United States Patent
Arai et al.

(10) Patent No.: US 9,812,652 B2
(45) Date of Patent: Nov. 7, 2017

(54) CYCLIC AZINE COMPOUND HAVING ADAMANTYL GROUP, PRODUCTION METHOD, AND ORGANIC ELECTROLUMINESCENT DEVICE CONTAINING IT AS CONSTITUENT COMPONENT

(71) Applicant: TOSOH CORPORATION, Yamaguchi (JP)

(72) Inventors: Nobumichi Arai, Kanagawa (JP); Keisuke Nomura, Kanagawa (JP); Tsuyoshi Tanaka, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 14/902,179

(22) PCT Filed: Jul. 8, 2014

(86) PCT No.: PCT/JP2014/068202
§ 371 (c)(1),
(2) Date: Dec. 30, 2015

(87) PCT Pub. No.: WO2015/005351
PCT Pub. Date: Jan. 15, 2015

(65) Prior Publication Data
US 2016/0372678 A1    Dec. 22, 2016

(30) Foreign Application Priority Data
Jul. 9, 2013 (JP) .................. 2013-143909

(51) Int. Cl.
| | | |
|---|---|---|
| C07D 251/24 | (2006.01) | |
| C07D 401/10 | (2006.01) | |
| C07C 309/65 | (2006.01) | |
| C09K 11/06 | (2006.01) | |
| H01L 51/50 | (2006.01) | |
| H05B 33/14 | (2006.01) | |
| H01L 51/00 | (2006.01) | |
| C07F 5/02 | (2006.01) | |
| C07D 401/14 | (2006.01) | |

(Continued)

(52) U.S. Cl.
CPC ........ *H01L 51/0067* (2013.01); *C07C 309/06* (2013.01); *C07D 251/24* (2013.01); *C07D 401/10* (2013.01); *C07D 401/14* (2013.01); *C07D 403/10* (2013.01); *C07F 5/025* (2013.01); *C09K 11/06* (2013.01); *H01L 51/0052* (2013.01); *H01L 51/0058* (2013.01); *H01L 51/0072* (2013.01); *C07C 2603/74* (2017.05); *C09K 2211/1011* (2013.01); *C09K 2211/1014* (2013.01); *H01L 51/5056* (2013.01); *H01L 51/5072* (2013.01)

(58) Field of Classification Search
CPC .. C07D 251/24; C07D 401/10; C07C 309/65; C09K 11/06; H01L 51/50; H01L 51/0032; H05B 33/14
USPC .................. 544/180; 345/82, 76, 72, 6, 727
See application file for complete search history.

(56) References Cited

U.S. PATENT DOCUMENTS

| | | | |
|---|---|---|---|
| 6,147,224 A | 11/2000 | Vuligonda et al. | |
| 6,403,638 B1 | 6/2002 | Vuligonda et al. | |
| 6,482,986 B1 | 11/2002 | Boigegrain et al. | |

(Continued)

FOREIGN PATENT DOCUMENTS

| | | |
|---|---|---|
| CN | 1328538 | 12/2001 |
| CN | 1355782 | 6/2002 |

(Continued)

OTHER PUBLICATIONS

Chinese Office Action issued in Counterpart Patent Appl. No. 201480033085.1, dated Nov. 30, 2016, along with an english translation thereof.
International Search Report issued in PCT/JP2014/068202, dated Aug. 19, 2014.
International Report on Patentability issued in PCT/JP2014/068202, dated Jul. 8, 2014.

*Primary Examiner* — Venkataraman Balasubramanian
(74) *Attorney, Agent, or Firm* — Greenblum and Bernstein, P.L.C.

(57) ABSTRACT

An azine compound represented by the formula (1), a method for its production and an organic electroluminescent device containing it as a constituent component.

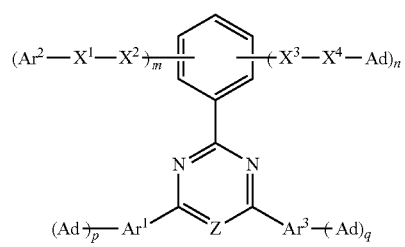

(1)

wherein Ad each independently represents a 1-adamantyl group, etc., p and q are each independently 0 or 1, $Ar^1$ and $Ar^2$ are each independently a single bond (but only when p is 1, or q is 1), or a pyridyl group which may be substituted by a phenyl group, etc., incidentally, Ad groups on $Ar^1$ and $Ar^2$ are each independently bonded to said pyridyl group, etc., $Ar^2$ is each independently a $C_{3-13}$ heteroaromatic group which may be substituted by a fluorine atom, etc., $X^1$, $X^2$, $X^3$ and $X^4$ are each independently a single bond, etc., m and n are each independently 0, 1 or 2, Z is a nitrogen atom, etc., n+p+q is 1, 2 or 3.

15 Claims, 1 Drawing Sheet

(51) Int. Cl.
  *C07D 403/10* (2006.01)
  *C07C 309/06* (2006.01)

(56) References Cited

U.S. PATENT DOCUMENTS

| | | |
|---|---|---|
| 2010/0249406 A1 | 9/2010 | Yamakawa et al. |
| 2012/0214993 A1 | 8/2012 | Aihara et al. |
| 2012/0313090 A1 | 12/2012 | Yamakawa et al. |

FOREIGN PATENT DOCUMENTS

| | | |
|---|---|---|
| CN | 101675038 | 3/2010 |
| CN | 102574813 | 7/2012 |
| JP | 2002-124385 | 4/2002 |
| JP | 2002-526516 | 8/2002 |
| JP | 2002-270374 | 9/2002 |
| JP | 2003-502306 | 1/2003 |
| JP | 2008-280330 | 11/2008 |
| JP | 2011-63584 | 3/2011 |
| JP | 2011-219444 | 11/2011 |
| WO | 2010/107244 | 9/2010 |

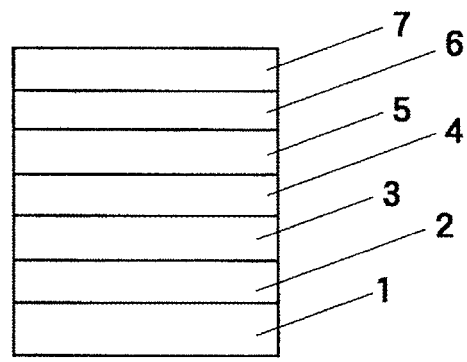

CYCLIC AZINE COMPOUND HAVING ADAMANTYL GROUP, PRODUCTION METHOD, AND ORGANIC ELECTROLUMINESCENT DEVICE CONTAINING IT AS CONSTITUENT COMPONENT

TECHNICAL FIELD

The present invention relates to a cyclic azine compound having an adamantyl group, a method for its production and an electroluminescent device containing it. More particularly, the present invention relates to a cyclic azine compound having a triazine skeleton or pyrimidine skeleton and an adamantyl skeleton combined, which is useful as a constituent component of an organic electroluminescent device, a method for its production, and an organic electroluminescent device having high efficiency, low voltage and high durability, wherein the cyclic azine compound is used in at least one layer of organic compound layers.

BACKGROUND ART

An organic electroluminescent device is a device wherein a luminous layer containing a luminescent material is sandwiched between a hole transport layer and an electron transport layer, and an anode and a cathode are further provided on the outside, so as to utilize emission of light (fluorescence or phosphorescence) at the time of deactivation of excitons formed by recombination of holes and electrons injected into the luminous layer, and it is applied not only to small size displays but also to large-screen televisions and lighting, etc. Here, the hole transport layer may sometimes be constituted as divided into a hole transport layer and a hole injection layer; the luminous layer may sometimes be constituted as divided into an electron blocking layer, a luminous layer and a hole blocking layer; and the electron transport layer may sometimes be constituted as divided into an electron transport layer and an electron injection layer. Further, there may be a case where as a carrier transport layer (an electron transport layer or a hole transport layer) in an organic electroluminescent device, a metal, an organic metal compound or a co-deposited film doped with an organic compound, is used.

Conventional organic electroluminescent devices were not put into practical use, since their drive voltage was high, their emission luminance or luminous efficiency was low, and their service life was remarkably low, as compared to inorganic light emitting diodes. Although recent organic EL devices have been gradually improved, with respect to luminous efficiency characteristics, drive voltage characteristic, long service life characteristics, further excellent material is required. Further, depending upon applications such as automotive applications, etc., high thermal resistance may sometimes be required, and the material is required to have a high glass transition temperature (Tg).

As electron transport materials excellent in long service life for organic electroluminescent devices, cyclic azine compounds disclosed in Patent Document 1 or 2 may be mentioned. However, with respect to the thermal resistance of the materials, as well as with respect to the service life and luminous efficiency of the organic electroluminescent devices, further improvement has been desired.

PRIOR ART DOCUMENTS

Patent Documents

Patent Document 1: JP-A-2011-063584
Patent Document 2: JP-A-2008-280330

DISCLOSURE OF INVENTION

Technical Problem

An object of the present invention is to provide a cyclic azine compound having an adamantyl group, a method for its production, and an electron transport material for an organic electroluminescent device having excellent thermal resistance, long service life or excellent luminous efficiency.

Solution to Problem

As a result of extensive studies to accomplish the above object, the present inventors have found that a cyclic azine compound having an adamantyl group introduced to a molecular terminal (hereinafter referred to also as "cyclic azine compound (1)") has high thermal resistance, and an organic electroluminescence device using the compound as an electron transport material, can be made to have a longer service life and a higher luminous efficiency, as compared with the case of using a conventional known material, and thus have completed the present invention.

That is, the present invention provides a cyclic azine compound represented by the following formula (1), a method for its production, and an organic electroluminescent device using it.

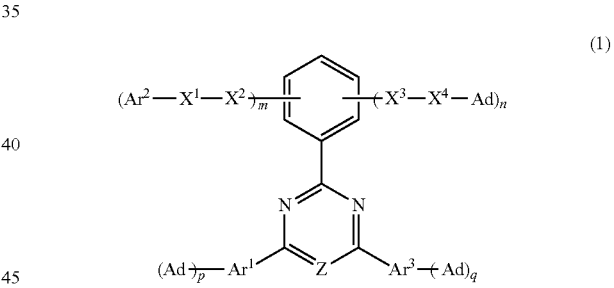

wherein Ad each independently represents a 1-adamantyl group ($Ad^1$) or a 2-adamantyl group ($Ad^2$):

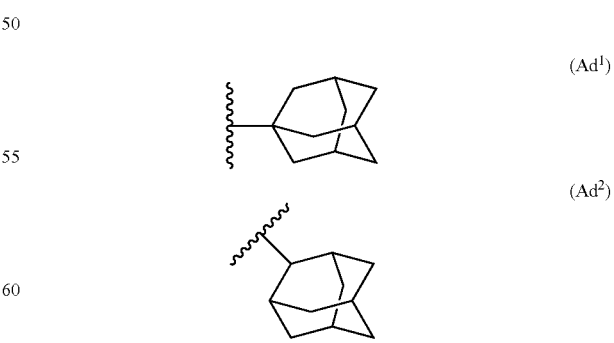

p and q are each independently 0 or 1,
$Ar^1$ and $Ar^3$ are each independently a single bond (but only when p is 1 or q is 1), a $C_{6-30}$ aromatic hydrocarbon group (which may have, as a substituent, a fluorine atom, a $C_{1-4}$ alkyl group, a C$_{6-18}$ aromatic hydrocarbon group, a C$_{6-18}$ aromatic hydrocarbon group substituted by a fluorine atom, a C$_{6-18}$ aromatic hydrocarbon group substituted by a C$_{1-4}$ alkyl group, a C$_{6-18}$ aromatic hydrocarbon group substituted by a C$_{3-13}$ heteroaromatic group, a C$_{3-13}$ heteroaromatic group, or a C$_{3-13}$ heteroaromatic group substituted by a C$_{1-4}$ alkyl group), or a pyridyl group which may be substituted by a phenyl group or a methyl group, incidentally, Ad groups on Ar$^1$ and Ar$^3$ are each independently bonded to said C$_{6-30}$ aromatic hydrocarbon group or said pyridyl group, Ar$^2$ is each independently a C$_{3-13}$ heteroaromatic group or a C$_{6-18}$ aromatic hydrocarbon group (these groups each independently may have, as a substituent, a fluorine atom, a C$_{1-4}$ alkyl group, a C$_{6-18}$ aromatic hydrocarbon group, a C$_{6-18}$ aromatic hydrocarbon group substituted by a fluorine atom, a C$_{6-18}$ aromatic hydrocarbon group substituted by a C$_{1-4}$ alkyl group, a C$_{6-18}$ aromatic hydrocarbon group substituted by a C$_{3-13}$ heteroaromatic group, a C$_{3-13}$ heteroaromatic group, or a C$_{3-13}$ heteroaromatic group substituted by a C$_{1-4}$ alkyl group), X$^1$, X$^2$, X$^3$ and X$^4$ are each independently a single bond or a C$_{4-14}$ arylene group (which may be substituted by a fluorine atom, a C$_{1-4}$ alkyl group, a phenyl group, a biphenyl group or a naphthyl group), m is 0, 1 or 2, n is 0, 1 or 2, Z is a nitrogen atom or a carbon atom, and n+p+q is 1, 2 or 3.

Advantageous Effects of Invention

By using the cyclic azine compound of the present invention, it is possible to provide an organic electroluminescent device having high thermal resistance and a long service life and being excellent in luminous efficiency.

BRIEF DESCRIPTION OF DRAWING

FIG. 1 a schematic cross-sectional view of an organic electroluminescent device prepared in Examples.

DESCRIPTION OF EMBODIMENTS

The present invention relates to the cyclic azine compound (1), a method for its production, and an organic electroluminescent device containing it, and substituents in the cyclic azine compound (1) are, respectively, defined as follows.

In the cyclic azine compound (1), Ad each independently represents a 1-adamantyl group (hereinafter referred to also as "Ad$^1$") or a 2-adamantyl group (hereinafter referred to also as "Ad$^2$").

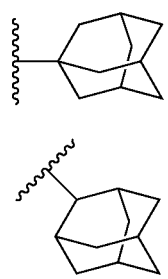

(Ad$^1$)

(Ad$^2$)

Among them, the 1-adamantyl group (Ad$^1$) is preferred from the viewpoint of excellent properties of the electron transport material.

Ar$^1$ and Ar$^3$ are each independently a single bond (but only when p is 1, or q is 1), a C$_{6-30}$ aromatic hydrocarbon group (which may have, as a substituent, a fluorine atom, a C$_{1-4}$ alkyl group, a C$_{6-18}$ aromatic hydrocarbon group, a C$_{6-18}$ aromatic hydrocarbon group substituted by a fluorine atom, a C$_{6-18}$ aromatic hydrocarbon group substituted by a C$_{1-4}$ alkyl group, a C$_{6-18}$ aromatic hydrocarbon group substituted by a C$_{3-13}$ heteroaromatic group, a C$_{3-13}$ heteroaromatic group, or a C$_{3-13}$ heteroaromatic group substituted by a C$_{1-4}$ alkyl group), or a pyridyl group which may be substituted by a phenyl group or a methyl group, The C$_{6-30}$ aromatic hydrocarbon group in Ar$^1$ and Ar$^3$ is not particularly limited, but a phenyl group, a biphenyl group, a naphthyl group, a phenanthryl group, an anthryl group, a pyrenyl group, a triphenylenyl group, a chrysenyl group, a fluoranthenyl group, an acenaphthylenyl group, a fluorenyl group, a benzofluorenyl group, etc. may be mentioned as preferred examples.

The C$_{1-4}$ alkyl group in Ar$^1$ and Ar$^3$ is not particularly limited, but a methyl group, an ethyl group, a n-propyl group, an isopropyl group, a n-butyl group, a sec-butyl group, a tert-butyl group, etc. may be mentioned as preferred examples.

The C$_{6-18}$ aromatic hydrocarbon group in Ar$^1$ and Ar$^3$ is not particularly limited, but a phenyl group, a biphenyl group, a naphthyl group, a phenanthryl group, an anthryl group, a pyrenyl group, a triphenylenyl group, a chrysenyl group, a fluoranthenyl group, an acenaphthylenyl group, a fluorenyl group, a benzofluorenyl group, etc. may be mentioned as preferred examples.

The C$_{6-18}$ aromatic hydrocarbon group substituted by a fluorine atom in Ar$^1$ and Ar$^3$ is not particularly limited, but a fluorophenyl group, a difluorobiphenyl group, a fluoronaphthyl group, a difluoronaphthyl group, a fluorophenanthryl group, a difluorophenanthryl group, a fluoroanthryl group, a difluoroanthryl group, a fluoropyrenyl group, a difluoropyrenyl group, a fluorotriphenylenyl group, a difluorotriphenylenyl group, a fluorochrysenyl group, a difluorochrysenyl group, a fluorofluoranthenyl group, a difluorofluoranthenyl group, a fluoroacenaphthylenyl group, a difluoroacenaphthylenyl group, etc. may be mentioned as preferred examples.

The C$_{6-18}$ aromatic hydrocarbon group substituted by a C$_{1-4}$ alkyl group in Ar$^1$ and Ar$^3$ is not particularly limited, but a methylphenyl group, a methylbiphenyl group, a methylnaphthyl group, a methylphenanthryl group, an anthryl group, a methylpyrenyl group, a methyltriphenylenyl group, a methylchrysenyl group, a methylfluoranthenyl group, a methylacenaphthylenyl group, a dimethylphenyl group, a dimethylbiphenyl group, a dimethylnaphthyl group, a dimethylphenanthryl group, an anthryl group, a dimethylpyrenyl group, a dimethyltriphenylenyl group, a dimethylchrysenyl group, a dimethylfluoranthenyl group, a dimethylacenaphthylenyl group, a di-dimethyl fluorenyl group, a dimethylbenzofluorenyl group, etc. may be mentioned as preferred examples.

The C$_{6-18}$ aromatic hydrocarbon group substituted by a C$_{3-13}$ heteroaromatic group in Ar$^1$ and Ar$^3$ is not particularly limited, but a pyridylphenyl group, a pyridylbiphenyl group, a pyridylnaphthyl group, a pyridylphenanthryl group, a pyridylanthryl group, a pyridylpyrenyl group, a pyridyltriphenylenyl group, a pyridylchrysenyl group, a pyridylfluoranthenyl group, a pyridylacenaphthylenyl group, a pyrimidylphenyl group, a pyrimidylbiphenyl group, a pyrimidylnaphthyl group, a pyrimidylphenanthryl group, a pyrimidylanthryl group, a pyrimidylpyrenyl group, a pyrimidyltriphenylenyl group, a pyrimidylchrysenyl group, a pyrimidylfluorantheny group, a pyrimidylacenaphthylenyl group, a pyrazylphenyl group, a pyrazylbiphenyl group, a pyrazylnaphthyl group, a pyrazylphenanthryl group, a pyrazylanthryl group, a pyrazylpyrenyl group, a pyrazyltriphenylenyl group, a pyrazylchrysenyl group, a pyrazylfluoranthenyl group, a pyrazylacenaphthylenyl group, a quinolylphenyl group, a quinolylbiphenyl group, a quinolylnaphthyl group, a quinolylphenanthryl group, a quinolylanthryl group, a quinolylpyrenyl group, a quinolyltriphenylenyl group, a quinolylchrysenyl group, a quinolylfluoranthenyl group, a quinolylacenaphthylenyl group, an isoquinolylphenyl group, an isoquinolylbiphenyl group, an isoquinolylnaphthyl group, isoquinolylphenanthryl group, an isoquinolylanthryl group, an isoquinolylpyrenyl group, isoquinolyltriphenylenyl group, an isoquinolylchrysenyl group, an isoquinolylfluoranthenyl group, an isoquinolylacenaphthylenyl group, etc. may be mentioned as preferred examples.

The $C_{3-13}$ heteroaromatic group in $Ar^1$ and $Ar^3$ is not particularly limited, but a pyridyl group, a pyrazyl group, a pyrimidyl group, a pyridazyl group, a triazyl group, a quinolyl group, an isoquinolyl group, a phenanthridyl group, a benzoquinolyl group, an acridyl group, etc. may be mentioned as preferred examples.

The $C_{3-13}$ heteroaromatic group substituted by a $C_{1-4}$ alkyl group in $Ar^1$ and $Ar^3$ is not particularly limited, but a methylpyridyl group, a methylpyrazyl group, a methylpyrimidyl group, a methylpyridazyl group, a methyltriazyl group, a methylquinolyl group, a methylisoquinolyl group, a methylphenanthridyl group, a methylbenzoquinolyl group, a methylacridyl group, a dimethylpyridyl group, a dimethylpyrazyl group, a dimethylpyrimidyl group, a dimethylpyridazyl group, a dimethyltriazyl group, a dimethylquinolyl group, a dimethylisoquinolyl group, a dimethylphenanthridyl group, a dimethylbenzoquinolyl group, a dimethylacridyl group, etc. may be mentioned as preferred examples.

As the pyridyl group which may be substituted by a phenyl group or a methyl group in $Ar^1$ and $Ar^3$, a 3-phenylpyridin-2-yl group, a 4-phenylpyridin-2-yl group, a 5-phenylpyridin-2-yl group, a 3-methylpyridin-2-yl group, a 4-methylpyridin-2-yl group, a 5-methylpyridin-2-yl group, etc. may be mentioned as preferred examples.

From the viewpoint of excellent electron transport material properties, $Ar^1$ and Ar3 are preferably a single bond (but only when p is 1, or q is 1), a phenyl group, a biphenyl group, a naphthyl group, a phenanthryl group, an anthryl group, a pyrenyl group, a triphenylenyl group, a chrysenyl group, a fluoranthenyl group, an acenaphthylenyl group, a pyridyl group, a pyrazyl group, a pyrimidyl group, a pyridazyl group, a triazyl group, a quinolyl group or an isoquinolyl group (these groups each independently may have, as a substituent, a methyl group, an ethyl group, a propyl group, an isopropyl group, a n-butyl group or a t-butyl group), more preferably a single bond (but only when p is 1, or q is 1), a phenyl group, a biphenyl group or a pyridyl group (these groups each independently may have, as a substituent, a methyl group or a t-butyl group), further preferably a single bond (but only when p is 1, or q is 1), a phenyl group or a biphenyl group.

As specific examples of the substituent represented by "-$Ar^1$-(Ad)p" and the substituent represented by "-$Ar^2$-(Ad)q", each independently, a 1-adamantyl group, a 2-adamantyl group, a 2-(1-adamantyl)phenyl group, a 3-(1-adamantyl) phenyl group, a 4-(1-adamantyl)phenyl group, a 3'-(1-adamantyl)biphenyl-2-yl group, a 3'-(1-adamantyl)biphenyl-3-yl group, a 3'-(1-adamantyl)biphenyl-4-yl group, a 4'-(1-adamantyl)biphenyl-2-yl group, a 4'-(1-adamantyl) biphenyl-3-yl group, a 4'-(1-adamantyl)biphenyl-4-yl group, a 5-(1-adamantyl)biphenyl-3-yl group, a 2-(2-adamantyl) phenyl group, a 3-(2-adamantyl)phenyl group, a 4-(2-adamantyl)phenyl group, a 3'-(2-adamantyl)biphenyl-2-yl group, a 3'-(2-adamantyl)biphenyl-3-yl group, a 3'-(2-adamantyl)biphenyl-4-yl group, a 4'-(2-adamantyl)biphenyl-2-yl group, a 4'-(2-adamantyl)biphenyl-3-yl group, a 4'-(2-adamantyl)biphenyl-4-yl group, a 5-(2-adamantyl)biphenyl-3-yl group, a phenyl group, a p-tolyl group, a m-tolyl group, an o-tolyl group, a 2,4-dimethylphenyl group, a 3,5-dimethylphenyl group, a mesityl group, a 2-ethylphenyl group, a 3-ethylphenyl group, a 4-ethylphenyl group, a 2,4-diethylphenyl group, a 3,5-diethylphenyl group, a 2-propylphenyl group, a 3-propylphenyl group, a 4-propylphenyl group, a 2,4-dipropylphenyl group, a 3,5-dipropylphenyl group, a 2-isopropylphenyl group, a 3-isopropylphenyl group, a 4-isopropylphenyl group, a 2,4-diisopropylphenyl group, a 3,5-diisopropylphenyl group, a 2-butylphenyl group, a 3-butylphenyl group, a 4-butylphenyl group, a 2,4-dibutylphenyl group, a 3,5-dibutylphenyl group, a 2-tert-butylphenyl group, a 3-tert-butylphenyl group, a 4-tert-butylphenyl group, a 2,4-di-tert-butylphenyl group, a 3,5-di-tert-butylphenyl group, a biphenyl-2-yl group, a biphenyl-3-yl group, a biphenyl-4-yl group, a 3-methylbiphenyl-4-yl group, a 2'-methylbiphenyl-4-yl group, a 4'-methylbiphenyl-4-yl group, a 2,2'-dimethylbiphenyl-4-yl group, a 2',4',6'-trimethylbiphenyl-4-yl group, a 6-methylbiphenyl-3-yl group, a 5-methylbiphenyl-3-yl group, a 2'-methylbiphenyl-3-yl group, a 4'-methylbiphenyl-3-yl group, a 6,2'-dimethylbiphenyl-3-yl group, a 2',4',6'-trimethylbiphenyl-3-yl group, a 5-methylbiphenyl-2-yl group, a 6-methylbiphenyl-2-yl group, a 2'-methylbiphenyl-2-yl group, a 4'-methylbiphenyl-2-yl group, a 6,2'-dimethylbiphenyl-2-yl group, a 2',4',6'-trimethylbiphenyl-2-yl group, a 3-ethylbiphenyl-4-yl group, a 4'-ethylbiphenyl-4-yl group, a 2',4',6'-triethylbiphenyl-4-yl group, a 6-ethylbiphenyl-3-yl group, a 4'-ethylbiphenyl-3-yl group, a 5-ethylbiphenyl-2-yl group, a 4'-ethylbiphenyl-2-yl group, a 2',4',6'-triethylbiphenyl-2-yl group, a 3-propylbiphenyl-4-yl group, a 4'-propylbiphenyl-4-yl group, a 2',4',6'-tripropylbiphenyl-4-yl group, a 6-propylbiphenyl-3-yl group, a 4'-propyl biphenyl-3-yl group, a 5-propylbiphenyl-2-yl group, a 4'-propylbiphenyl-2-yl group, a 2',4',6'-tripropylbiphenyl-2-yl group, a 3-isopropylbiphenyl-4-yl group, a 4'-isopropylbiphenyl-4-yl group, a 2',4',6'-triisopropyl biphenyl-4-yl group, a 6-isopropylbiphenyl-3-yl group, a 4'-isopropylbiphenyl-3-yl group, a 5-isopropylbiphenyl-2-yl group, a 4'-isopropylbiphenyl-2-yl group, a 2',4',6'-triisopropylbiphenyl-2-yl group, a 3-butylbiphenyl-4-yl group, a 4'-butylbiphenyl-4-yl group, a 2',4',6'-tributylbiphenyl 4-yl group, a 6-butylbiphenyl-3-yl group, a 4'-butylbiphenyl-3-yl group, a 5-butylbiphenyl-2-yl group, a 4'-butylbiphenyl-2-yl group, a 2',4',6'-tributylbiphenyl-2-yl group, a 3-tert-butylbiphenyl-4-yl group, a 4'-tert-butylbiphenyl-4-yl group, a 2',4',6'-tri tert-butylbiphenyl-4-yl group, a 6-tert-butylbiphenyl-3-yl group, a 4'-tert-butyl-biphenyl-3-yl group, a 5-tert-butylbiphenyl-2-yl group, a 4'-tert-butylbiphenyl-2-yl group, a 2',4',6'-tri-tert-butylbiphenyl-2-yl group, a 2-pyridyl group, a 3-pyridyl group, a 4-pyridyl group, a 2-methylpyridin-3-yl group, a 2-methylpyridin-4-yl group, a 2-methylpyridin-5-yl group, a 2-methylpyridin-6-yl group, a 3-methylpyridin-2-yl group, a 3-methylpyridin-4-yl group, a 3-methylpyridin-5-yl group, a 3-methylpyridin-6-yl group, a 4-methylpyridin-2-yl group, a 4-methylpyridin-3-yl group, a 2,6-dimethylpyridin-3-yl group, a 2,6-dimethylpyridin-4-yl group, a 3,6-dimethylpyridin-2-yl group, a 3,6-dimethylpyridin-4-yl group, a 3,6-dimethylpyridin 5-yl group, a 2-phenylpyridin-6-yl group, a 3-phenylpyridin-6-yl group, a 4-phenylpyridin-6-yl group, a 5-phenylpyridin-6-yl group, a 2-phenylpyridin-3-yl group, a 2-phenylpyridin-5-yl group, a 3-phenylpyridin-5-yl group, a 4-phenylpyridin-3-yl group, a 3-phenylpyridin-4-yl group, a 2-phenylpyridin-4-yl group, a 2-(2-pyridyl)phenyl group, a 3-(2-pyridyl)phenyl group, a 4-(2-pyridyl)phenyl group, a 2-(3-pyridyl)phenyl group, a 3-(3-pyridyl)phenyl group, a 4-(3-pyridyl)phenyl group, a 2-(4-pyridyl)phenyl group, a 3-(4-pyridyl)phenyl group, a 4-(4-pyridyl)phenyl group, a 1-naphthyl group, a 2-naphthyl group, a 1-phenylnaphthalen-2-yl group, a 1-phenylnaphthalen-3-yl group, a 1-phenylnaphthalen-4-yl group, a 1-phenylnaphthalen-5-yl group, a 1-phenylnaphthalen-6-yl group, a 1-phenylnaphthalen-7-yl group, a 1-phenylnaphthalen-8-yl group, a 2-phenylnaphthalen-1-yl group, a 2-phenylnaphthalen-3-yl group, a 2-phenylnaphthalen-4-yl group, a 2-phenylnaphthalen-5-yl group, a 2-phenylnaphthalen-6-yl group, a 2-phenylnaphthalen-7-yl group, a 2-phenylnaphthalen-8-yl group, a 1-methylnaphthalen-4-yl group, a 1-methylnaphthalen-5-yl group, a 1-methylnaphthalen-6-yl group, a 1-methylnaphthalen-7-yl group, a 1-methylnaphthalen-8-yl group, a 2-methylnaphthalen-1-yl group, a 2-methylnaphthalen-3-yl group, a 2-methylnaphthalen-4-yl group, a 2-methylnaphthalen-5-yl group, a 2-methylnaphthalen-6-yl group, a 2-methylnaphthalen-7-yl group, a 2-methylnaphthalen-8-yl group, a 1-phenanthryl group, a 2-phenanthryl group, a 3-phenanthryl group, a 4-phenanthryl group, a 9-phenanthryl group, a 1-phenylphenanthren-2-yl group, a 1-phenylphenanthren-3-yl group, a 1-phenylphenanthren-4-yl group, a 1-phenylphenanthren-5-yl group, a 1-phenylphenanthren-6-yl group, a 1-phenylphenanthren-7-yl group, a 1-phenylphenanthren-8-yl group, a 1-phenylphenanthren-9-yl group, a 1-phenylphenanthren-10-yl group, a 2-phenylphenanthren-1-yl group, a 2-phenylphenanthren-3-yl group, a 2-phenylphenanthren-4-yl group, a 2-phenylphenanthren-5-yl group, a 2-phenylphenanthren-6-yl group, a 2-phenylphenanthren-7-yl group, a 2-phenylphenanthren-8-yl group, a 2-phenylphenanthren-9-yl group, a 2-phenylphenanthren-10-yl group, a 3-phenylphenanthren-1-yl group, a 3-phenylphenanthren-2-yl group, a 3-phenylphenanthren-4-yl group, a 3-phenylphenanthren-5-yl group, a 3-phenylphenanthren-6-yl group, a 3-phenylphenanthren-7-yl group, a 3-phenylphenanthren-8-yl group, a 3-phenylphenanthren-9-yl group, a 3-phenylphenanthren-10-yl group, a 4-phenylphenanthren-1-yl group, a 4-phenylphenanthren-2-yl group, a 4-phenylphenanthren-3-yl group, a 4-phenylphenanthren-5-yl group, a 4-phenylphenanthren-6-yl group, a 4-phenylphenanthren-7-yl group, a 4-phenylphenanthren-8-yl group, a 4-phenylphenanthren-9-yl group, a 4-phenylphenanthren-10-yl group, a 1-methylphenanthren-2-yl group, a 1-methylphenanthren-3-yl group, a 1-methylphenanthren-4-yl group, a 1-methylphenanthren-5-yl group, a 1-methylphenanthren-6-yl group, a 1-methylphenanthren-7-yl group, a 1-methylphenanthren-8-yl group, a 1-methylphenanthren-9-yl group, a 1-methylphenanthren-10-yl group, a 2-methylphenanthren-1-yl group, a 2-methylphenanthren-3-yl group, a 2-methylphenanthren-4-yl group, a 2-methylphenanthren-5-yl group, a 2-methylphenanthren-6-yl group, a 2-methylphenanthren-7-yl group, a 2-methylphenanthren-8-yl group, a 2-methylphenanthren-9-yl group, a 2-methylphenanthren-10-yl group, a 3-methylphenanthren-1-yl group, a 3-methylphenanthren-2-yl group, a 3-methylphenanthren-4-yl group, a 3-methylphenanthren-5-yl group, a 3-methylphenanthren-6-yl group, a 3-methylphenanthren-7-yl group, a 3-methylphenanthren-8-yl group, a 3-methylphenanthren-9-yl group, a 3-methylphenanthren-10-yl group, a 4-methylphenanthren-1-yl group, a 4-methylphenanthren-2-yl group, a 4-methylphenanthren-3-yl group, a 4-methylphenanthren-5-yl group, a 4-methylphenanthren-6-yl group, a 4-methylphenanthren-7-yl group, a 4-methylphenanthren-8-yl group, a 4-methylphenanthren-9-yl group, a 4-methylphenanthren-10-yl group, a 1-anthryl group, a 2-anthryl group, a 9-anthryl group, a 1-phenylanthracen-2-yl group, a 1-phenylanthracen-3-yl group, a 1-phenylanthracen-4-yl group, a 1-phenylanthracen-5-yl group, a 1-phenylanthracen-6-yl group, a 1-phenylanthracen-7-yl group, a 1-phenylanthracen-8-yl group, a 1-phenylanthracen-9-yl group, a 1-phenylanthracen-10-yl group, a 2-phenylanthracen-1-yl group, a 2-phenylanthracen-3-yl group, a 2-phenylanthracen-4-yl group, a 2-phenylanthracen-5-yl group, a 2-phenylanthracen-6-yl group, a 2-phenylanthracen-7-yl group, a 2-phenylanthracen-8-yl group, a 2-phenylanthracen-9-yl group, a 2-phenylanthracen-10-yl group, a 9-phenylanthracen-1-yl group, a 9-phenylanthracen-2-yl group, a 9-phenylanthracen-3-yl group, a 9-phenylanthracen-4-yl group, a 9-phenylanthracen-5-yl group, a 1-pyrenyl group, a 2-pyrenyl group, a 4-pyrenyl group, a 1-phenylpyren-2-yl group, a 1-phenylpyren-3-yl group, a 1-phenylpyren-4-yl group, a 1-phenylpyren-5-yl group, a 1-phenylpyren-6-yl group, a 1-phenylpyrene-7-yl group, a 1-phenylpyrene-8-yl group, a 1-phenylpyren-9-yl group, a 1-phenylpyren-10-yl group, a 2-phenylpyren-1-yl group, a 2-phenylpyren-3-yl group, a 2-phenylpyren-4-yl group, a 2-phenylpyren-5-yl group, 2-phenylpyren-6-yl group, a 2-phenylpyren-7-yl group, a 2-phenylpyren-8-yl group, a 2-phenylpyren-9-yl group, a 2-phenylpyren-10-yl group, a 9-phenylpyren-1-yl group, a 9-phenylpyren-2-yl group, a 9-phenylpyren-3-yl group, a 9-phenylpyren-4-yl group, a 9-phenylpyren-5-yl group, a 9-phenylpyren-6-yl group, a 9-phenylpyren-7-yl group, a 9-phenylpyren-8-yl group, a 9-phenylpyren-10-yl group, a 1-methylpyren-2-yl group, a 1-methylpyren-3-yl group, a 1-methylpyren-4-yl group, a 1-methylpyren-5-yl group, a 1-methylpyren-6-yl group, a 1-methylpyren-7-yl group, a 1-methylpyren-8-yl group, a 1-methylpyren-9-yl group, a 1-methylpyren-10-yl group, a 2-methylpyren-1-yl group, a 2-methylpyren-3-yl group, a 2-methylpyren-4-yl group, a 2-methylpyren-5-yl group, a 2-methylpyren-6-yl group, a 2-methylpyren-7-yl group, a 2-methylpyren-8-yl group, a 2-methylpyren-9-yl group, a 2-methylpyren-10-yl group, a 9-methylpyren-1-yl group, a 9-methylpyren-2-yl group, a 9-methylpyren-3-yl group, a 9-methylpyren-4-yl group, a 9-methylpyren-5-yl group, a 9-methylpyren-6-yl group, a 9-methylpyren-7-yl group, a 9-methylpyren-8-yl group, a 9-methylpyren-10-yl group, a fluoranthen-1-yl group, a fluoranthen-1-yl group, a fluoranthen-2-yl group, a fluoranthen-3-yl group, a fluoranthen-4-yl group, a fluoranthen-5-yl group, a fluoranthen-6-yl group, a fluoranthen-7-yl group, fluoranthen-8-yl group, a fluoranthen-9-yl group, a fluoranthen-10-yl group, a triphenylen-1-yl group, a triphenylen-2-yl group, an acenaphthylen-1-yl group, an acenaphthylen-3-yl group, an acenaphthylen-4-yl group, an acenaphthylen-5-yl group, a chrysen-1-yl group, a chrysen-2-yl group, a chrysen-5-yl group, a chrysen-6-yl group, etc. may be mentioned as preferred examples.

Among these substituents, from the viewpoint of excellent electron transport material properties, each independently, a phenyl group, a p-tolyl group, a biphenyl-3-yl group, a biphenyl-4-yl group, a 3-(2-pyridyl)phenyl group, a 4-(2-pyridyl)phenyl group, a 3-(3-pyridyl)phenyl group, a 4-(3-pyridyl)phenyl group, a 2-pyridyl group, a 3-pyridyl group, a 2-phenylpyridin-6-yl group, a 2-phenylpyridin-5-yl group, a 2-phenylpyridin-4-yl group, a 3-phenylpyridin-5-yl group, a 3-phenylpyridin-6-yl group, a 1-naphthyl group or a 2-naphthyl group is more preferred, and each independently, a phenyl group, a p-tolyl group, a biphenyl-3-yl group or a biphenyl-4-yl group is further preferred.

Incidentally, Ad groups on $Ar^1$ and $Ar^3$ are each independently bonded to said $C_{6-30}$ aromatic hydrocarbon group or said pyridyl group.

$Ar^2$ is each independently a $C_{3-13}$ heteroaromatic group or a $C_{6-18}$ aromatic hydrocarbon group (these groups each independently may have, as a substituent, a fluorine atom, a $C_{1-4}$ alkyl group, a $C_{6-18}$ aromatic hydrocarbon group, a $C_{6-18}$ aromatic hydrocarbon group substituted by a fluorine atom, a $C_{6-18}$ aromatic hydrocarbon group substituted by a $C_{1-4}$ alkyl group, a $C_{6-18}$ aromatic hydrocarbon group substituted by a $C_{3-13}$ heteroaromatic group, a $C_{3-13}$ heteroaromatic group, or a $C_{3-13}$ heteroaromatic group substituted by a $C_{1-4}$ alkyl group).

The following substituents in $Ar^2$ are the same as the substituents exemplified in $Ar^1$.
(1) a $C_{3-13}$ heteroaromatic group,
(2) a $C_{6-18}$ aromatic hydrocarbon group,
(3) a $C_{1-4}$ alkyl group,
(4) a $C_{6-18}$ aromatic hydrocarbon group substituted by a fluorine atom,
(5) a $C_{6-18}$ aromatic hydrocarbon groups substituted by a $C_{1-4}$ alkyl group,
(6) a $C_{6-18}$ aromatic hydrocarbon group substituted by a $C_{3-13}$ heteroaromatic group,
(7) a $C_{3-13}$ heteroaromatic group substituted by a $C_{1-4}$ alkyl group.

From the viewpoint of excellent electron transport material properties, $Ar^2$ is preferably a pyridyl group, a pyrazyl group, a pyridazyl group, a pyrimidyl group, a triazyl group, a quinolyl group, an isoquinolyl group, a naphthyridyl group, a quinazolyl group, a quinoxalyl group, a benzoquinolyl group, an acridyl group, a phenanthridyl group, a phenanthrolyl group, a phenyl group, a biphenyl group, a naphthyl group, a phenanthryl group, an anthryl group, a pyrenyl group, a triphenylenyl group, a chrysenyl group, a fluoranthenyl group or an acenaphthylenyl group (these groups each independently may have, as a substituent, a methyl group, a phenyl group, a naphthyl group, a phenanthryl group, an anthryl group, a pyrenyl group, a triphenylenyl group, a pyridyl group, a pyrimidyl group, a pyrazyl group, a triazyl group, a quinolyl group or an isoquinolyl group), more preferably a phenyl group, a biphenyl group, a pyridyl group, a pyrazyl group, a pyrimidyl group, an isoquinolyl group, a quinolyl group, a phenanthridyl group, a phenanthryl group, an anthryl group, a fluoranthenyl group or a triphenylenyl group (these groups each independently may have, as a substituent, a methyl group, a phenyl group, a naphthyl group or a pyridyl group), further preferably a pyridyl group, a quinolyl group or an isoquinolyl group.

$Ar^2$ is not particularly limited, but specifically, a 2-pyridyl group, a 3-pyridyl group, a 4-pyridyl group, a 2-methylpyridin-3-yl group, a 2-methylpyridin-4-yl group, a 2-methylpyridin-5-yl group, a 2-methylpyridin-6-yl group, a 3-methylpyridin-2-yl group, a 3-methylpyridin-4-yl group, a 3-methylpyridin-5-yl group, a 3-methylpyridin-6-yl group, a 4-methylpyridin-2-yl group, a 4-methylpyridin-3-yl group, a 2,6-dimethylpyridin-3-yl group, a 2,6-dimethylpyridin-4-yl group, a 3,6-dimethylpyridin-2-yl group, a 3,6-dimethylpyridin-4-yl group, a 3,6-dimethylpyridin-5-yl group, a pyridin-6-yl group, a 5-phenylpyridine-6-yl group, a 2-phenylpyridin-3-yl group, a 2-phenylpyridine-5-yl group, a 3-phenylpyridin-5-yl group, a 4-phenylpyridin-3-yl group, a 3-phenylpyridin-4-yl group, a 2-phenylpyridin-4-yl group, a 2,4-diphenylpyridin-2-yl group, a 2,6-diphenylpyridin-4-yl group, a 4-(1-naphthyl)-2-phenylpyridin-6-yl group, a 4-(2-naphthyl)-2-phenylpyridin-6-yl group, a 2-(1-naphthyl)-4-phenylpyridin-6-yl group, a 2-(2-naphthyl)-4-phenylpyridin-6-yl group, a 2,4-di(1-naphthyl)pyridin-2-yl group, a 2,4-di(2-naphthyl)pyridin-2-yl group, a 2,6-di(1-naphthyl)pyridin-4-yl group, a 2,6-di(2-naphthyl)pyridin-4-yl group, a 2-pyrimidyl group, a 4-pyrimidyl group, a 5-pyrimidyl group, a 4,6-dimethylpyrimidin-2-yl group, a 4,6-diphenylpyrimidin-2-yl group, a 5-phenylpyrimidin-2-yl group, a quinolin-2-yl group, a quinolin-3-yl group, a quinolin-4-yl group, a quinolin-5-yl group, a quinolin-6-yl group, a quinolin-7-yl group, a quinolin-8-yl group, a quinolin-9-yl group, a 2-methylquinolin-3-yl group, a 2-methylquinolin-4-yl group, a 2-methylquinolin-5-yl group, a 2-methylquinolin-6-yl group, a 2-methylquinolin-7-yl group, a 2-methylquinolin-8-yl group, an isoquinolin-1-yl group, an isoquinolin-3-yl group, an isoquinolin-4-yl group, an isoquinolin-5-yl group, an isoquinolin-6-yl group, an isoquinolin-7-yl group, an isoquinolin-8-yl group, a pyrazyl group, a 2-phenylpyrazin-5-yl group, a 2-phenylpyrazin-6-yl group, a 2-methylpyrazin-5-yl group, a 2-methylpyrazin-6-yl, a pyridazin-3-yl group, a pyridazin-4-yl group, a 3-phenylpyridazin-4-yl group, a 3-phenylpyridazin-5-yl group, a 3-phenylpyridazin-6-yl group, a 4-phenylpyridazin-3-yl group, a 4-phenylpyridazine-5-yl group, a 4-phenylpyridazin-6-yl group, a 5-phenylpyridazin-3-yl group, a 5-phenylpyridazin-3-yl group, a 5-phenylpyridazin-4-yl group, a 5-phenylpyridazin-6-yl group, a 6-phenylpyridazin-3-yl group, a 6-phenylpyridazin-4-yl group, a 6-phenylpyridazine-5-yl group, a 3-methylpyridazin-5-yl group, a 3-methylpyridazin-6-yl group, a 4-methylpyridazin-3-yl group, a 4-methylpyridazin-5-yl group, a 4-methylpyridazin-6-yl group, a 5-methylpyridazin-3-yl group, 5-methylpyridazin-3-yl group, a 5-methylpyridazin-4-yl group, a 5-methylpyridazin-6-yl group, a 6-methylpyridazin-3-yl group, a 6-methylpyridazin-4-yl group, a 6-methylpyridazine-5-yl group, a triazyl group, a 2,4-diphenyltriazin-6-yl, a 2,4-dimethyltriazin-6-yl group, a naphthyridin-2-yl group, a naphthyridin-3-yl group, a naphthyridin-4-yl group, a quinoxalin-2-yl group, a quinoxalin-5-yl group, a quinoxalin-6-yl group, a 2,3-dimethylquinoxalin-5-yl group, a 2,3-dimethylquinoxalin-6-yl group, a quinazolin-2-yl group, a quinazolin-4-yl group, a quinazolin-5-yl group, a quinazolin-6-yl group, a quinazolin-7-yl group, a quinazolin-8-yl group, a phenanthridin-1-yl group, a phenanthridin-2-yl group, a phenanthridin-3-yl group, a phenanthridin-4-yl group, a phenanthridin-6-yl group, a phenanthridin-7-yl group, a phenanthridin-8-yl group, a phenanthridin-9-yl group, a phenanthridin-10-yl group, a 1,10-phenanthrolin-2-yl group, a 1,10-phenanthrolin-3-yl group, a 1,10-phenanthrolin-4-yl group, a 1,10-phenanthrolin-5-yl group, an acridin-1-yl group, an acridin-2-yl group, an acridin-3-yl group, an acridin-4-yl group, an acridin-9-yl group, a phenazin-1-yl group, a phenazin-2-yl group, a benzo[h]quinolyl group, a benzo[f]quinolyl group, a 1-naphthyl group, a 2-naphthyl group, a 1-phenyl-naphthalen-2-yl group, a 1-phenylnaphthalen-3-yl group, a 1-phenylnaphthalen-4-yl group, a 1-phenylnaphthalen-5-yl group, a 1-phenylnaphthalen-6-yl group, a 1-phenylnaphthalen-7-yl group, a 1-phenylnaphthalen-8-yl group, a 2-phenylnaphthalen-1-yl group, a 2-phenylnaphthalen-3-yl group, a 2-phenylnaphthalen-4-yl group, a 2-phenylnaphthalen-5-yl group, a 2-phenylnaphthalen-6-yl group, a 2-phenylnaphthalen-7-yl group, a 2-phenylnaphthalen-8-yl group, a 1-methylnaphthalen-4-yl group, a 1-methylnaphthalen-5-yl group, a 1-methylnaphthalen-6-yl group, a 1-methylnaphthalen-7-yl group, a 1-methylnaphthalen-8-yl group, a 2-methylnaphthalen-1-yl group, a 2-methylnaphthalen-3-yl group, a 2-methylnaphthalen-4-yl group, a 2-methylnaphthalen-5-yl group, a 2-methylnaphthalen-6-yl group, a 2-methylnaphthalen-7-yl group, a 2-methylnaphthalen-8-yl group, a 1-phenanthryl group, a 2-phenanthryl group, a 3-phenanthryl group, a 4-phenanthryl group, a 9-phenanthryl group, a 1-phenylphenanthren-2-yl group, a 1-phenylphenanthren-3-yl group, a 1-phenylphenanthren-4-yl group, a 1-phenylphenanthren-5-yl group, a 1-phenylphenanthren-6-yl group, a 1-phenylphenanthren-7-yl group, a 1-phenylphenanthren-8-yl group, a 1-phenylphenanthren-9-yl group, a 1-phenylphenanthren-10-yl group, a 2-phenylphenanthren-1-yl group, a 2-phenylphenanthren-3-yl group, a 2-phenylphenanthren-4-yl group, a 2-phenylphenanthren-5-yl group, a 2-phenylphenanthren-6-yl group, a 2-phenylphenanthren-7-yl group, a 2-phenylphenanthren-8-yl group, a 2-phenylphenanthren-9-yl group, a 2-phenylphenanthren-10-yl group, a 3-phenylphenanthren-1-yl group, a 3-phenylphenanthren-2-yl group, a 3-phenylphenanthren-4-yl group, a 3-phenylphenanthren-5-yl group, a 3-phenylphenanthren-6-yl group, a 3-phenylphenanthren-7-yl group, a 3-phenylphenanthren-8-yl group, a 3-phenylphenanthren-9-yl group, a 3-phenylphenanthren-10-yl group, a 4-phenylphenanthren-1-yl group, a 4-phenylphenanthren-2-yl group, a 4-phenylphenanthren-3-yl group, a 4-phenylphenanthren-5-yl group, a 4-phenylphenanthren-6-yl group, a 4-phenylphenanthren-7-yl group, a 4-phenylphenanthren-8-yl group, a 4-phenylphenanthren-9-yl group, a 4-phenylphenanthren-10-yl group, a 1-methylphenanthren-2-yl group, a 1-methylphenanthren-3-yl group, a 1-methylphenanthren-4-yl group, a 1-methylphenanthren-5-yl group, a 1-methylphenanthren-6-yl group, a 1-methylphenanthren-7-yl group, a 1-methylphenanthrene-8-yl group, a 1-methylphenanthren-9-yl group, a 1-methylphenanthren-10-yl group, a 2-methylphenanthren-1-yl group, a 2-methylphenanthren-3-yl group, a 2-methylphenanthren-4-yl group, a 2-methylphenanthren-5-yl group, a 2-methylphenanthren-6-yl group, a 2-methylphenanthren-7-yl group, a 2-methylphenanthren-8-yl group, a 2-methylphenanthren-9-yl group, a 2-methylphenanthren-10-yl group, a 3-methylphenanthren-1-yl group, a 3-methylphenanthren-2-yl group, a 3-methylphenanthren-4-yl group, a 3-methylphenanthren-5-yl group, a 3-methylphenanthren-6-yl group, a 3-methylphenanthren-7-yl group, a 3-methylphenanthren-8-yl group, a 3-methylphenanthren-9-yl group, a 3-methylphenanthren-10-yl group, a 4-methylphenanthren-1-yl group, a 4-methylphenanthren-2-yl group, a 4-methylphenanthren-3-yl group, a 4-methylphenanthren-5-yl group, a 4-methylphenanthren-6-yl group, a 4-methylphenanthren-7-yl group, a 4-methylphenanthren-8-yl group, a 4-methylphenanthren-9-yl group, a 4-methylphenanthren-10-yl group, a 1-anthryl group, a 2-anthryl group, a 9-anthryl group, a 1-phenylanthracen-2-yl group, a 1-phenylanthracen-3-yl group, a 1-phenylanthracen-4-yl group, a 1-phenylanthracen-5-yl group, a 1-phenylanthracen-6-yl group, a 1-phenylanthracen-7-yl group, a 1-phenylanthracen-8-yl group, a 1-phenylanthracen-9-yl group, a 1-phenylanthracene-10-yl group, a 2-phenylanthracen-1-yl group, a 2-phenylanthracen-3-yl group, a 2-phenylanthracen-4-yl group, a 2-phenylanthracen-5-yl group, a 2-phenylanthracen-6-yl group, a 2-phenylanthracen-7-yl group, a 2-phenylanthracen-8-yl group, a 2-phenylanthracen-9-yl group, a 2-phenylanthracen-10-yl group, a 9-phenylanthracen-1-yl group, a 9-phenylanthracene-2-yl group, a 9-phenylanthracen-3-yl group, a 9-phenylanthracen-4-yl group, a 9-phenylanthracen-5-yl group, a 1-pyrenyl group, a 2-pyrenyl group, a 4-pyrenyl group, a 1-phenylpyren-2-yl group, a 1-phenylpyren-3-yl group, a 1-phenylpyren-4-yl group, a 1-phenylpyren-5-yl group, a 1-phenylpyren-6-yl group, a 1-phenylpyren-7-yl group, a 1-phenylpyren-8-yl group, a 1-phenylpyren-9-yl group, a 1-phenylpyren-10-yl group, a 2-phenylpyren-1-yl group, a 2-phenylpyren-3-yl group, a 2-phenylpyren-4-yl group, a 2-phenylpyren-5-yl group, a 2-phenylpyren-6-yl group, a 2-phenylpyren-7-yl group, a 2-phenylpyren-8-yl group, a 2-phenylpyren-9-yl group, a 2-phenylpyren-1-yl group, a 9-phenylpyren-1-yl group, a 9-phenylpyren-2-yl group, a 9-phenylpyren-3-yl group, a 9-phenylpyren-4-yl group, a 9-phenylpyren-5-yl group, a 9-phenylpyren-6-yl group, a 9-phenylpyren-7-yl group, a 9-phenylpyren-8-yl group, a 9-phenylpyren-10-yl group, a 1-methylpyren-2-yl group, a 1-methylpyren-3-yl group, a 1-methylpyren-4-yl group, a 1-methylpyren-5-yl group, a 1-methylpyren-6-yl group, a 1-methylpyren-7-yl group, a 1-methylpyren-8-yl group, a 1-methylpyren-9-yl group, a 1-methylpyren-10-yl group, a 2-methylpyren-1-yl group, a 2-methylpyren-3-yl group, a 2-methylpyren-4-yl group, a 2-methylpyren-5-yl group, a 2-methylpyren-6-yl group, a 2-methylpyren-7-yl group, a 2-methylpyren-8-yl group, a 2-methylpyren-9-yl group, a 2-methylpyren-10-yl group, a 9-methylpyren-1-yl group, a 9-methylpyren-2-yl group, a 9-methylpyren-3-yl group, a 9-methylpyren-4-yl group, a 9-methylpyren-5-yl group, a 9-methylpyren-6-yl group, a 9-methylpyren-7-yl group, a 9-methylpyren-8-yl group, a 9-methylpyren-10-yl group, a fluoranthen-1-yl group, a fluoranthen-1-yl group, a fluoranthen-2-yl group, a fluoranthen-3-yl group, a fluoranthen-4-yl group, a fluoranthen-5-yl group, a fluoranthen-6-yl group, a fluoranthen-7-yl group, a fluoranthen-8-yl group, a fluoranthen-9-yl group, a fluoranthen-10-yl group, a triphenylen-1-yl group, a triphenylen-2-yl group, an acenaphthylen-1-yl group, an acenaphthylen-3-yl group, an acenaphthylen-4-yl group, an acenaphthylen-5-yl group, a chrysen-1-yl group, a chrysen-2-yl group, a chrysen-5-yl group, a chrysen-6-yl group, etc. may be mentioned as preferred examples.

Among these, from the viewpoint of excellent electron transport material properties, a 2-pyridyl group, a 3-pyridyl group, a 4-pyridyl group, a 2-methylpyridin-6-yl group, a 3-methylpyridin-6-yl group, a 4-methylpyridin-6-yl group, a 2-methylpyridin-5-yl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-pyrimidyl group, a 4,6-dimethylpyrimidyl group or a pyrazyl group is preferred; a 2-pyridyl group, a 3-pyridyl group, a 2-quinolyl group, a 3-quinolyl group, a 8-quinolyl group, a 1-isoquinolyl group, a 3-isoquinolyl group, a 4-isoquinolyl group, a 9-phenanthryl group, a 9-anthryl group, a 1-pyrenyl group, a fluoranthen-3-yl group or a triphenylene-2-yl group is more preferred; and a 3-pyridyl group, a 2-pyridyl group, a 3-quinolyl group or a 4-isoquinolyl group is further preferred.

$X^1$, $X^2$, $X^3$ and $X^4$ are each independently a single bond or a $C_{4-14}$ arylene group (which may be substituted by a fluorine atom, a $C_{1-4}$ alkyl group, a phenyl group, a biphenyl group or a naphthyl group).

In $X^1$, $X^2$, $X^3$ and $X^4$, the $C_{4-14}$ arylene group (which may be substituted by a fluorine atom, a $C_{1-4}$ alkyl group, a phenyl group, a biphenyl group or a naphthyl group), is not particularly limited, but a phenylene group, a fluorophenylene group, a methylphenylene group, a dimethylphenylene group, a naphthylene group, a fluoronaphthylene group, a methylnaphthylene group, a pyridylene group, a fluoropyridylene group, a methylpyridylene group, a dimethylpyridylene group, a pyrazylene group, a fluoropyrazylene group, a methylpyrazylene group, a pyrimidylene group, a fluoropyrimidylene group, a methylpyrimidylene group, a dimethylpyrimidylene group, a phenylpyridylene group, a naphthylpyridylene group or a biphenylpyridylene group may be mentioned as a preferred example.

From the viewpoint of good performance of the organic electroluminescent device, $X^1$, $X^2$, $X^3$ and $X^4$ are each independently preferably a phenylene group, a naphthylene group, a pyridylene group, a pyrazylene group, a pyrimidylene group (these groups may be substituted by a fluorine atom, a methyl group or a phenyl group) or a single bond. Further, from the viewpoint of easy synthesis, $X^1$, $X^2$, $X^3$ and $X^4$ are each independently more preferably a phenylene group, a pyridylene group (these groups may be substituted by a fluorine atom, a methyl group or a phenyl group) or a single bond, further preferably a phenylene group, a pyridylene group or a single bond.

m is 0, 1 or 2. Among them, m is preferably 0 or 1, more preferably 1.

n is 0, 1 or 2. Among them, n is preferably 0 or 1, more preferably 1.

Z is a nitrogen atom or a carbon atom. Among them, from the viewpoint of excellent electron transport material properties, a nitrogen atom is preferred.

n+p+q is 1, 2 or 3. That is, the cyclic azine compound of the present invention (1) is characterized by having at least one adamantyl group in its molecule. Particularly, from the viewpoint of excellent electron transport material properties, it is preferred that n+p+q is 1 or 2.

In an organic electroluminescent device wherein the cyclic azine compound (1) of the present invention is used as a part of the constituent components of the organic electroluminescent device, it is possible to obtain such effects as high luminous efficiency, long service life, lowering of the voltage, etc. In particular, when the cyclic azine compound (1) is used as a material of the electron transport layer, such effects will be remarkable.

The following (A-1) to (A-456) may be exemplified as particularly preferred specific examples of the compound represented by the formula (1), but the present invention is not limited thereto.

Here, in (A-1) to (A-456), $Ad^1$ represents a 1-adamantyl group, and $Ad^2$ represents a 2-adamantyl group.

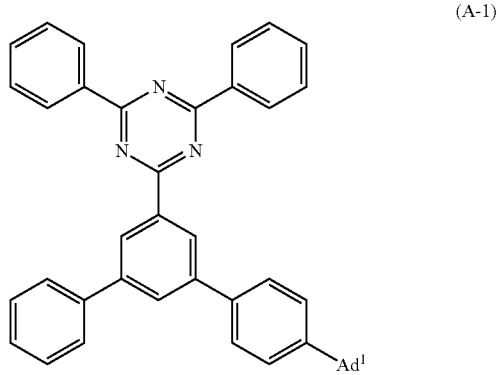

(A-1)

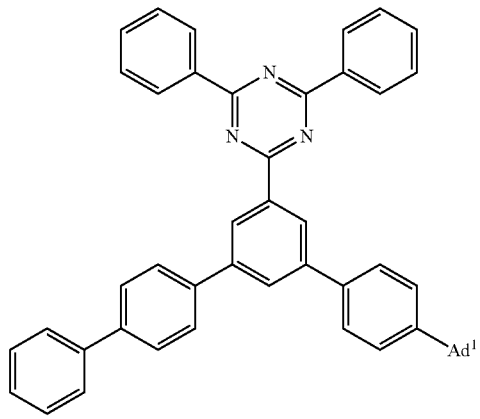

(A-2)

(A-3)

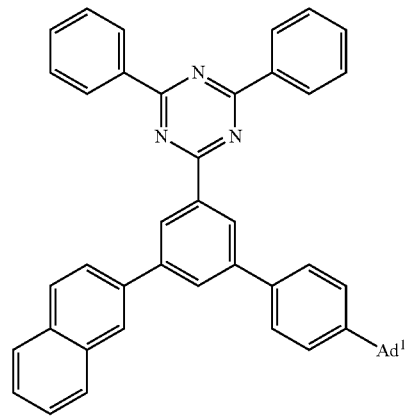

(A-4)

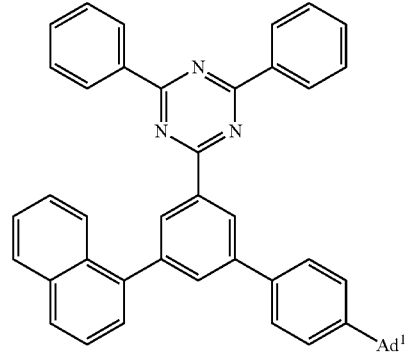

(A-5)

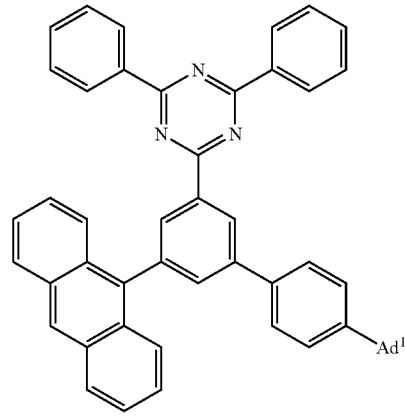

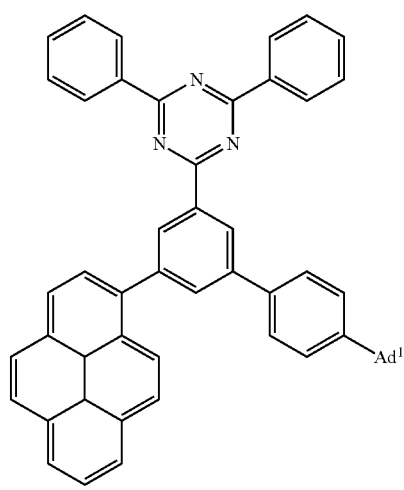
(A-6)
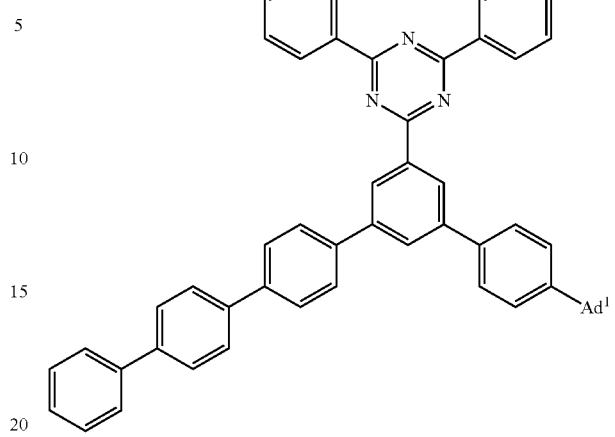
(A-9)
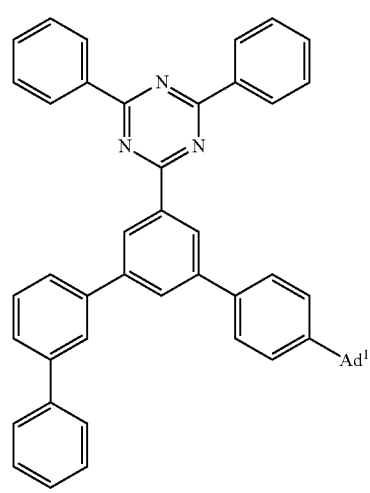
(A-7)
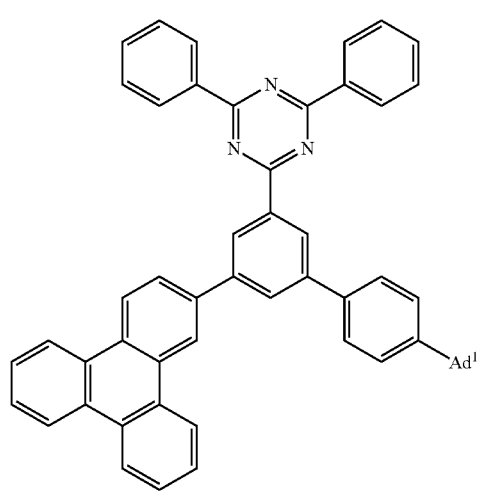
(A-10)
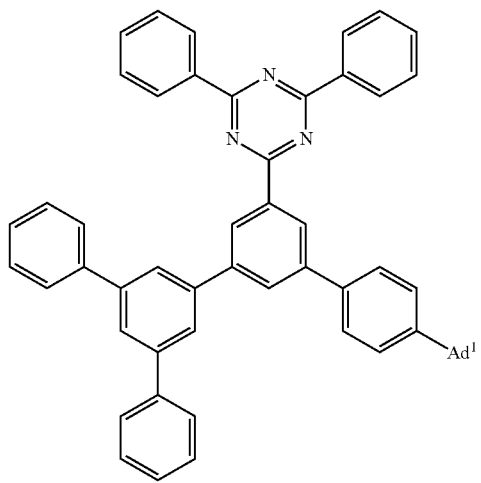
(A-8)
(A-11)

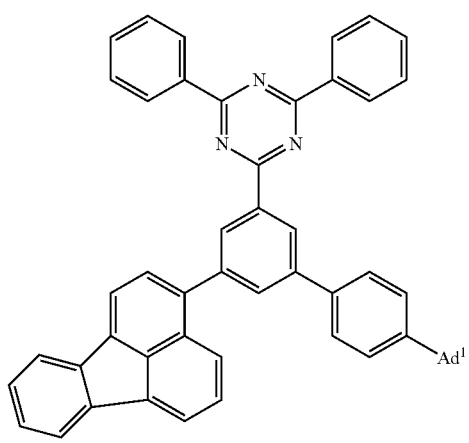
(A-12)
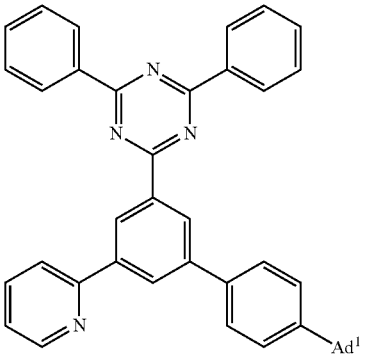
(A-16)
(A-13)
(A-17)
(A-14)
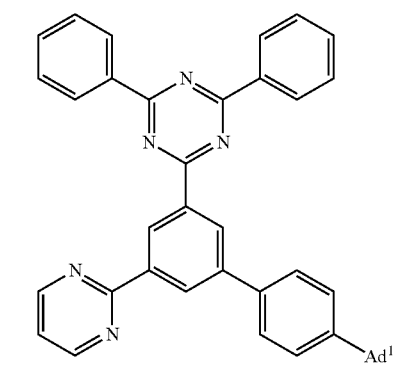
(A-18)
(A-15)
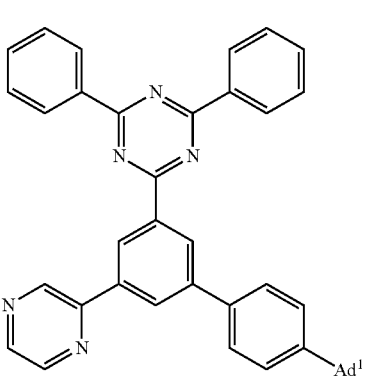
(A-19)
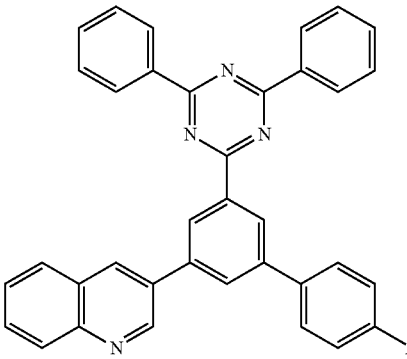

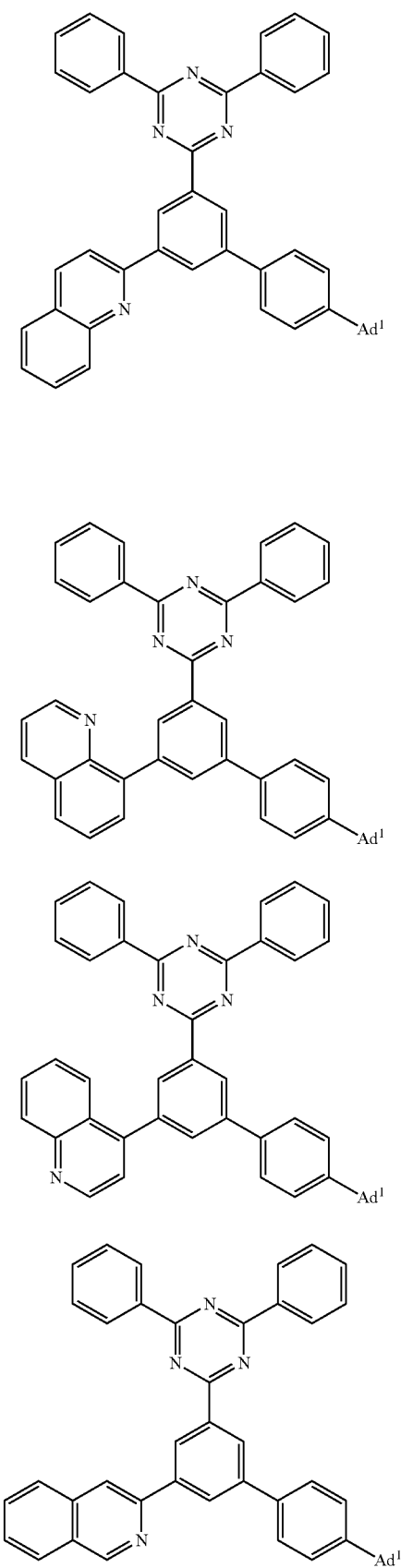
(A-20)
(A-21)
(A-22)
(A-23)
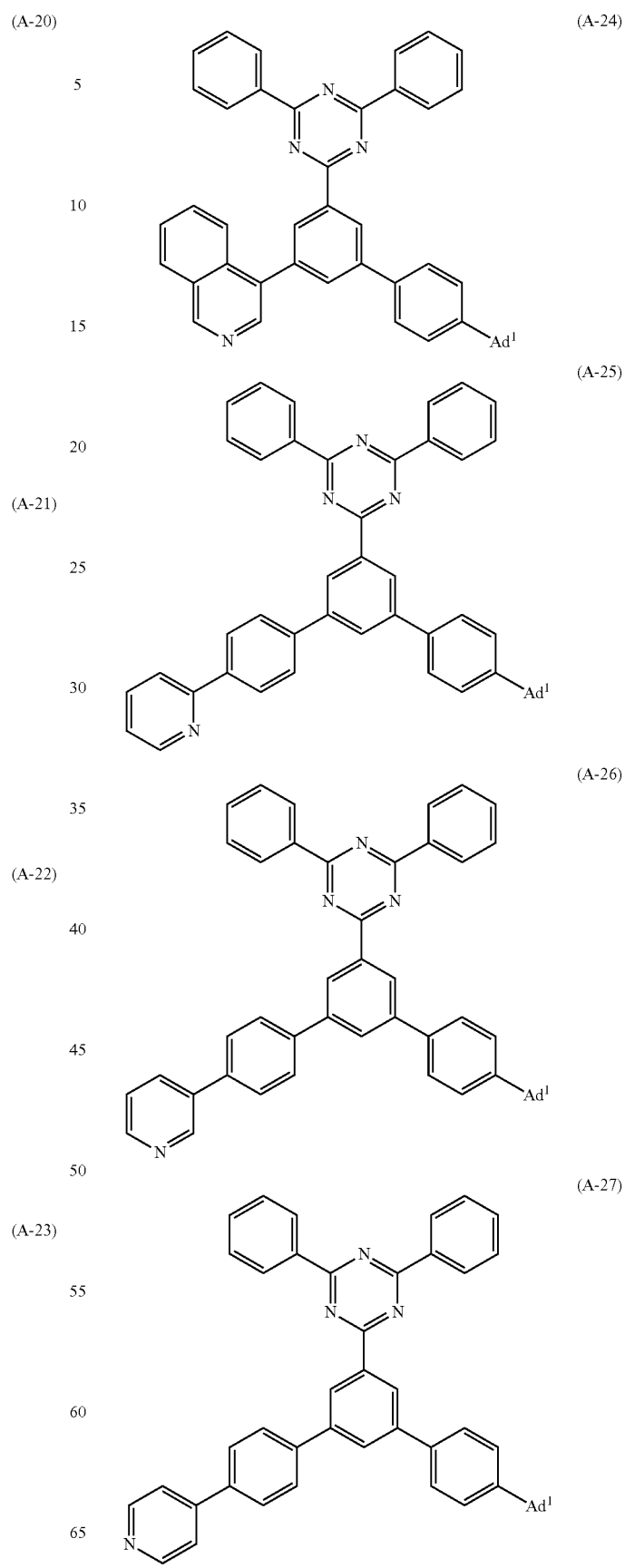
(A-24)
(A-25)
(A-26)
(A-27)

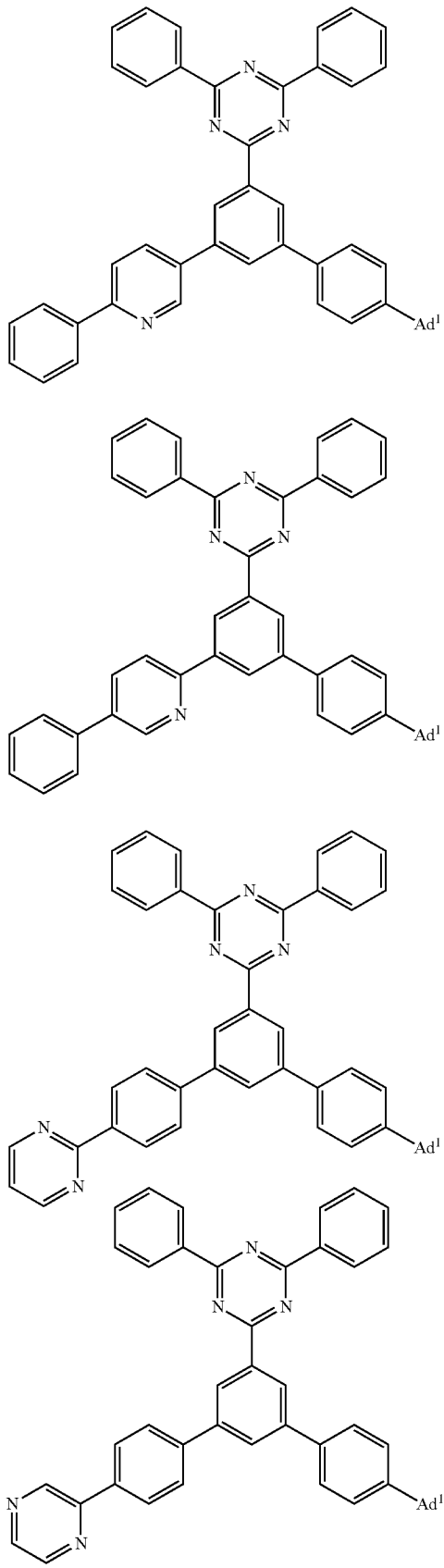
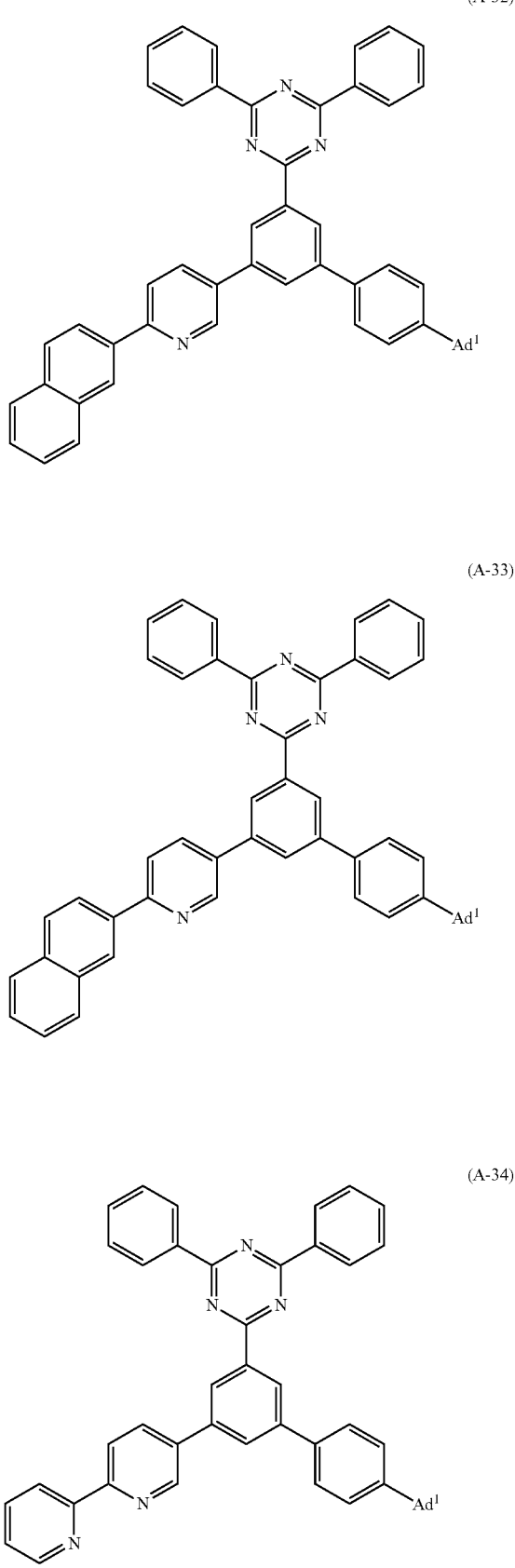

(A-35)
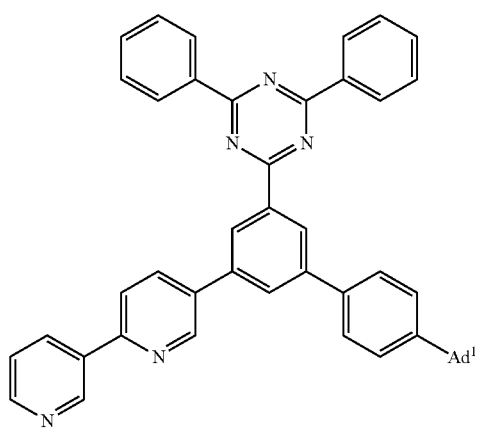
(A-36)
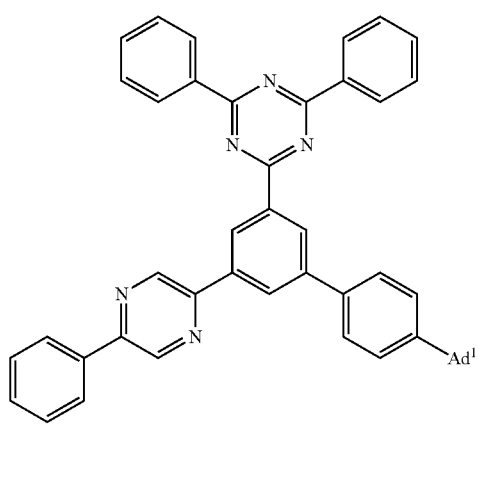
(A-37)
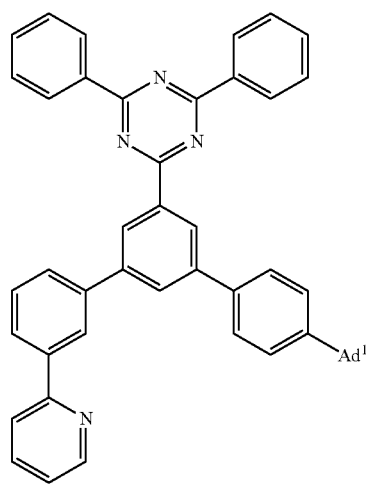
(A-38)
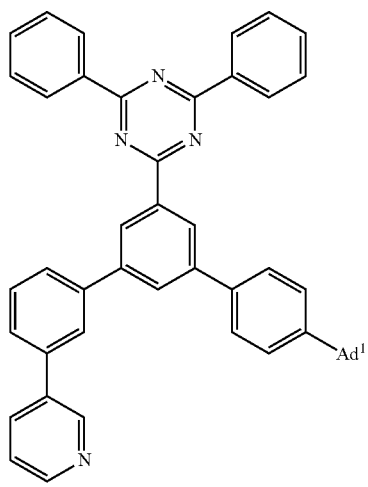
(A-39)
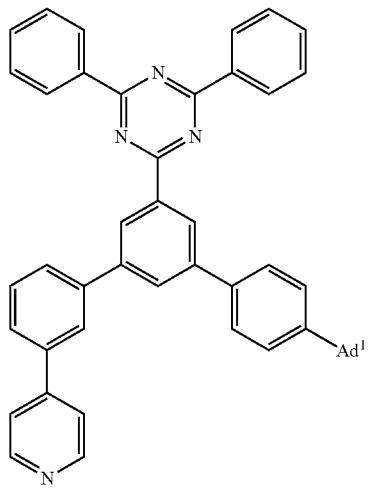
(A-40)
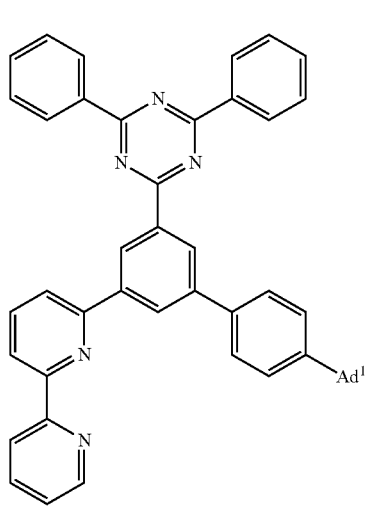

(A-41) 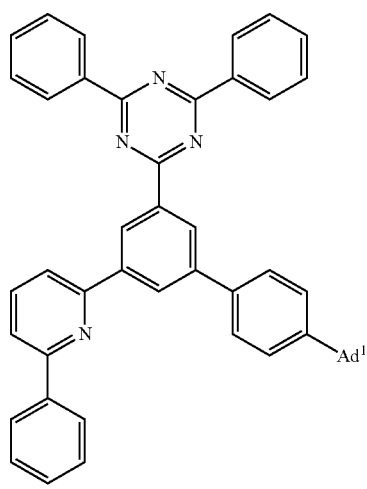
(A-44) 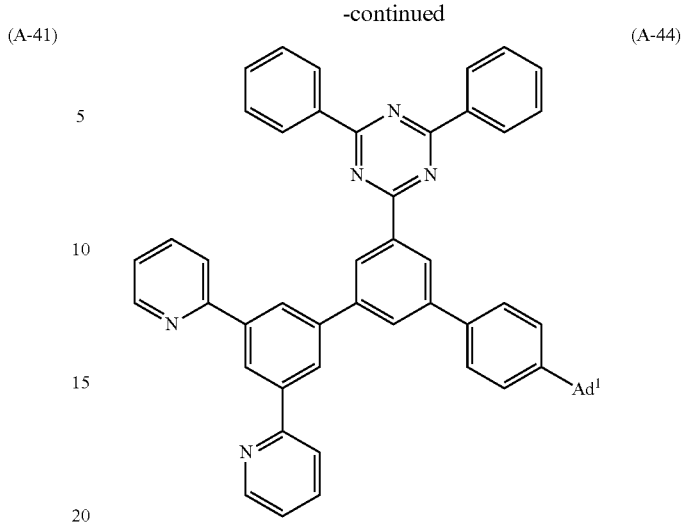
(A-42) 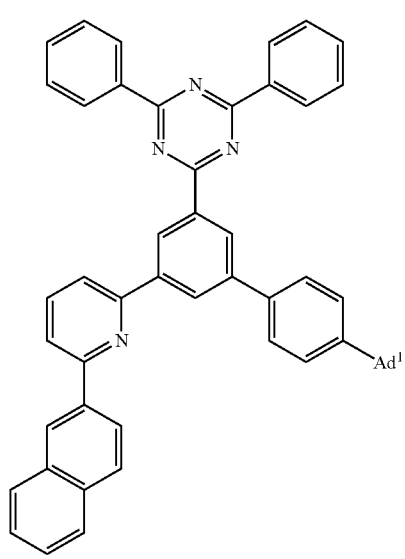
(A-45) 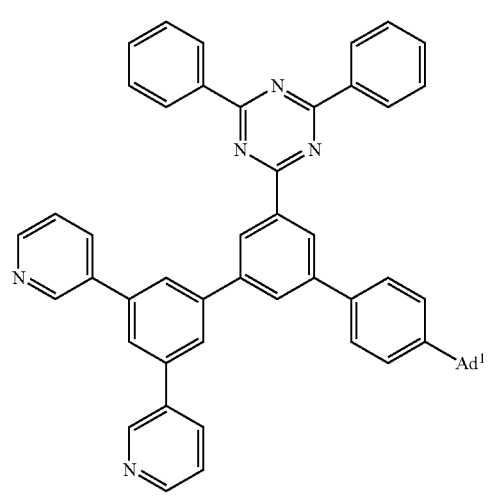
(A-43) 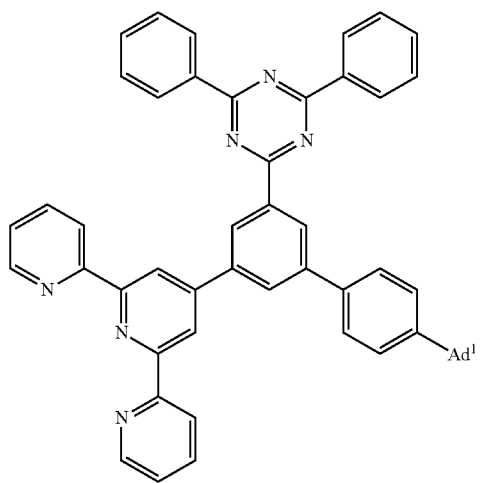
(A-46) 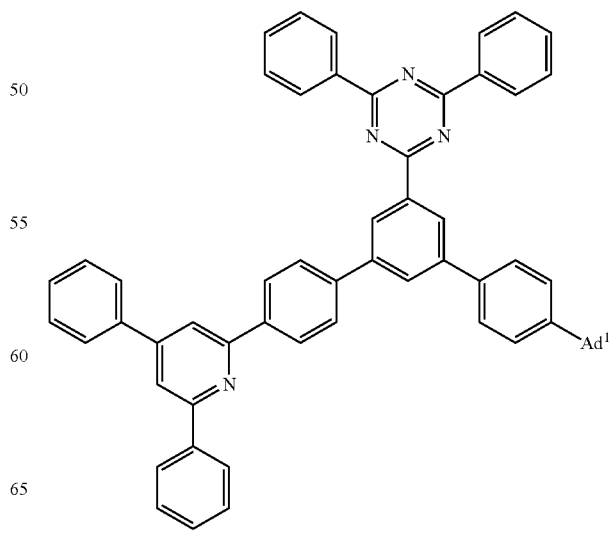

(A-47)
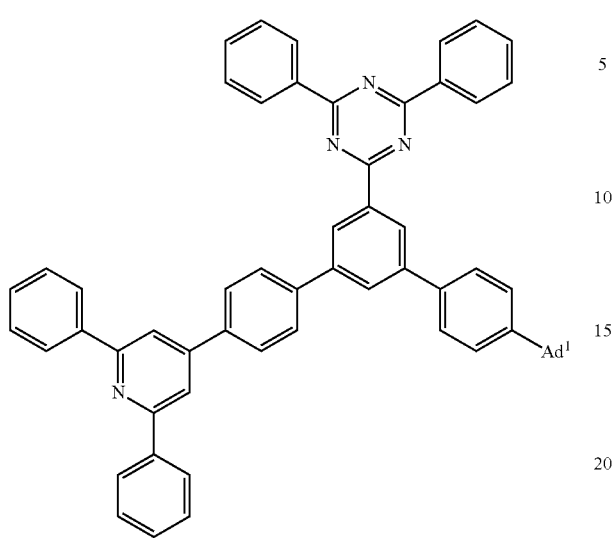
(A-48)
(A-49)
(A-50)
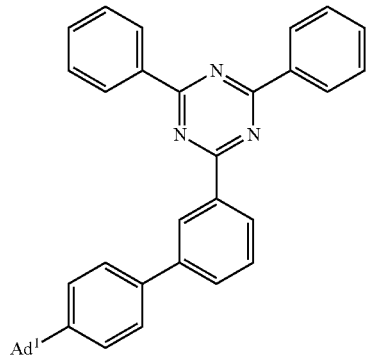
(A-51)
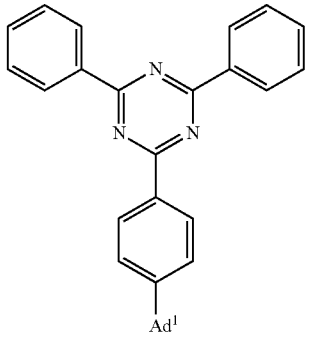
(A-52)
(A-53)
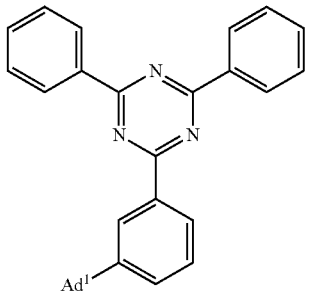

(A-54)
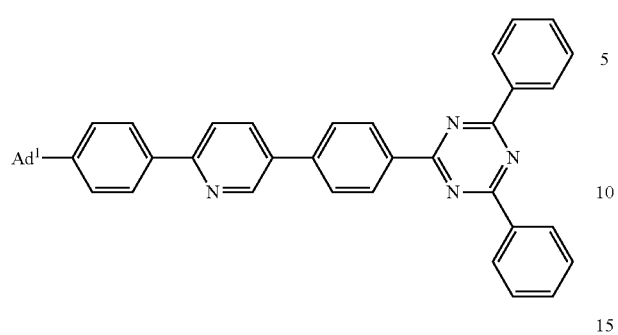
(A-58)
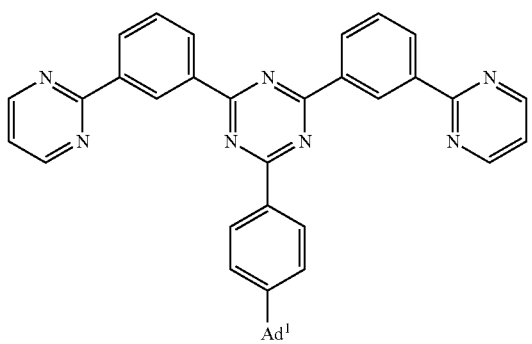
(A-55)
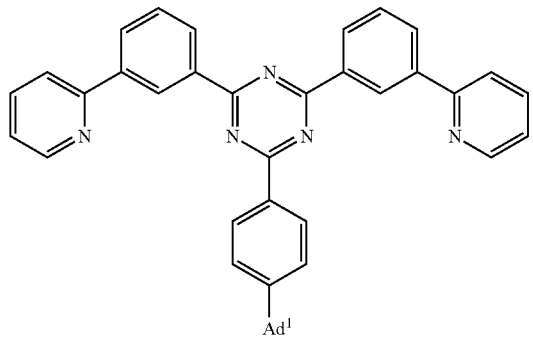
(A-59)
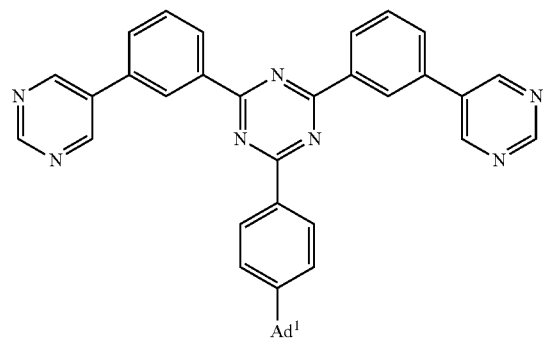
(A-56)
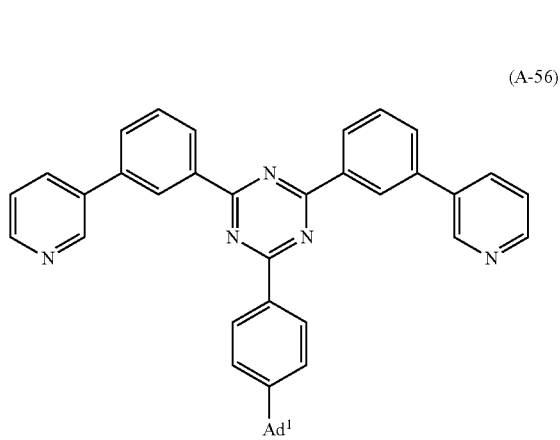
(A-60)
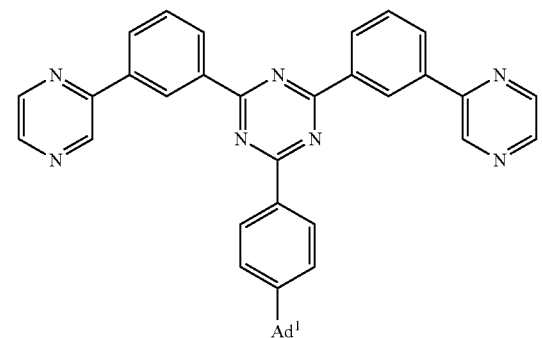
(A-57)
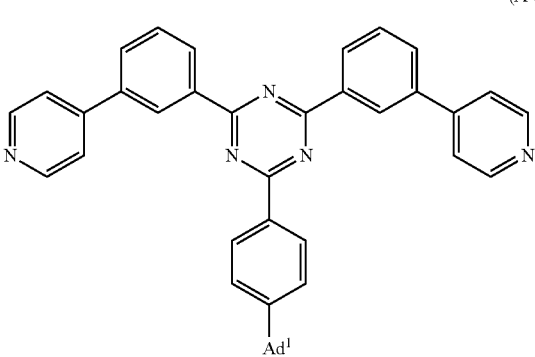
(A-61)
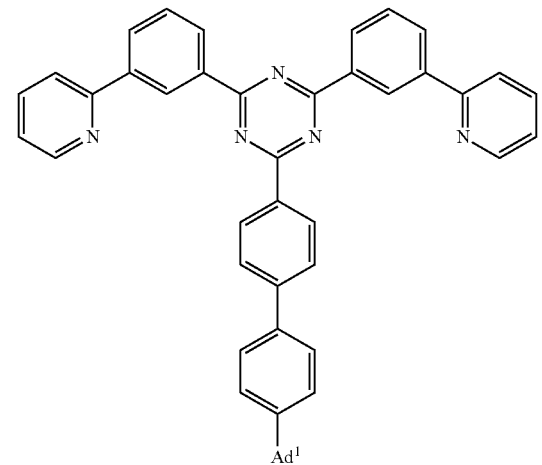

(A-62)
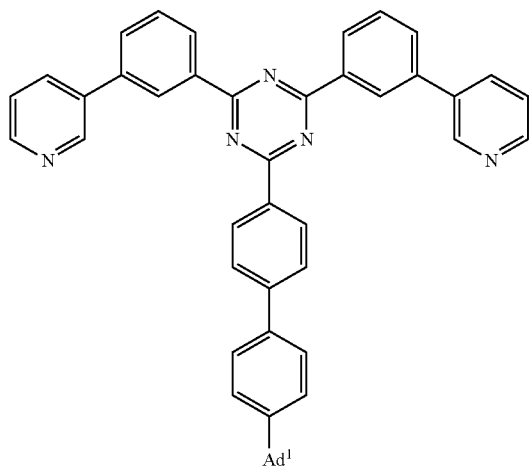
(A-63)
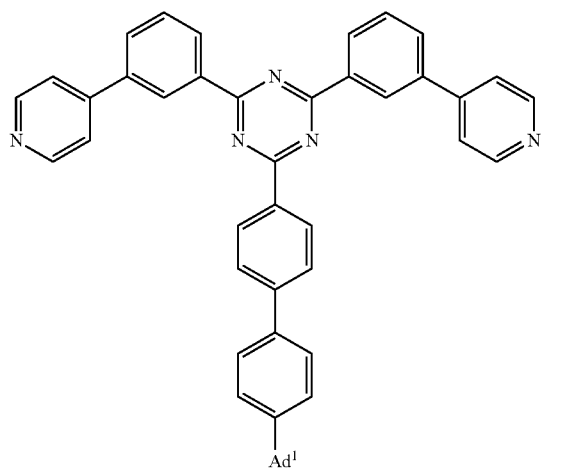
(A-64)
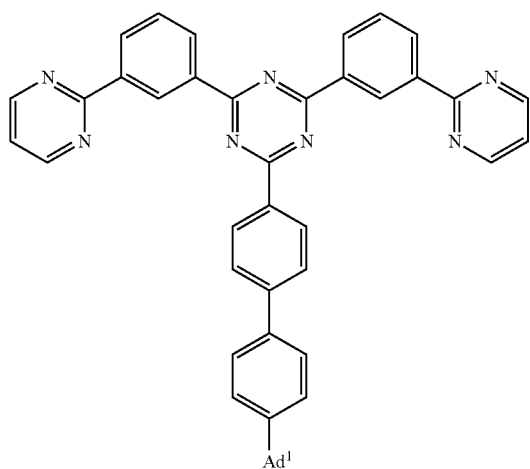
(A-65)
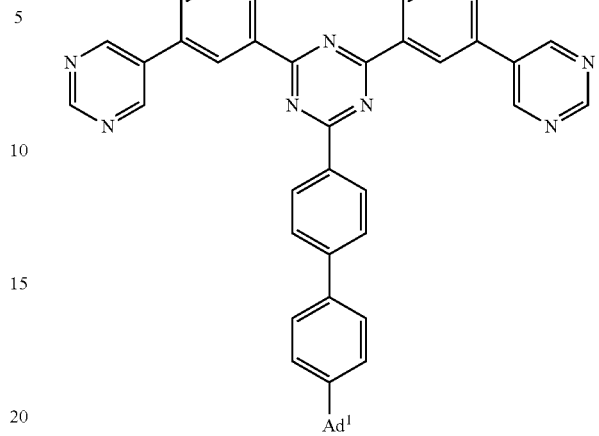
(A-66)
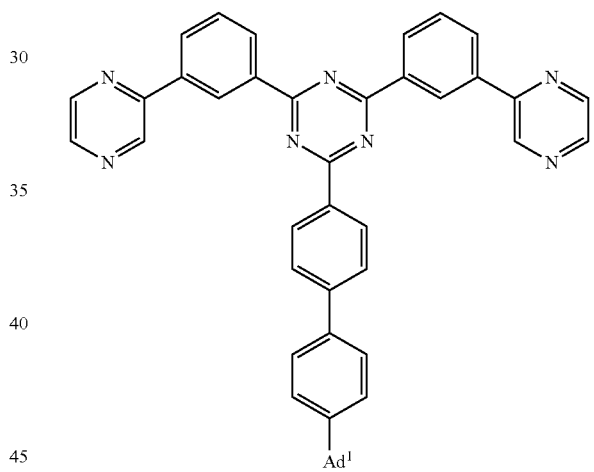
(A-67)
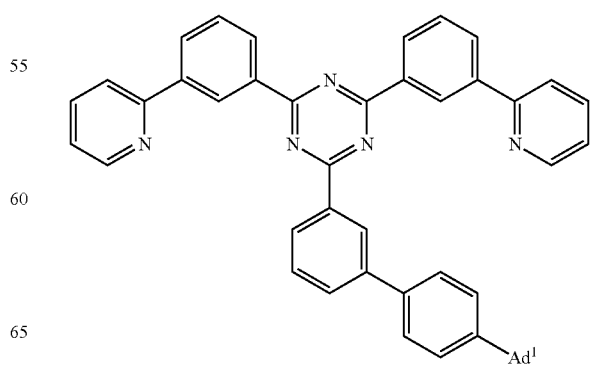

-continued
(A-68)
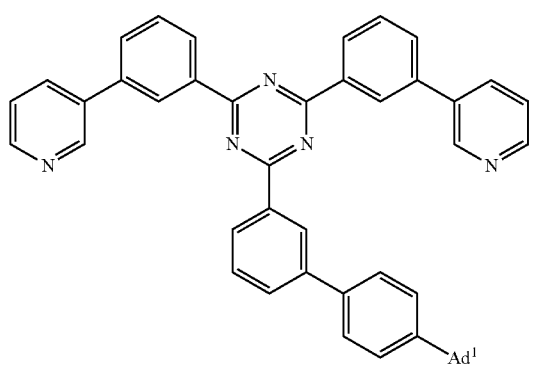
(A-69)
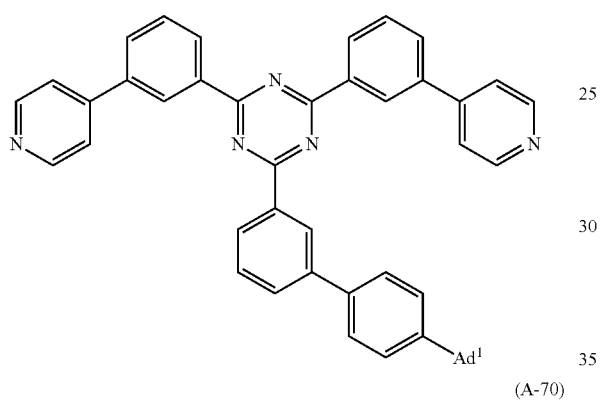
(A-70)
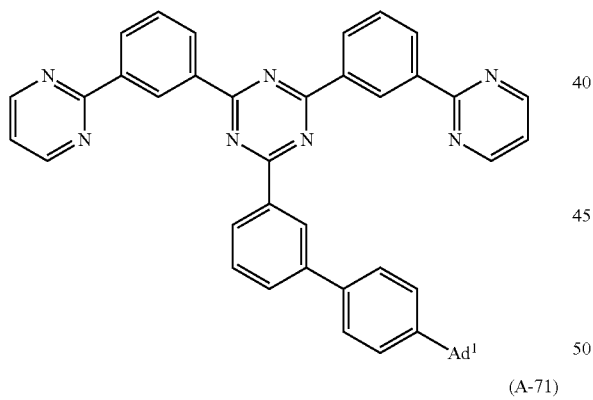
(A-71)
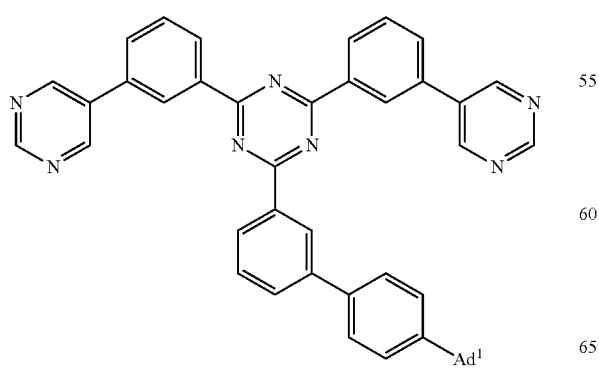
-continued
(A-72)
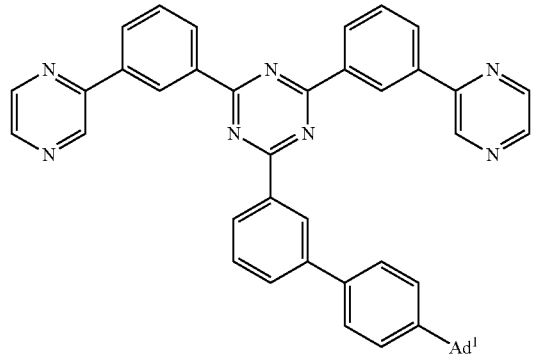
(A-73)
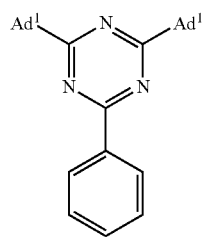
(A-74)
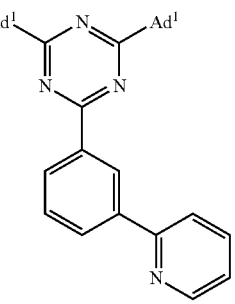
(A-75)
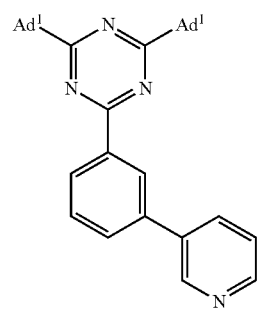
(A-76)
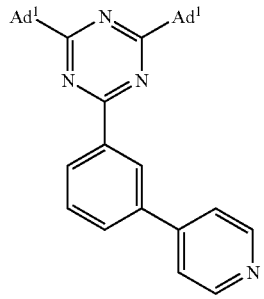

-continued
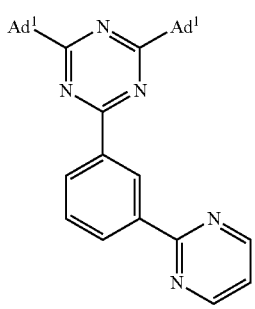
(A-77)
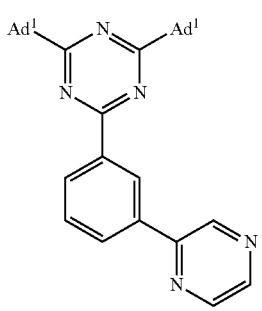
(A-78)
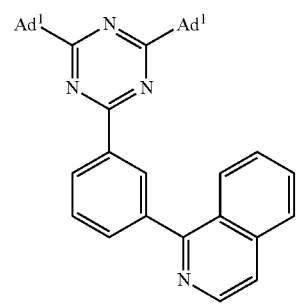
(A-79)
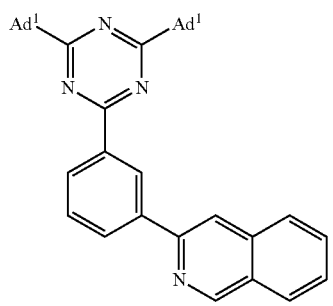
(A-80)
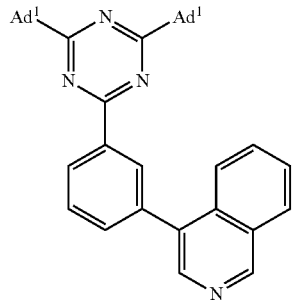
(A-81)
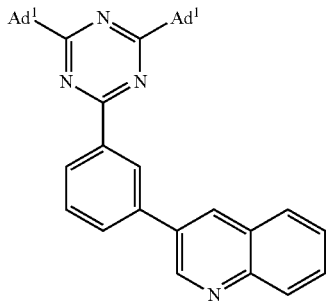
(A-82)
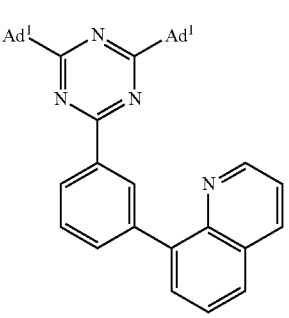
(A-83)
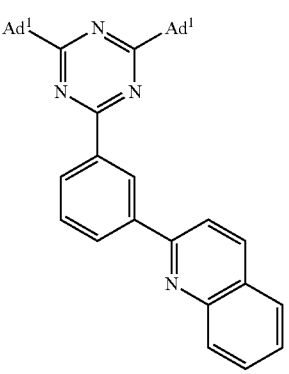
(A-84)
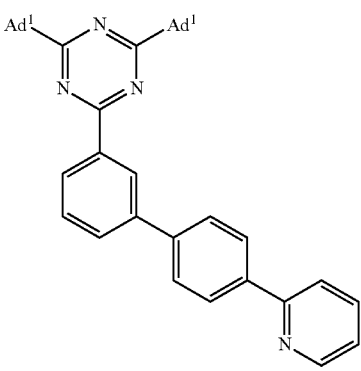
(A-85)

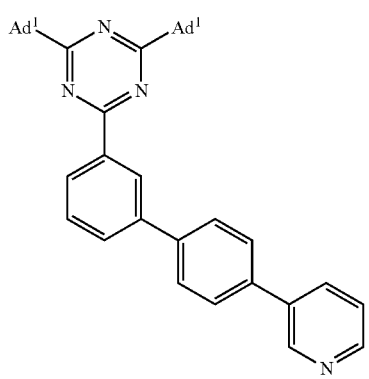 (A-86)
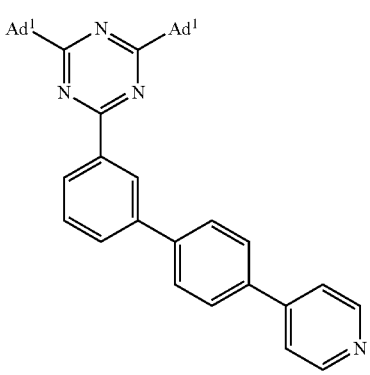 (A-87)
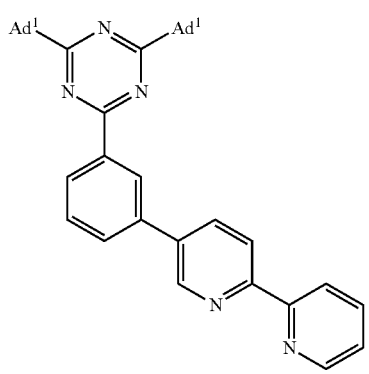 (A-88)
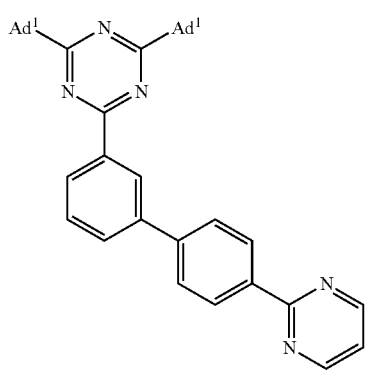 (A-89)
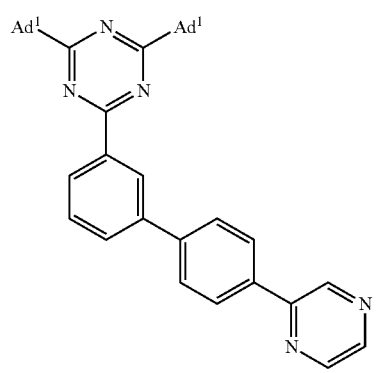 (A-90)
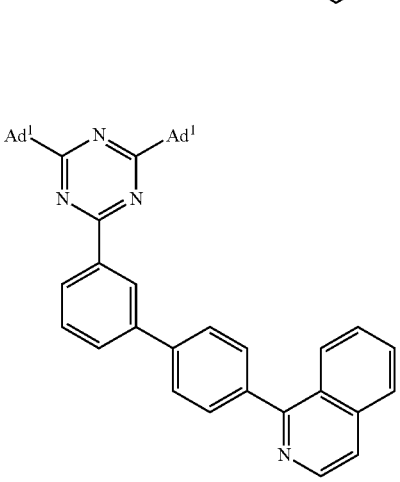 (A-91)
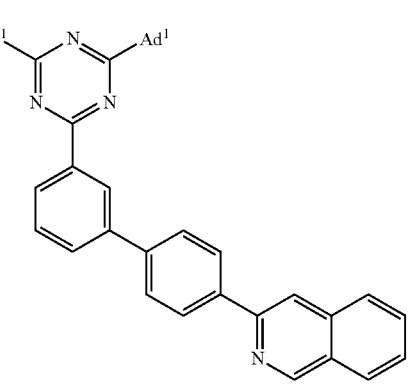 (A-92)
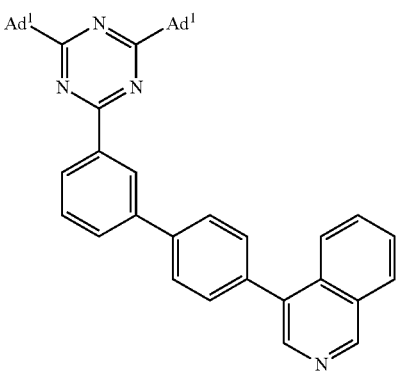 (A-93)

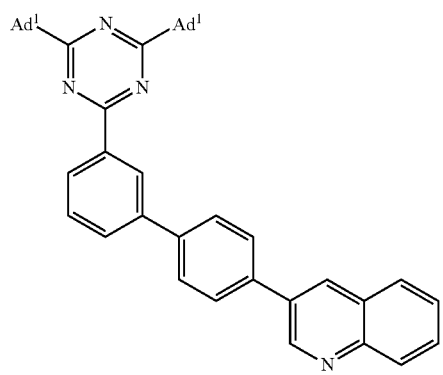
(A-94)
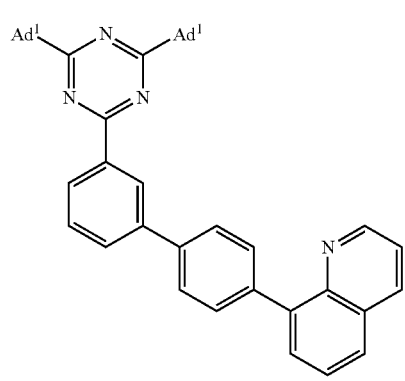
(A-95)
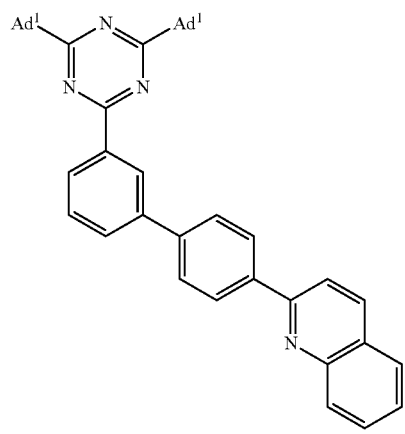
(A-96)
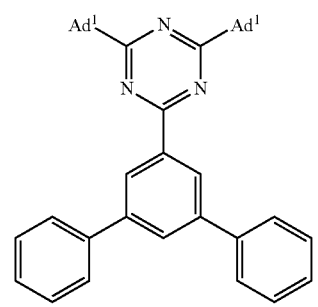
(A-97)
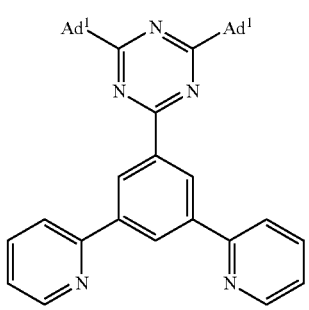
(A-98)
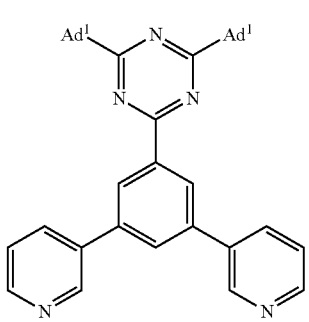
(A-99)
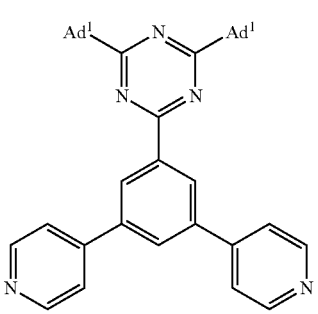
(A-100)
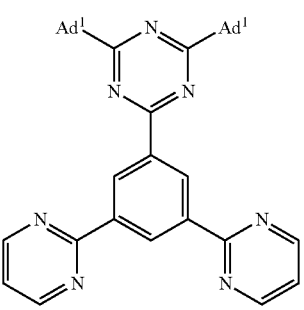
(A-101)
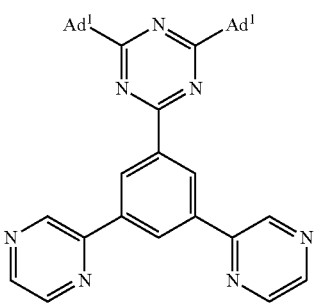
(A-102)

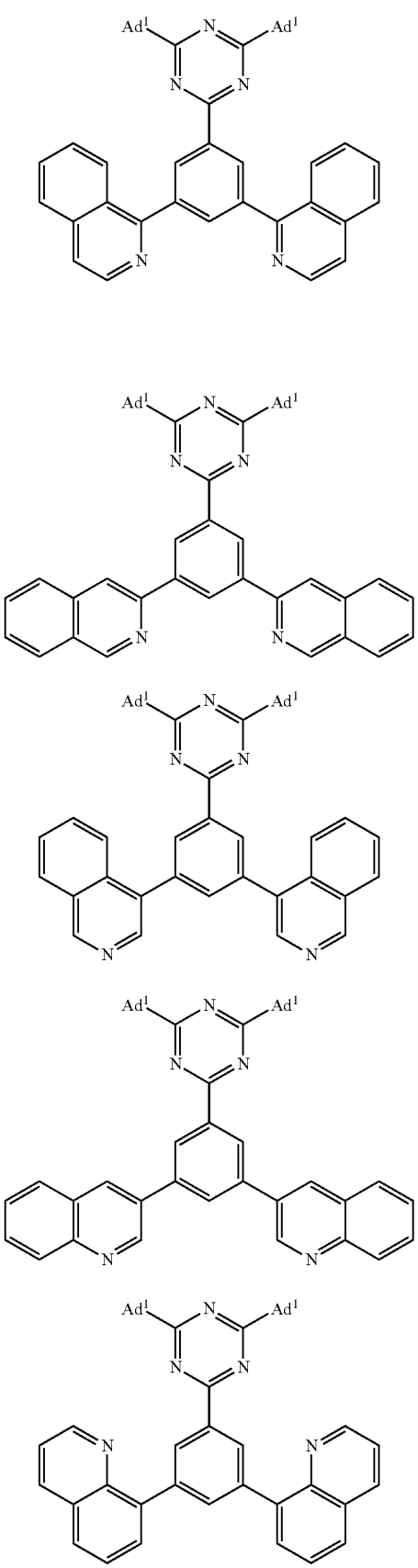
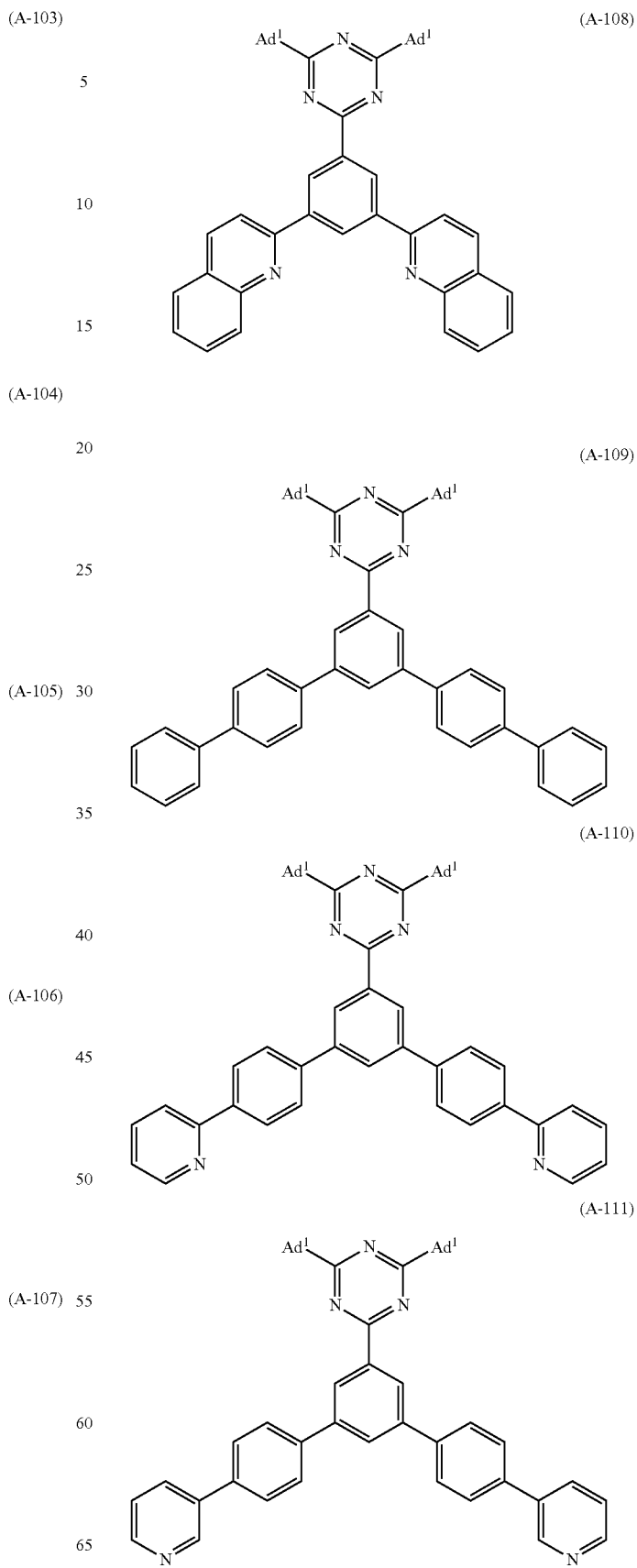

(A-112)
(A-113)
(A-114)
(A-115)
(A-116)
(A-117)
(A-118)
(A-119)
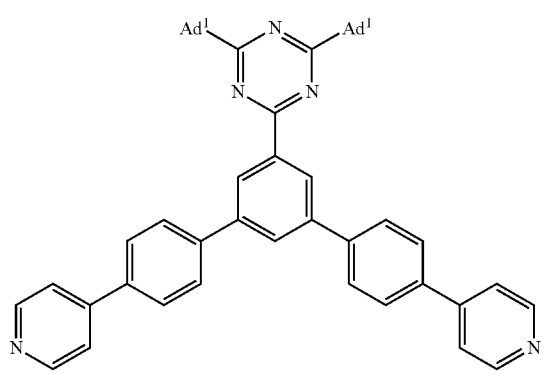
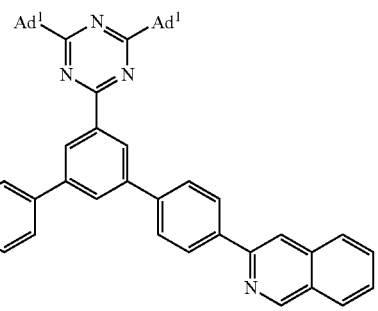
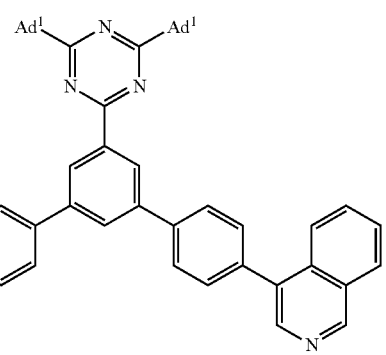
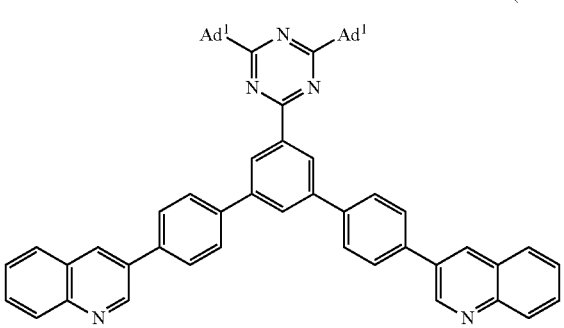
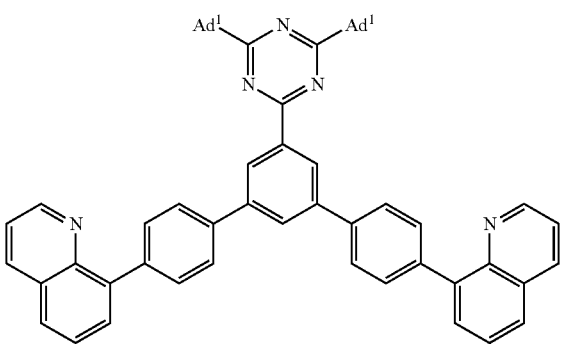

(A-120) 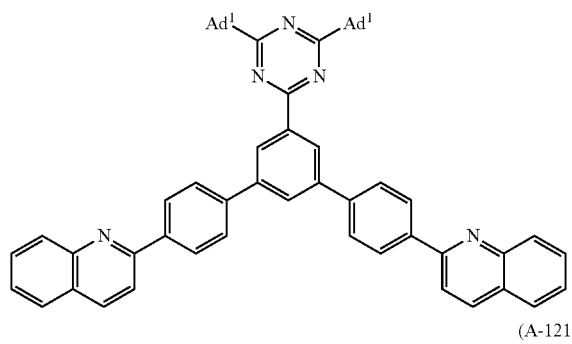
(A-121) 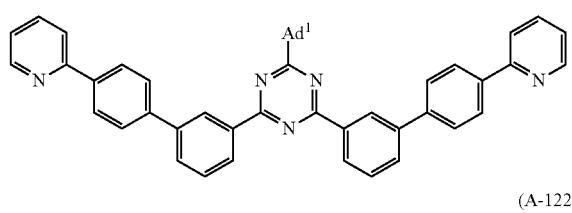
(A-122) 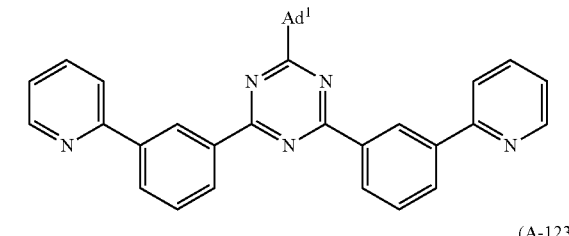
(A-123) 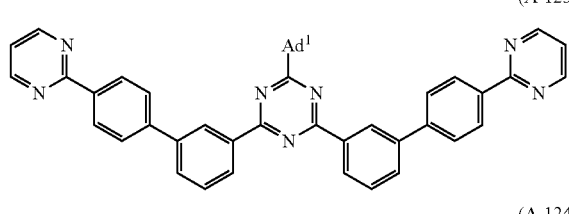
(A-124) 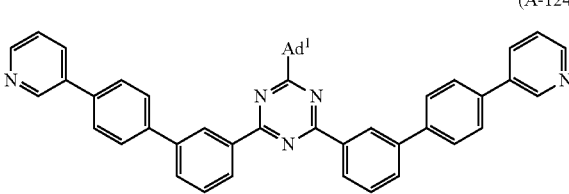
(A-125) 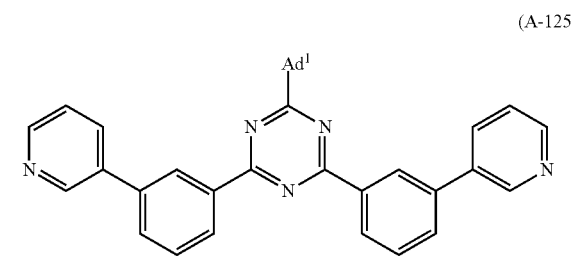
(A-126) 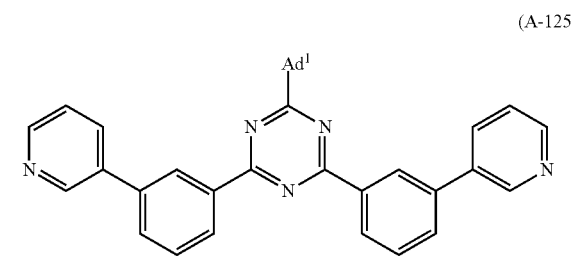
(A-127) 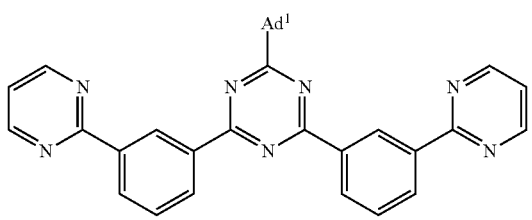
(A-128) 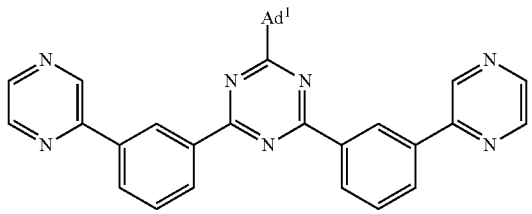
(A-129) 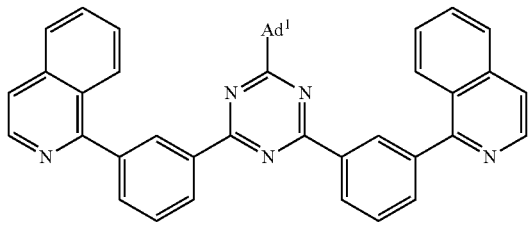
(A-130) 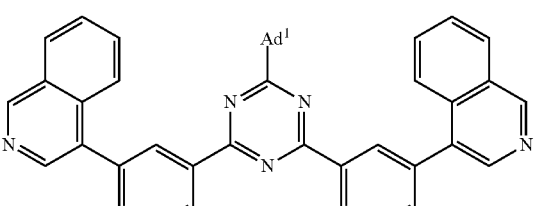
(A-131) 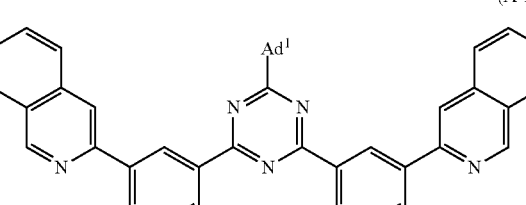
(A-132) 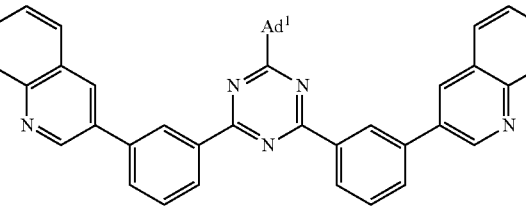

(A-133) 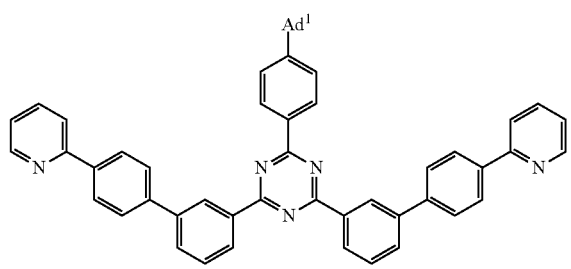
(A-138) 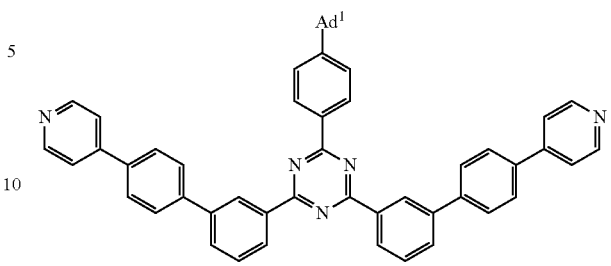
(A-134) 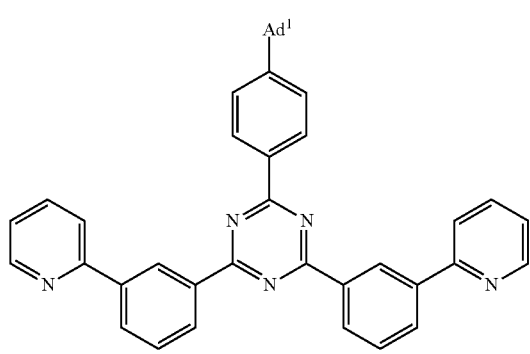
(A-139) 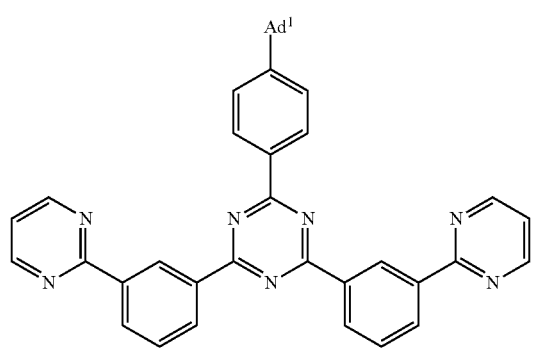
(A-135) 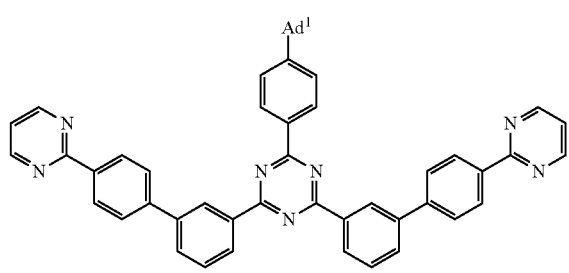
(A-140) 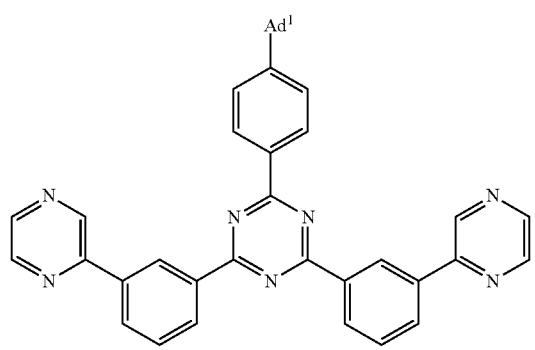
(A-136) 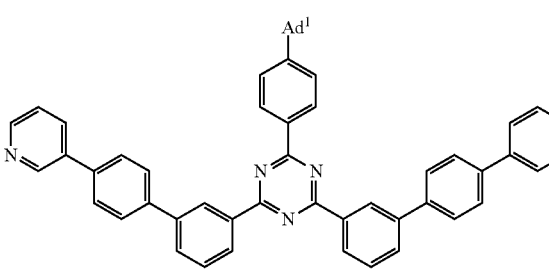
(A-141) 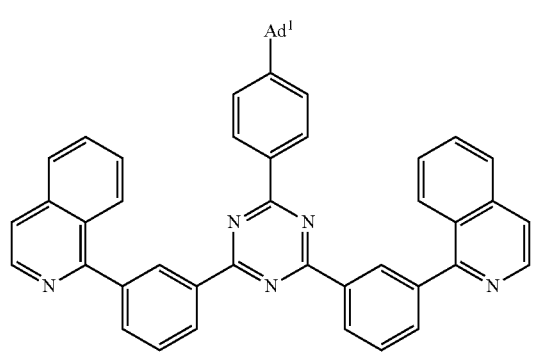
(A-137)

(A-142)
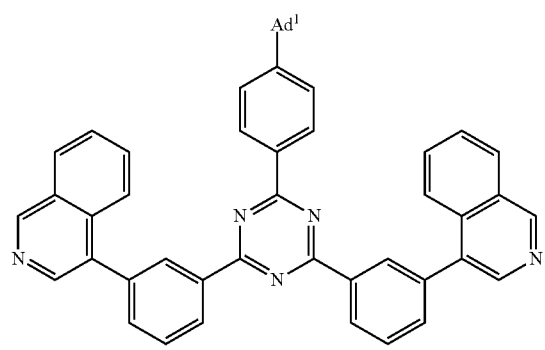
(A-143)
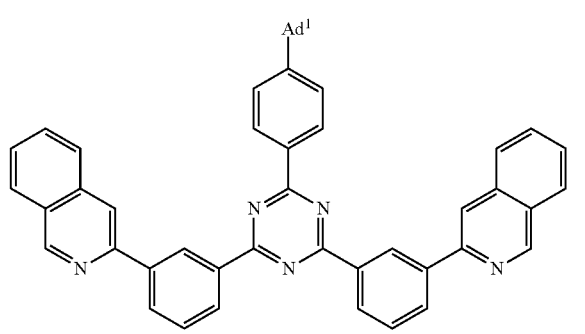
(A-144)
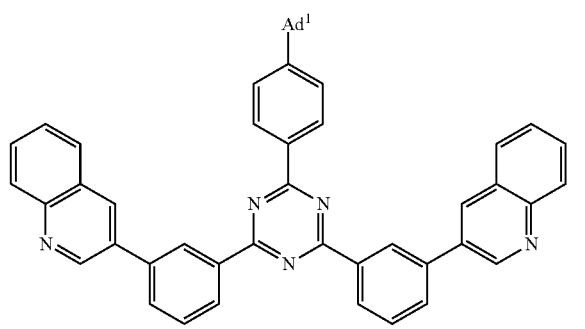
(A-145)
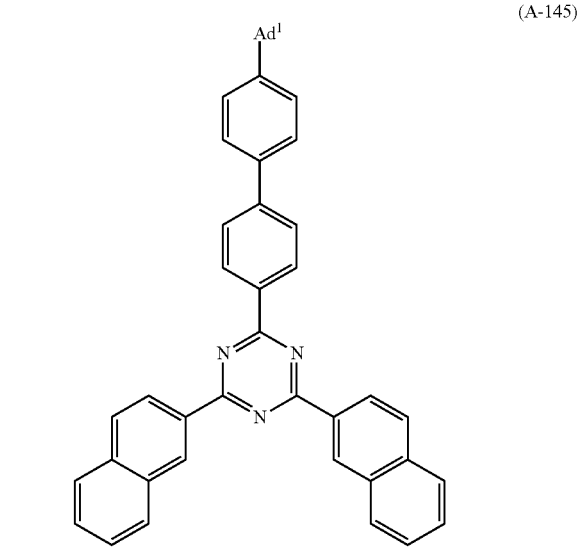
(A-146)
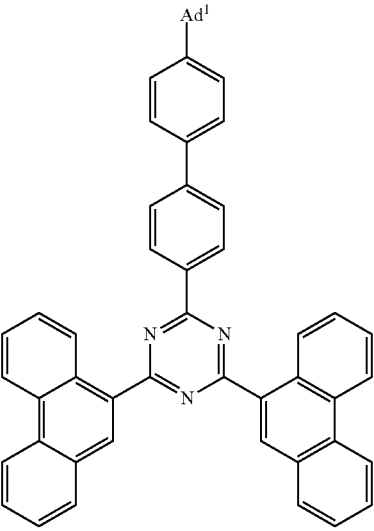
(A-147)
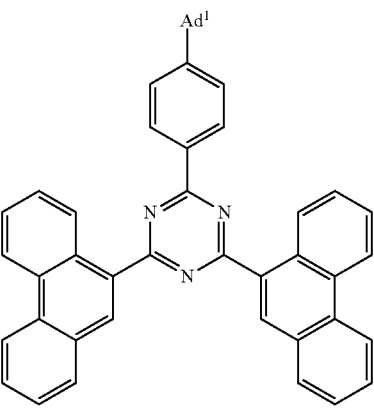
(A-148)
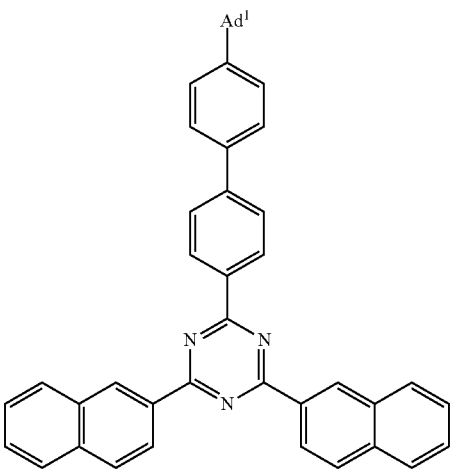

(A-149)
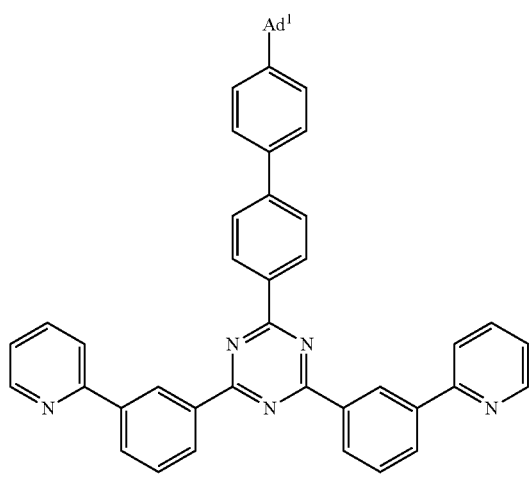
(A-150)
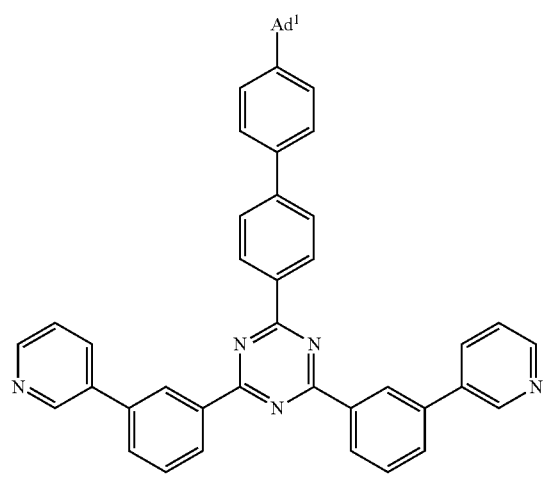
(A-151)
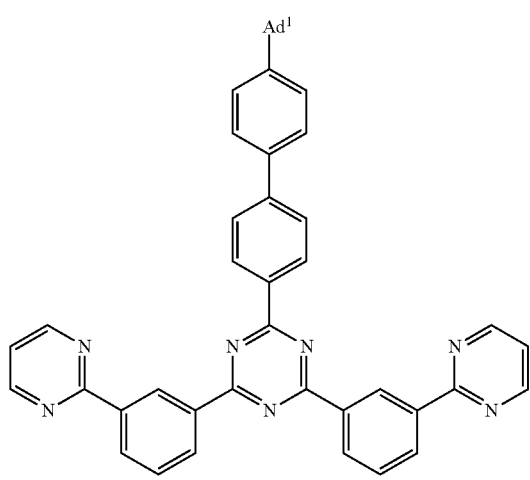
(A-152)
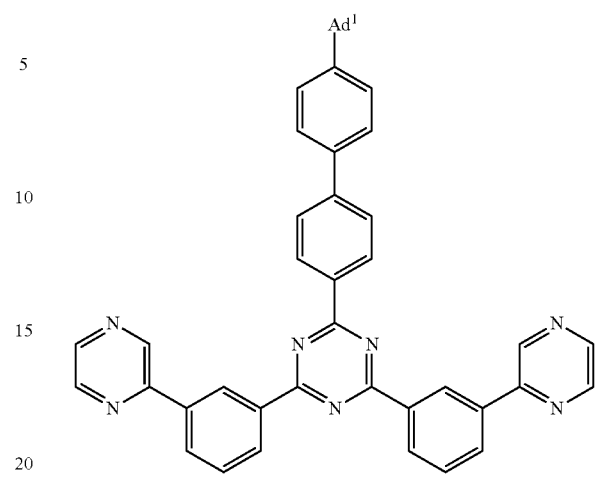
(A-153)
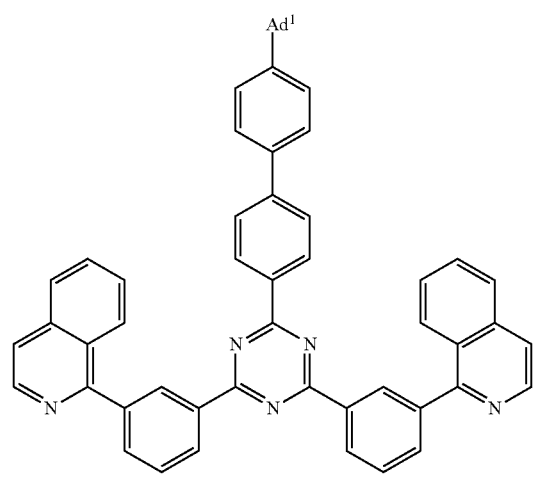
(A-154)
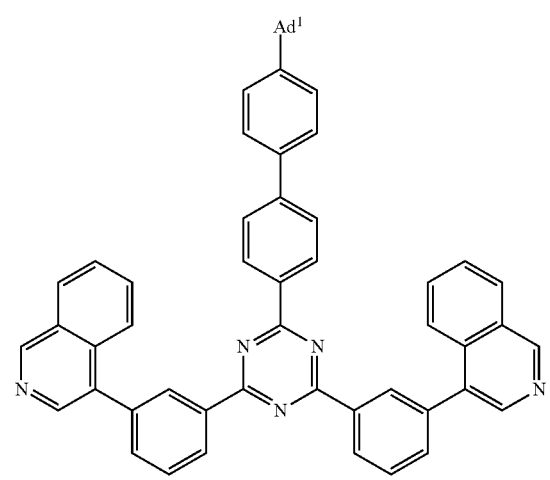

(A-155)
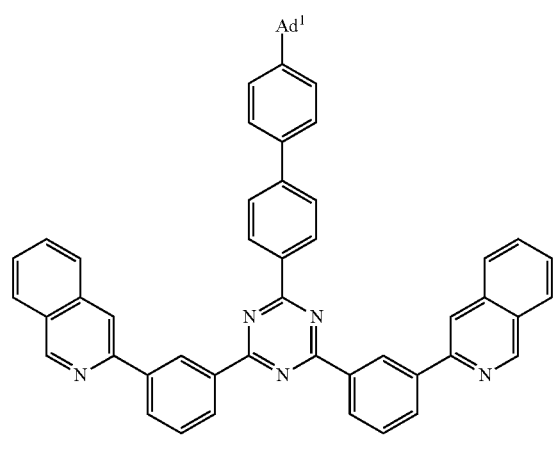
(A-158)
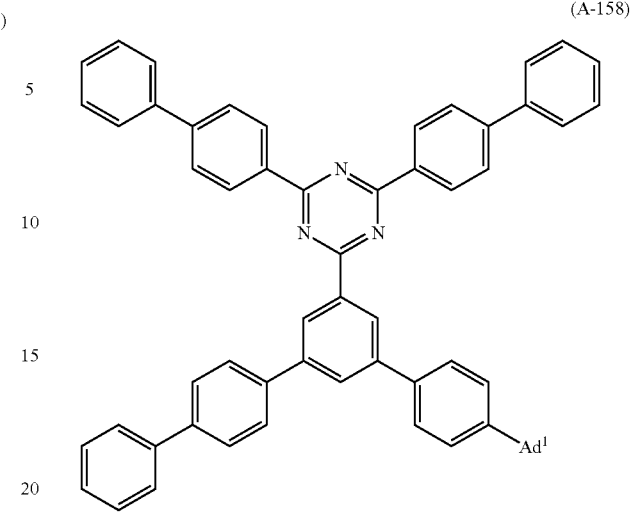
(A-156)
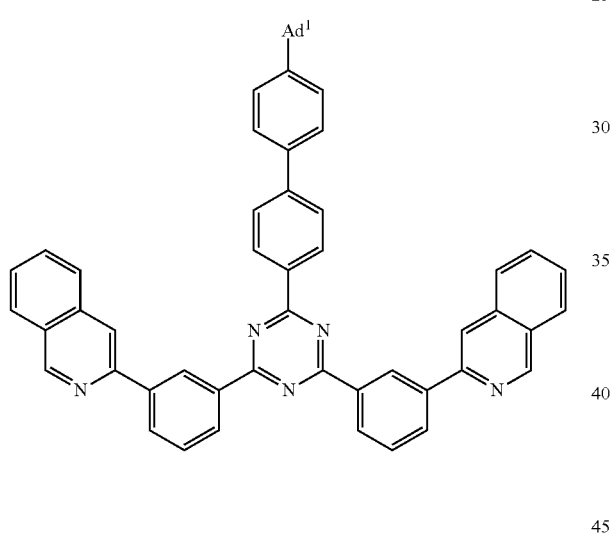
(A-159)
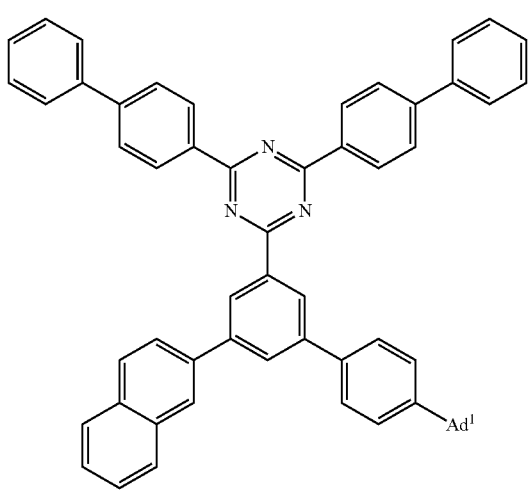
(A-157)
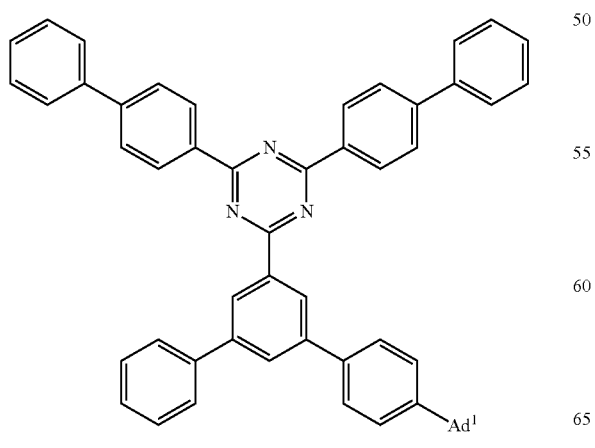
(A-160)
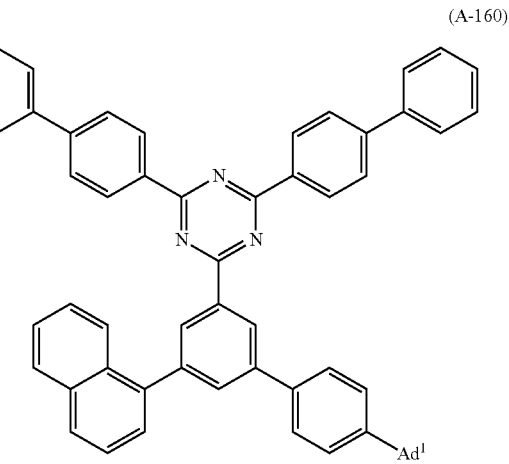

(A-161)
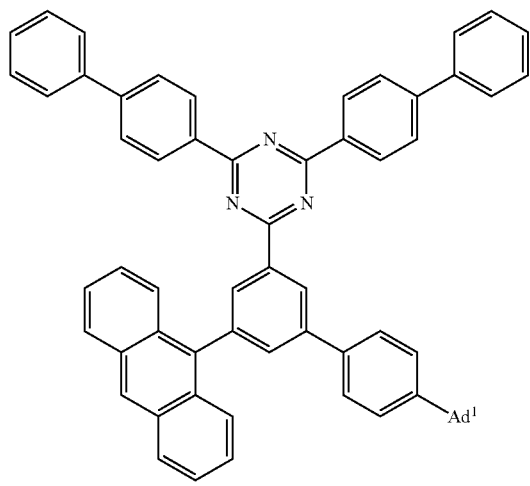
(A-162)
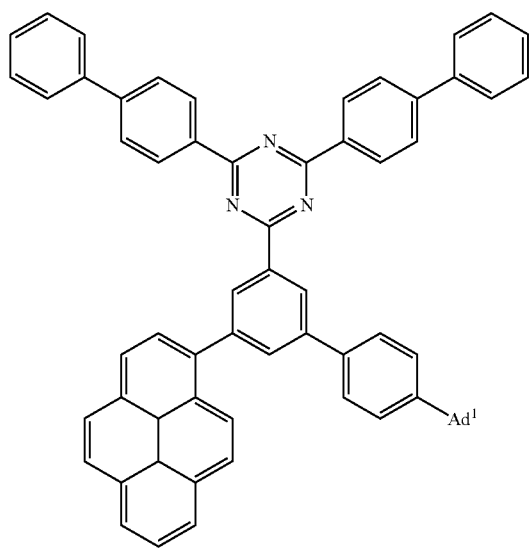
(A-163)
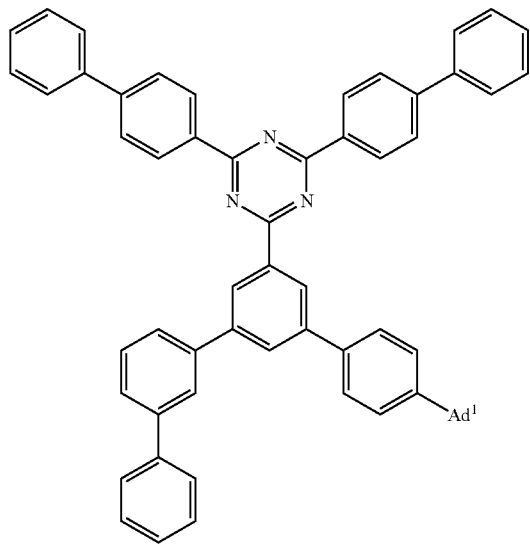
(A-164)
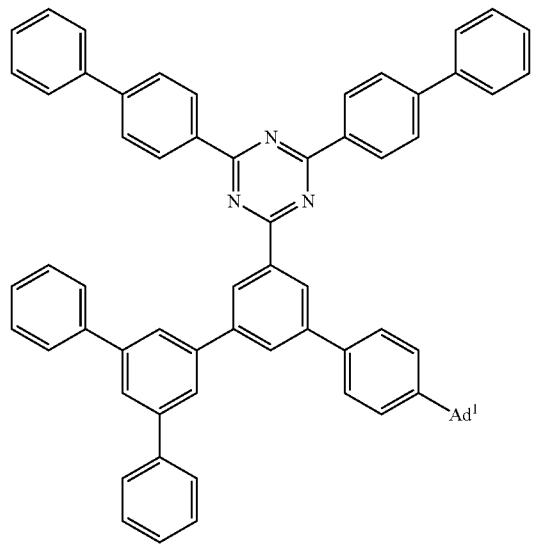
(A-165)
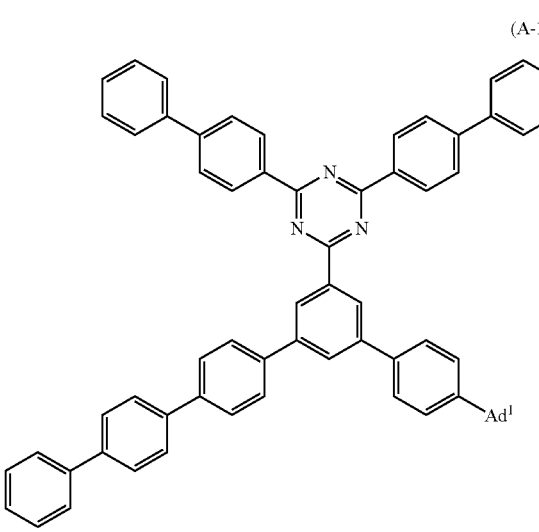
(A-166)
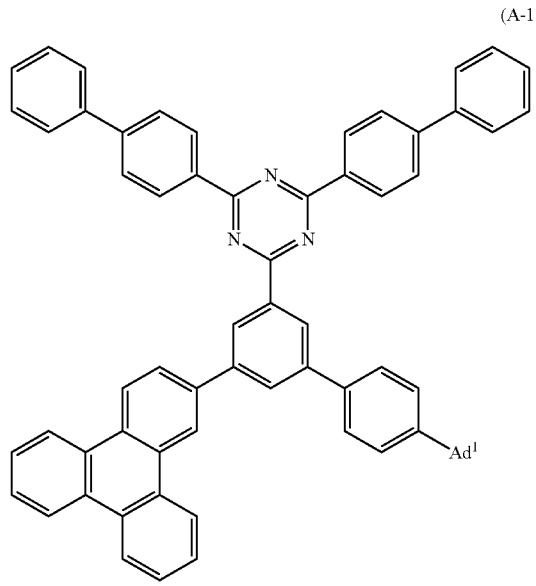

(A-167)
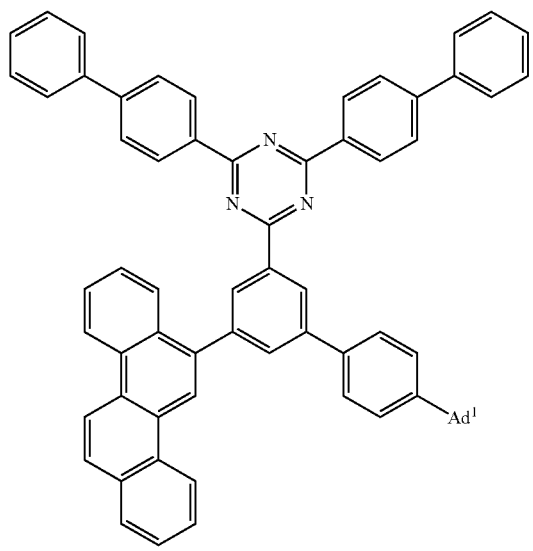
(A-170)
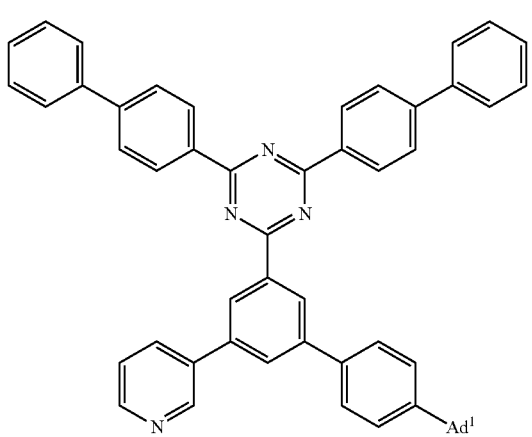
(A-168)
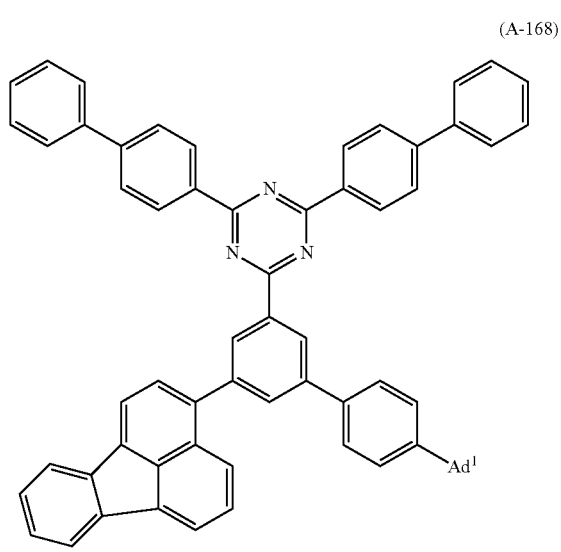
(A-171)
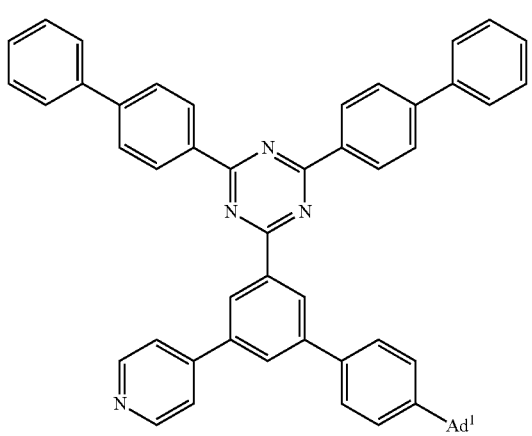
(A-169)
(A-172)
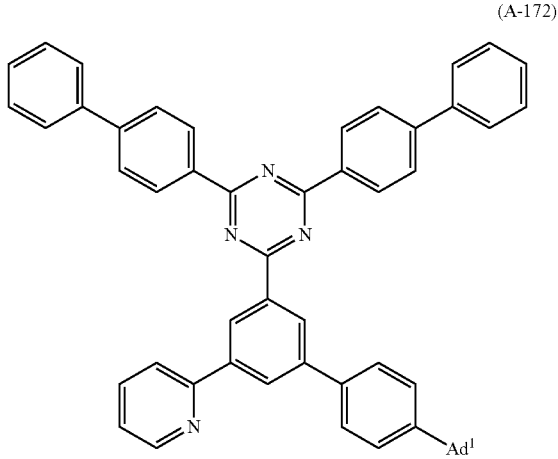

(A-173)
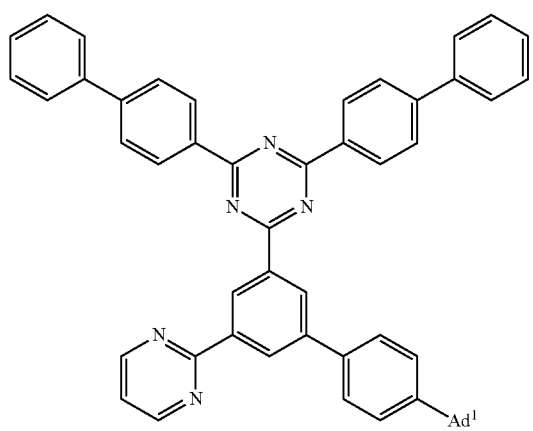
(A-174)
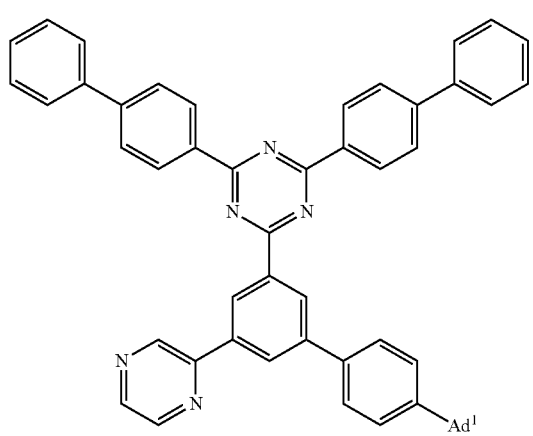
(A-175)
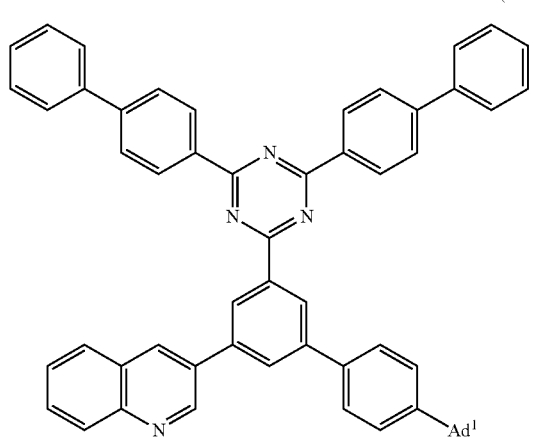
(A-176)
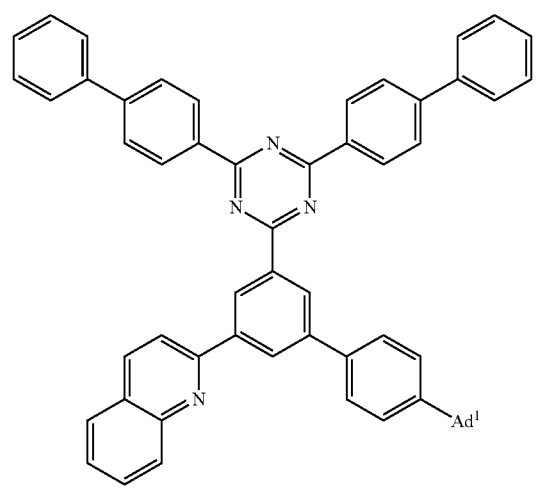
(A-177)
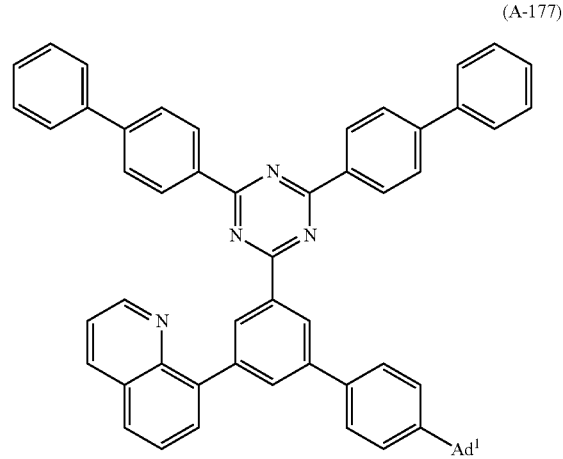
(A-178)
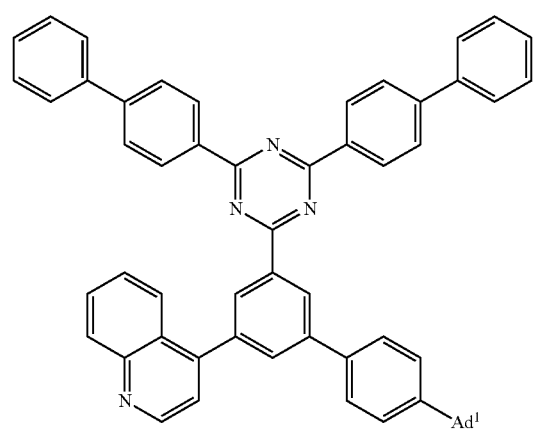

(A-179)
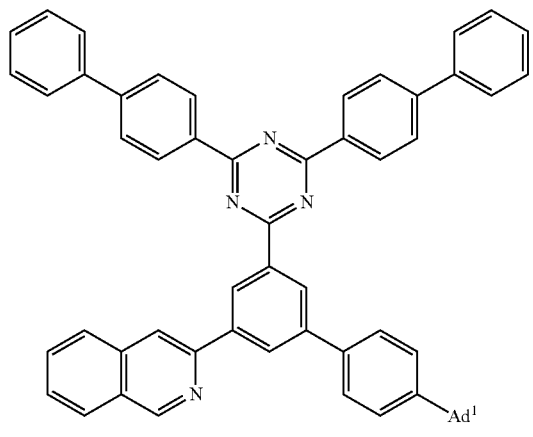
(A-180)
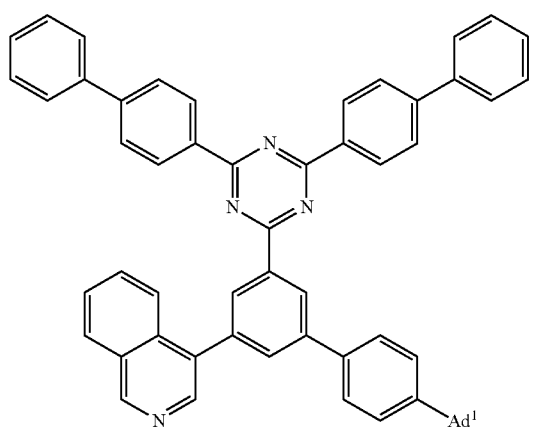
(A-181)
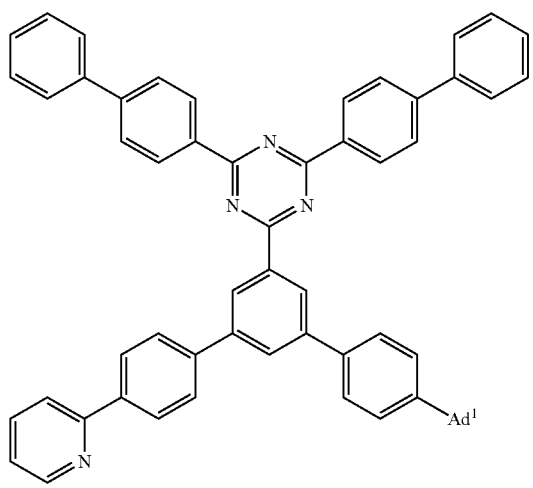
(A-182)
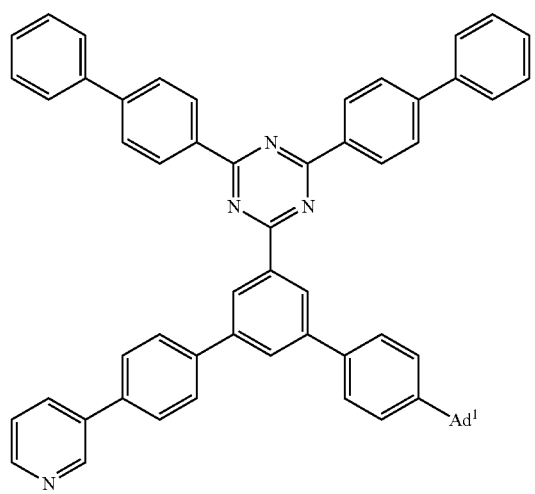
(A-183)
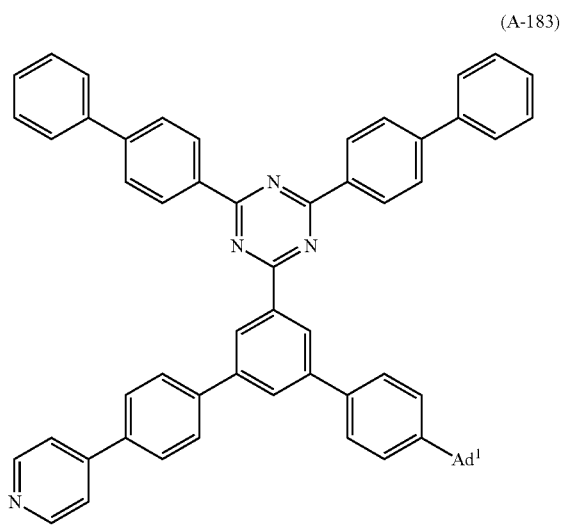
(A-184)
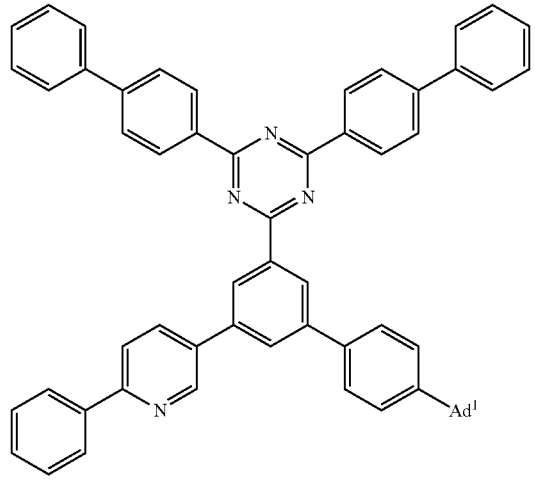

(A-185)
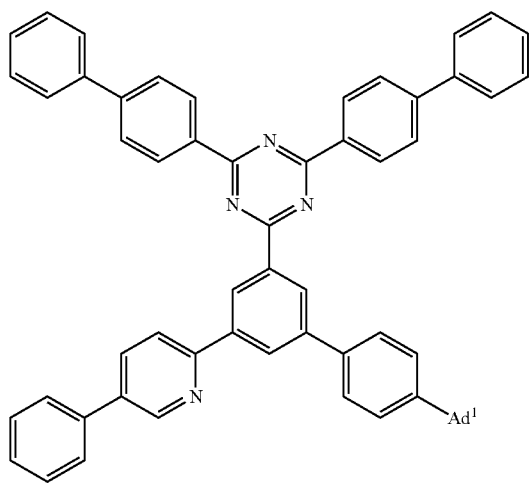
(A-188)
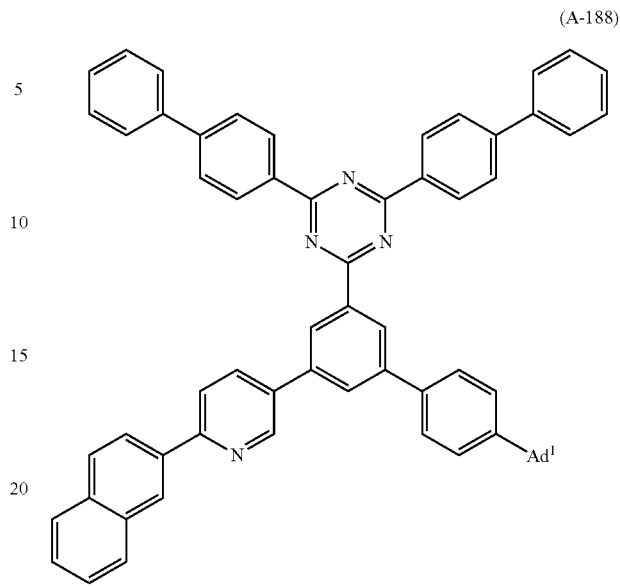
(A-186)
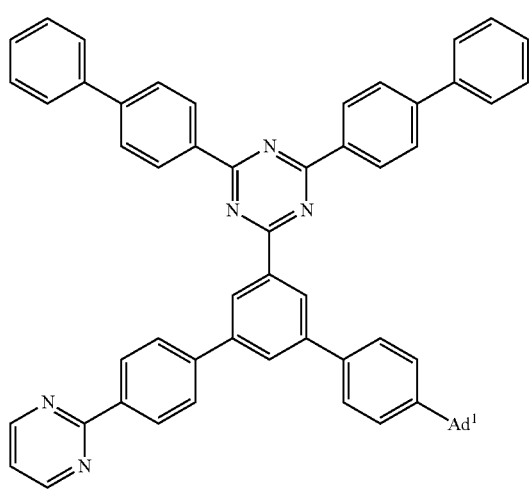
(A-189)
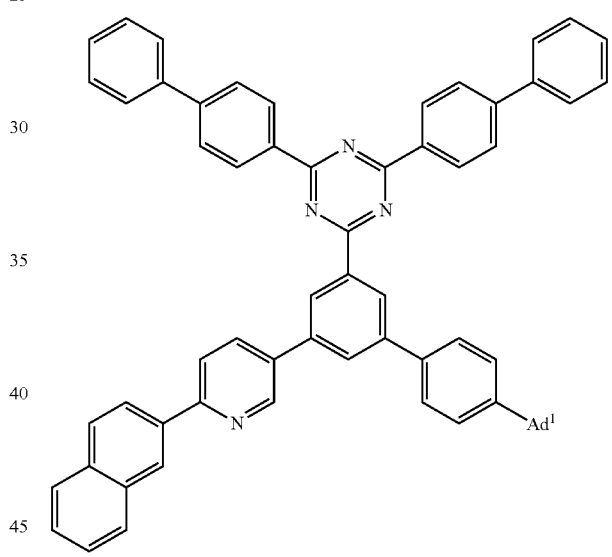
(A-187)
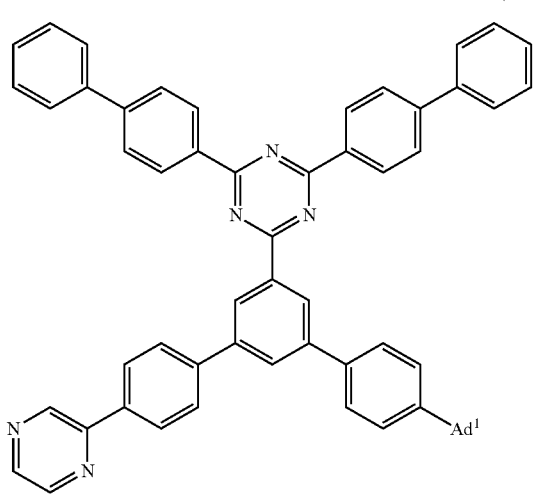
(A-190)
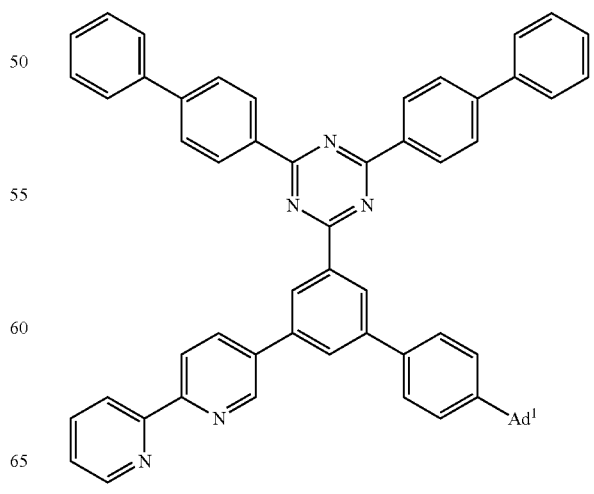

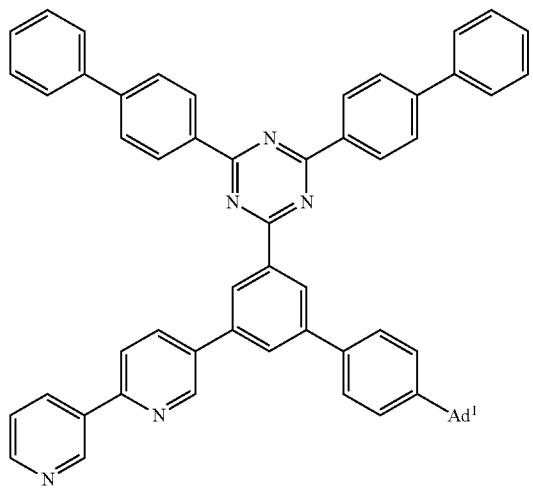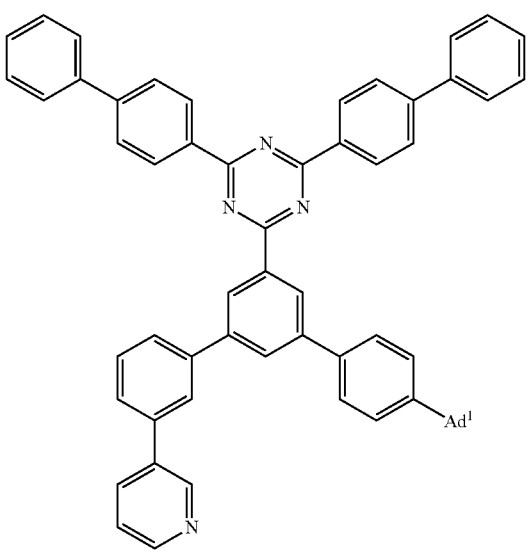

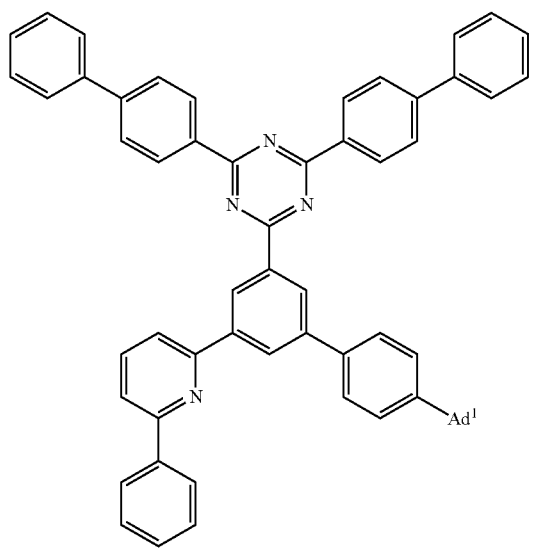
(A-197)
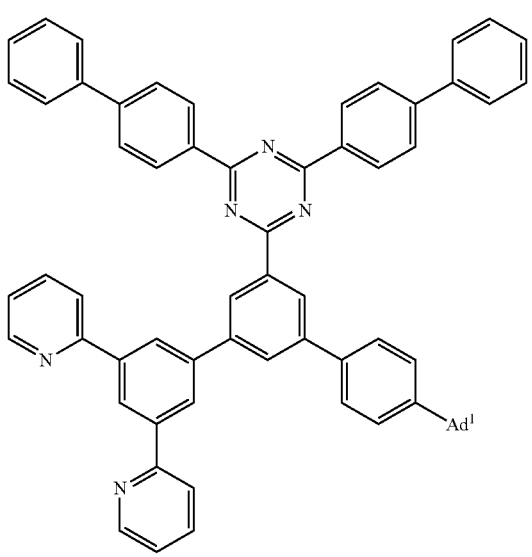
(A-200)
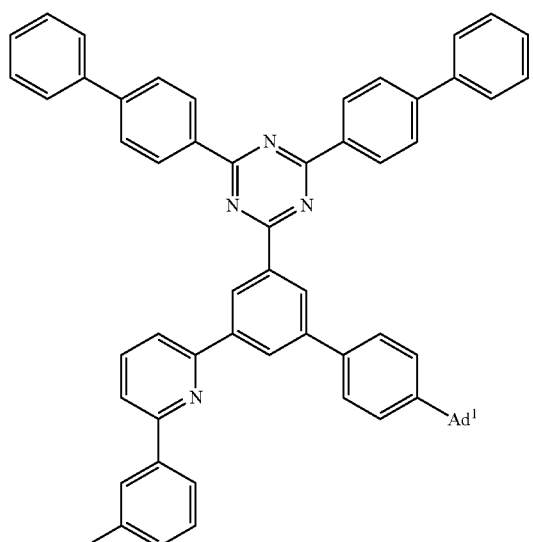
(A-198)
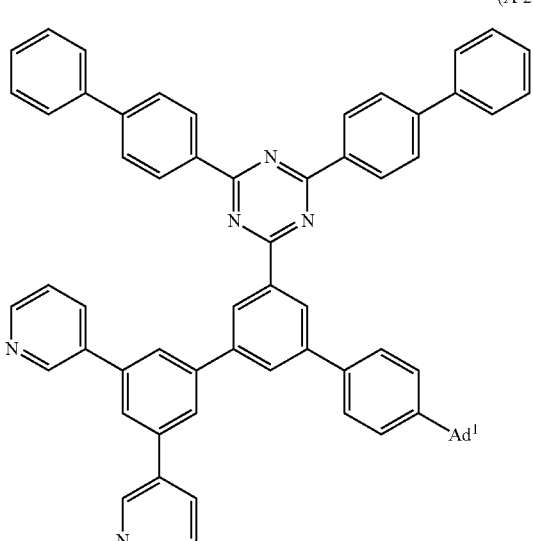
(A-201)
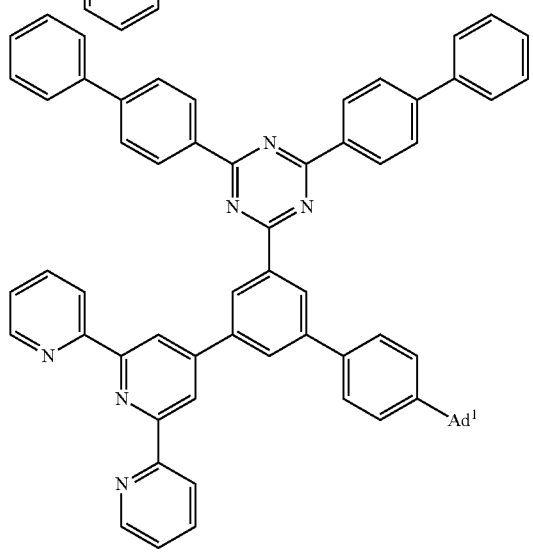
(A-199)
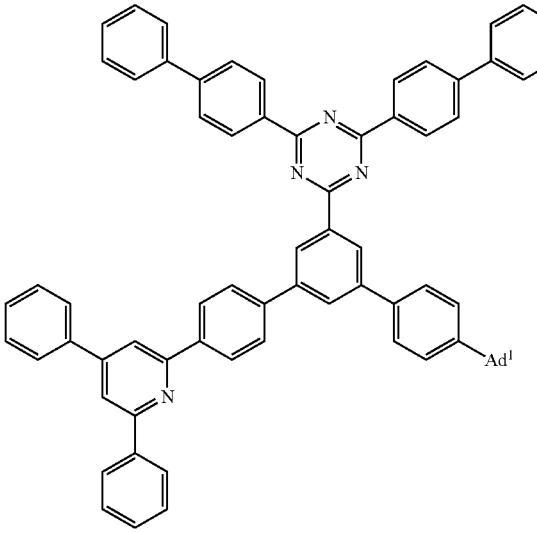
(A-202)

(A-203)
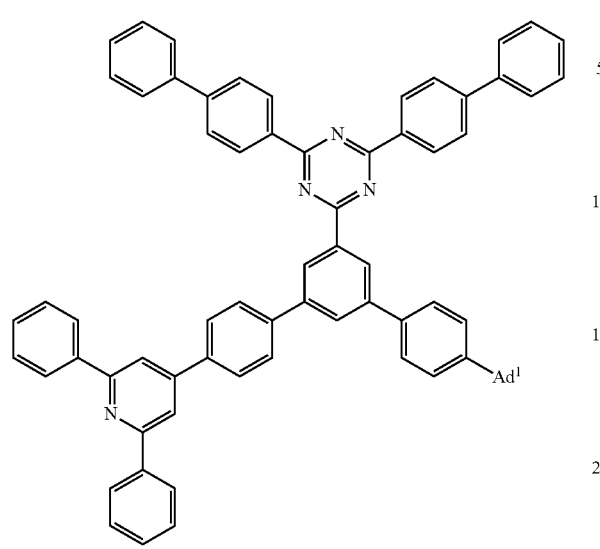
(A-204)
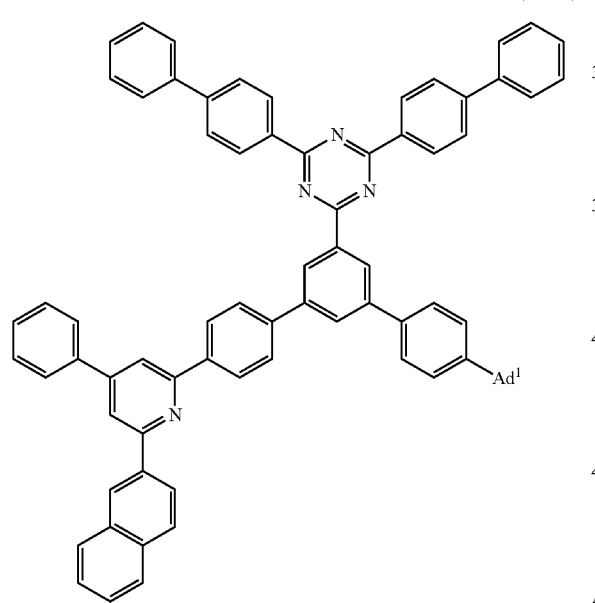
(A-205)
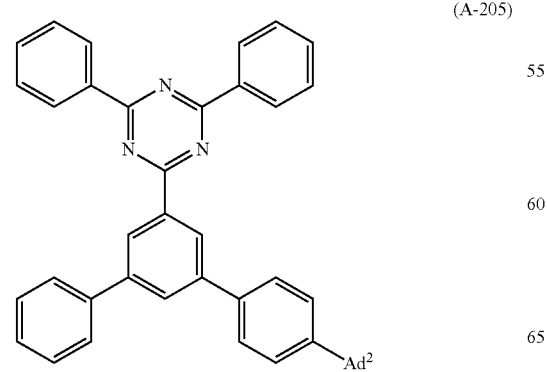
(A-206)
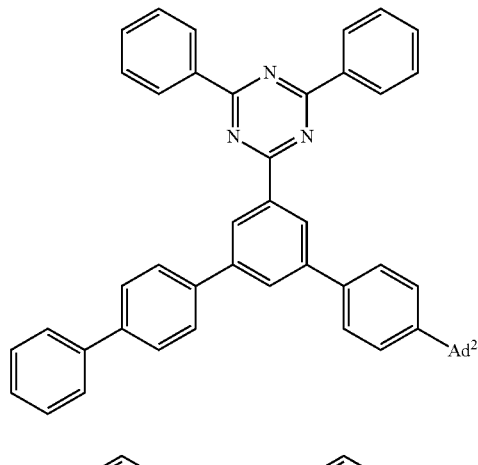
(A-207)
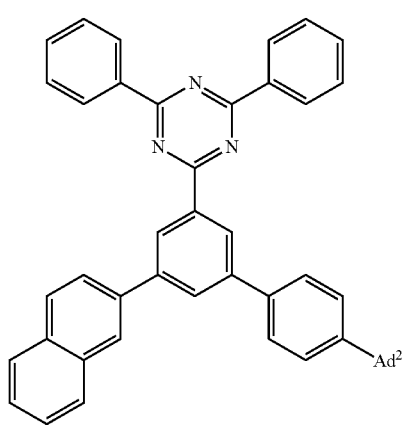
(A-208)
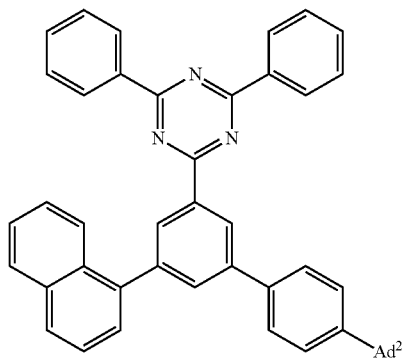
(A-209)
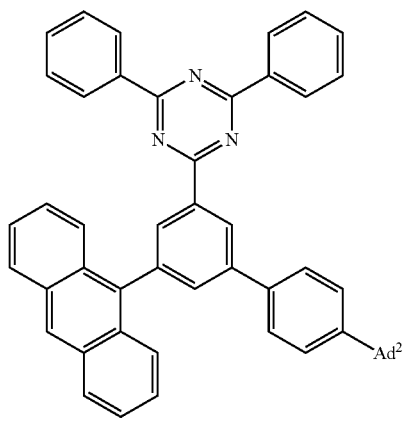

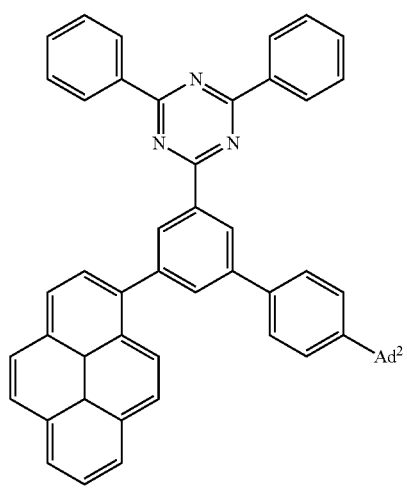
(A-210)
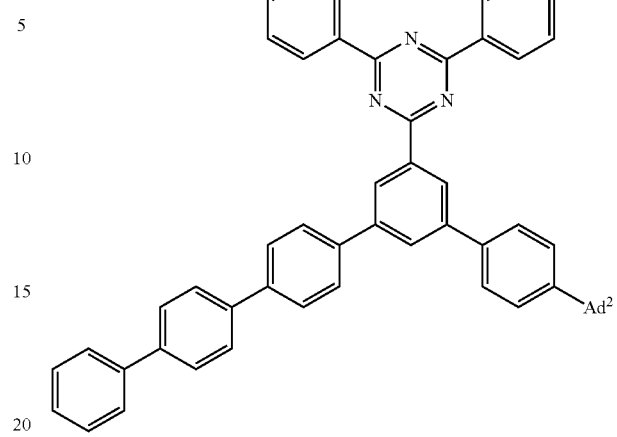
(A-213)
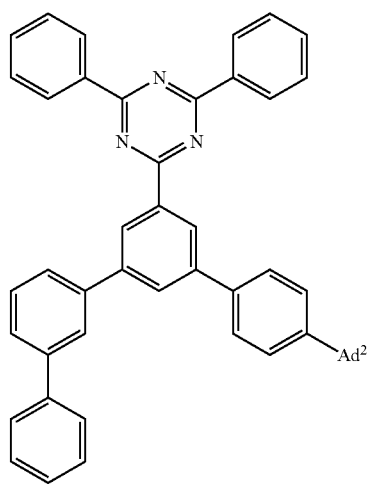
(A-211)
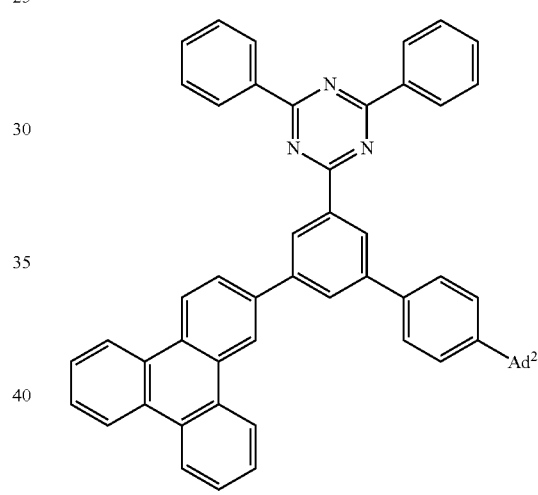
(A-214)
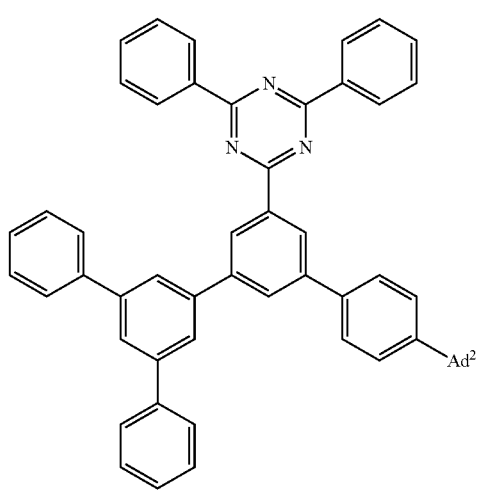
(A-212)
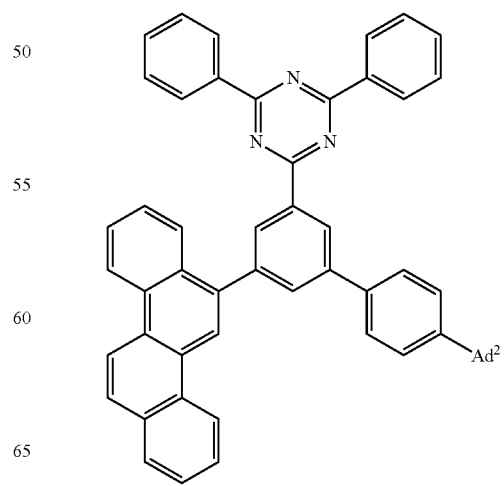
(A-215)

-continued
(A-216)
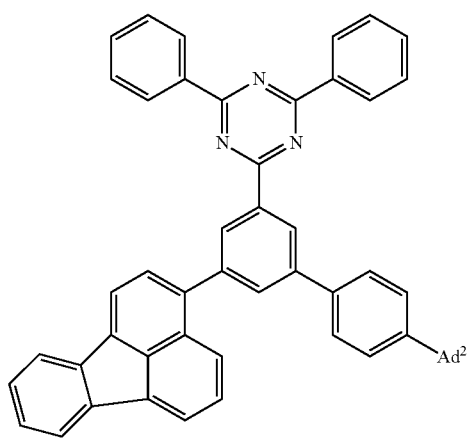
(A-217)
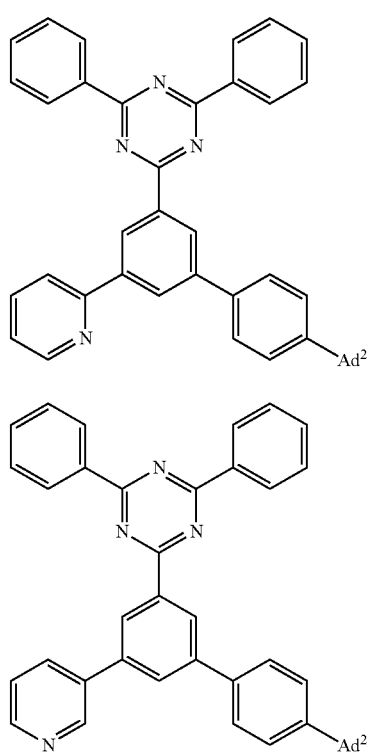
(A-218)
(A-219)
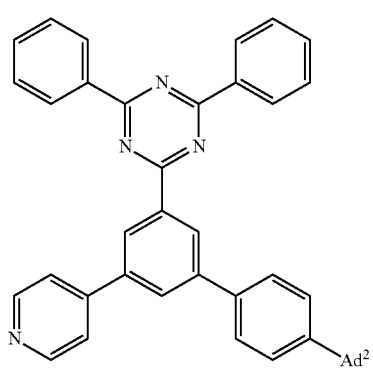
-continued
(A-220)
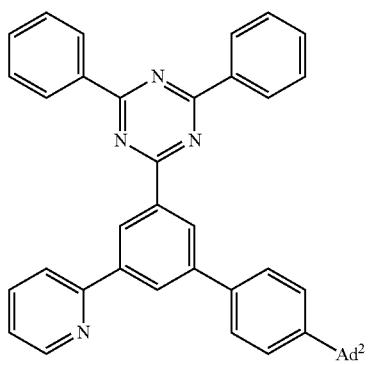
(A-221)
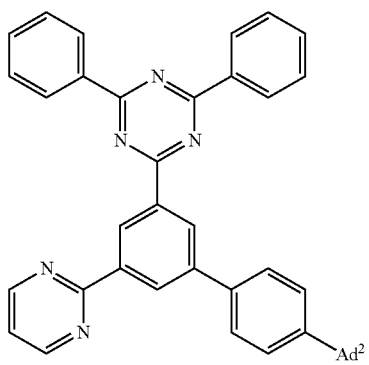
(A-222)
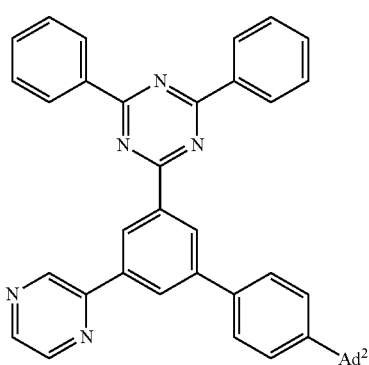
(A-223)
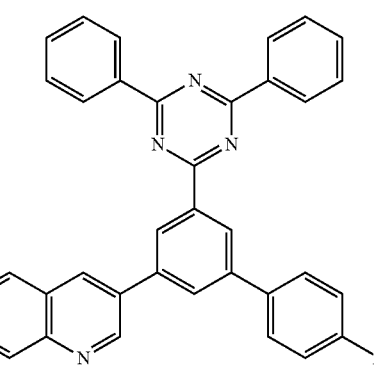

(A-224)
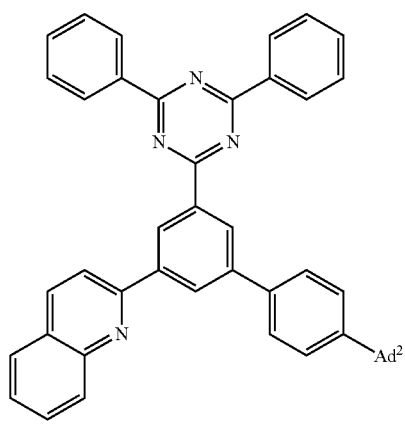
(A-225)
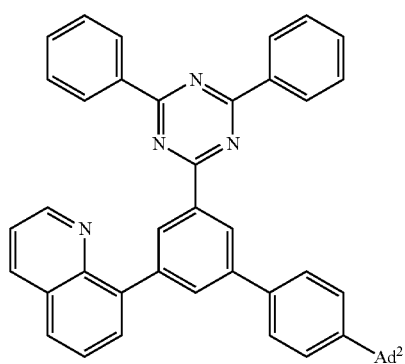
(A-226)
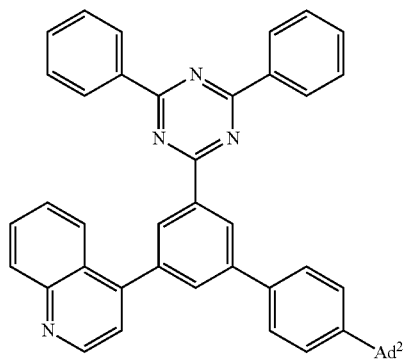
(A-227)
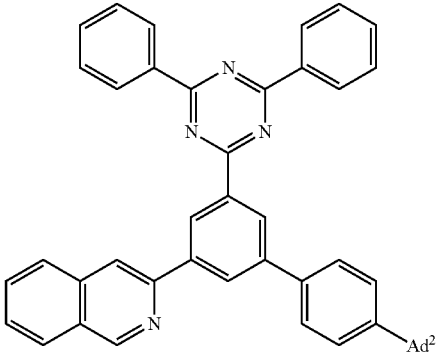
(A-228)
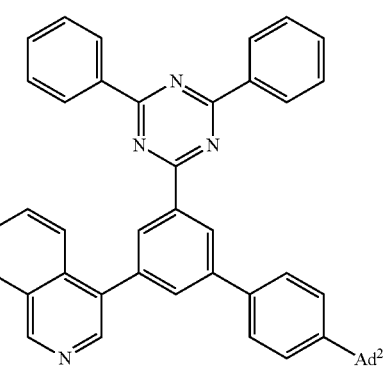
(A-229)
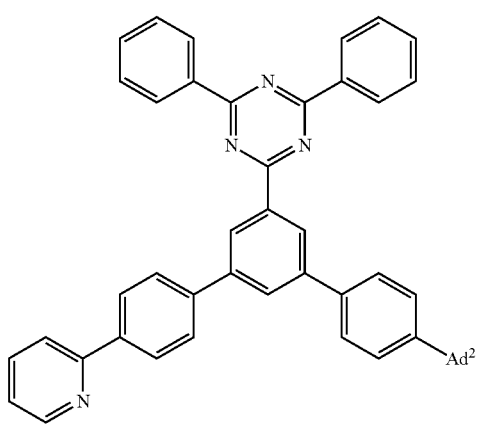
(A-230)
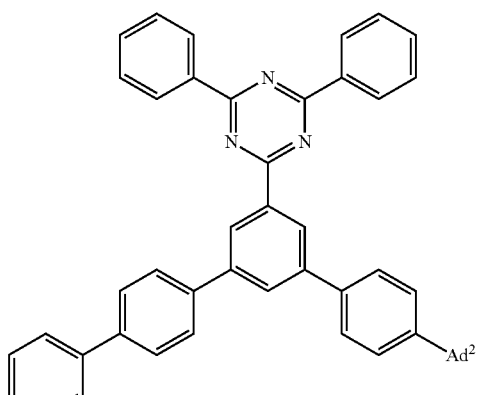
(A-231)
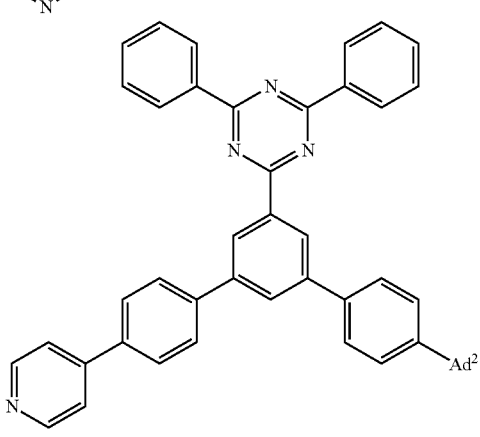

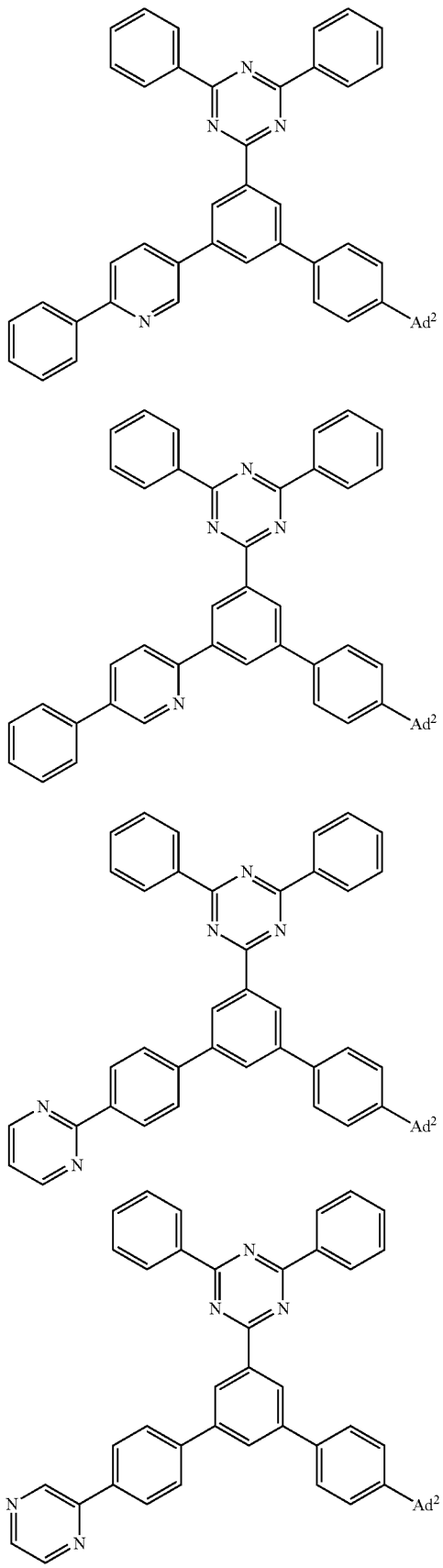
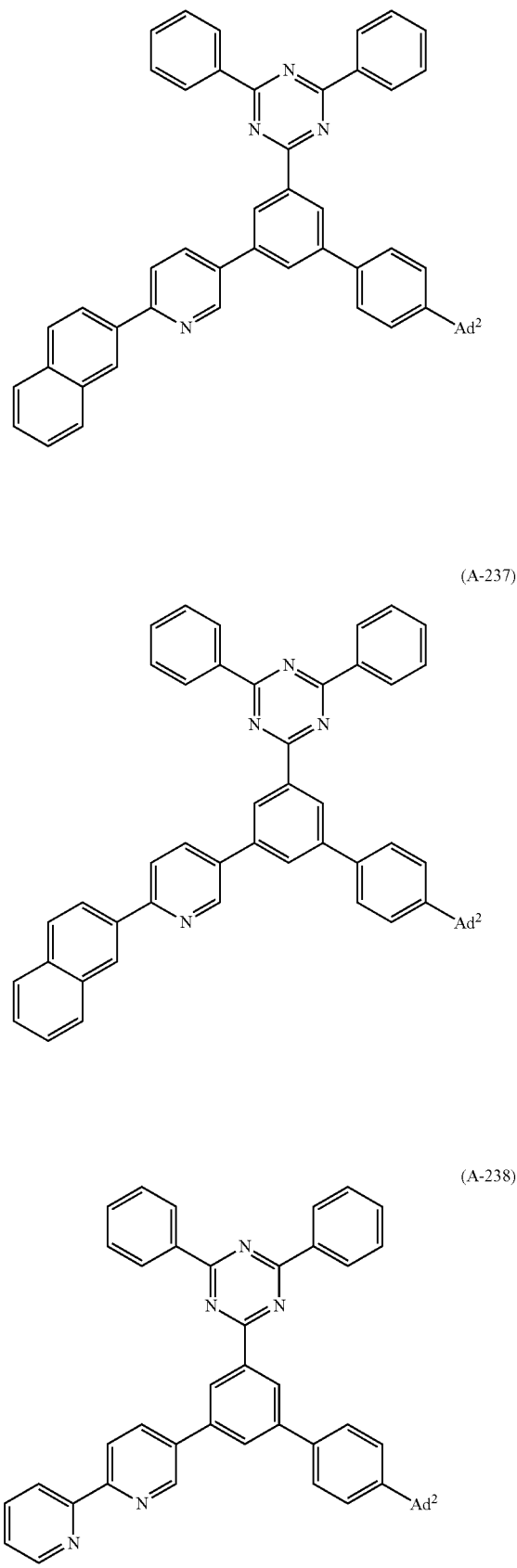

(A-239)
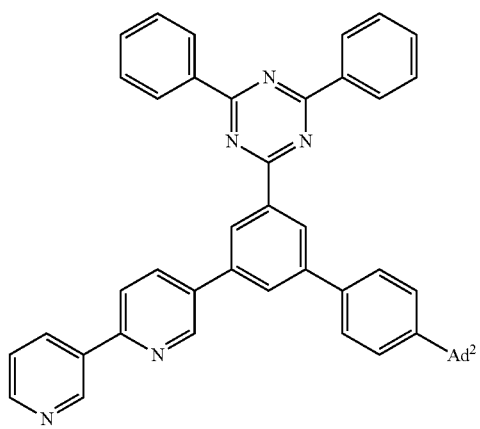
(A-240)
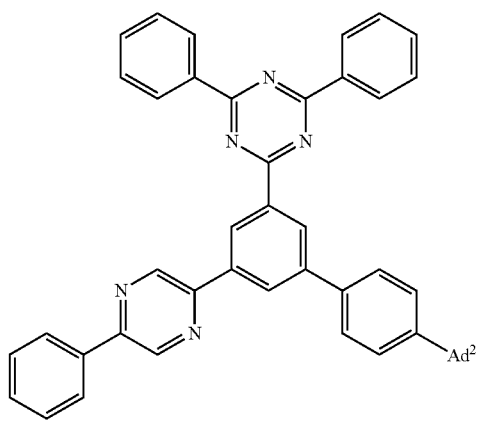
(A-241)
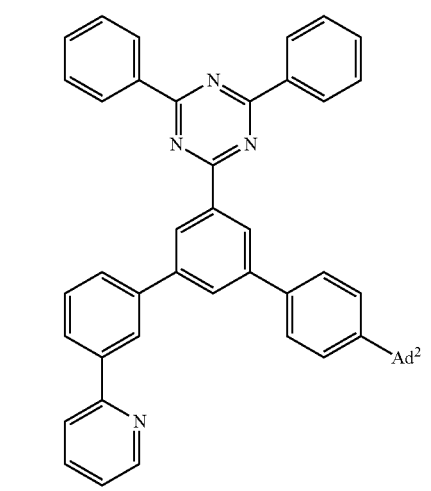
(A-242)
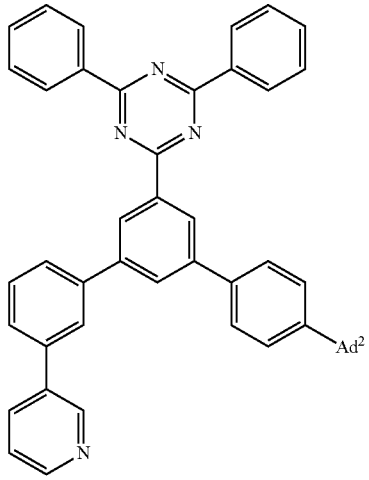
(A-243)
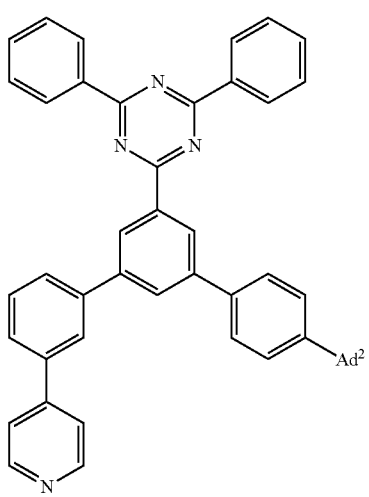
(A-244)
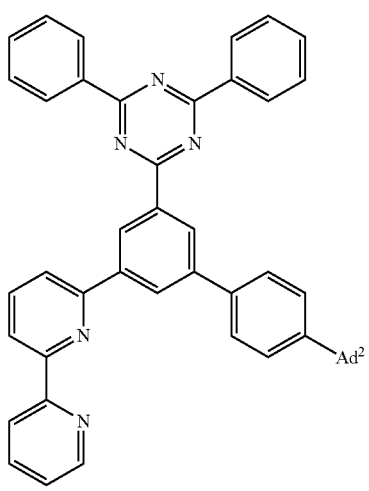

(A-245)
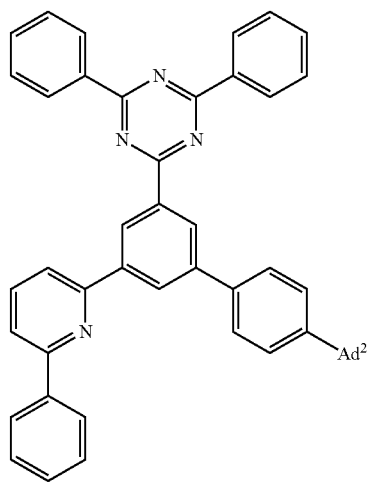
(A-248)
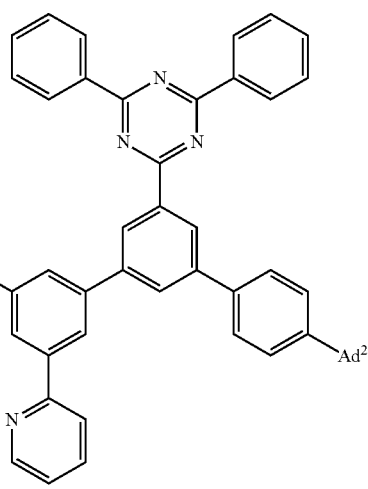
(A-246)
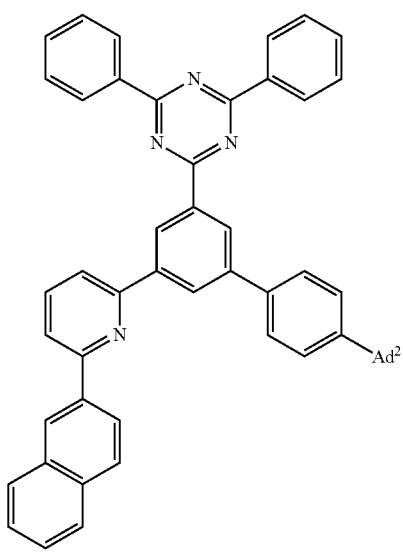
(A-249)
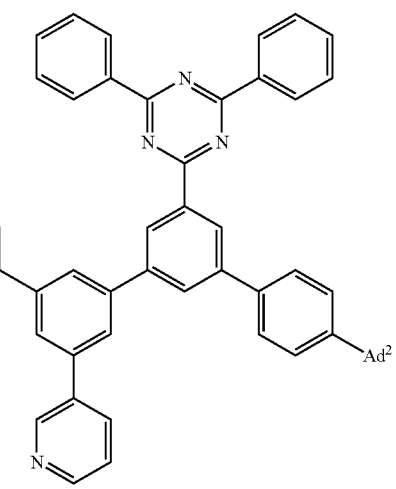
(A-247)
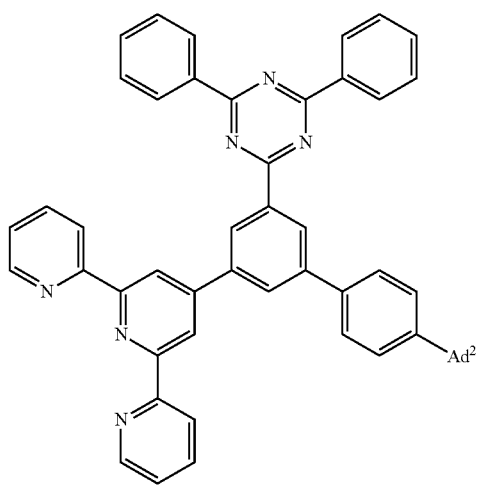
(A-250)
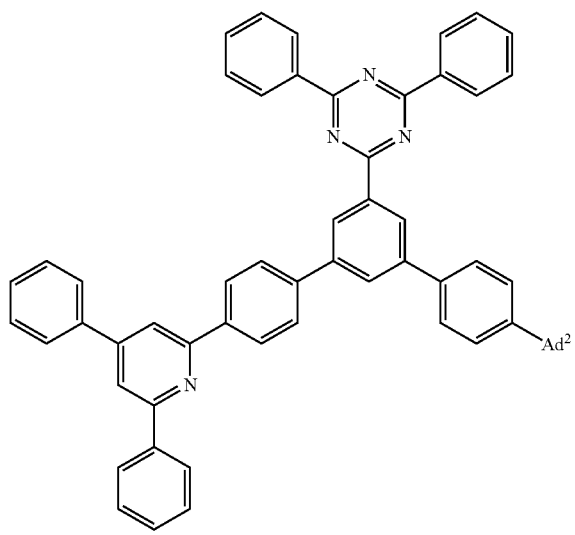

(A-251)
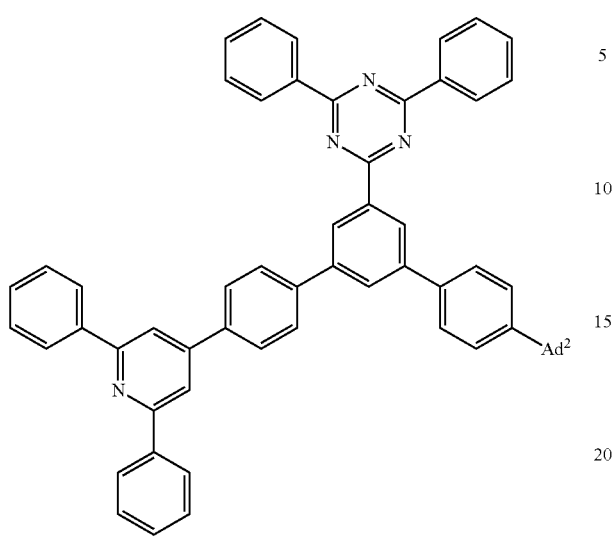
(A-254)
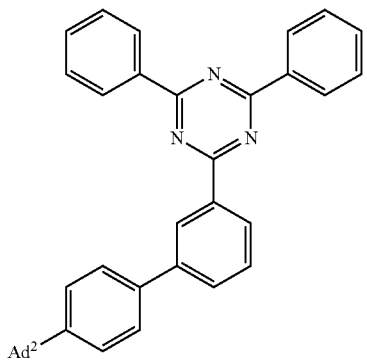
(A-252)
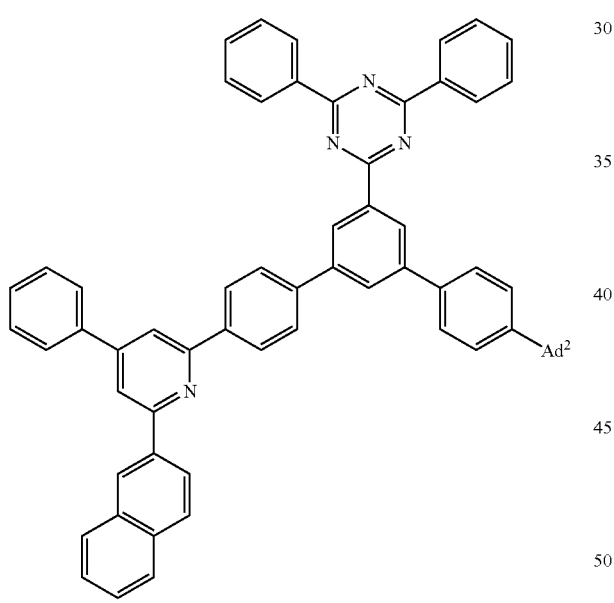
(A-255)
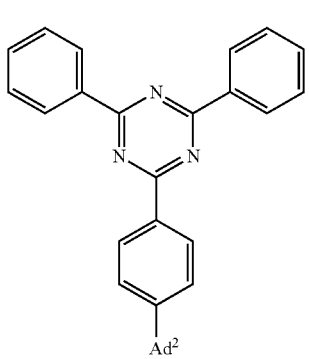
(A-256)
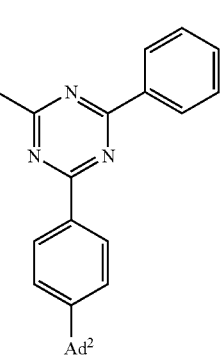
(A-253)
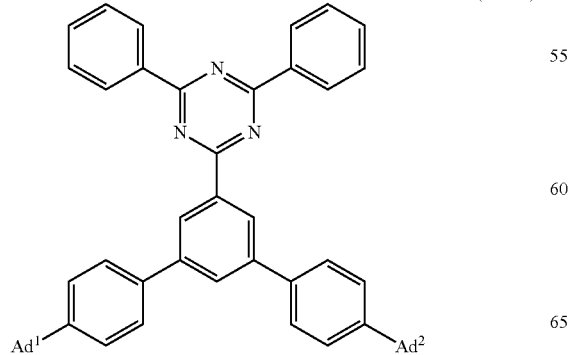
(A-257)
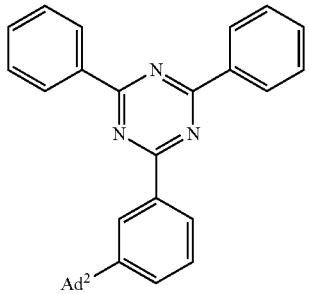

-continued
(A-258)
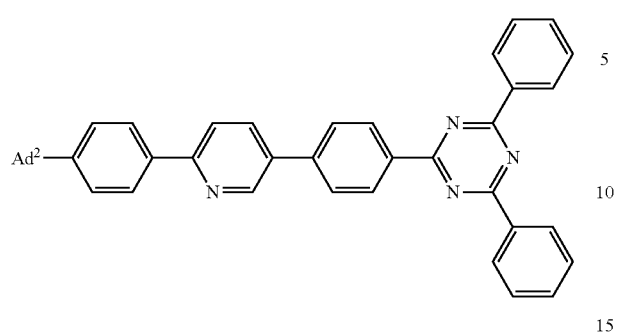
(A-262)
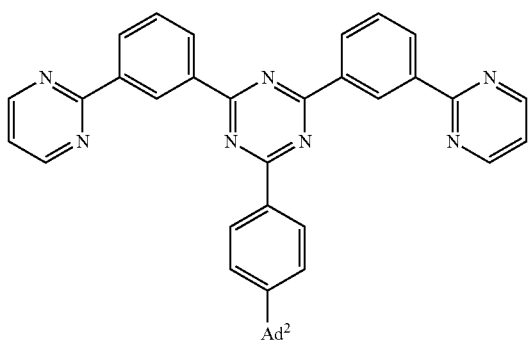
(A-259)
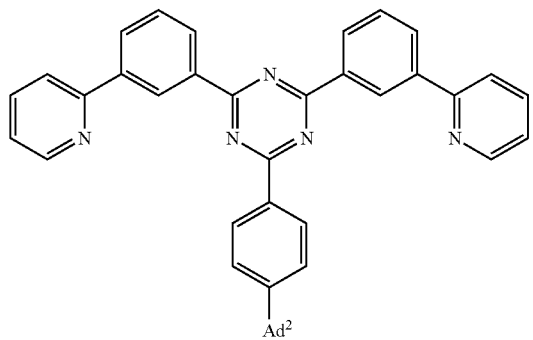
(A-263)
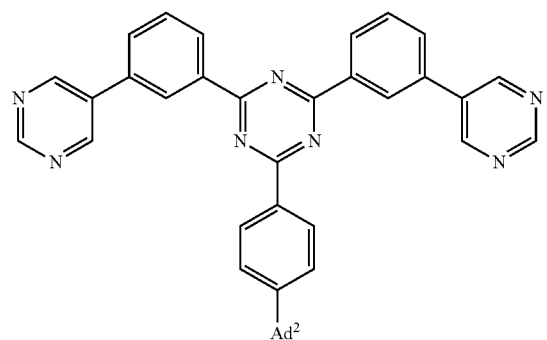
(A-260)
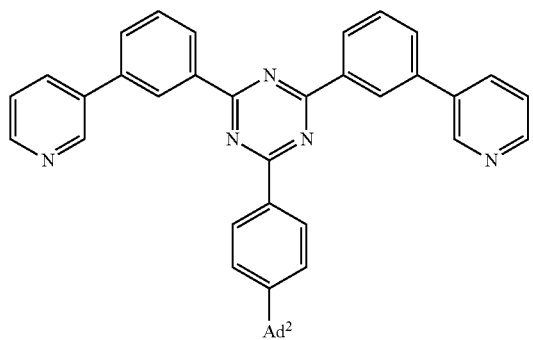
(A-264)
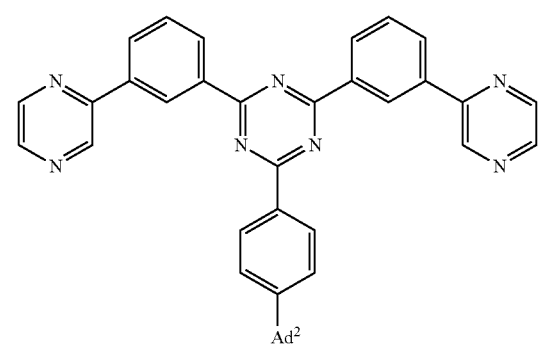
(A-261)
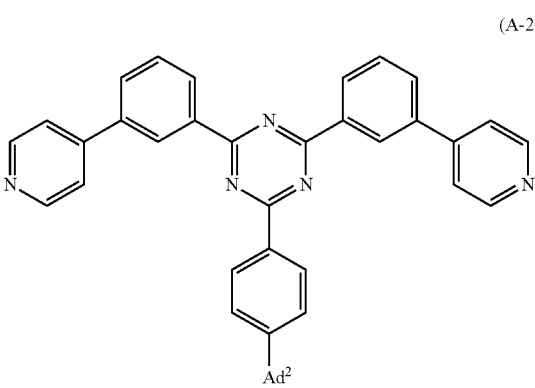
(A-265)
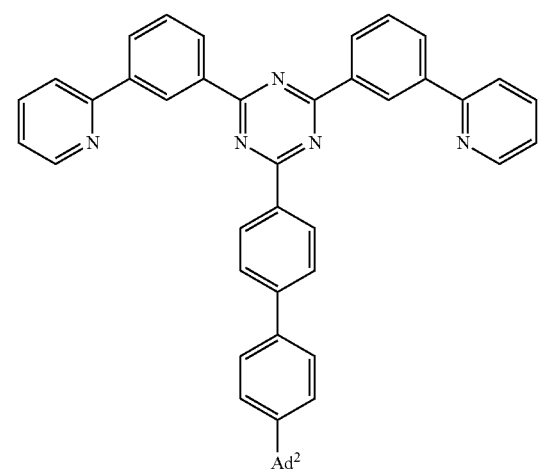

(A-266)
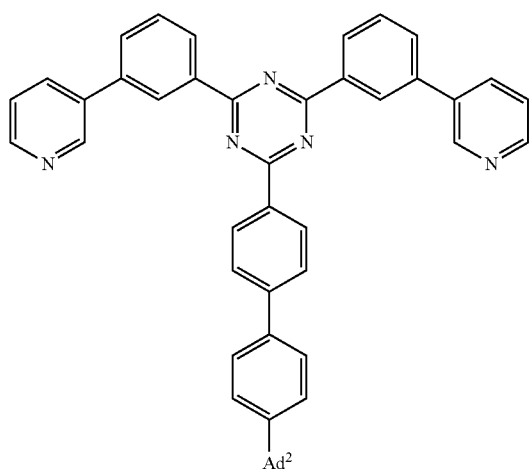
(A-269)
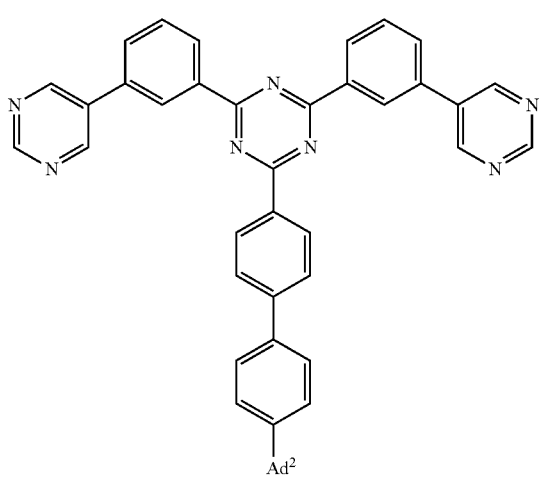
(A-267)
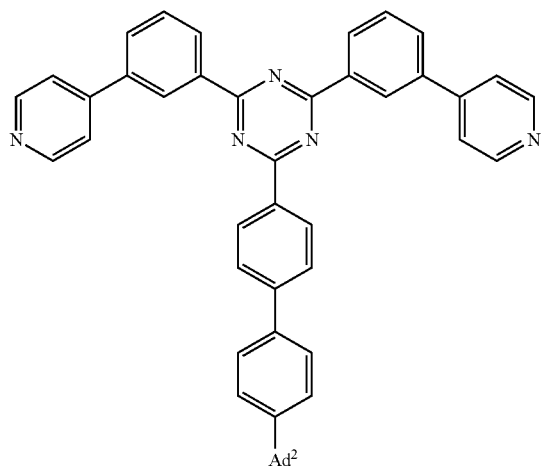
(A-270)
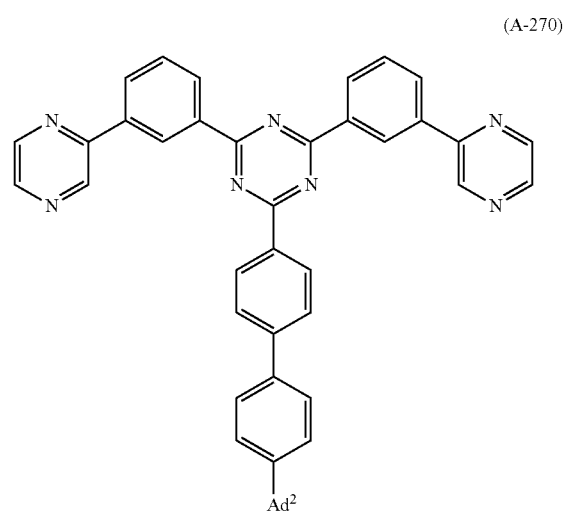
(A-268)
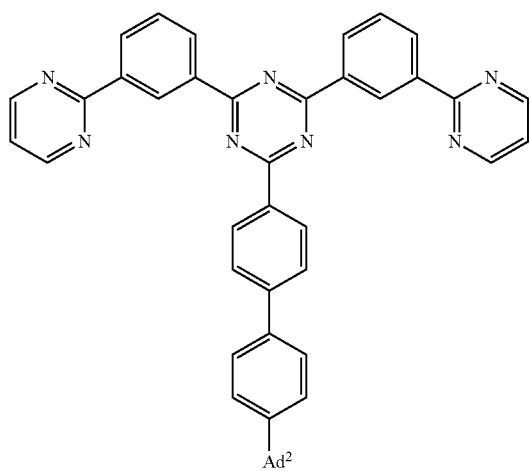
(A-271)
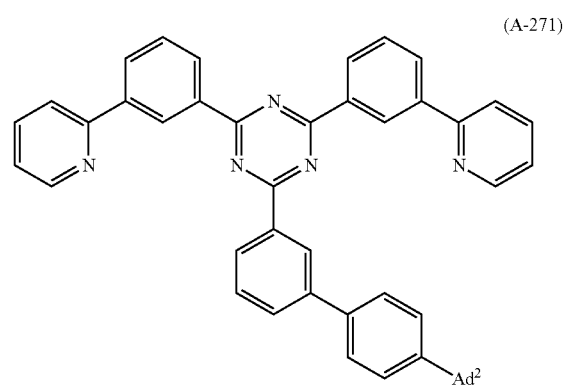

(A-272) 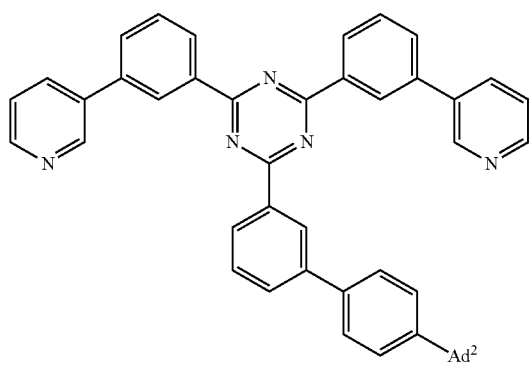
(A-273) 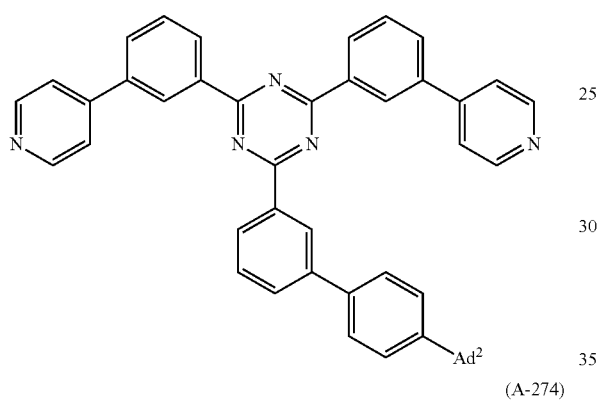
(A-274) 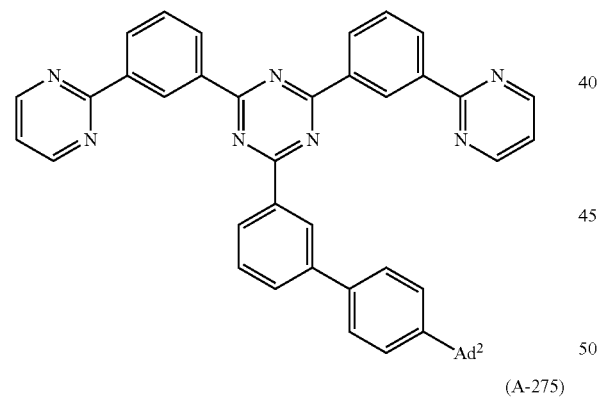
(A-275) 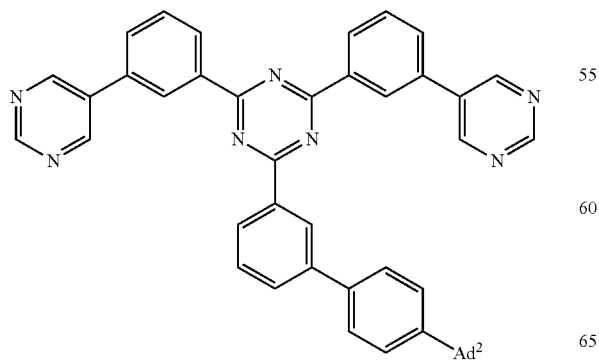
(A-276) 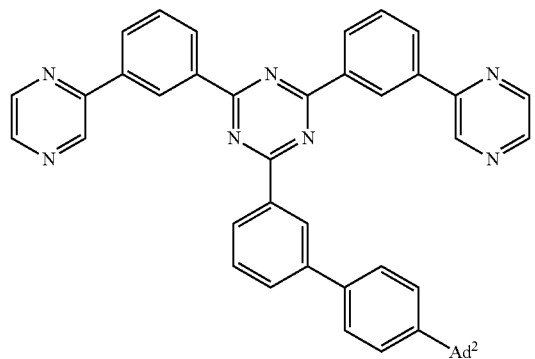
(A-277) 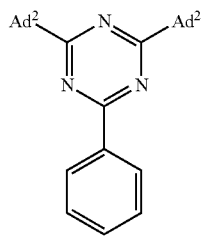
(A-278) 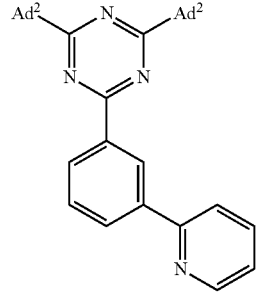
(A-279) 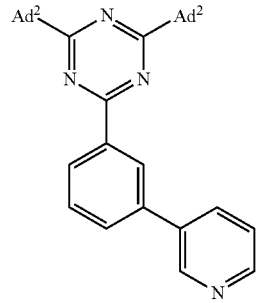
(A-280) 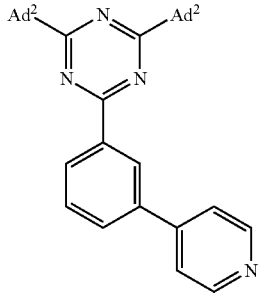

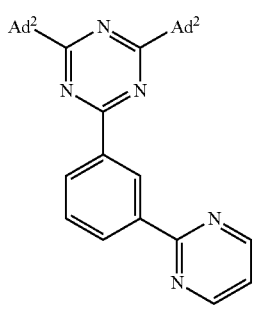
(A-281)
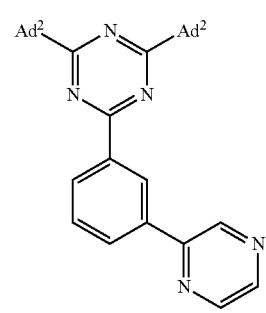
(A-282)
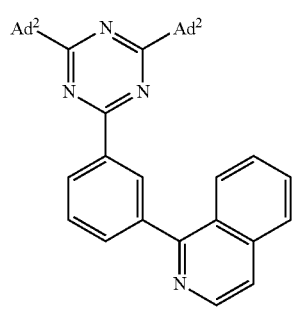
(A-283)
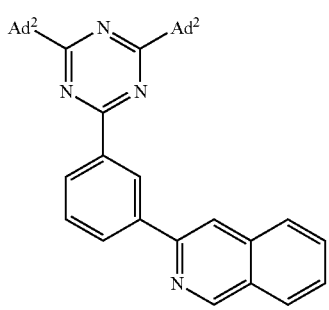
(A-284)
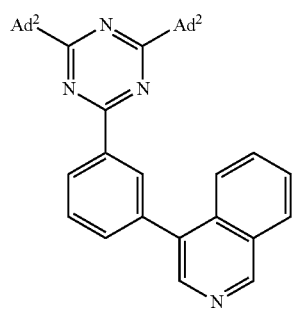
(A-285)
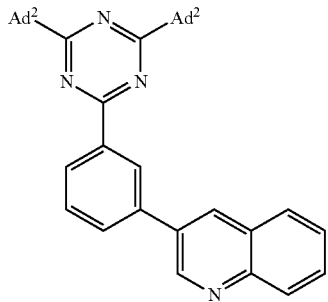
(A-286)
(A-287)
(A-288)
(A-289)

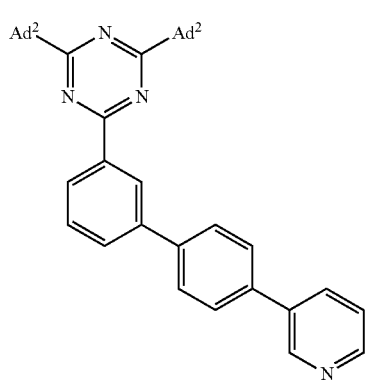
(A-290)
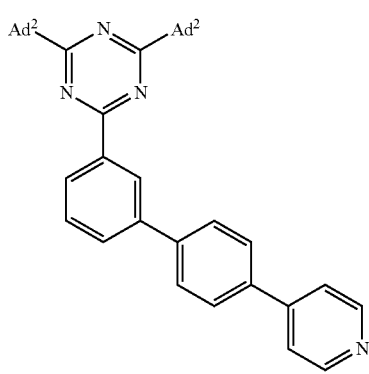
(A-291)
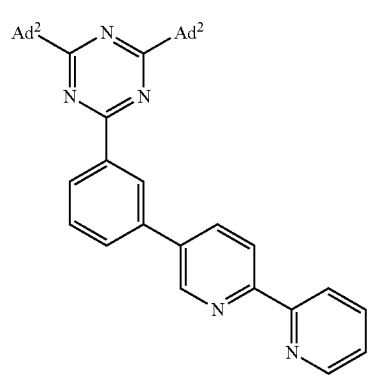
(A-292)
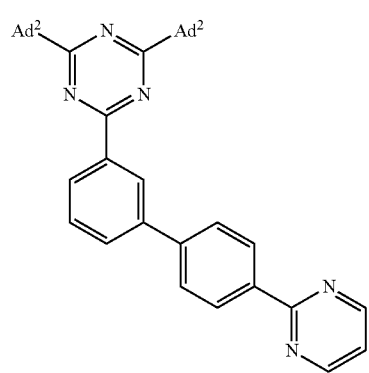
(A-293)
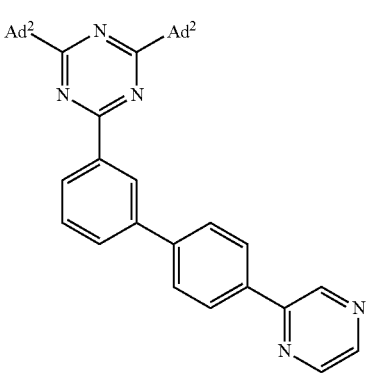
(A-294)
(A-295)
(A-296)
(A-297)

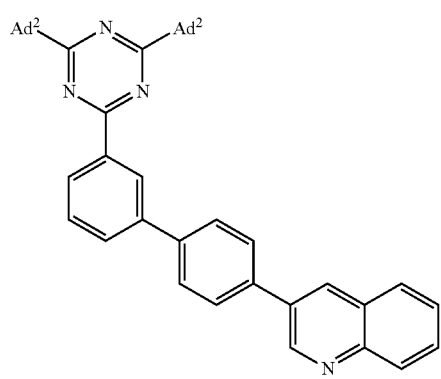
(A-298)
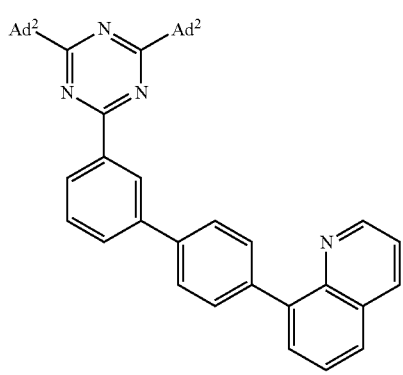
(A-299)
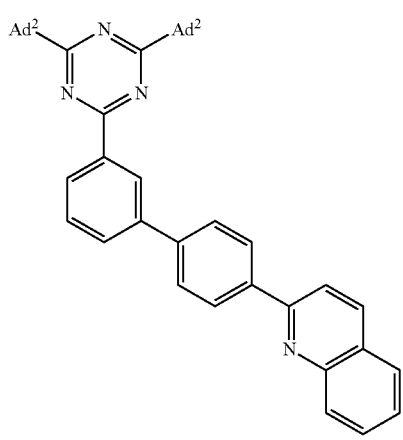
(A-300)
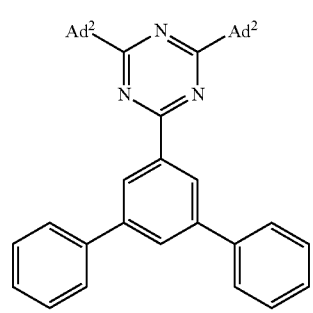
(A-301)
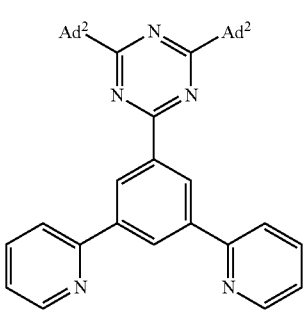
(A-302)
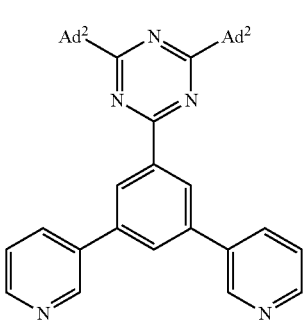
(A-303)
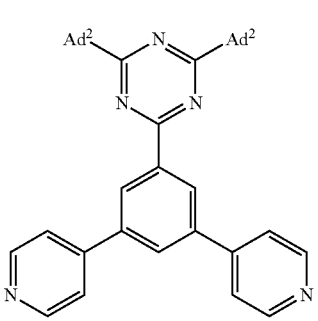
(A-304)
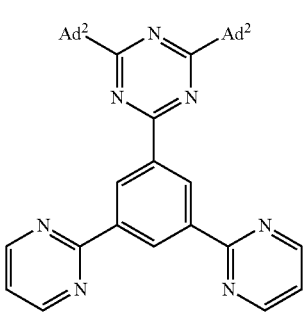
(A-305)
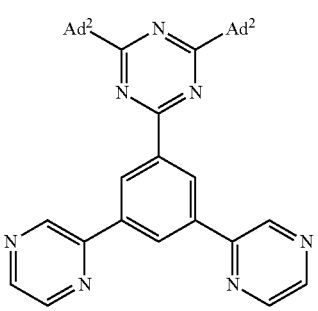
(A-306)

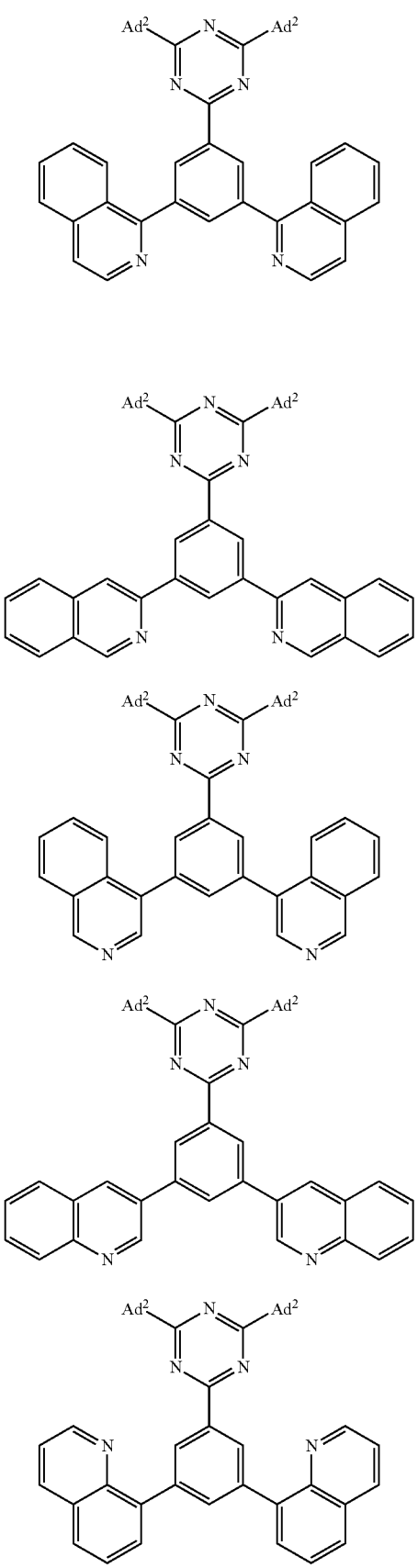
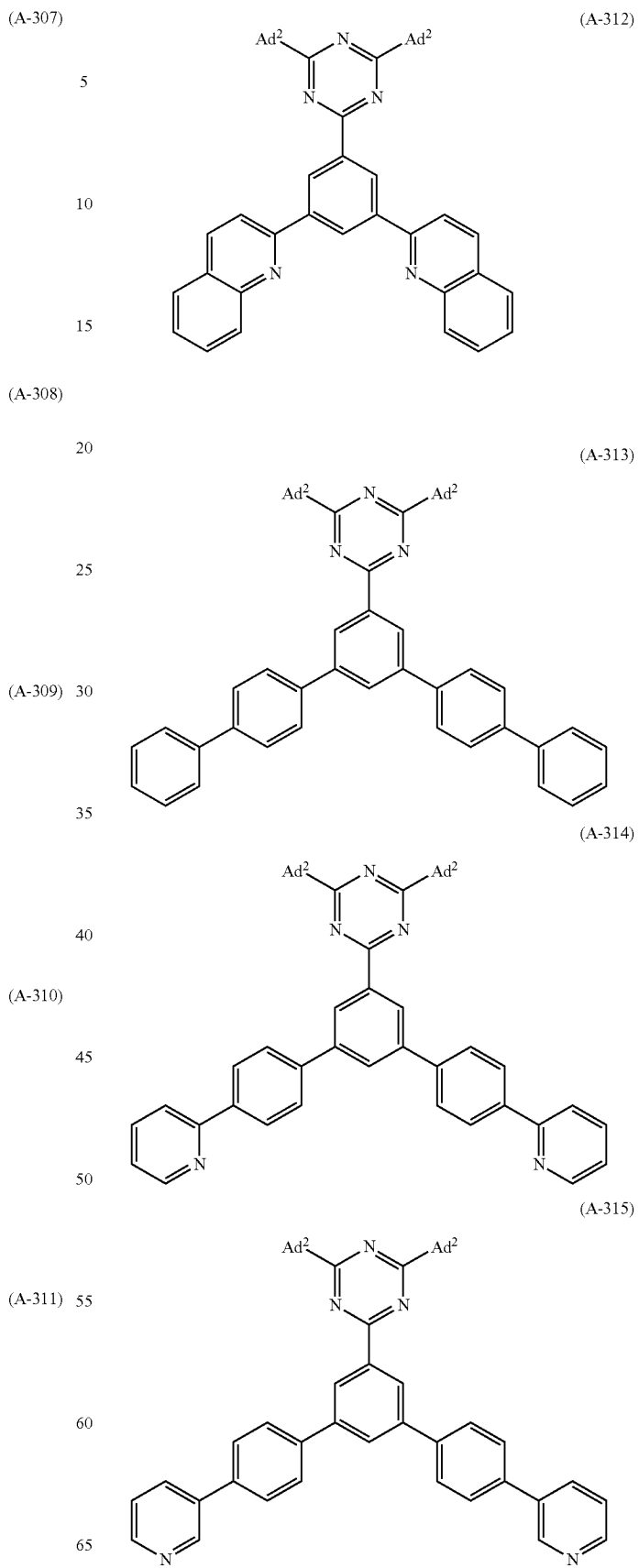

(A-316)
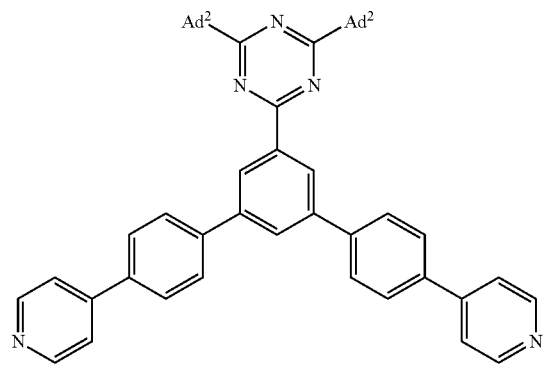
(A-320)
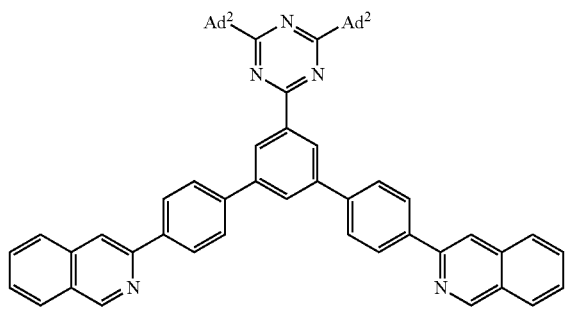
(A-317)
(A-321)
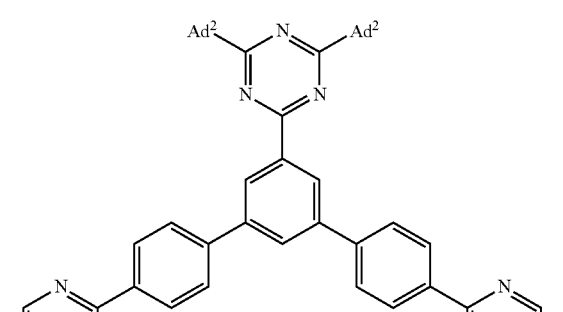
(A-318)
(A-322)
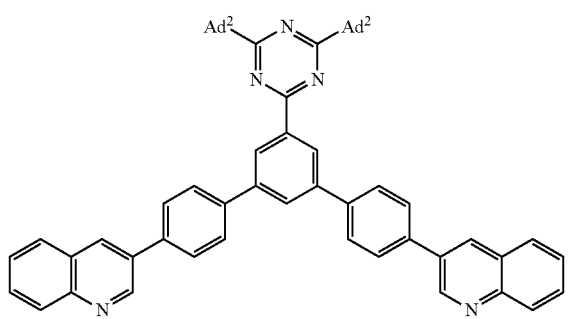
(A-319)
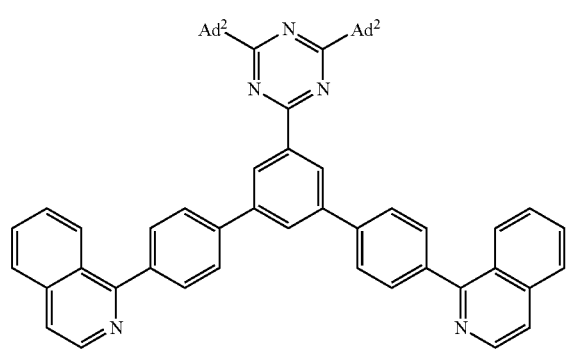
(A-323)

(A-324)
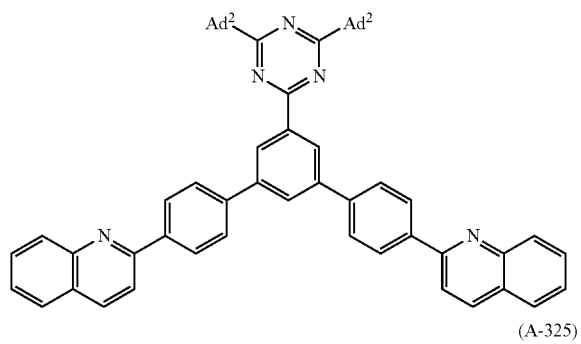
(A-325)
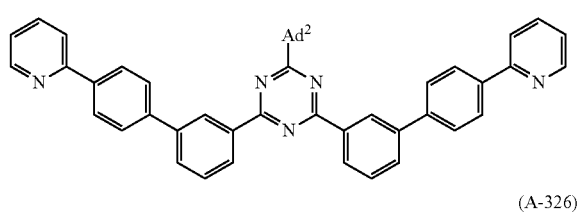
(A-326)
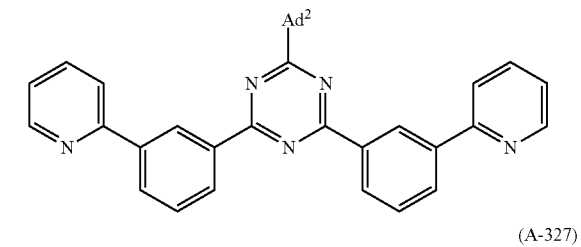
(A-327)
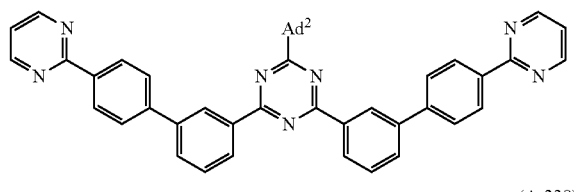
(A-328)
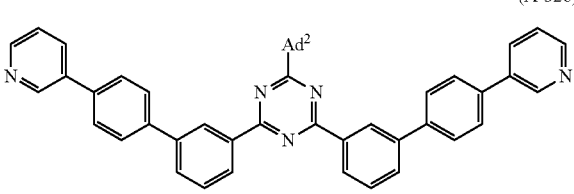
(A-329)
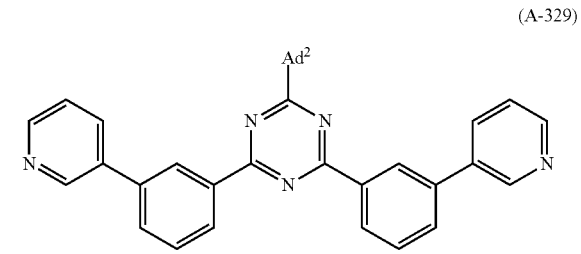
(A-330)
(A-331)
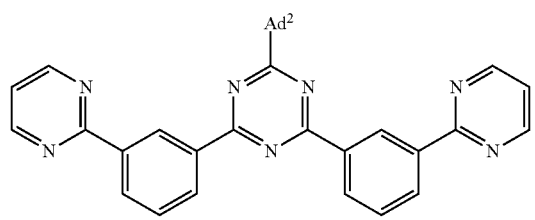
(A-332)
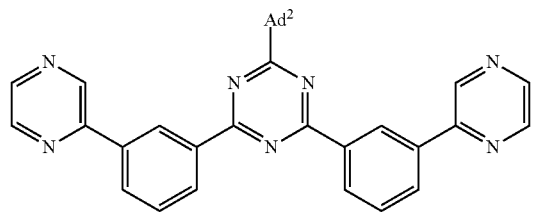
(A-333)
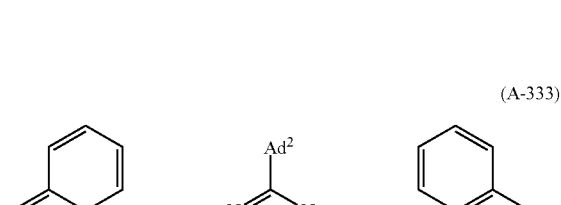
(A-334)
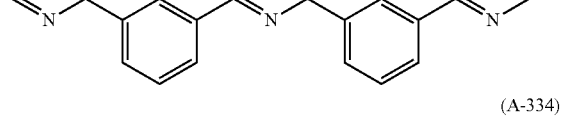
(A-335)
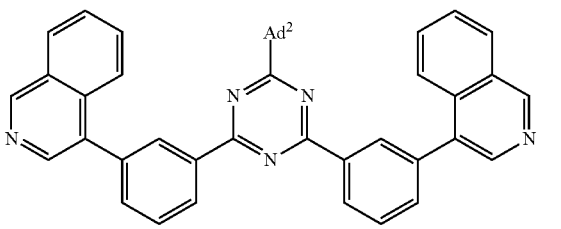
(A-336)
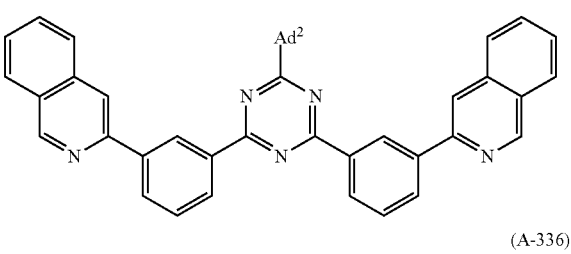

(A-337)
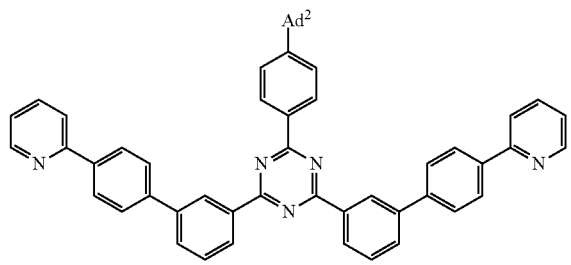
(A-338)
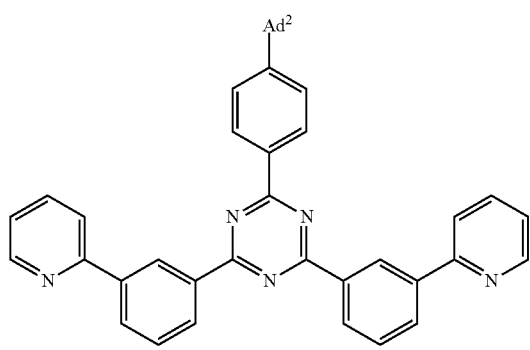
(A-339)
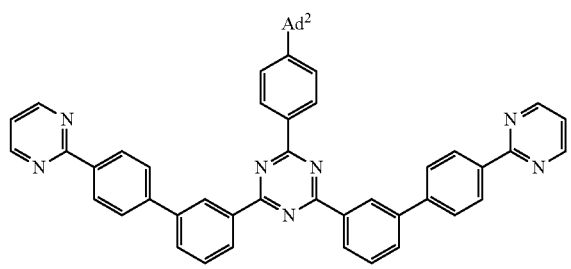
(A-340)
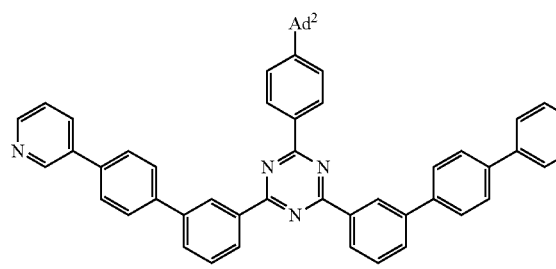
(A-341)
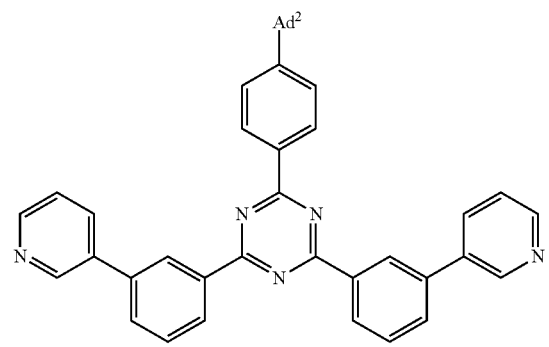
(A-342)
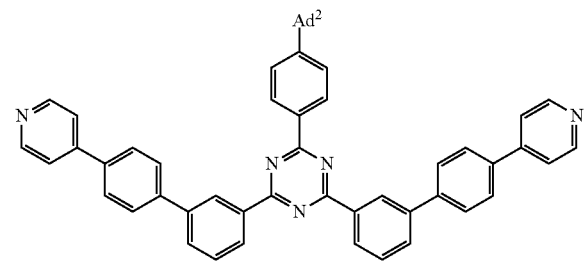
(A-343)
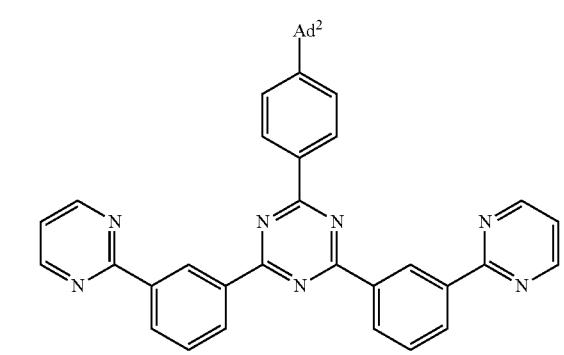
(A-344)
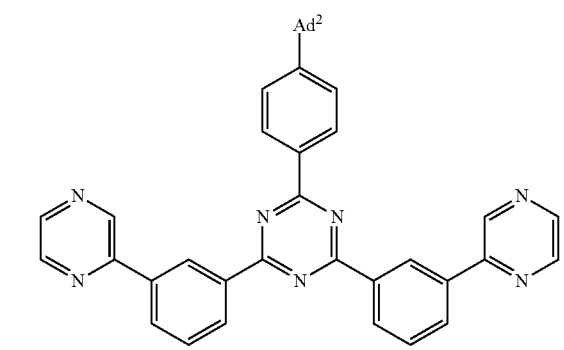
(A-345)
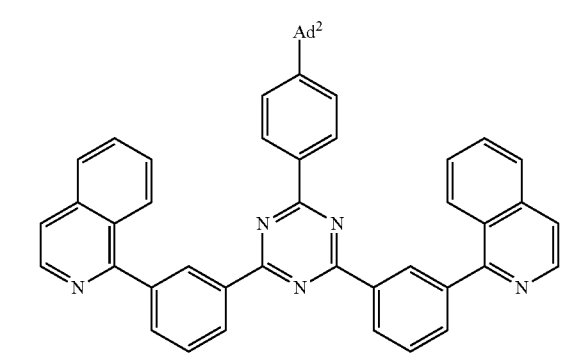

(A-346)
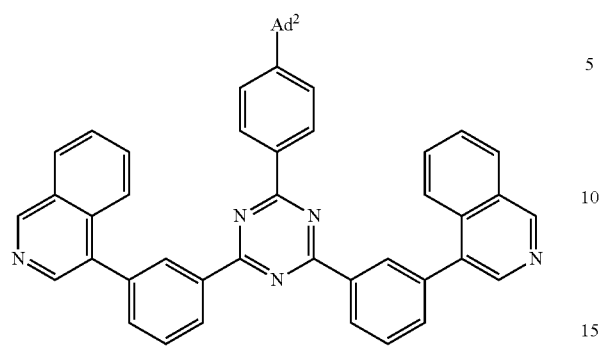
(A-347)
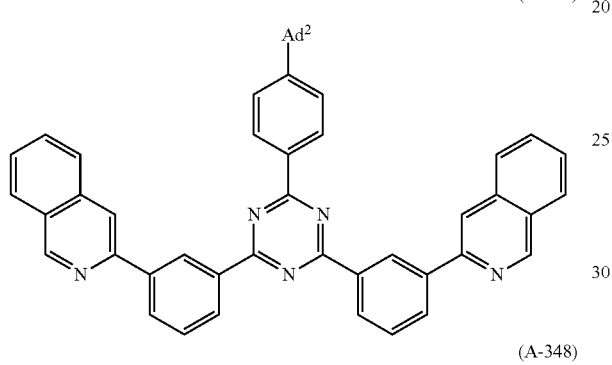
(A-348)
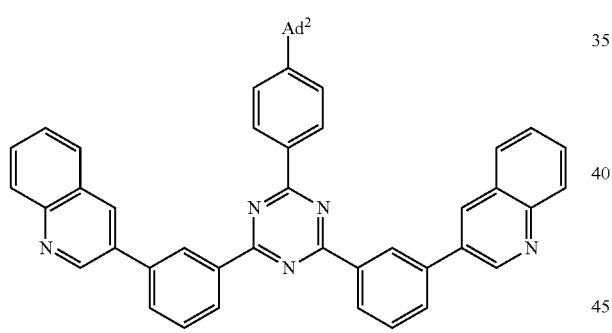
(A-349)
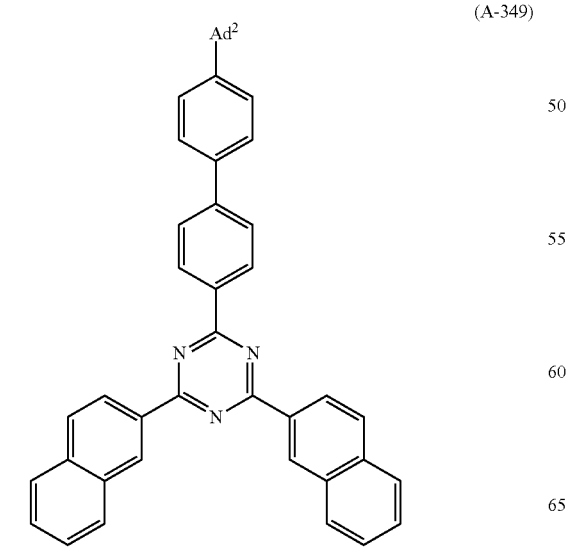
(A-350)
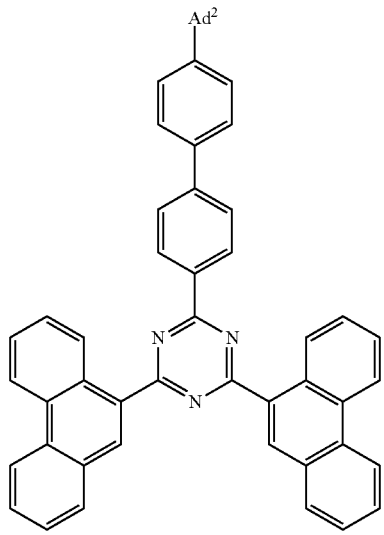
(A-351)
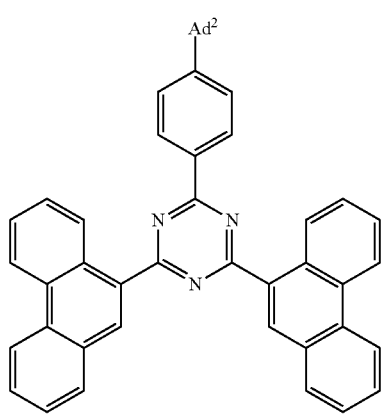
(A-352)

(A-353)
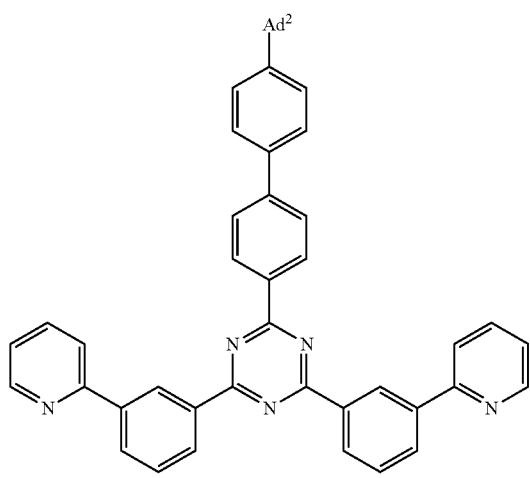
(A-356)
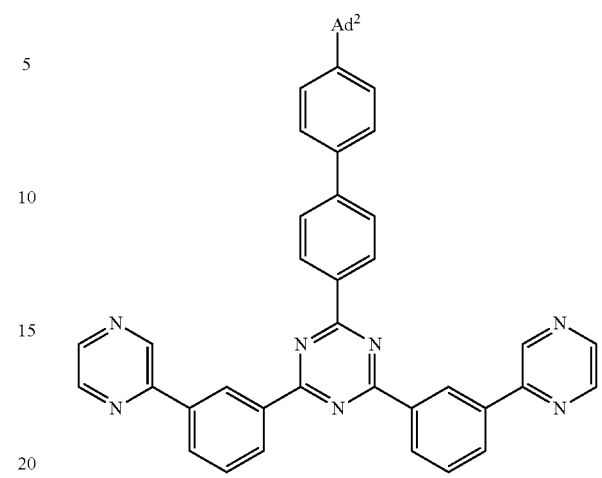
(A-354)
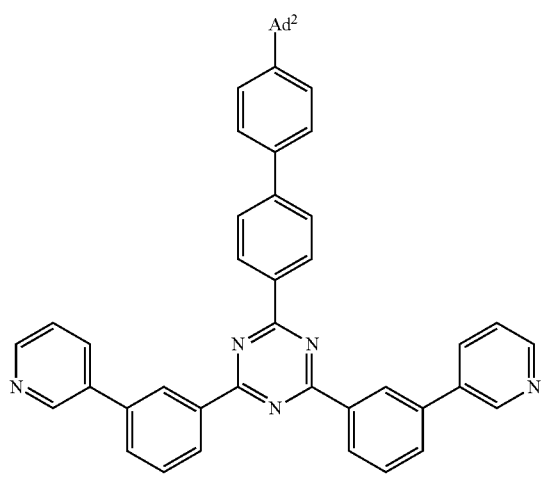
(A-357)
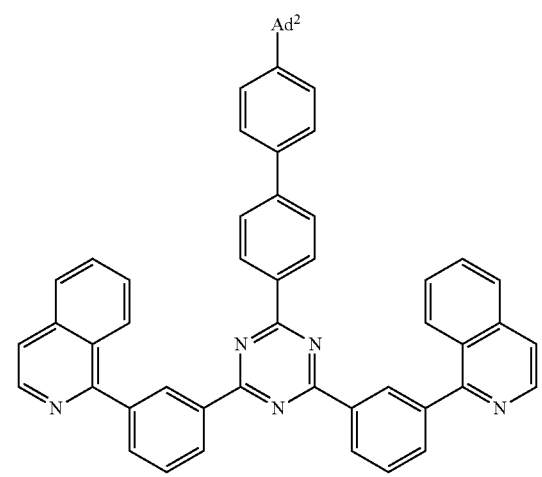
(A-355)
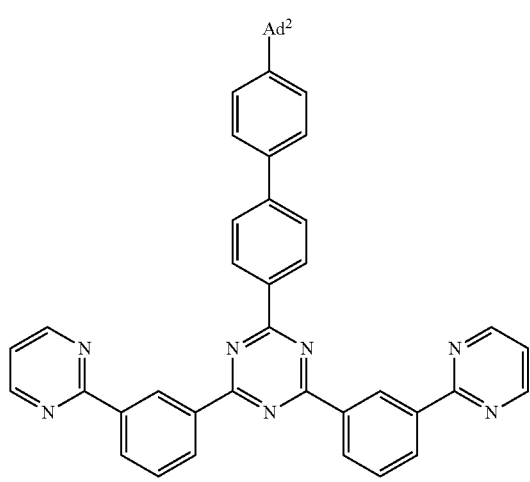
(A-358)
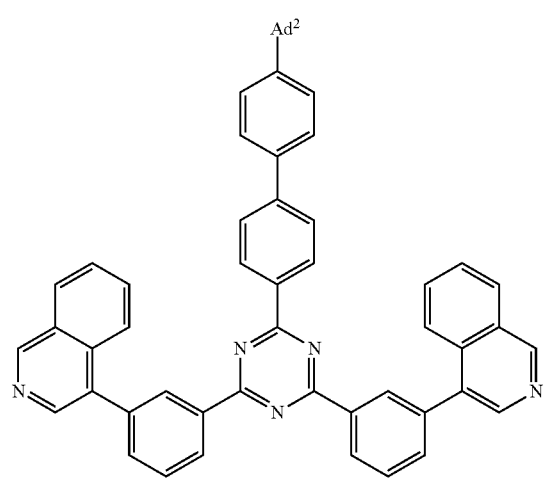

(A-359)
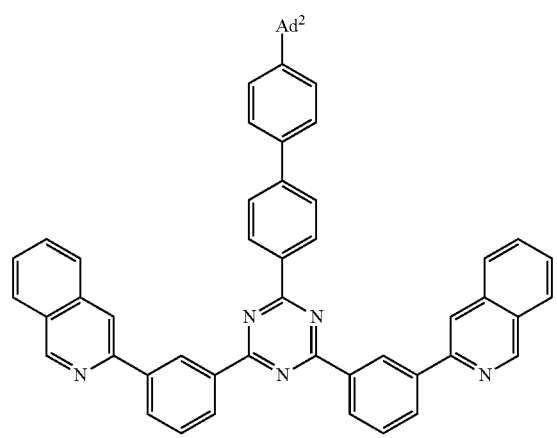
(A-362)
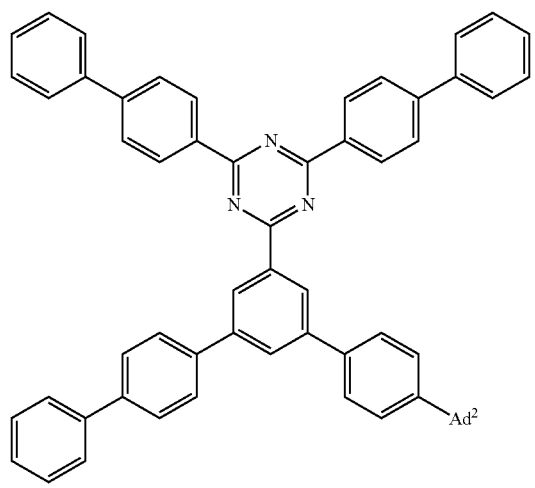
(A-360)
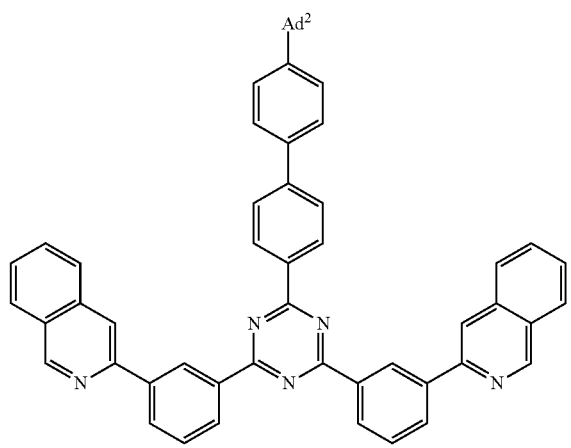
(A-363)
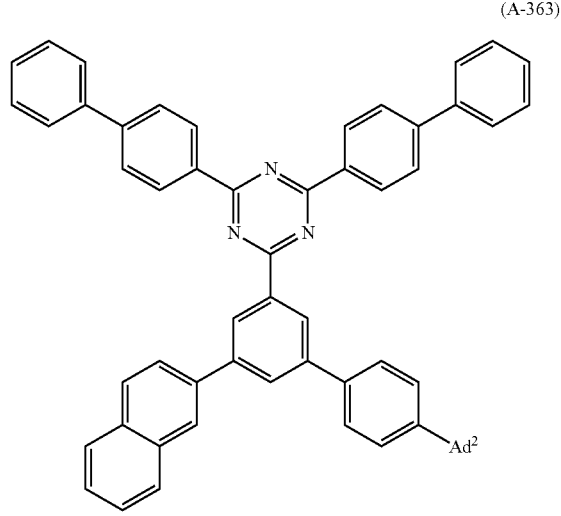
(A-361)
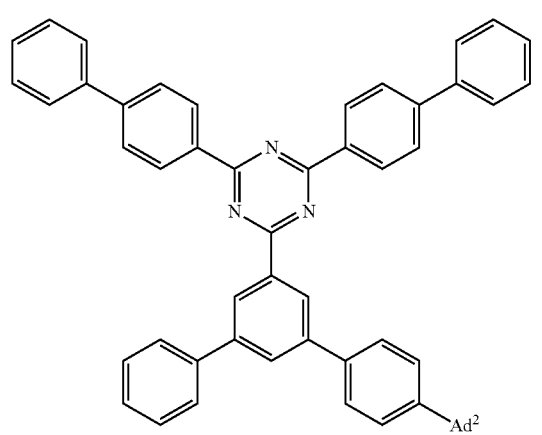
(A-364)
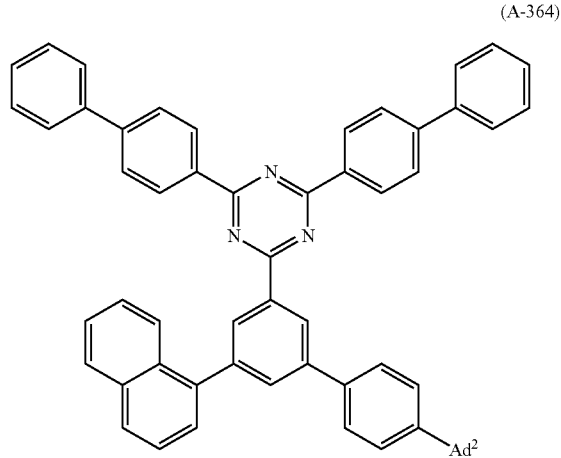

(A-365)
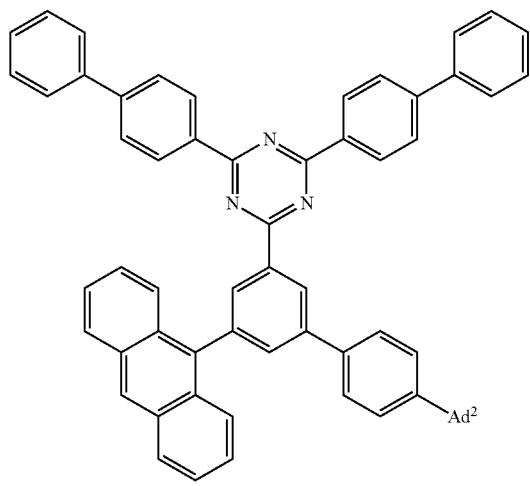
(A-366)
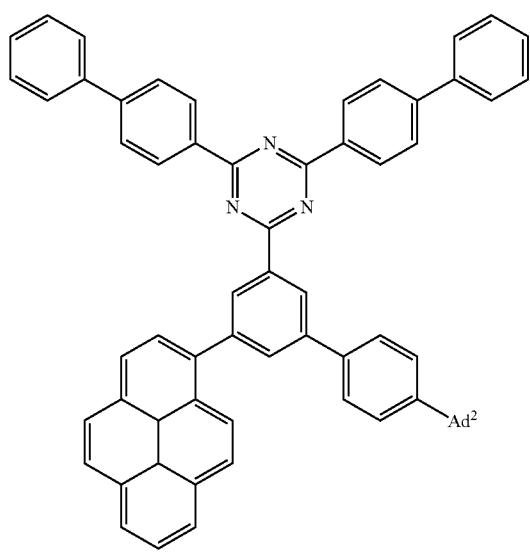
(A-367)
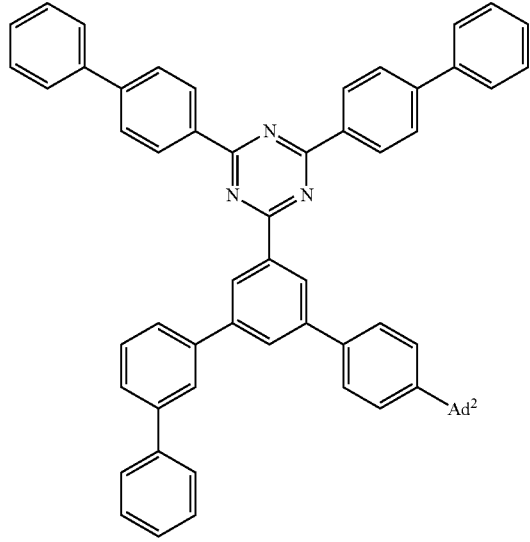
(A-368)
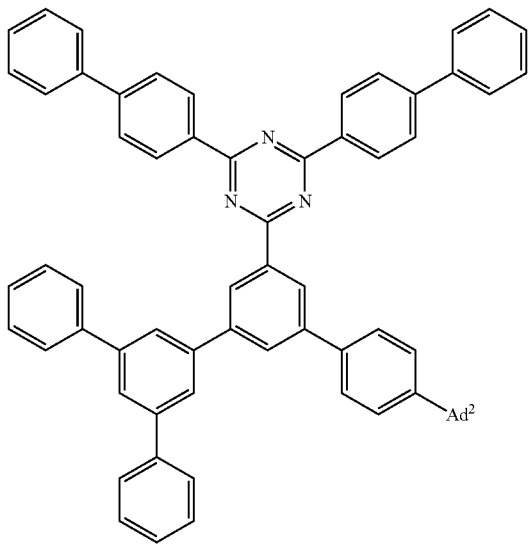
(A-369)
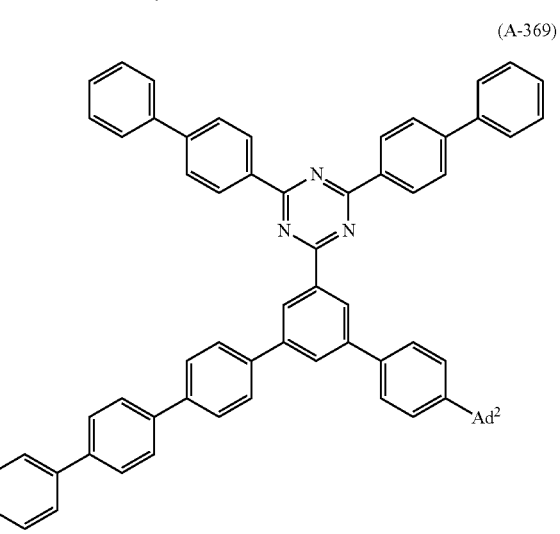
(A-370)
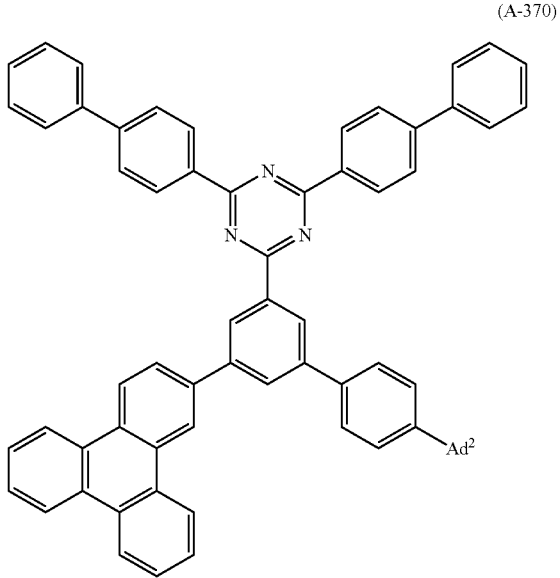

(A-371)
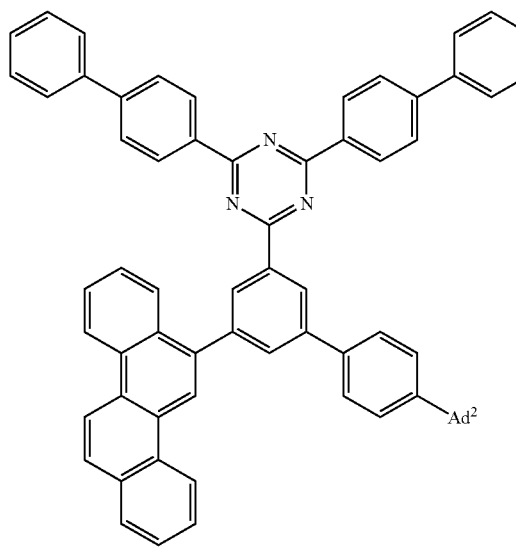
(A-372)
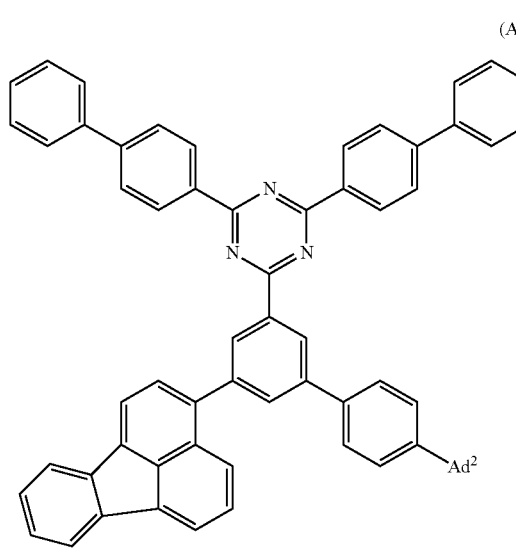
(A-373)
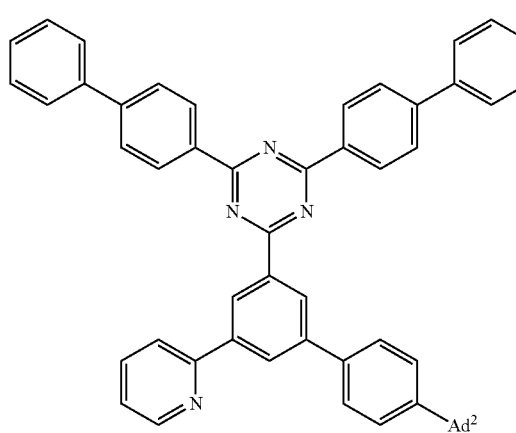
(A-374)
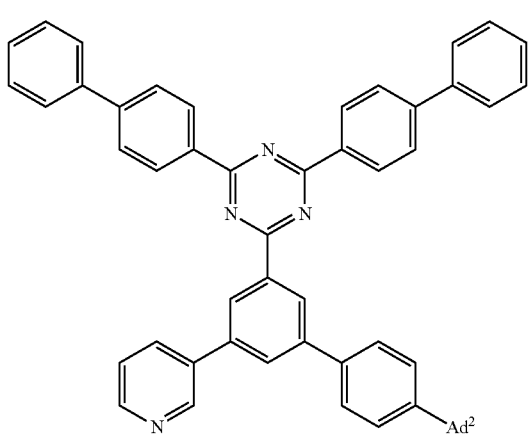
(A-375)
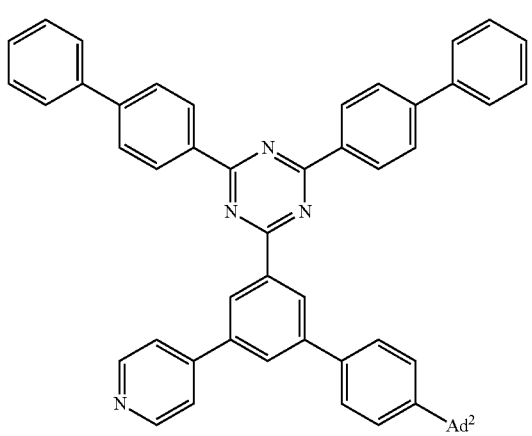
(A-376)
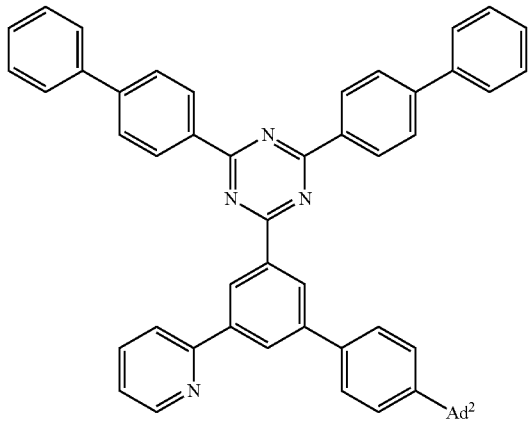

(A-377)
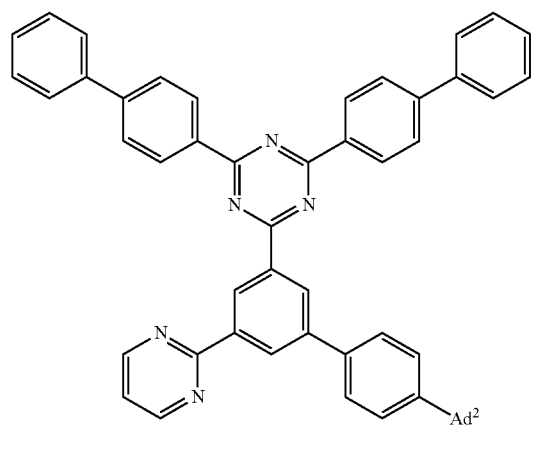
(A-378)
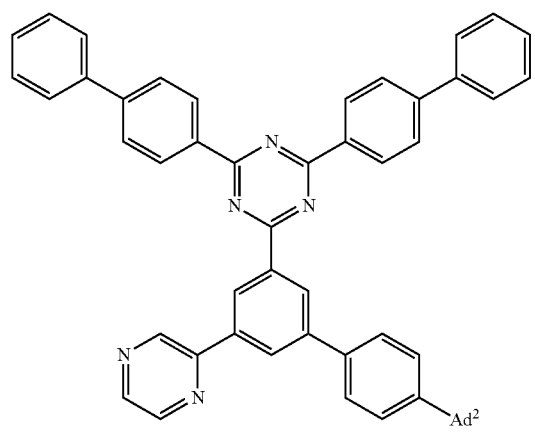
(A-379)
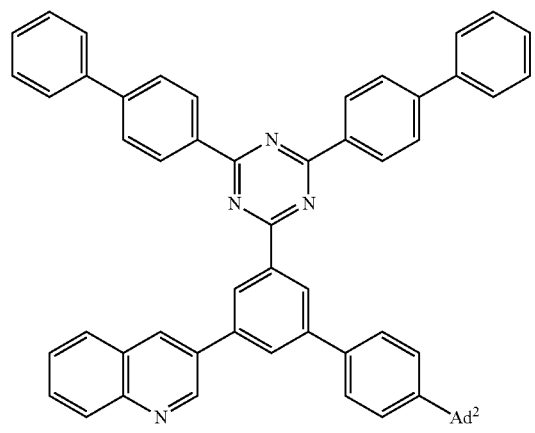
(A-380)
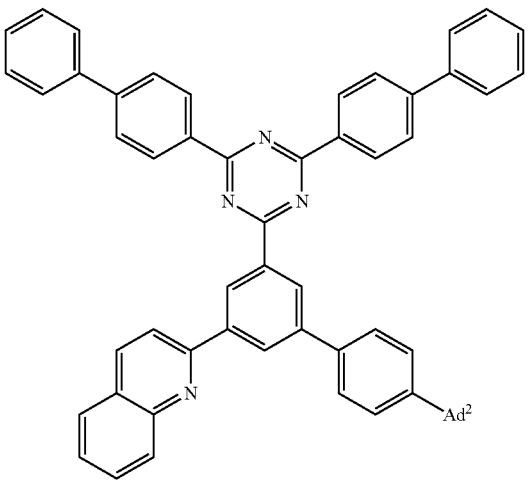
(A-381)
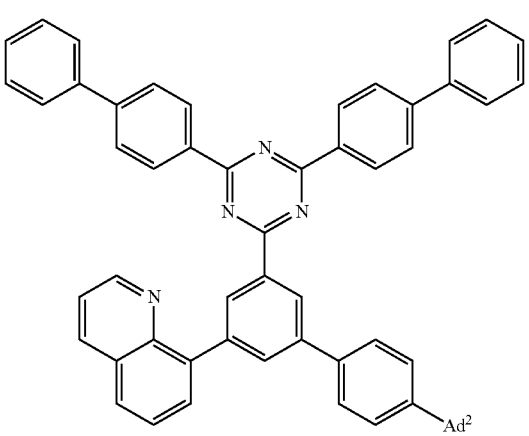
(A-382)
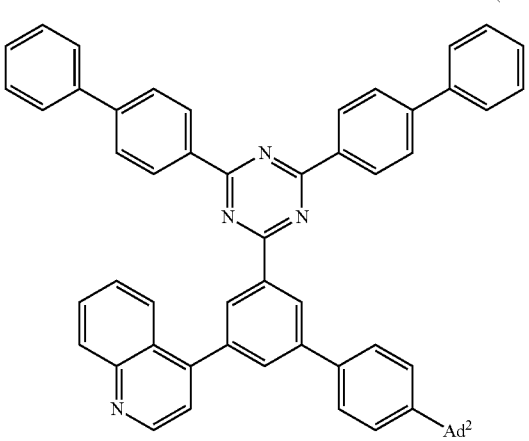

(A-383)
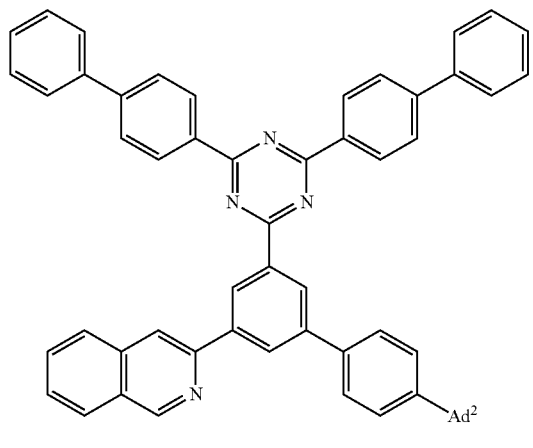
(A-384)
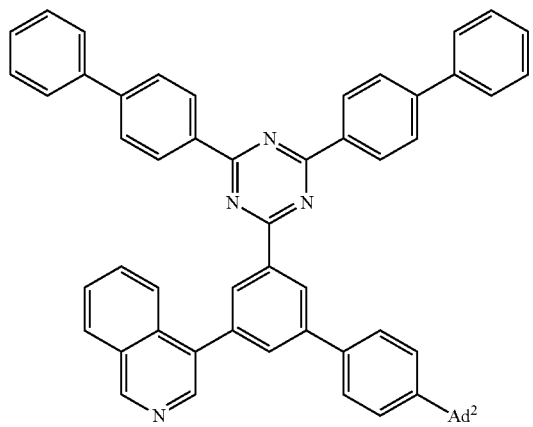
(A-385)
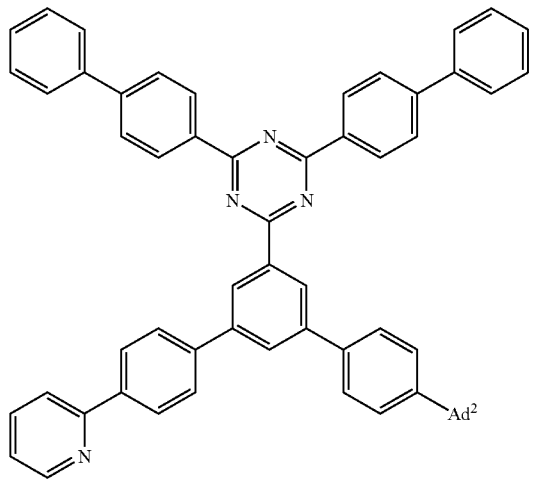
(A-386)
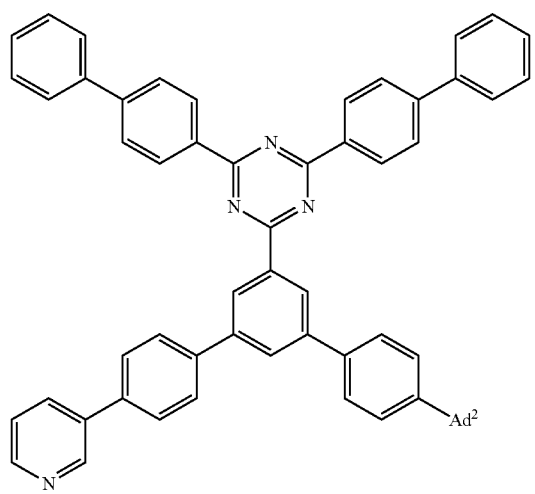
(A-387)
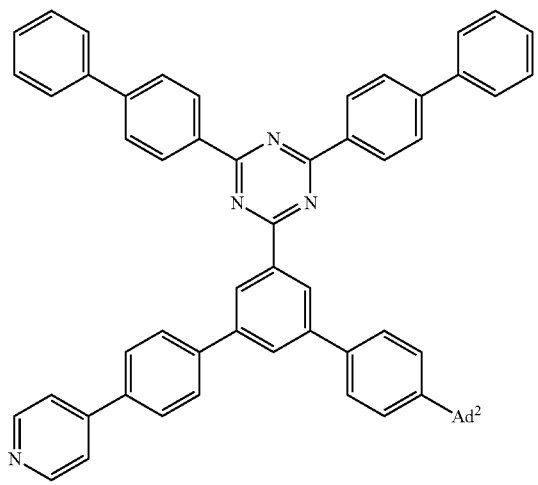
(A-388)
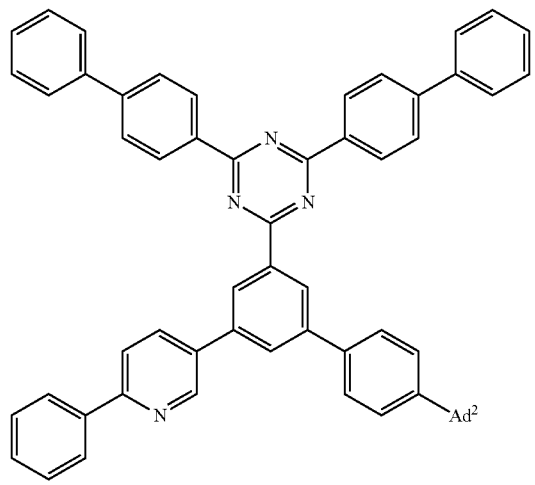

-continued
(A-389)
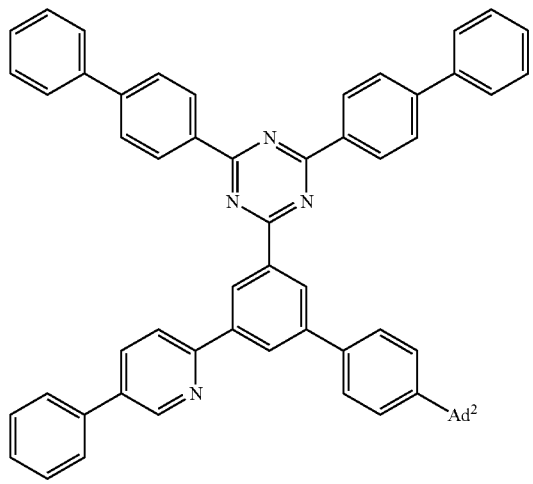
(A-390)
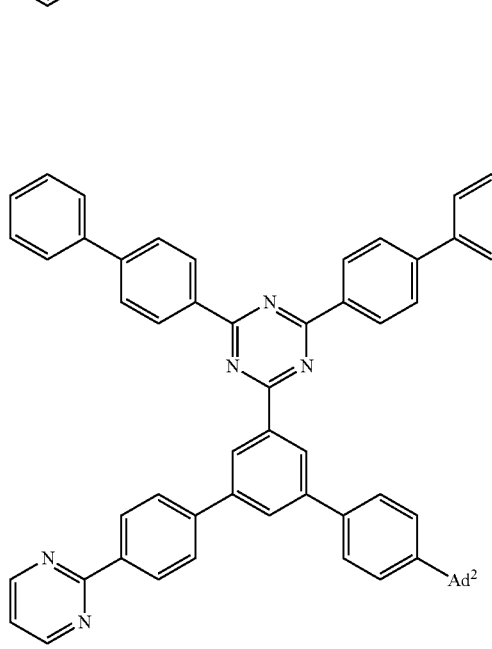
(A-391)
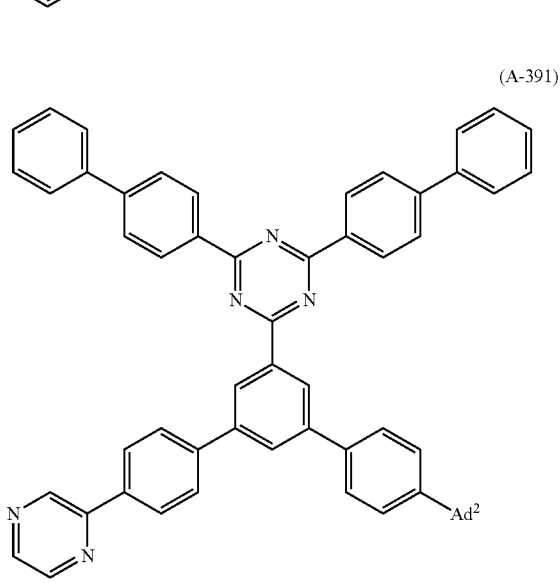
-continued
(A-392)
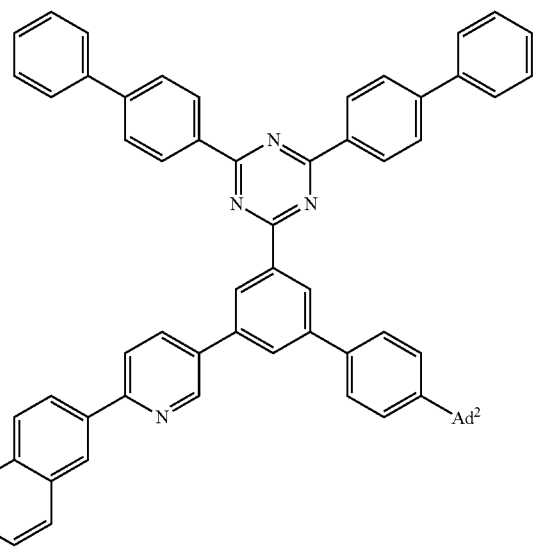
(A-393)
(A-394)

(A-395)
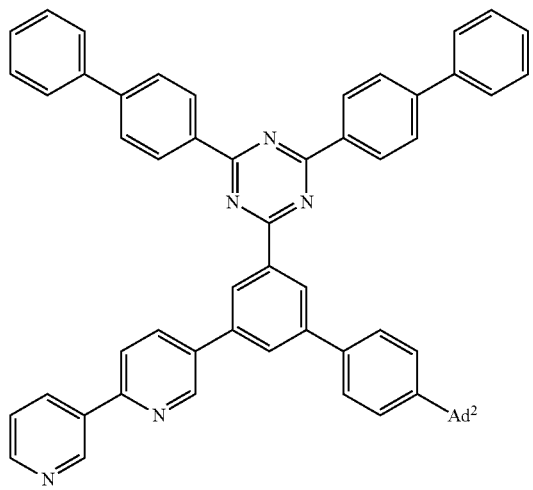
(A-396)
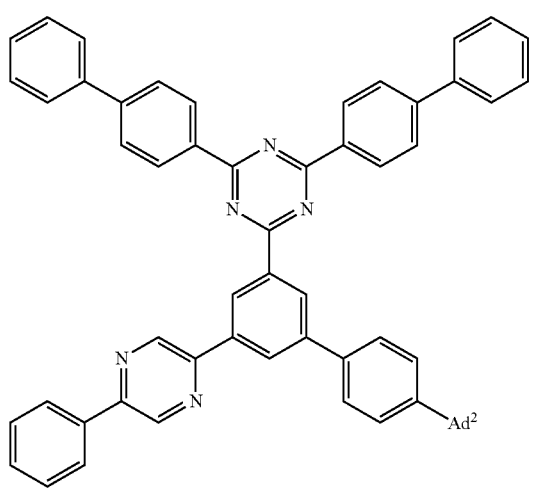
(A-397)
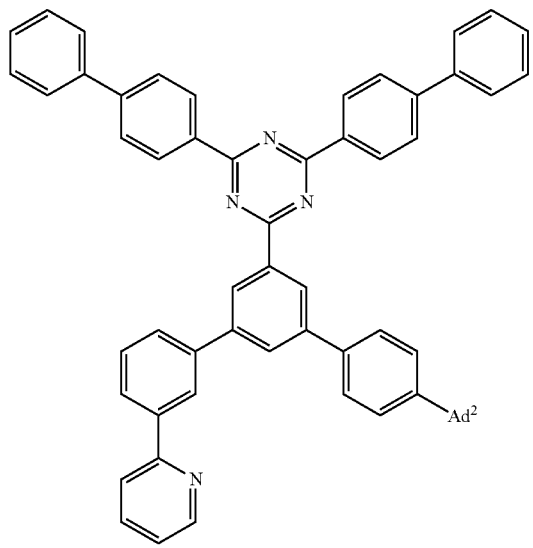
(A-398)
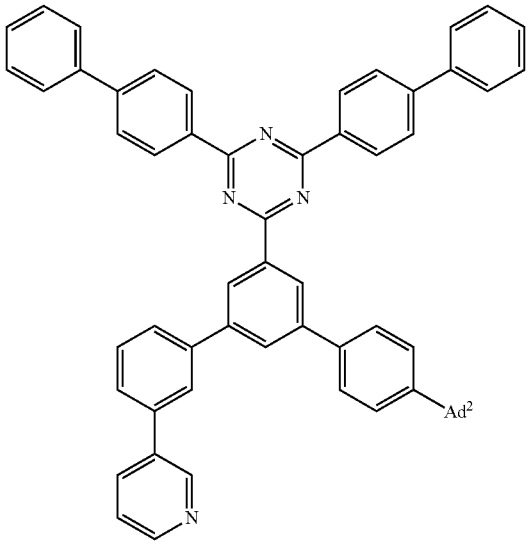
(A-399)
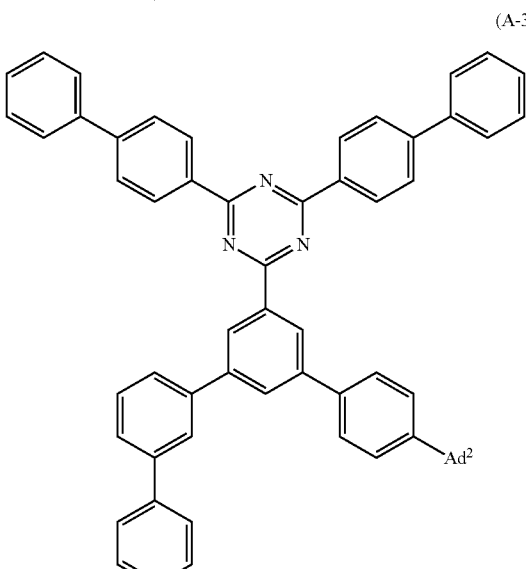
(A-400)
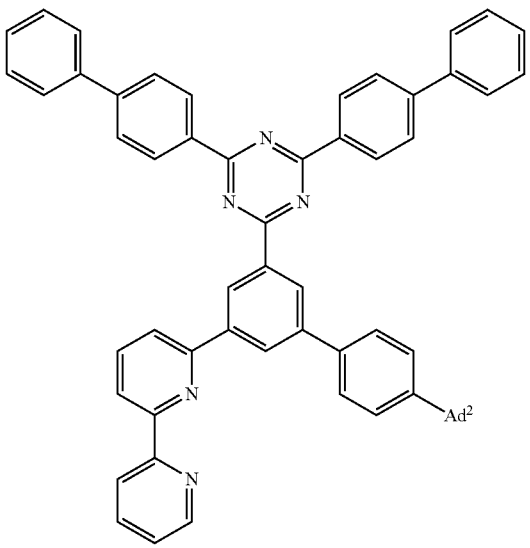

-continued
(A-401)
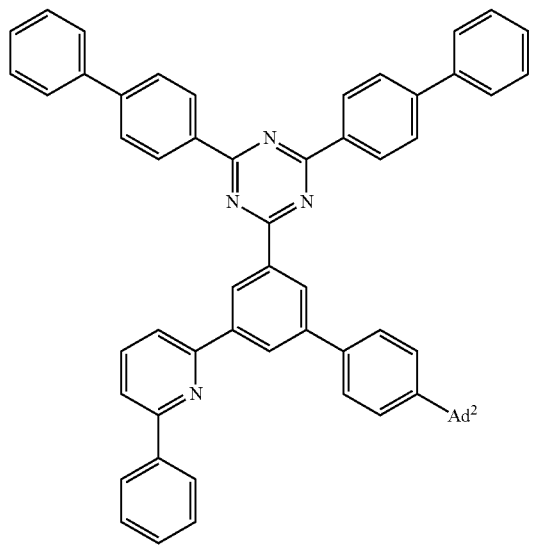
(A-402)
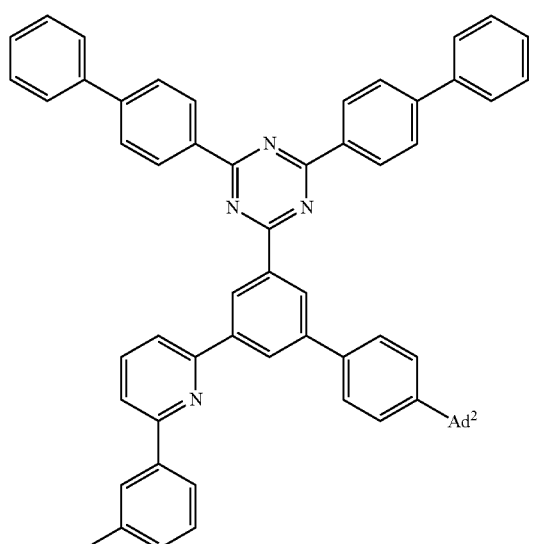
(A-403)
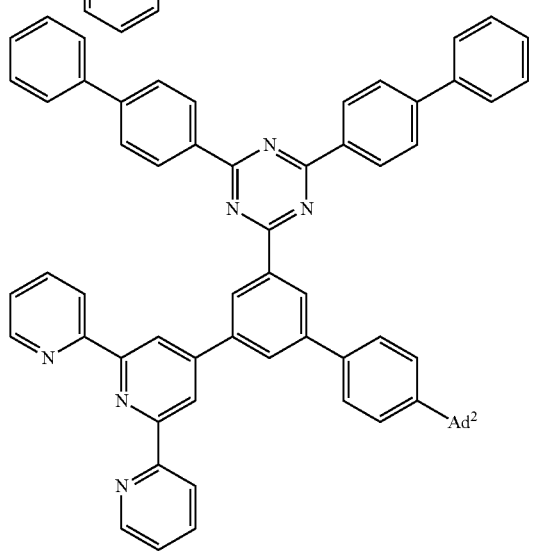
-continued
(A-404)
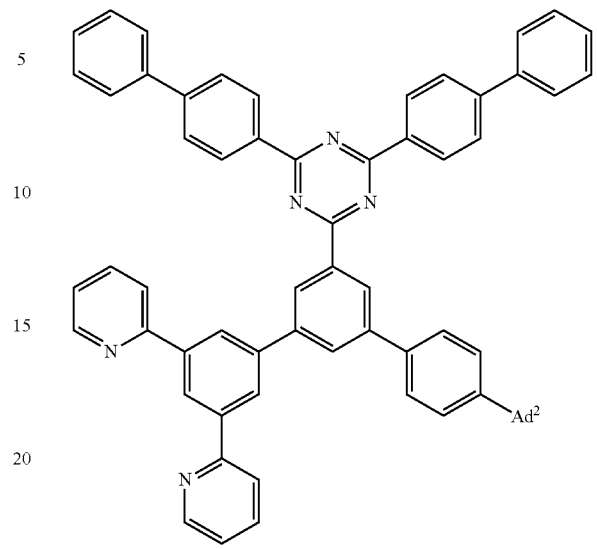
(A-405)
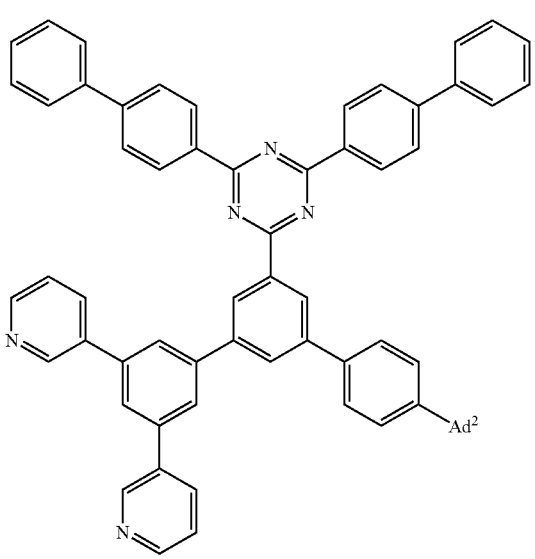
(A-406)
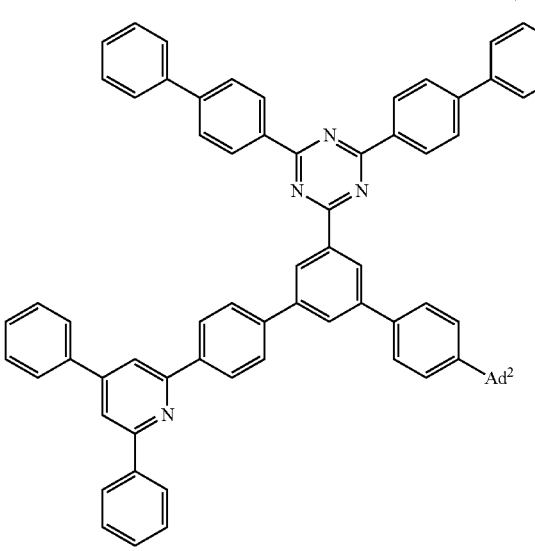

(A-407)
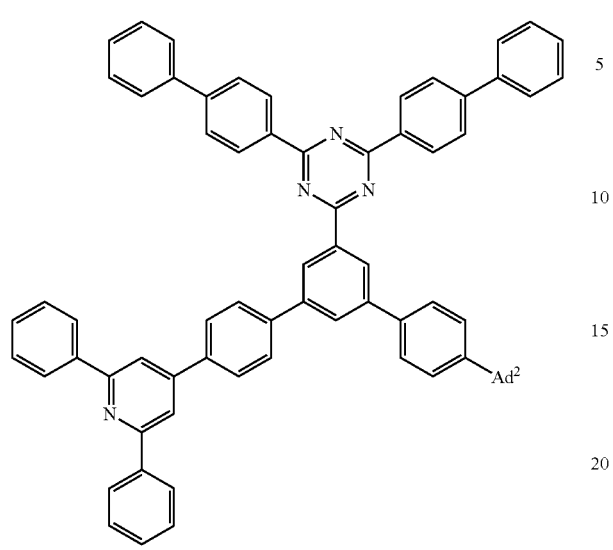
(A-408)
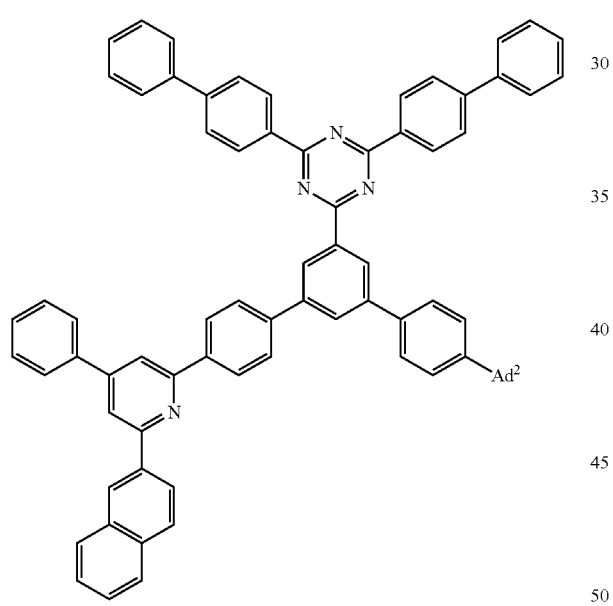
(A-409)
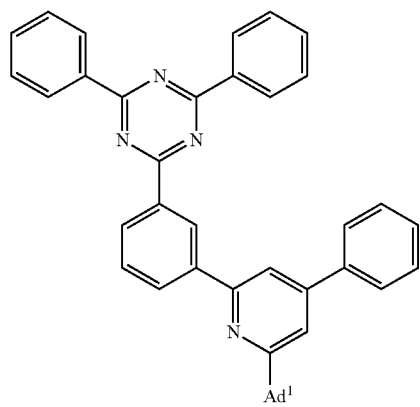
(A-410)
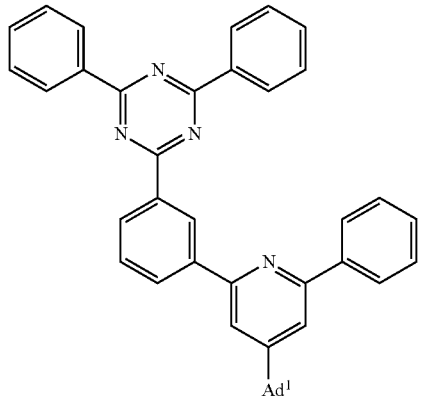
(A-411)
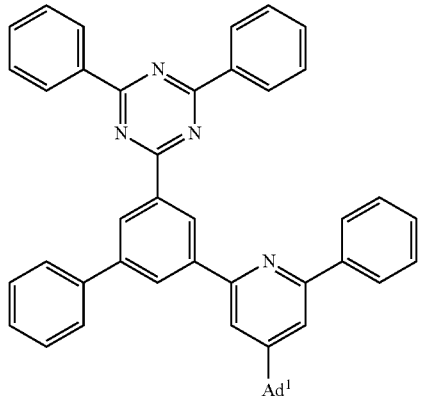
(A-412)
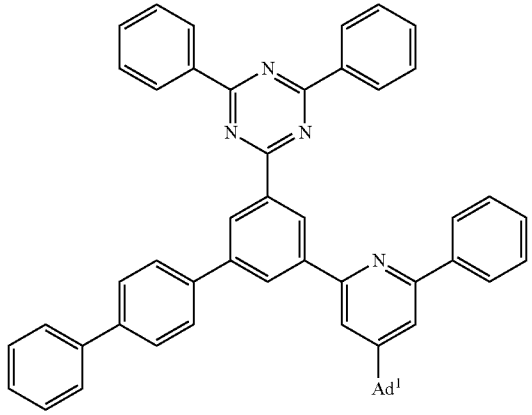

(A-413) 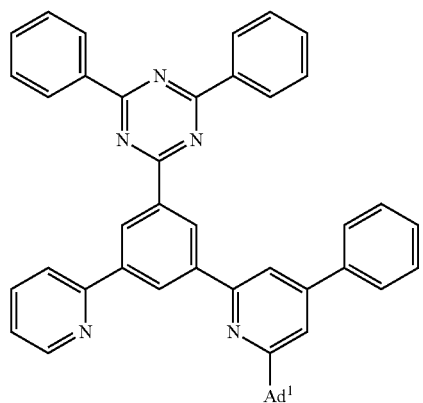
(A-414) 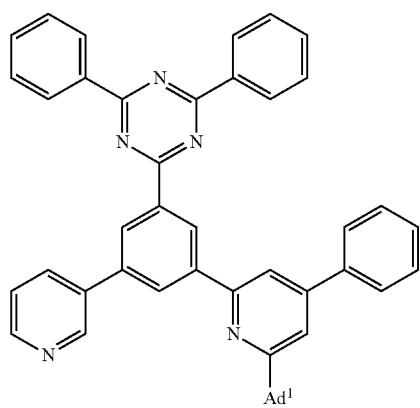
(A-415) 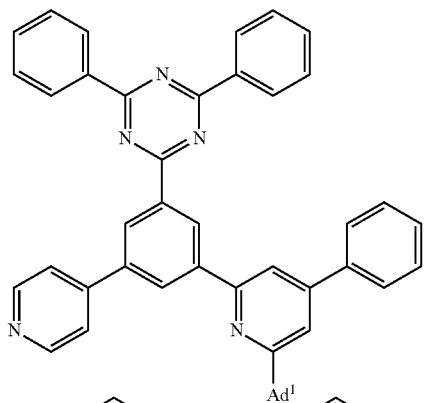
(A-416) 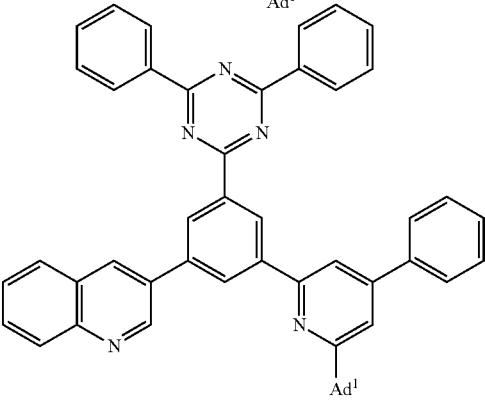
(A-417) 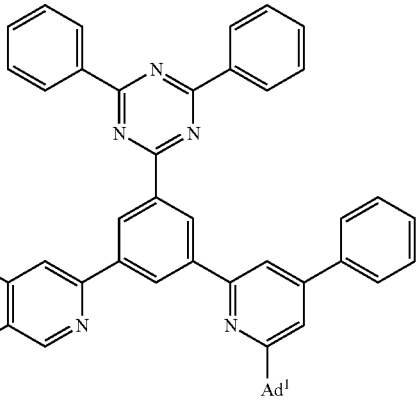
(A-418) 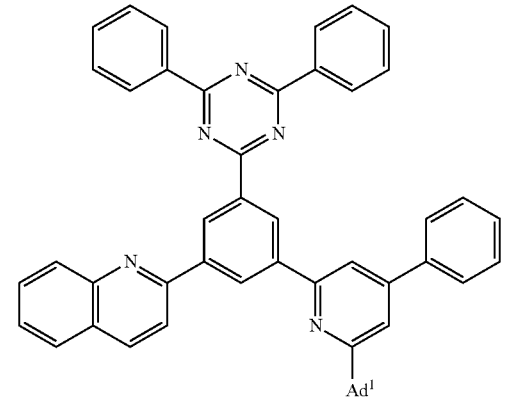
(A-419) 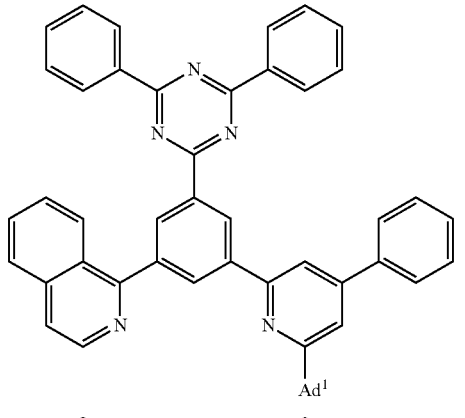
(A-420) 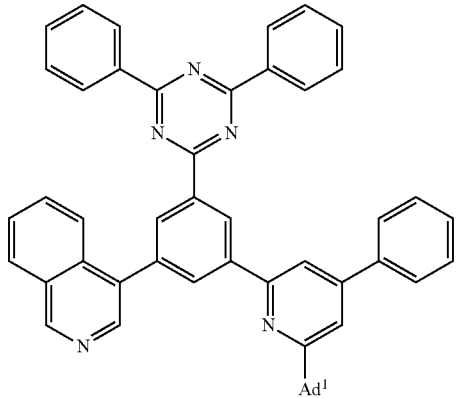

(A-421) 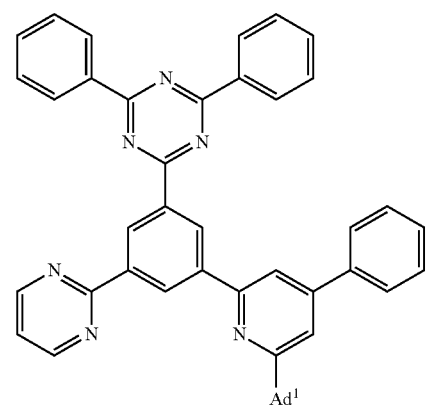
(A-422) 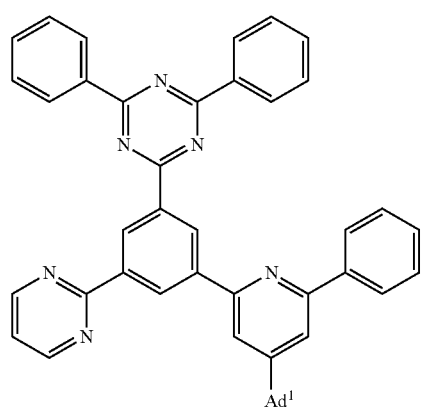
(A-423) 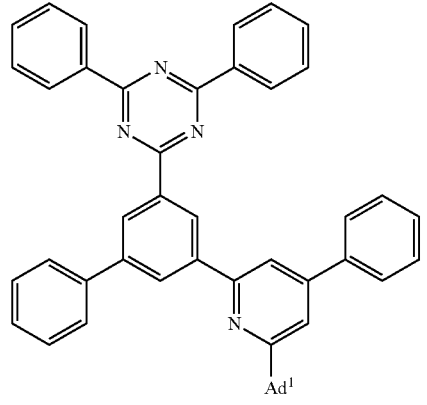
(A-424) 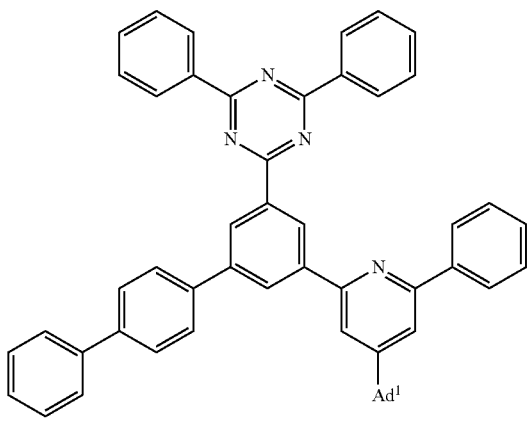
(A-425) 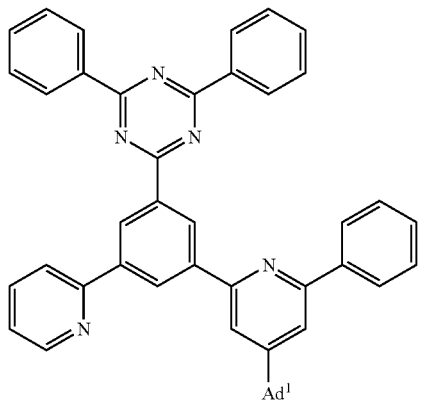
(A-426) 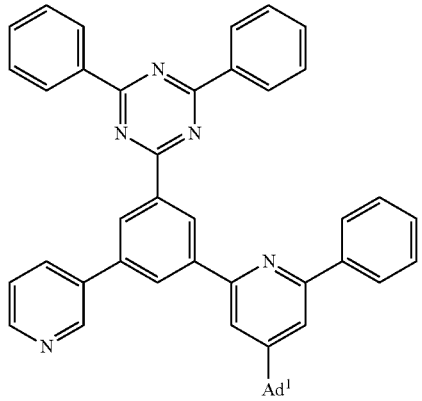
(A-427) 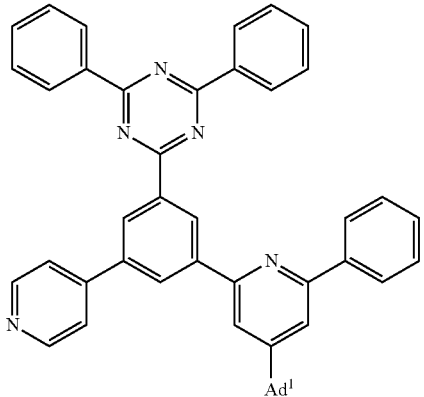
(A-428) 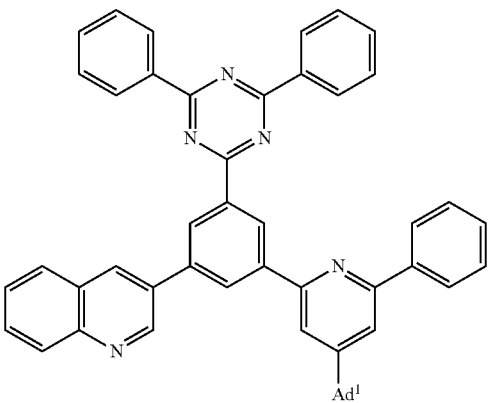

(A-429)
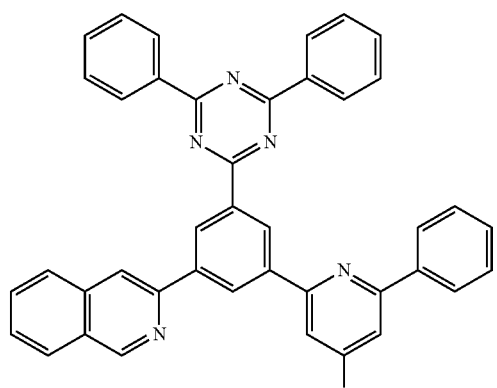
(A-430)
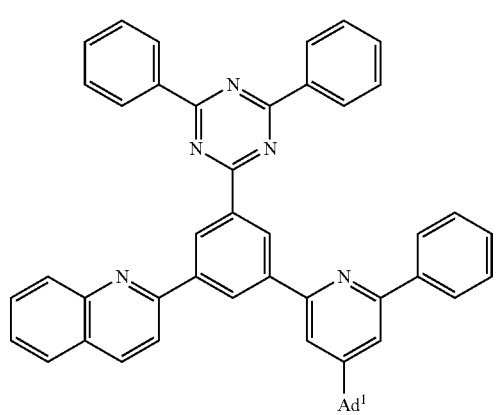
(A-431)
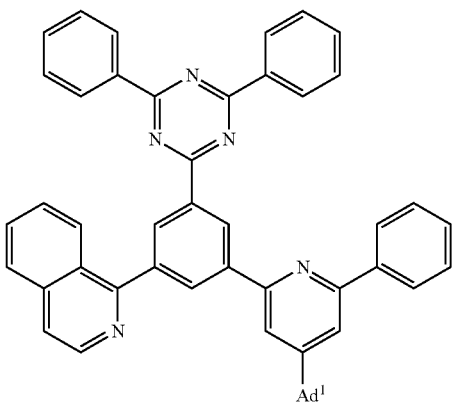
(A-432)
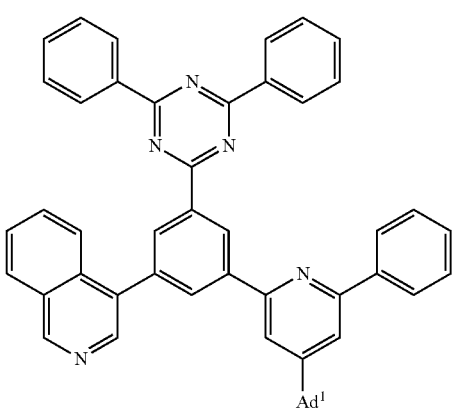
(A-433)
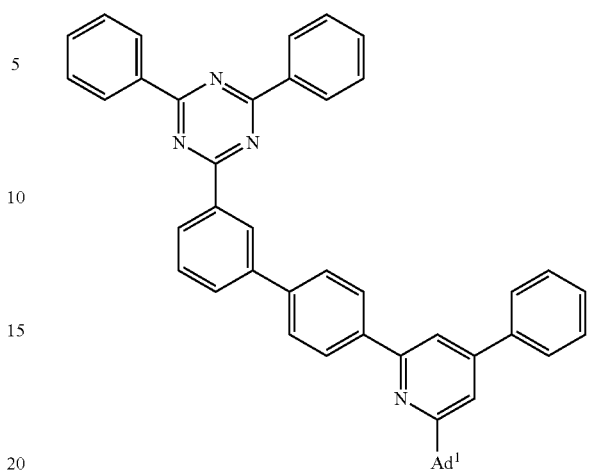
(A-434)
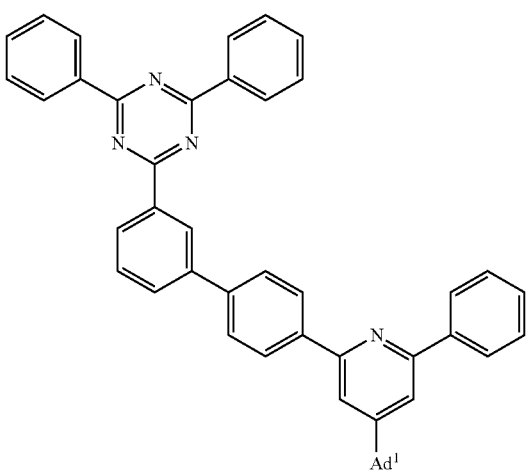
(A-435)
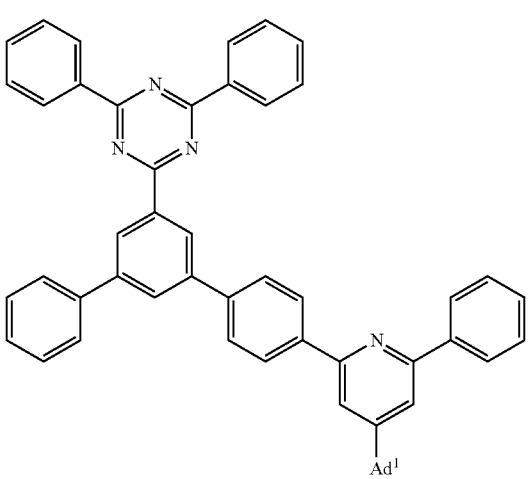

(A-436)
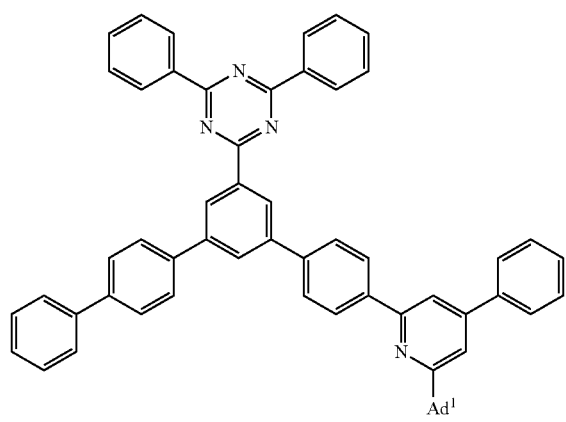
(A-439)
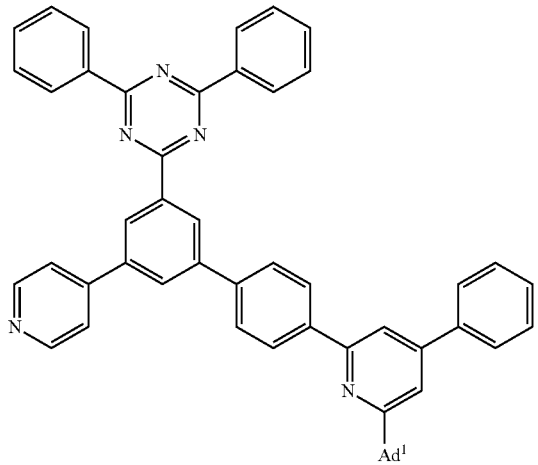
(A-437)
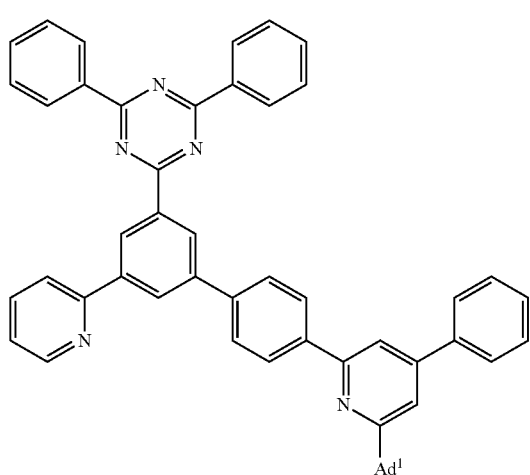
(A-440)
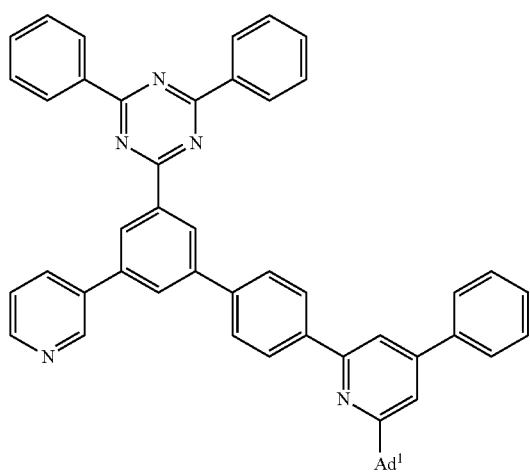
(A-438)
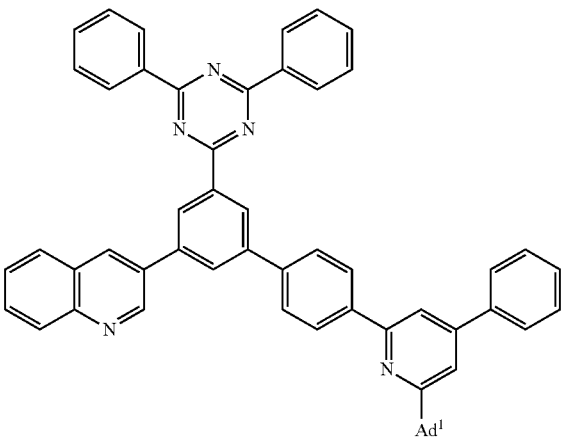
(A-441)

(A-442)
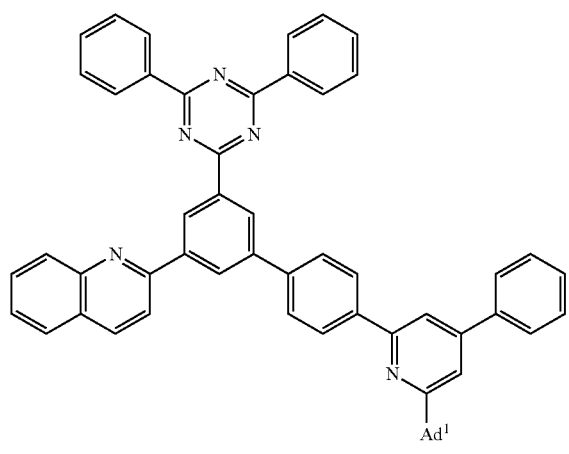
(A-443)
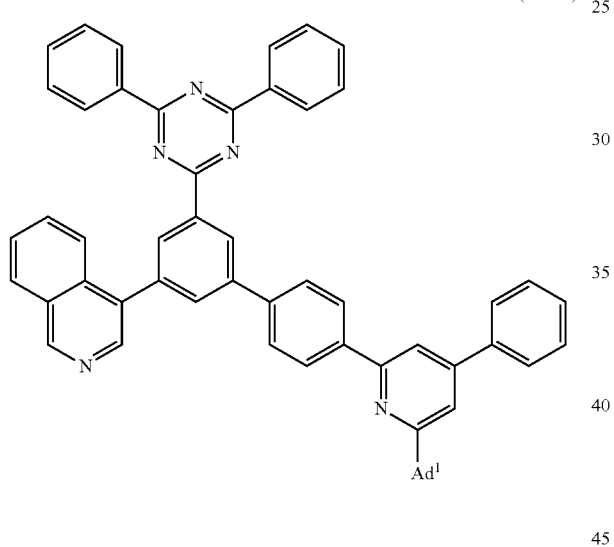
(A-444)
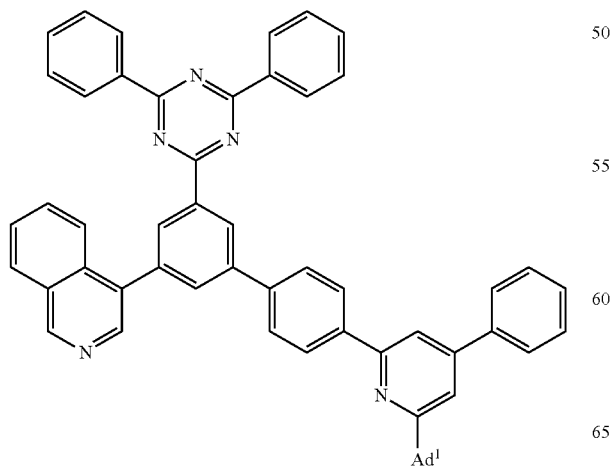
(A-445)
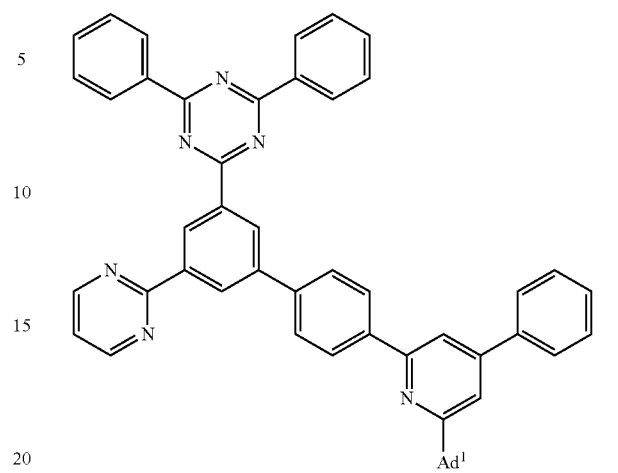
(A-446)
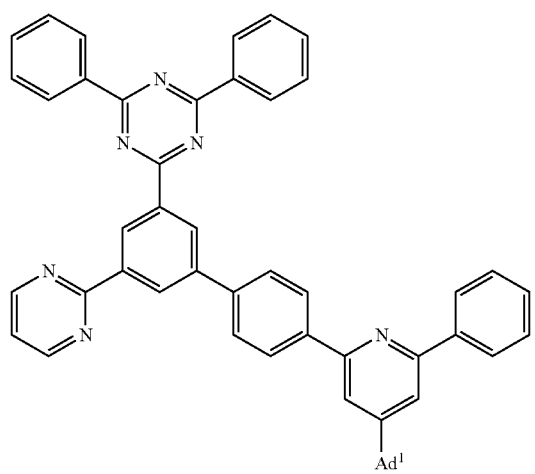
(A-447)
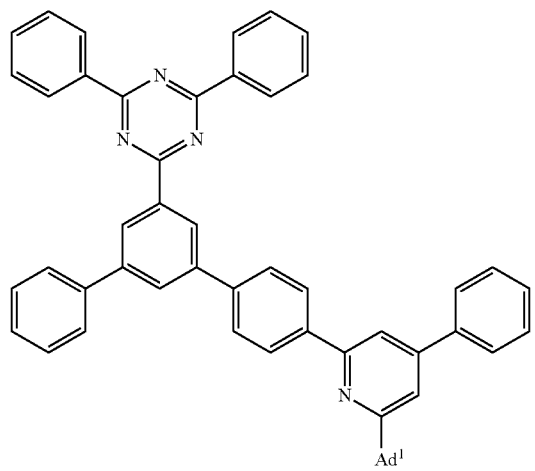

(A-448)
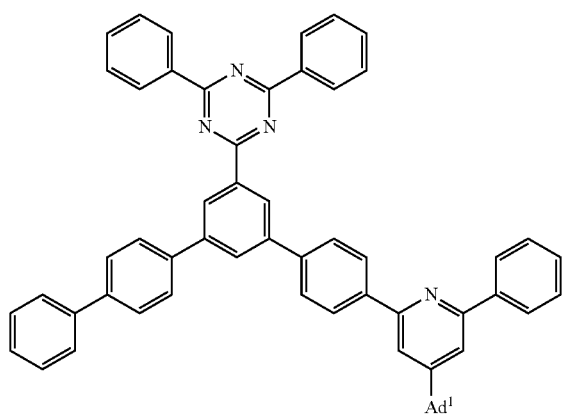
(A-451)
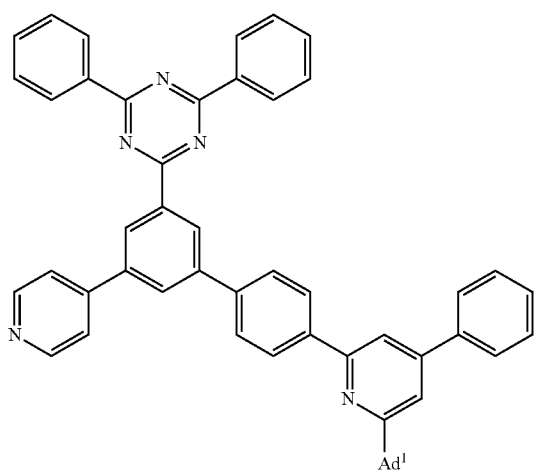
(A-449)
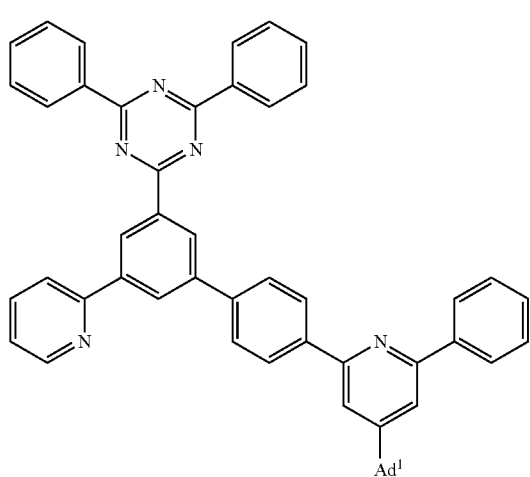
(A-452)
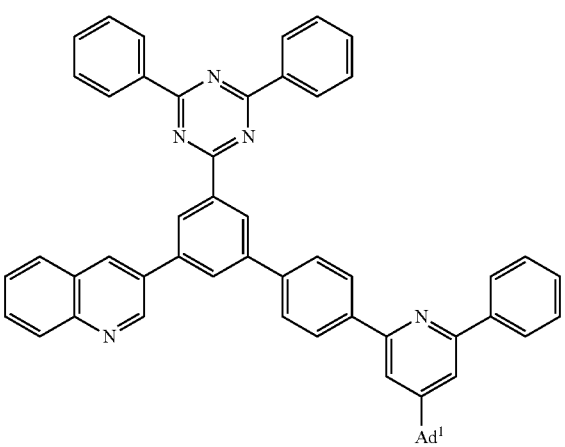
(A-450)
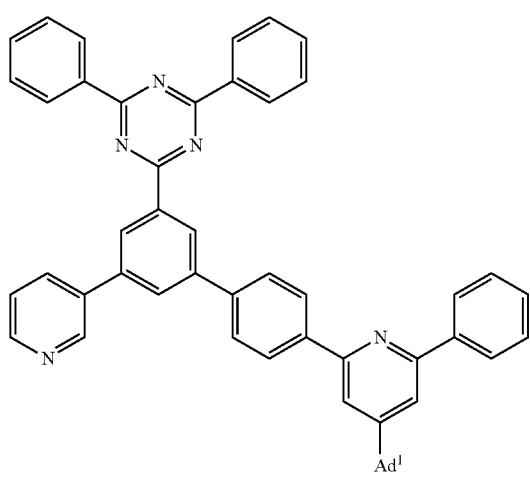
(A-453)
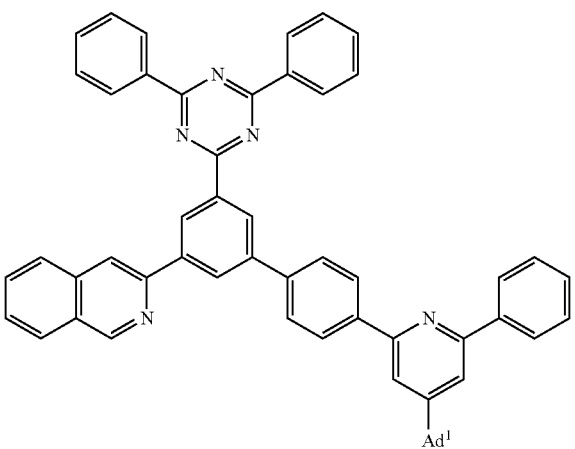

-continued (A-454)

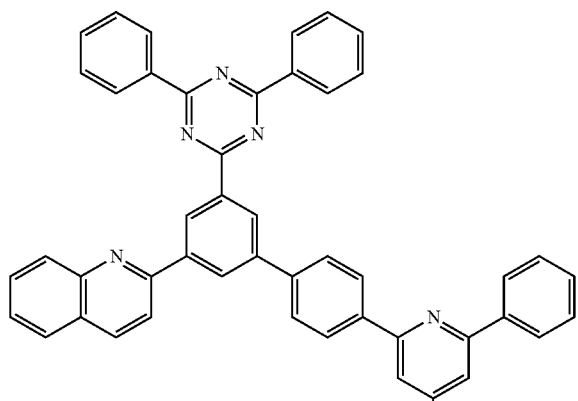

(A-455)

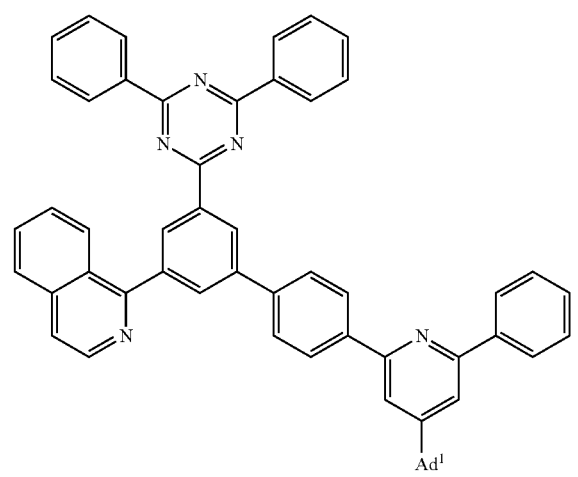

(A-456)

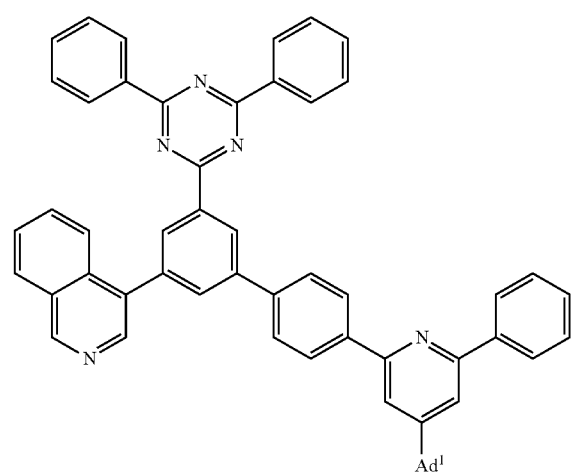

Now, the methods for producing cyclic azine compounds (1) of the present invention will be described.

The cyclic azine compounds (1) of the present invention can be prepared by the methods shown by the following reaction formulae (1) to (4), in the presence or absence of a base and in the presence of a palladium catalyst.

Reaction Formula (1);

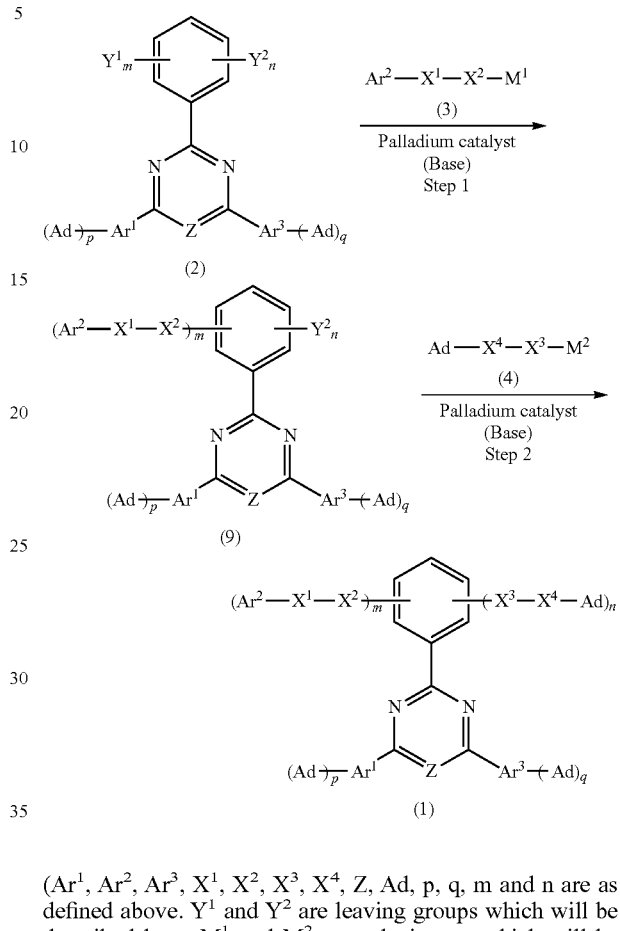

($Ar^1$, $Ar^2$, $Ar^3$, $X^1$, $X^2$, $X^3$, $X^4$, Z, Ad, p, q, m and n are as defined above. $Y^1$ and $Y^2$ are leaving groups which will be described later. $M^1$ and $M^2$ are substituents which will be described later.)

Reaction Formula (2);

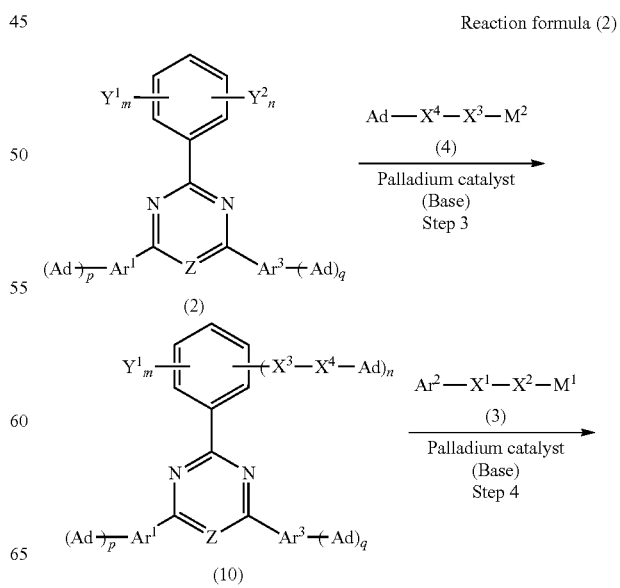

-continued

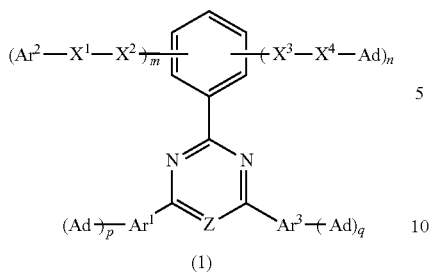

(1)

($Ar^1$, $Ar^2$, $Ar^3$, $X^1$, $X^2$, $X^3$, $X^4$, Z, Ad, p, q, m and n are as defined above. $Y^1$ and $Y^2$ are leaving groups which will be described later. $M^1$ and $M^2$ are substituents which will be described later.)

Reaction Formula (3);

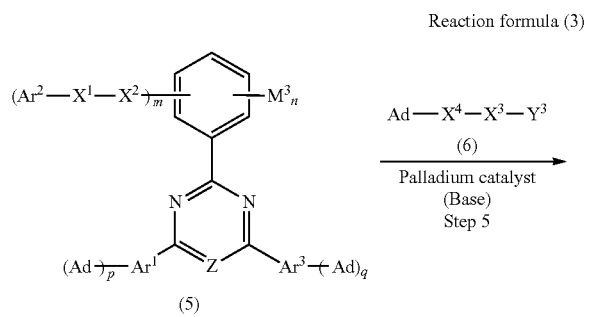

Reaction formula (3)

($Ar^1$, $Ar^2$, $Ar^3$, $X^1$, $X^2$, $X^3$, $X^4$, Z, Ad, p, q, m and n are as defined above. $Y^3$ is a leaving group which will be described later. $M^3$ is a substituent which will be described later.)

Reaction Formula (4):

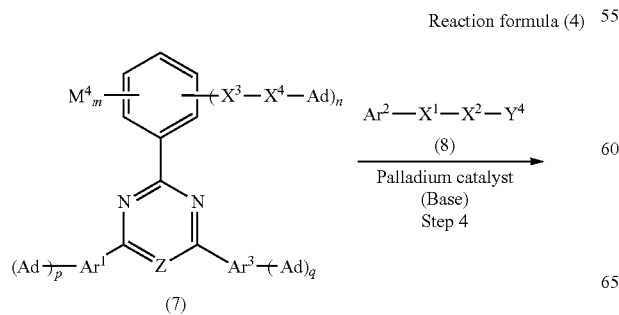

Reaction formula (4)

($Ar^1$, $Ar^2$, $Ar^3$, $X^1$, $X^2$, $X^3$, $X^4$, Z, Ad, p, q, m and n are as defined above. $Y^4$ is a leaving group which will be described later. $M^4$ is a substituent which will be described later.)

In the following, the compound represented by the formula (2) will be referred to as the compound (2). The same applies to the compounds (3) to (10).

The compound (3) to be used in the reaction formula (1) or reaction formula (2) can be prepared using the method disclosed in, for example, JP-A-2008-280330 (paragraphs [0061] to [0076]), or JP-A-2001-335516 (paragraphs [0047] to [0082]). As the compound (3), the following (B-1) to (B-22) may be exemplified, but the present invention is not limited thereto.

(B-1)

(B-2)

(B-3)

(B-4)

(B-5)

(B-6)

(B-7)

(B-8)

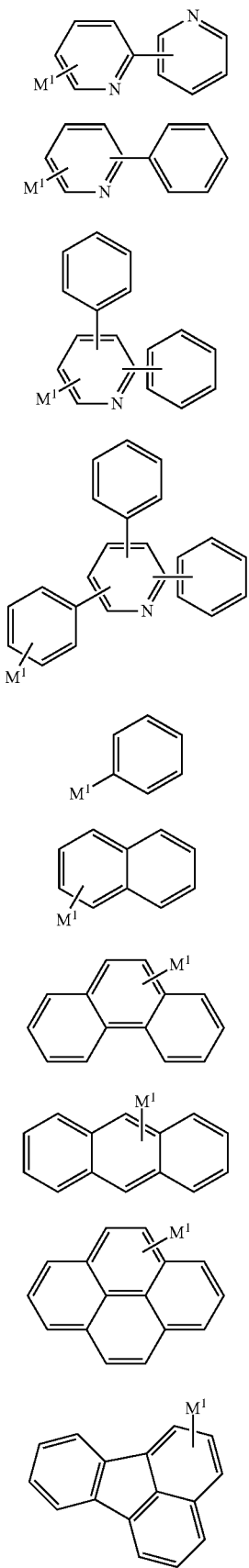

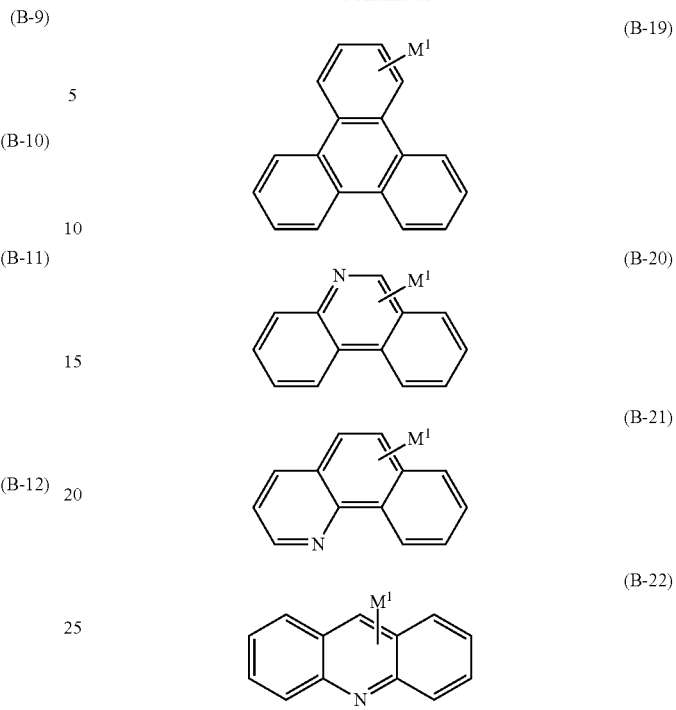

As ZnR¹ and MgR² represented by M¹ in the above (B-1) to (B-22), ZnCl, ZnBr, ZnI, MgCl, MgBr, MgI, etc. may be exemplified. As Sn(R³)₃ represented by M¹, Sn(Me)₃, Sn(Bu)₃, etc. may be exemplified.

$R^1$ and $R^2$ are each independently a chlorine atom, a bromine atom or an iodine atom, and $R^3$ is a $C_{1-4}$ alkyl group or a phenyl group.

As B(OR⁴)₂ represented by M¹, B(OH)₂, B(OMe)₂, B(OⁱPr)₂, B(OBu)₂, etc. may be exemplified. Further, as examples of B(OR⁴)₂ in a case where the two R⁴ together form a ring containing an oxygen atom and a boron atom, groups represented by the following (C-1) to (C-6) may be exemplified, and the group represented by (C-2) is preferred from the viewpoint of good yield.

$R^4$ is a hydrogen atom, a $C_{1-4}$ alkyl group or a phenyl group, and the two $R^4$ in B(OR⁴)₂ may be the same or different. Or, the two $R^4$ may together form a ring containing an oxygen atom and a boron atom.

(C-4) 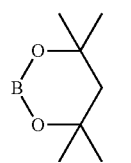

(C-5) 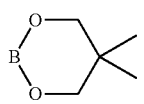

(C-6) 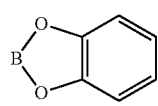

The compound (4) to be used in the reaction formula (1) or reaction formula (2) can be prepared by using the method disclosed in, for example, JP-A-2008-280330 (paragraphs [0061] to [0076]), or JP-A-2001-335516 (paragraphs [0047] to [0082]). As $M^2$ in the compound (4), the same substituents as the above $M^1$ may be exemplified. As the compound (4), the following (D-1) to (D-12) may be exemplified, but the present invention is not limited thereto. Here, Ad in (D-1) to (D-12) represents a 1-adamantyl group or a 2-adamantyl group.

(D-1) Ad—M²

(D-2) 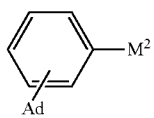

(D-3) 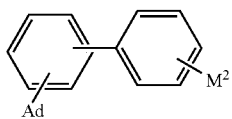

(D-4) 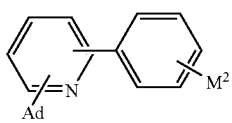

(D-5) 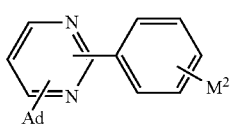

(D-6) 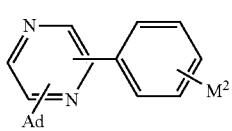

(D-7) 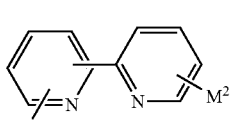

(D-8) 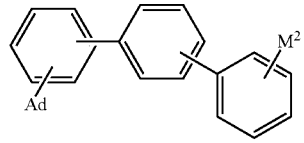

(D-9) 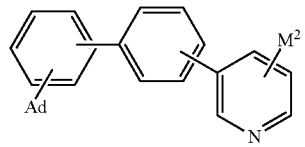

(D-10) 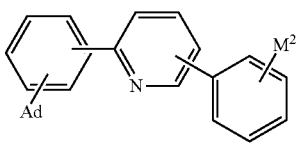

(D-11) 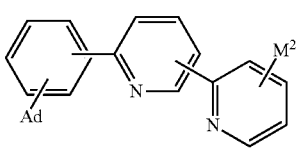

(D-12) 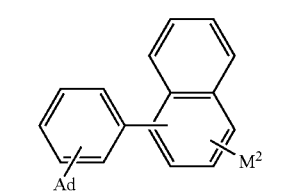

As the compound (6) to be used in the reaction formula (3), a skeleton having $M^2$ in the above compound (4) replaced by $Y^3$ may be exemplified As the compound (8) to be used in the reaction formula (4), a skeleton having $M^1$ in the above compound (3) replaced by $Y^4$ may be exemplified.

$Y^3$ in the compound (6) and $Y^4$ in the compound (8) each independently represents a leaving group and is not particularly limited, but, for example a chlorine atom, a bromine atom, an iodine atom or a triflate may be mentioned. Among them, from the viewpoint of good reaction yield, a bromine atom or a chlorine atom is preferred. However, from the availability of raw materials, it is preferred in some cases to use a triflate.

$Y^1$ and $Y^2$ in the compound (2) each independently represents a leaving group and is not particularly limited, but, for example a chlorine atom, a bromine atom, an iodine atom or a triflate may be mentioned. Among them, from the viewpoint of good reaction yield, a bromine atom or a chlorine atom is preferred. Further, in order to improve the selectivity of the reaction, it is further preferred that $Y^1$ and $Y^2$ represent different leaving groups.

"Step 1" in the reaction formula (1) is a method for obtaining a compound (9) as a synthetic intermediate by reacting the compound (2) with the compound (3) in the presence or absence of a base and in the presence of a palladium catalyst, and it is possible to obtain the desired product in good yield by applying reaction conditions of common coupling reactions, such as the Suzuki-Miyaura reaction, the Negishi reaction, the Tamao-Kumada reaction, the Stille reaction, etc.

As the palladium catalyst which may be used in the "Step 1", a salt such as palladium chloride, palladium acetate, palladium trifluoroacetate, palladium nitrate, etc. may be exemplified. Further, a complex compound such as π-allyl palladium chloride dimer, palladium acetylacetonate, tris (dibenzylideneacetone) dipalladium, dichlorobis (triphenylphosphine) palladium, tetrakis(triphenylphosphine) palladium, dichloro(1,1'-bis (diphenylphosphino)ferrocene) palladium, etc. may be exemplified. Among them, a palladium complex having a tertiary phosphine as a ligand is more preferred from the viewpoint of good reaction yield. From the viewpoint of availability and good reaction yield, a palladium complex having a triphenylphosphine as a ligand is particularly preferred.

The palladium complex having a tertiary phosphine as a ligand may also be prepared in the reaction system by adding a tertiary phosphine to a palladium salt or complex compound. As the tertiary phosphine which may be used in such a case, triphenylphosphine, trimethylphosphine, tributylphosphine, tri(tert-butyl)phosphine, tricyclohexylphosphine, tert-butyldiphenylphosphine, 9,9-dimethyl-4,5-bis (diphenylphosphino)xanthene, 2-(diphenylphosphino)-2'-(N,N-dimethylamino) biphenyl, 2-(di-tert-butylphosphino) biphenyl, 2-(dicyclohexylphosphino) biphenyl, bis(diphenylphosphino)methane, 1,2-bis(diphenylphosphino)ethane, 1,3-bis(diphenylphosphino)propane, 1,4-bis(diphenylphosphino)butane, 1,1'-bis(diphenylphosphino)ferrocene, tri(2-furyl) phosphine, tri(o-tolyl) phosphine, tris(2,5-xylyl) phosphine, (±)-2,2'-bis(diphenylphosphino)-1, 1'-binaphthyl, 2-dicyclohexylphosphino-2',4',6'-triisopropyl biphenyl, etc., may be exemplified. From the viewpoint of availability and good reaction yield, 2-dicyclohexylphosphino-2',4',6'-triisopropyl biphenyl or triphenylphosphine is preferred. The molar ratio of the tertiary phosphine to the palladium salt or complex compound is preferably from 1:10 to 10:1, and from the viewpoint of good reaction yield, from 1:2 to 5:1 is more preferred.

As the base which may be used in the "Step 1", sodium hydroxide, potassium hydroxide, sodium carbonate, potassium carbonate, lithium carbonate, cesium carbonate, potassium phosphate, sodium phosphate, sodium fluoride, potassium fluoride, cesium fluoride, etc. may be exemplified. From the viewpoint of good yield, potassium carbonate is preferred. The molar ratio of the base to the compound (3) is preferably from 1:2 to 10:1, and from the viewpoint of good yield, from 1:1 to 3:1 is more preferred.

The molar ratio of the compound (2) to the compound (3) to be used in the "Step 1" is preferably from 1:2 to 5:1, and from the viewpoint of good yield, from 1:1 to 1:3 is more preferred.

As the solvent which may be used in the "Step 1", water, dimethyl sulfoxide, dimethylformamide, tetrahydrofuran, 1,4-dioxane, dimethoxyethane, toluene, benzene, diethyl ether, ethanol, methanol, xylene, etc. may be exemplified, and these solvents may be used suitably in combination. From the viewpoint of good yield, it is preferred to use a mixed solvent of dioxane or THF and water.

The reaction temperature in the "Step 1" may be chosen appropriately from 0 to 150° C., and from the viewpoint of good yield, it is more preferably chosen from 50 to 100° C.

The compound (9) may be prepared by a usual processing after the end of the "Step 1". At that time, by-products formed by a reaction of both $Y^1$ and $Y^2$ of the compound (2) with the compound (3), will be treated and separated by e.g. recrystallization, column chromatography, sublimation, etc.

Further, the compound (9) may be purified, as the case requires, by recrystallization, column chromatography, sublimation, etc.

"Step 2" is a method for obtaining the cyclic azine compound (1) of the present invention by reacting the compound (9) with a compound (4), in the presence or absence of a base, and it is possible to obtain the desired product in good yield by applying the reaction conditions of common coupling reactions, such as the Suzuki-Miyaura reaction, the Negishi reaction, the Tamao-Kumada reaction, the Stille reaction, etc.

In the "Step 2", it is possible to select the same reaction conditions as mentioned in the "Step 1". However, they need not be the same reaction conditions as in the "Step 1". Further, without isolating the compound (9) as a synthetic intermediate, the compound (4) may be added to the reaction system in the "Step 1" to synthesize a cyclic azine compound (1). After completion of the "Step 2", the obtained cyclic azine compound (1) may be purified, as the case requires, by recrystallization, column chromatography, sublimation, etc.

"Step 3" in the reaction formula (2) is a method for obtaining a compound (10) as a synthetic intermediate, by reacting the compound (2) with a compound (4) in the presence or absence of a base and in the presence of a palladium catalyst, and it is possible to obtain the desired product in good yield by applying the reaction conditions of common coupling reactions, such as the Suzuki-Miyaura reaction, the Negishi reaction, the Tamao-Kumada reaction, the Stille reaction, etc. In the "Step 3", the same reaction conditions as the conditions mentioned in the "Step 1" may be selected for use. However, they need not be the same reaction conditions as in the "Step 1". After completion of the "Step 3", the obtained compound (10) may be purified, as the case requires, by e.g. recrystallization, column chromatography or sublimation.

"Step 4" is a method for obtaining the cyclic azine compound (1) of the present invention by reacting the compound (10) with a compound (3) in the presence or absence of a base and in the presence of a palladium catalyst, and it is possible to obtain the desired product in good yield by applying the reaction conditions of common coupling reactions, such as the Suzuki-Miyaura reaction, the Negishi reaction, the Tamao-Kumada reaction, the Stille reaction, etc.

In the "Step 4", the same reaction conditions as the conditions mentioned in the "Step 1" may be selected for use. However, they need not be the same reaction conditions as in the "Step 1". Further, without isolating the compound (10) as a synthetic intermediate, the compound (3) may be added to the reaction system in the "Step 3" to synthesize a cyclic azine compound (1). After completion of the "Step 4", the obtained cyclic azine compound (1) may be purified, as the case requires, by e.g. recrystallization, column chromatography or sublimation.

The compound (5) to be used in the "Step 5" in the reaction formula (3) may be synthesized from the compound (9) by using a common reaction of synthesizing an organometallic compound (e.g. Angew. Chem. Int. Ed. 2007, 46, 5359-5363).

"Step 5" is a method for obtaining the cyclic azine compound (1) of the present invention by reacting the compound (5) with a compound (6) in the presence or absence of a base and in the presence of a palladium catalyst, and it is possible to obtain the desired product in good yield by applying the reaction conditions of common coupling reactions, such as the Suzuki-Miyaura reaction, the Negishi reaction, the Tamao-Kumada reaction, the Stille reaction, etc.

As the palladium catalyst which may be used in the "Step 5", the same palladium catalyst as mentioned in the "Step 1" may be mentioned. Among them, a palladium complex having a tertiary phosphine as a ligand is more preferred from the viewpoint of good reaction yield. From the viewpoint of availability and good reaction yield, a palladium complex having a triphenylphosphine as a ligand is particularly preferred.

The palladium complex having a tertiary phosphine as a ligand may also be prepared in the reaction system by adding a tertiary phosphine to a palladium salt or complex compound. As the tertiary phosphine which may be used in such a case, the same tertiary phosphine as mentioned in the "Step 1" may be mentioned. From the viewpoint of availability and good reaction yield, 2-dicyclohexylphosphino-2',4',6'-triisopropyl biphenyl or triphenylphosphine is preferred. The molar ratio of the tertiary phosphine to the palladium salt or complex compound is preferably from 1:10 to 10:1, and from the viewpoint of good reaction yield, from 1:2 to 5:1 is more preferred.

As the base which may be used in the "Step 5", the same base as mentioned in the "Step 1" may be mentioned. The molar ratio of the base to the compound (5) is preferably from 1:2 to 10:1, and from the viewpoint of good yield, from 1:1 to 3:1 is more preferred.

The molar ratio of the compound (5) to the compound (6) used in the "Step 5" is preferably from 1:5 to 2:1, and from the viewpoint of good yield, from 1:1 to 1:3 is more preferred.

As the solvent which may be used in the "Step 5", the same solvent as mentioned in the "Step 1" may be mentioned. From the viewpoint of good yield, it is preferred to use a mixed solvent of dioxane or THF and water.

The reaction temperature in the "Step 5" may be suitably selected from 0 to 150° C., and from the viewpoint of good yield, from 50 to 100° C. is preferred. After completion of the "Step 5", the obtained cyclic azine compound (1) may be purified, as the case requires, by e.g. recrystallization, column chromatography or sublimation.

The compound (7) to be used in the "Step 6" in the reaction formula (4) may be synthesized from the compound (10) by using a common reaction of synthesizing an organometallic compound (e.g. Angew. Chem. Int. Ed. 2007, 46, 5359-5363).

"Step 6" is a method for obtaining the cyclic azine compound (1) of the present invention by reacting the compound (7) with a compound (8) in the presence or absence of a base and in the presence of a palladium catalyst, and it is possible to obtain the desired product in good yield by applying the reaction conditions of common coupling reactions, such as the Suzuki-Miyaura reaction, the Negishi reaction, the Tamao-Kumada reaction, the Stille reaction, etc.

In the "Step 6", the same reaction conditions as mentioned in the "Step 5" may be selected for use. However, they need not be the same reaction conditions as in the "Step 5". After the completion of the "Step 6", the obtained cyclic azine compound (1) may be purified, as the case requires, by e.g. recrystallization, column chromatography or sublimation.

Further, the cyclic azine compound (1) of the present invention may be prepared by reacting an adamantane compound represented by the following formula (11) and/or (12) with a compound represented by (2') in the presence of a palladium catalyst, or in the presence of a base and a palladium catalyst.

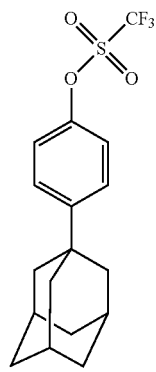

(11)

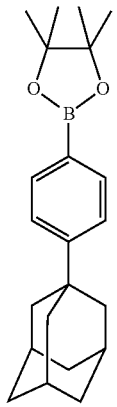

(12)

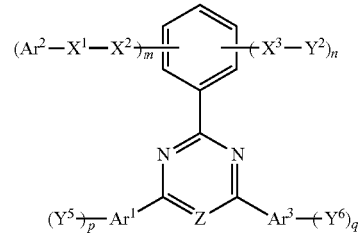

(2')

($Ar^1$, $Ar^2$, $Ar^3$, $X^1$, $X^2$, $X^3$, Z, p, q, m and n are the same as defined in formula (1). $Y^2$, $Y^5$ and $Y^6$ each independently represents a leaving group which will be described later.)

In the compound (2'), $Y^5$ and $Y^6$ each independently represents a leaving group and is not particularly limited, but, for example, a chlorine atom, a bromine atom, an iodine atom, a triflate, etc., may be mentioned. Among them, from the viewpoint of good reaction yield, a bromine atom or a chlorine atom is preferred. Further, in order to improve the selectivity of the reaction, $Y^2$, $Y^5$ and $Y^6$ are more preferably different leaving groups.

With respect to the palladium catalyst, the base, the solvent, the reaction conditions, etc. in the above coupling reaction, it is possible to apply exactly the same materials, reaction conditions, etc. as used in, for example, the "Step 1".

Here, the compounds represented by the formulae (11) and (12) are extremely useful compounds as production intermediates for the production of organic electroluminescent device materials, and they are novel compounds.

The cyclic azine compound (1) of the present invention is preferably used as part of the constituent components of an organic electroluminescent device. In particular, when it is used as an electron transport layer, better effects such as longer service life, higher efficiency, lower voltages, etc. than a conventional device, can be obtained.

Further, at the time of using the cyclic azine compound (1) of the invention as a material for an organic electroluminescence device, it is possible to use it in the form of a co-deposited film with an optional organometallic species, organic compound or inorganic compound.

The cyclic azine compound (1) of the present invention exhibits good electron transport characteristics and thus may preferably be used as the material for an organic thin film layer having an electron transport property, such as a luminous layer, an electron transport layer, an electron injection layer, etc. in an organic electroluminescent device.

The method for producing a thin film for an organic electroluminescent device comprising a cyclic azine compound (1) of the present invention is not particularly limited, and film formation by a vacuum vapor deposition method is possible. The film formation by a vacuum vapor deposition method may be carried out by using a general purpose vacuum vapor deposition apparatus. The vacuum degree in the vacuum chamber at the time of forming a film by a vacuum vapor deposition method, is preferably at a level of from $1 \times 10^{-2}$ to $1 \times 10^{-6}$ Pa, more preferably from $1 \times 10^{-4}$ to $1 \times 10^{-6}$ Pa, which can be reached by a commonly used diffusion pump, turbomolecular pump, cryopump or the like, in consideration of the production tact time and production cost for the production of an organic electroluminescent device.

The deposition rate is preferably from 0.005 to 1.0 nm/sec., more desirably from 0.01 to 0.3 nm/sec., although it may depend on the thickness of the film to be formed.

The cyclic azine compound (1) of the present invention has a high solubility in chloroform, dichloromethane, 1,2-dichloroethane, chlorobenzene, toluene, ethyl acetate, tetrahydrofuran, etc., and therefore, its film formation may be possible by a spin coating method, an ink-jet method, a casting method, a dipping method, etc., using a general-purpose device.

A typical structure of an organic electroluminescent device whereby the effects of the present invention are obtainable, comprises a substrate, an anode, a hole injection layer, a hole transport layer, a luminous layer, an electron transport layer, and a cathode.

The anode and cathode in the organic electroluminescent device are connected to a power source via an electrical conductor. By applying a potential between the anode and the cathode, the organic electroluminescent device is operated. Holes are injected from the anode into the organic electroluminescent device, and electrons are injected by the cathode into the organic electroluminescent device.

The organic electroluminescent device is typically placed on a substrate, and the anode or cathode may be in contact with the substrate. The electrode in contact with the substrate is, for convenience sake, referred to as the lower electrode. Usually, the lower electrode is an anode, but the structure is not limited to such a form in the organic electroluminescent device of the present invention.

The substrate, may be light transmissive or opaque depending on the intended direction of light emission. Light transmission properties can be confirmed by the electroluminescence light emission through the substrate. Usually, a transparent glass or plastic is employed as the substrate. The substrate may have a composite structure comprising multiple material layers.

In a case where the electroluminescence light emission is confirmed through the anode, the anode is formed of a material which permits or substantially permits the light emission to pass therethrough.

As a common transparent anode (anode) material to be used in the present invention, indium-tin oxide (ITO), indium-zinc oxide (IZO) or tin oxide may be mentioned. Further, another metal oxide, such as aluminum- or indium-doped tin oxide, magnesium-indium oxide, or nickel-tungsten oxide may also preferably be used.

In addition to these oxides, a metal nitride, such as gallium nitride, a metal selenide, such as zinc selenide, or a metal sulfide, such as zinc sulfide, may also be used as the anode. The anode may be modified with a plasma-deposited fluorocarbon.

In a case where the electroluminescence light emission is confirmed only through the cathode, the transmission characteristics of the anode is not critical, and a transparent, opaque or reflective optional conductive material may be employed. As an example of such a conductor for this application, gold, iridium, molybdenum, palladium, platinum or the like may be mentioned.

A hole injection layer may be provided between an anode and a hole transport layer. The material for the hole injection layer serves to improve the film forming properties of an organic material layer such as a hole transport layer or a hole injection layer and to facilitate injection of holes into the hole transport layer. As examples of the material suitable for use in the hole injection layer, a porphyrin compound, a plasma vapor deposition type fluorocarbon polymer, and an amine having an aromatic ring such as a biphenyl group, a carbazole group, etc., such as m-MTDATA (4,4',4"-tris[(3-methylphenyl)phenylamino]triphenylamine), 2T-NATA (4,4',4"-tris[(N-naphthalen-2-yl)-N-phenylamino]triphenylamine), triphenylamine, tritolylamine, tolyldiphenylamine, N,N'-diphenyl-N,N'-bis(3-methylphenyl)-1,1'-biphenyl-4,4'-diamine, N,N,N',N'-tetrakis(4-methylphenyl)-1,1'-biphenyl-4,4'-diamine, MeO-TPD (N,N,N',N'-tetrakis(4-methoxyphenyl)-1,1'-biphenyl-4,4'-diamine), N,N'-diphenyl-N,N'-dinaphthyl-1,1'-biphenyl-4,4'-diamine, N,N'-bis(methylphenyl)-N, N'-bis(4-n-butylphenyl)phenanthrene-9,10-diamine, N,N'-diphenyl-N,N'-bis(9-phenylcarbazol-3-yl)-1,1'-biphenyl-4,4'-diamine, etc. may be mentioned.

The hole transport layer in the organic electroluminescence device, preferably contains at least one hole transport compound (hole transport material), for example, an aromatic tertiary amine. An aromatic tertiary amine is a compound which contains at least one trivalent nitrogen atom, the trivalent nitrogen atom is bonded only to carbon atoms, and at least one of such carbon atoms forms an aromatic ring. Specifically, the aromatic tertiary amine may be an arylamine, such as a monoarylamine, a diarylamine, a triarylamine or a polymeric arylamine.

As the hole transport material, it is possible to use an aromatic tertiary amine having at least one amine group. Further, it is possible to use a polymeric hole transport material. For example, poly(N-vinylcarbazole) (PVK), polythiophene, polypyrrole, polyaniline, etc. may be used.

Specifically, NPD (N, N'-bis(naphthalen-1-yl)-N, N'-diphenyl-1,1'-biphenyl-4,4'-diamine), α-NPD (N,N'-di(1-naphthyl)-N,N'-diphenyl-1,1'-biphenyl-4,4'-diamine), TPBi (1,3,5-tris(1-phenyl-1H-benzimidazol-2-yl)benzene), TPD (N,N'-bis(3-methylphenyl)-N, N'-diphenyl-1,1'-biphenyl-4, 4'-diamine), etc. may be mentioned.

Between the hole injection layer and the hole transport layer, a layer containing dipyrazino[2,3-f: 2',3'-h]quinoxaline-2,3,6,7,10,11-hexa-carbonitrile (HAT-CN) may be provided as a charge generation layer.

The luminous layer in an organic electroluminescent device contains a phosphorescent or fluorescent material, and in such a case, electron-hole pairs are recombined in this region, whereupon light emission is caused as a result. The luminous layer may be formed of a single material containing both low molecular and polymer substances, but more usually, it is formed of a host material doped with a guest compound, so that light emission is primarily from the dopant, and it can emit any color.

As the host material in the luminous layer, a compound having a biphenyl group, a fluorenyl group, a triphenylsilyl group, a carbazole group, a pyrenyl group or an anthranyl group, may, for example, be mentioned.

Specifically, DPVBi (4,4'-bis(2,2-diphenyl-vinyl)-1,1'-biphenyl), BCzVBi (4,4'-bis(9-ethyl-3-carbazovinylene)-1,1'-biphenyl), TBADN (2-tert-butyl-9,10-di(2-naphthyl) anthracene), ADN (9,10-di(2-naphthyl)anthracene), CBP (4,4'-bis(carbazol-9-yl) biphenyl), CDBP (4,4'-bis(carbazol-9-yl)-2,2'-dimethyl-biphenyl), 9,10-bis(biphenyl) anthracene, etc. may be mentioned.

The host material in the luminous layer may be an electron transport material as defined below, a hole transport material as defined above, another material that supports the hole-electron recombination, or a combination of these materials.

As examples of a fluorescent dopant, anthracene, tetracene, xanthene, perylene, rubrene, coumarin, rhodamine and quinacridone, a dicyanomethylenepyran compound, a thiopyran compound, a polymethine compound, a pyrylium or thiapyrilium compound, a fluorene derivative, a periflanthene derivative, an indenoperylene derivative, a bis(azinyl) amine boron compound, a bis(azinyl)methane compound, a carbostyril compound, etc. may be mentioned.

As an example of a useful phosphorescent dopant, an organic metal complex of transition metal such as iridium, platinum, palladium, osmium, etc. may be mentioned.

As examples of a dopant, Alq$_3$ (tris(8-hydroxyquinoline) aluminum)), DPAVBi (4,4'-bis[4-(di-para-tolylamino) styryl] biphenyl), perylene, Ir(PPy)$_3$ (tris(2-phenylpyridine) iridium (III), FIrPic (bis(3,5-difluoro-2-(2-pyridyl)phenyl-(2-carboxypyridyl)iridium (III), etc. may be mentioned.

The thin film-forming material to be used for forming an electron transport layer in the organic electroluminescent device of the present invention is the cyclic azine compound of the present invention (1). Here, the electron transporting layer may also contain other electron transport materials. As such other electron transport materials, an alkali metal complex, an alkaline earth metal complex, an earth metal complex, etc. may be mentioned.

As a preferred alkali metal complex, alkali earth metal complex or earth metal complex, for example, lithium 8-hydroxyquinolinate (Liq), zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris (8-hydroxyquinolinate), beryllium bis(10-hydroxybenzo[h] quinolinate), zinc bis(10-hydroxybenzo[h]quinolinate), chlorogallium bis(2-methyl-8-quinolinate), gallium bis(2-methyl-8-quinolinato) (o-cresolate), aluminum bis(2-methyl-8-quinolinato)-1-naphtholate, gallium bis(2-methyl-8-quinolinato)-2-naphtholate, etc. may be mentioned.

Between the luminous layer and the electron transport layer, a hole blocking layer may be provided for the purpose of improving the carrier balance. As a preferred compound as such a hole blocking layer, BCP (2,9-dimethyl-4,7-diphenyl-1,10-phenanthroline), Bphen (4,7-diphenyl-1,10-phenanthroline), BAlq (aluminum bis(2-methyl-8-quinolinato)-4-(phenyl-phenolate)), beryllium bis(10-hydroxybenzo[h]quinolinate)), etc. may be mentioned.

In the organic electroluminescent device of the present invention, an electron injection layer may be provided for the purpose of improving the electron injection property and device characteristics (for example, luminous efficiency, low voltage driving, or high durability).

As a preferred compound as such an electron injecting layer, fluorenone, anthraquinodimethane, diphenoquinone, thiopyran dioxide, oxazole, oxadiazole, triazole, imidazole, perylenetetracarboxylic acid, deflection fluorenylidenemethane isopropylidene methane, anthraquinodimethane or anthrone may be mentioned. Further, inorganic compounds like the above-mentioned metal complexes and alkali metal oxides, alkaline earth oxides, rare earth oxides, alkali metal halides, alkaline earth halides, rare earth halides, various oxides, nitrides and oxynitrides such as SiOx, AlOx, SiNx, SiON, AlON, GeOx, LiOx, LiON, TiOx, TiON, TaOx, TaON, TaNx, C, etc. may also be used.

In a case where light emission is viewed only through the anode, the cathode to be used in the present invention may be formed of substantially optional conductive material. As a preferred cathode material, sodium, a sodium-potassium alloy, magnesium, lithium, a magnesium/copper mixture, a magnesium/silver mixture, a magnesium/aluminum mixture, a magnesium/indium mixture, an aluminum/aluminum oxide (Al$_2$O$^3$) mixture, indium, a lithium/aluminum mixture, a rare earth metal, etc. may be mentioned.

EXAMPLES

Now, the present invention will be described in further detail with reference to Examples and Reference Examples, but it should be understood that the present invention is by no means limited thereto.

Synthesis Example 1

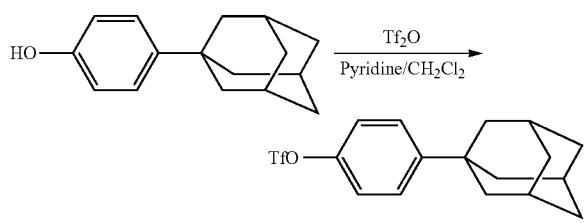

Under an argon stream, 4-(1-adamantyl)phenol (3.77 g, 16.5 mmol) was suspended in dichloromethane (40 mL), and pyridine (2.66 mL, 33.0 mmol) was added. The obtained mixed solution was cooled to 0° C., a solution having anhydrous trifluoromethanesulfonic acid (5.59 g, 19.8 mmol) and dichloromethane (20 mL) mixed, was dropped slowly over a period of 15 minutes. The obtained reaction solution was stirred for 2 hours at 0° C. and then stirred at room temperature for 15 hours. After completion of the stirring, chloroform (30 mL) and a 2M HCl aqueous solution (30 mL) were added to the reaction solution and mixed by shaking, whereupon only the organic layer was taken out. The organic layer was dehydrated by addition of magnesium sulfate and filtered. By distilling off low-boiling point components from the organic layer, a yellowish white solid of 4-(1-adamantyl)phenyl triflate (amount: 5.50 g, yield: 92.4%) was obtained as the desired compound.

¹H-NMR (CDCl₃): 1.76 (brq, J=12.0 Hz, 6H), 1.88 (d, J=2.9 Hz, 6H), 2.09 (brs, 3H), 7.18 (d, J=9.0 Hz, 2H), 7.40 (d, J=9.1 Hz, 2H).

Synthesis Example 2

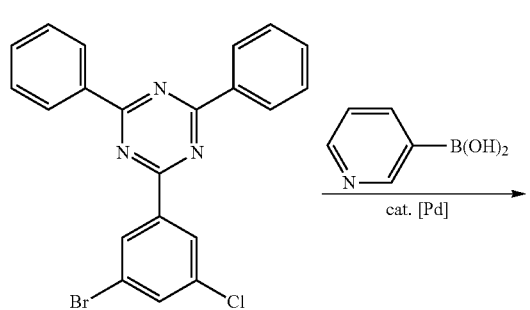

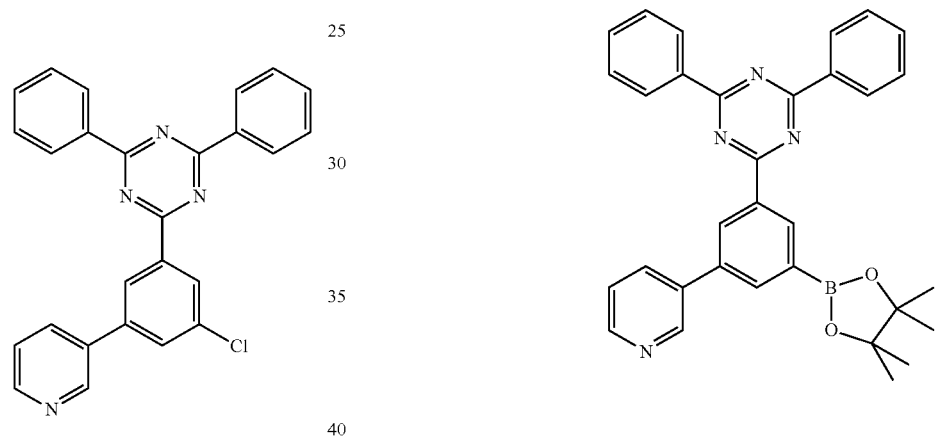

Under an argon stream, 2-(3-bromo-5-chlorophenyl)-4,6-diphenyl-1,3,5-triazine (25.0 g, 59.1 mmol), 3-pyridine boronic acid (12.0 g, 97.6 mmol), tetrakistriphenylphosphine palladium (2.05 g, 1.77 mmol) and potassium carbonate (24.5 g, 177 mmol) were suspended in a mixed solvent of tetrahydrofuran (500 mL) and water (177 mL), followed by heating to 70° C. and stirring for 18 hours. After the stirring, the reaction solvent was distilled off, and chloroform and water were added for dissolution again. Only the organic layer was taken out, and it was dehydrated by addition of magnesium sulfate and filtered. Low boiling point components in the obtained organic layer were distilled off, and the obtained gray white solid was purified by recrystallization with toluene, to obtain a gray white solid of 2-[5-chloro-3-(3-pyridyl) phenyl]-4,6-diphenyl-1,3,5-triazine (amount: 22.6 g, yield: 90.9%) as the desired product.

¹H-NMR (CDCl₃): 7.45 (dd, J=7.6 Hz, 4.8 Hz, 1H), 7.56-7.65 (m, 6H), 7.78 (t, J=1.9 Hz, 1H), 7.99 (d, J=7.9 Hz, 1H), 8.68 (dd, J=4.8 Hz, 1.6 Hz, 1H), 8.74-8.76 (m, 1H), 8.76 (d, J=6.5 Hz, 4H), 8.86 (brs, 1H), 8.99 (d, J=2.2 Hz, 1H).

Synthesis Example 3

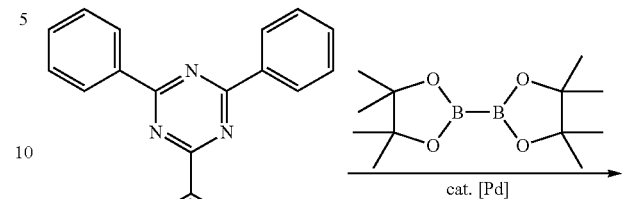

Under an argon stream, 2-[5-chloro-3-(3-pyridyl) phenyl]-4,6-diphenyl-1,3,5-triazine (10.0 g, 23.8 mmol), bis(pinacolato)diboron (9.07 g, 35.7 mmol), potassium acetate (7.01 g, 71.4 mmol), palladium acetate (53.4 mg, 0.238 mmol) and 2-dicyclohexylphosphino-2',4',6'-triisopropyl biphenyl (227 mg, 0.476 mmol) were suspended in 1,4-dioxane (400 mL), followed by heating to 100° C. and stirring for 18 hours. Then, 500 mL of chloroform and 100 mL of water were added to the reaction solution and mixed by shaking, whereupon only the organic layer was taken out. The organic layer was dehydrated by addition of magnesium sulfate and filtered. After low-boiling point components in the obtained organic layer were distilled off, and the organic layer was dissolved in 150 mL of chloroform. To this chloroform solution, 1,000 mL of hexane was added, followed by stirring for 1 hour, whereupon the formed precipitate was collected by filtration, to obtain a white solid of 4,6-diphenyl-2-[3-(3-pyridyl)-5-4,4,5,5-tetramethyl-1,3,2-dioxaborolan-2-yl)phenyl]-1,3,5-triazine (9.58 g, yield: 78.6%) as the desired product.

¹H-NMR (CDCl₃): 1.42 (s, 12H), 7.43 (ddd, J=7.8 Hz, 4.8 Hz, 0.7 Hz, 1H), 7.56-7.64 (m, 6H), 8.06 (ddd, J=7.8 Hz, 2.3 Hz, 1.6 Hz, 1H), 8.23 (dd, J=2.1 Hz, 1.0 Hz, 1H), 8.65 (dd, J=4.9 Hz, 1.6 Hz, 1H), 8.79 (dd, J=8.0 Hz, 1.4 Hz, 4H), 9.04 (dd, J=2.5 Hz, 0.8 Hz, 1H), 9.08 (t, J=1.9 Hz, 1H), 9.16 (dd, J=1.7 Hz, 1.1 Hz, 1H).

Example 1

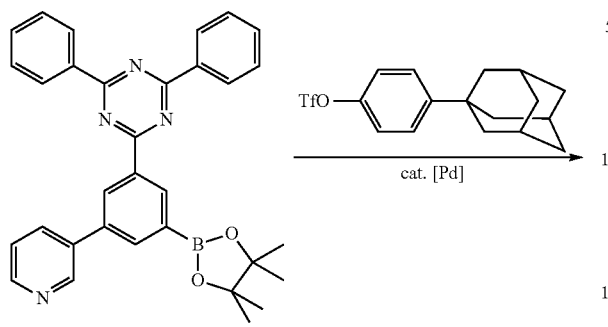

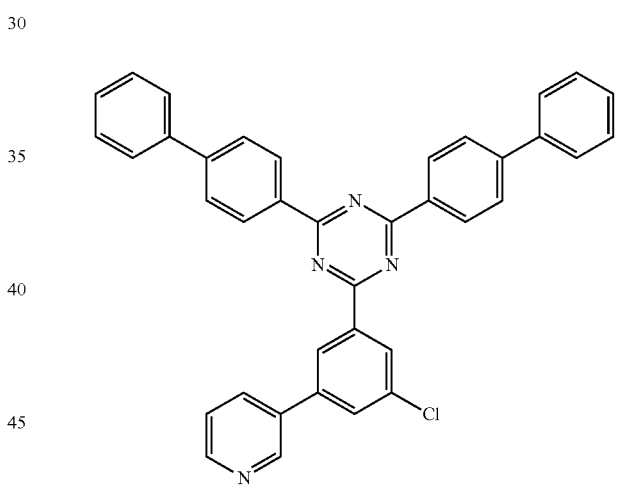

Under an argon stream, 4,6-diphenyl-2-[3-(3-pyridyl)-5-(4,4,5,5-tetramethyl-1,3,2-dioxaborolan-2-yl)phenyl]-1,3,5-triazine (1.50 g, 2.93 mmol), 4-(1-adamantyl)phenyl triflate (1.58 g, 4.40 mmol), palladium acetate (13.2 mg, 0.0586 mmol), 2-dicyclohexylphosphino-2',4',6'-triisopropyl biphenyl (55.9 mg, 0.117 mmol) and potassium carbonate (1.05 g, 7.62 mmol) were suspended in a mixed solvent of tetrahydrofuran (16 mL) and water (7.3 mL), followed by heating to 70° C. and stirring for 18 hours. After cooling to room temperature, water (30 mL) was added to the reaction mixture, and the precipitate was collected by filtration. The obtained precipitate was purified by silica gel chromatography (developing solvent:mixed solvent of chloroform and hexane in a ratio of 1:2 (volume ratio, the same applies hereinafter)) and by recrystallization from toluene, to obtain a white solid of 2-[4'(1-adamantyl)-5-(3-pyridyl)biphenyl-3-yl]-4,6-diphenyl-1,3,5-triazine (Compound A-14) (amount: 1.06 g, yield: 60.6%) as the desired product.

$^1$H-NMR (CDCl$_3$): 1.80 (brs, 6H), 2.00 (brd, J=2.8 Hz, 6H), 2.14 (brs, 3H), 7.45 (dd, J=7.9 Hz, 4.8 Hz, 1H), 7.54 (d, J=8.5 Hz, 2H), 7.56-7.64 (m, 6H), 7.75 (d, J=8.5 Hz, 2H), 8.00 (t, J=1.9 Hz, 1H), 8.07 (d, J=8.0 Hz, 1H), 8.67 (dd, J=4.8 Hz, 1.6 Hz, 1H), 8.79 (dd, J=8.1 Hz, 1.8 Hz, 4H), 8.94 (t, J=1.6 Hz, 1H), 9.02 (t, J=1.6 Hz, 1H), 9.06 (d, J=1.9 Hz, 1H).

Tg of the obtained compound A-14 was 129° C.

Synthesis Example 4

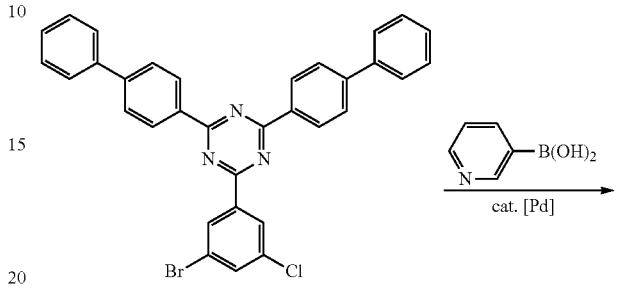

Under an argon stream, 2-(3-bromo-5-chlorophenyl)-4,6-bis(biphenyl-4-yl)-1,3,5-triazine (4.00 g, 6.96 mmol), 3-pyridineboronic acid (1.03 g, 8.35 mmol), tetrakistriphenylphosphine palladium (160.9 mg, 0.139 mmol) and potassium carbonate (2.31 g, 16.7 mmol) were suspended in a mixed solvent of tetrahydrofuran (200 mL) and water (16 mL), followed by heating to 70° C. and stirring for 18 hours. After the stirring, 200 mL of water was added to the reaction mixture, and the precipitate was collected by filtration. The obtained product was purified by recrystallization with toluene, to obtain a gray white solid of 4,6-bis(biphenyl-4-yl)-2-[5-chloro-3-(3-pyridyl)phenyl]-1,3,5-triazine (amount: 3.19 g, yield: 80.0%) as the desired product.

$^1$H-NMR (CDCl$_3$): 7.41 (t, J=7.3 Hz, 2H), 7.45-7.52 (m, 5H), 7.71 (dd, J=8.3 Hz, 1.4 Hz, 4H), 7.80 (t, J=1.9 Hz, 1H), 7.82 (d, J=8.7 Hz, 4H), 8.02 (ddd, J=7.9 Hz, 2.4 Hz, 1.6 Hz, 1H), 8.69 (dd, J=4.9 Hz, 1.7 Hz, 1H), 8.80 (dd, J=2.1 Hz, 1.5 Hz, 1H), 8.84 (d, J=8.7 Hz, 4H), 8.89 (t, J=1.6 Hz, 1H), 9.01 (dd, J=2.5 Hz, 0.8 Hz, 1H).

Synthesis Example 5

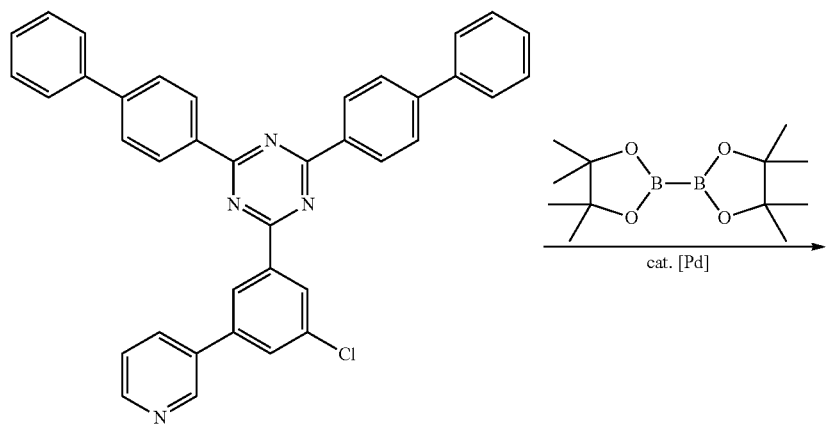

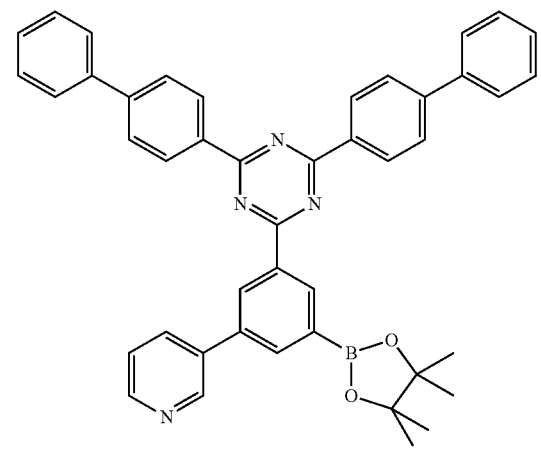

Under an argon atmosphere, 4,6-bis(biphenyl-4-yl)-2-[5-chloro-3-(3-pyridyl) phenyl]-1,3,5-triazine (2.89 g, 5.04 mmol), bis(pinacolato)diboron (1.92 g, 7.56 mmol), potassium carbonate (2.09 g, 15.1 mmol), palladium acetate (11.3 mg, 0.0504 mmol) and 2-dicyclohexylphosphino-2',4',6'-triisopropyl biphenyl (48.1 mg, 0.101 mmol) were suspended in 1,4-dioxane (200 mL), followed by heating to 100° C. and stirring for 18 hours. Then, 700 mL of chloroform and 100 mL of water were added to the reaction solution and mixed by shaking, whereupon only the organic layer was taken out. The organic layer was dehydrated by addition of magnesium sulfate and filtered. After low-boiling point components in the obtained organic layer were distilled off, the organic layer was dispersed in 200 mL of hexane, followed by stirring for one hour. After the stirring, the precipitate is collected by filtration, to obtain a white solid of 4,6-bis(biphenyl-4-yl)-2-[3-(3-pyridyl)-5-(4,4,5,5-tetramethyl-1,3,2-dioxaborolan-2-yl)phenyl]-1,3,5-triazine (amount: 3.30 g, yield: 98.5%) as the desired product.

$^1$H-NMR (CDCl$_3$): 1.43 (s, 12H), 7.38-7.45 (m, 3H), 7.50 (t, J=7.7 Hz, 4H), 7.71 (dd, J=8.5 Hz, 1.4 Hz, 4H), 7.83 (d, J=8.6 Hz, 4H), 8.08 (ddd, J=7.8 Hz, 2.4 Hz, 1.7 Hz, 1H), 8.27 (dd, J=2.0 Hz, 1.0 Hz, 1H), 8.66 (dd, J=5.0 Hz, 1.6 Hz, 1H), 8.88 (d, J=8.7 Hz, 4H), 9.05 (dd, J=2.5 Hz, 0.8 Hz, 1H), 9.10 (t, J=1.8 Hz, 1H), 9.19 (dd, J=1.7 Hz, 1.1 Hz, 1H).

Example 2

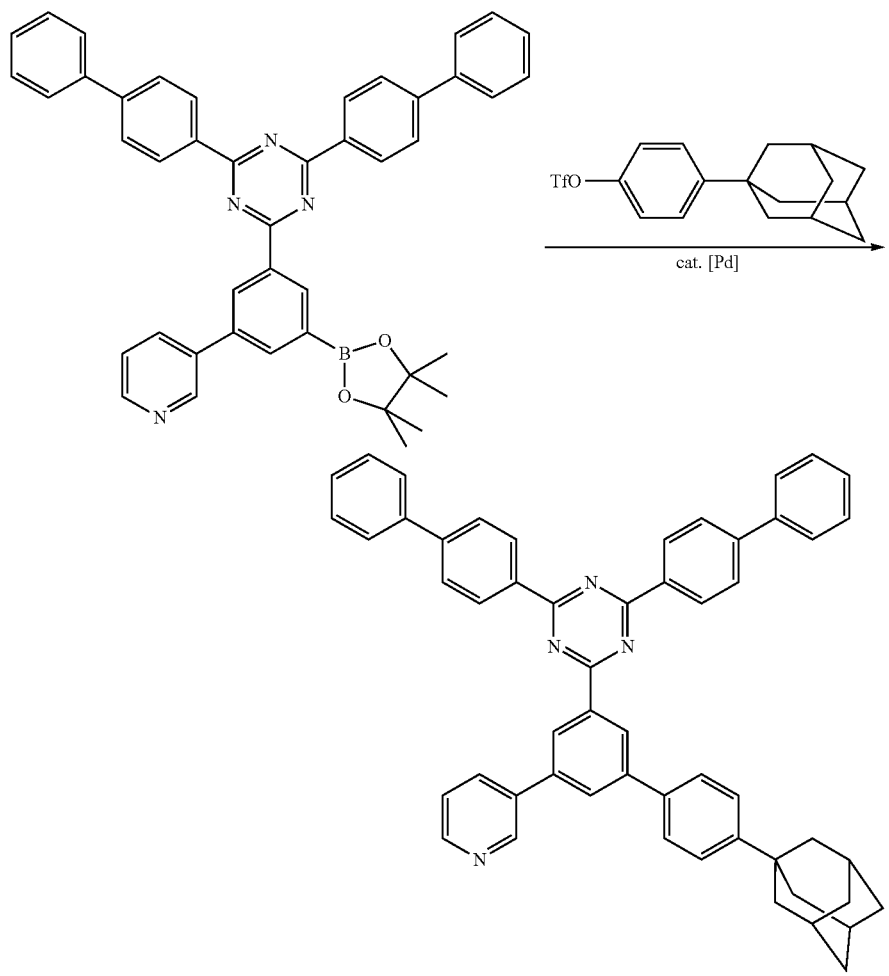

Under an argon stream, 4,6-bis(biphenyl-4-yl)-2-[3-(3-pyridyl)-5-(4,4,5,5-tetramethyl-1,3,2-dioxaborolan-2-yl)phenyl]-1,3,5-triazine (1.50 g, 2.26 mmol), 4-(1-adamantyl)phenyl triflate (1.22 g, 3.39 mmol), palladium acetate (5.07 mg, 0.0226 mmol), 2-dicyclohexylphosphino-2',4',6'-triisopropyl biphenyl (21.6 mg, 0.0452 mmol) and potassium carbonate (0.810 g, 5.87 mmol) were suspended in a mixed solvent of tetrahydrofuran (75 mL) and water (6 mL), followed by heating to 70° C. and stirring for 17 hours. After cooling to room temperature, water (50 mL) was added to the reaction mixture, and the precipitate was collected by filtration. The obtained precipitate was purified by silica gel chromatography (developing solvent:mixed solvent of chloroform and hexane in a ratio of 1:2) and by recrystallization with toluene, to obtain a white solid of 4,6-bis(biphenyl-4-yl)-2-[4'-(1-adamantyl)-5-(3-pyridyl)biphenyl-3-yl]-1,3,5-triazine (Compound A-170) (amount: 0.970 g of, yield: 57.3%) as the desired product.

$^1$H-NMR (CDCl$_3$): 1.81 (brs, 6H), 2.01 (brs, 6H), 2.14 (brs, 3H), 7.39-7.52 (m, 7H), 7.55 (d, J=8.5 Hz, 2H), 7.71 (d, J=7.0 Hz, 4H), 7.76 (d, J=8.5 Hz, 2H), 7.81 (d, J=8.5 Hz, 4H), 8.0 (t, J=1.8 Hz, 1H), 8.08 (ddd, J=1.7 Hz, 2.3 Hz, 7.9 Hz, 1H), 8.68 (dd, J=4.9 Hz, 1.6 Hz, 1H), 8.86 (d, J=8.6 Hz, 4H), 8.95 (t, J=1.6 Hz, 1H), 9.05 (t, J=1.6 Hz, 1H), 9.07 (d, J=1.7 Hz, 1H).

Tg of the obtained compound A-170 was 155° C.

Synthesis Example 6

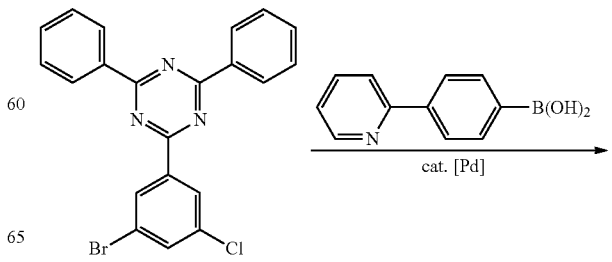

163
-continued

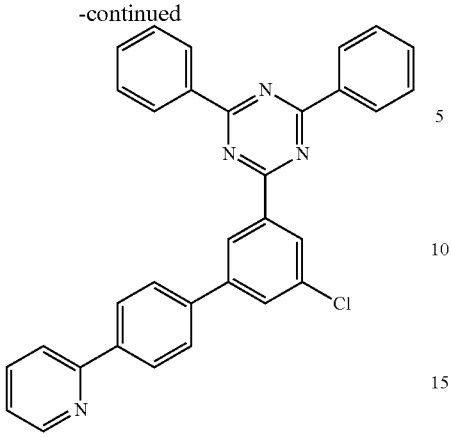

Under an argon stream, 2-(3-bromo-5-chlorophenyl)-4,6-diphenyl-1,3,5-triazine (14.8 g, 34.9 mmol), 4-(2-pyridyl)phenylboronic acid (9.04 g, 45.4 mmol) and tetrakis triphenylphosphine palladium (808 mg, 0.699 mmol a) were suspended in tetrahydrofuran (250 mL), followed by heating to 60° C. To this suspension, a 10 mass % NaOH aqueous solution (40 mL, 105 mmol) was dropwise slowly added, followed by stirring for 3 hours. After cooling to room temperature, water (90 mL) was added to the reaction mixture, and the precipitate was collected by filtration. The obtained precipitate was purified by recrystallization with toluene, to obtain a white solid of 2-[5-chloro-4'-(2-pyridyl)biphenyl-3-yl]-4,6-diphenyl-1,3,5-triazine (amount: 15.4 g, yield: 88.5%) as the desired product.

$^1$H-NMR (CDCl$_3$): 7.27 (ddd, J=5.7 Hz, 4.6 Hz, 2.3 Hz, 1H), 7.56-7.65 (m, 6H), 7.77-7.85 (m, 5H), 8.16 (d, J=8.6 Hz, 2H), 8.72-8.74 (m, 2H), 8.77 (dd, J=8.2 Hz, 1.4 Hz, 4H), 8.92 (t, J=1.6 Hz, 1H).

Synthesis Example 7

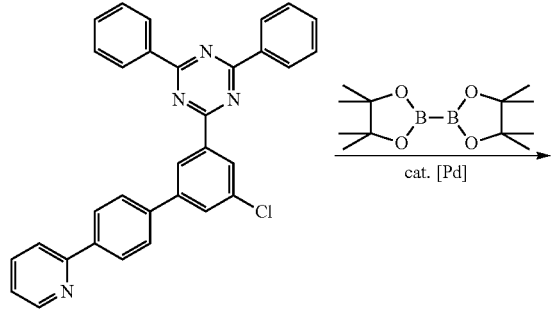

164
-continued

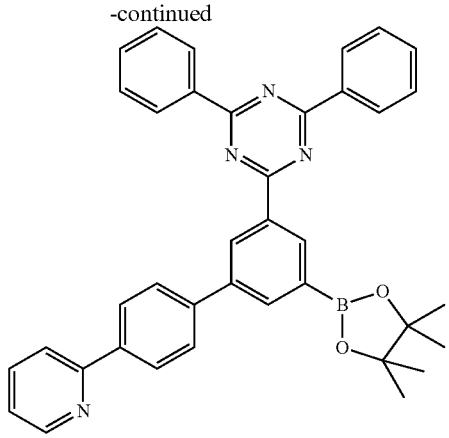

Under an argon stream, 2-[5-chloro-4'-(2-pyridyl)biphenyl-3-yl]-4,6-diphenyl-1,3,5-triazine (6.86 g, 13.8 mmol), bis(pinacolato)diboron (5.26 g, 20.7 mmol), potassium acetate (4.06 g, 41.4 mmol), palladium acetate (31.0 mg, 0.138 mmol) and 2-dicyclohexylphosphino-2',4',6'-triisopropyl biphenyl (131.5 mg, 0.276 mmol) were suspended in 1,4-dioxane (20 mL), followed by heating to 100° C. and stirring for 4 hours. Then, 200 mL of chloroform and 50 mL of water were added to the reaction solution and mixed by shaking, whereupon only the organic layer was taken out. The organic layer was dehydrated by addition of magnesium sulfate and filtered. After low-boiling point components in the obtained organic layer were distilled off, the organic layer was dissolved in 100 mL of chloroform. To this chloroform solution, 700 mL of hexane was added and stirred for 1 hour, and the formed precipitate was collected by filtration, to obtain a white solid of 4,6-diphenyl-2-[4'-(2-pyridyl)-5-(4,4,5,5-tetramethyl-1,3,2-dioxaborolan-2-yl)biphenyl-3-yl]-1,3,5-triazine (8.10 g, yield: 99.7%) as the desired product.

$^1$H-NMR (CDCl$_3$): 1.43 (s, 12H), 7.23-7.27 (m, 1H), 7.56-7.64 (m, 6H), 7.78 (ddd, J=7.8 Hz, 7.8 Hz, 1.8 Hz, 1H), 7.81 (d, J=7.7 Hz, 1H), 7.90 (d, J=8.5 Hz, 2H), 8.14 (d, J=8.5 Hz, 2H), 8.33 (dd, J=1.9 Hz, 1.1 Hz, 1H), 8.73 (ddd, J=4.8 Hz, 1.7 Hz, 1.1 Hz, 1H), 8.81 (dd, J=7.8 Hz, 1.6 Hz, 4H), 9.12-9.14 (m, 2H).

Example 3

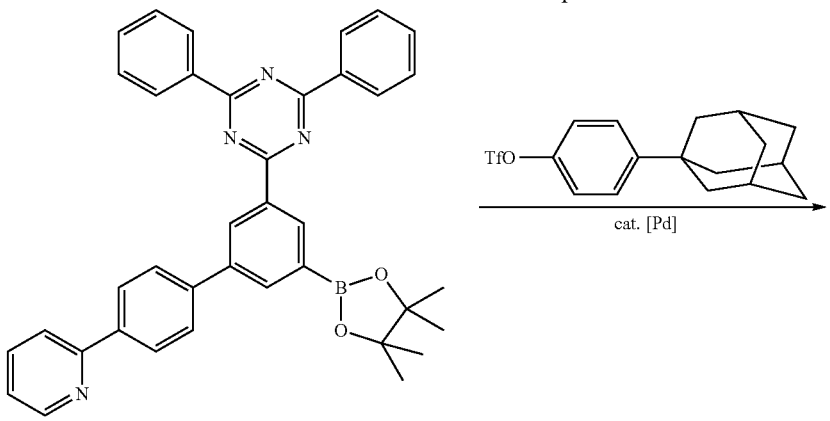

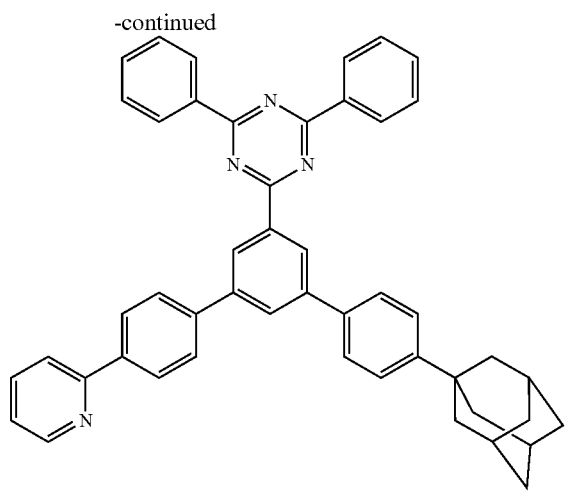

Under an argon stream, 4,6-diphenyl-2-[4'-(2-pyridyl)-5-(4,4,5,5-tetramethyl-1,3,2-dioxaborolan-2-yl)biphenyl-3-yl]-1,3,5-triazine (300 mg, 0.510 mmol), 4-(1-adamantyl)phenyl triflate (203 mg, 0.663 mmol), palladium acetate (2.25 mg, 0.0102 mmol), 2-dicyclohexylphosphino-2',4',6'-triisopropyl biphenyl (9.72 mg, 0.0204 mmol) and potassium carbonate (141 mg, 1.02 mmol) were suspended in a mixed solvent of tetrahydrofuran (3.00 mL) and water (1.30 mL), followed by heating to 70° C. and stirring for 22 hours. After cooling to room temperature, water (5 mL) was added to the reaction mixture, and the precipitate was collected by filtration. The obtained precipitate was purified by silica gel chromatography (developing solvent:mixed solvent of chloroform and hexane in a ratio of 1:2) and by recrystallization with toluene, to obtain a white solid of 2-[4''-(1-adamantyl)-4-(2-pyridyl)-[1,1':3',1'']-terphenyl-5'-yl]-4,6-diphenyl-1,3,5-triazine (Compound A-25) (amount: 278 mg, yield: 81.0%) as the desired product.

$^1$H-NMR (CDCl$_3$): 1.81 (brs, 6H), 2.00 (brd, d=2.8 Hz, 6H), 2.14 (brs, 3H), 7.24-7.27 (m, 1H), 7.53-7.64 (m, 8H), 7.76 (d, J=8.5 Hz, 2H), 7.79 (dd, J=7.2 Hz, 1.8 Hz, 1H), 7.83 (d, J=7.7 Hz, 1H), 7.90 (d, J=8.7 Hz, 2H), 8.08 (t, J=1.7 Hz, 1H), 8.17 (d, J=8.5 Hz, 2H), 8.73 (ddd, J=4.9 Hz, 1.8 Hz, 1.1 Hz, 1H), 8.80 (dd, J=8.1 Hz, 1.8 Hz, 4H), 8.98 (t, J=1.6 Hz, 1H), 9.00 (t, J=1.6 Hz, 1H).

Tg of the obtained compound A-25 was 147° C.

Example 4

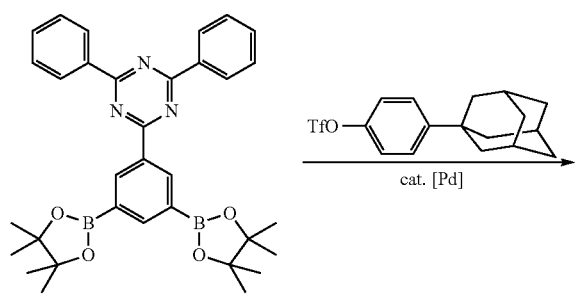

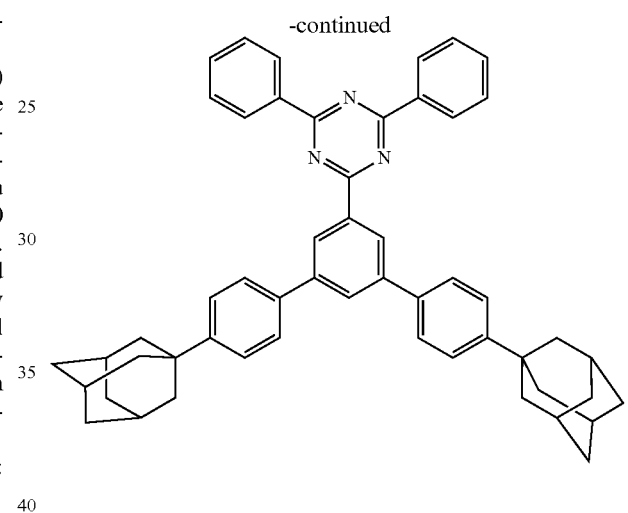

Under an argon stream, 4,6-diphenyl-2-[3,5-bis(4,4,5,5-tetramethyl-1,3,2-dioxaborolan-2-yl)phenyl]-1,3,5-triazine (1.50 g, 2.67 mmol), 4-(1-adamantyl)phenyl triflate (2.69 g, 7.46 mmol), palladium acetate (12.0 mg, 0.0534 mmol), 2-dicyclohexylphosphino-2',4',6'-triisopropyl biphenyl (50.9 mg, 0.107 mmol) and potassium carbonate (0.959 g, 6.94 mmol) were suspended in a mixed solvent of tetrahydrofuran (15 mL) and water (6.5 mL), followed by heating to 70° C. and stirring for 20 hours. After cooling to room temperature, water (30 mL) was added to the reaction mixture, and the precipitate was collected by filtration. The obtained precipitate was purified by silica gel chromatography (developing solvent:mixed solvent of chloroform and hexane in a ratio of 1:2) and recrystallization from toluene to obtain a white solid of 2-[4,4''-bis(1-adamantyl)-[1,1':3',1'']-terphenyl-5'-yl]-4,6-diphenyl-1,3,5-triazine (Compound A-49) (amount: 1.07 g, yield: 54.9%) as the desired product.

$^1$H-NMR (CDCl$_3$): 1.80 (brs, 12H), 2.00 (brd, J=2.6 Hz, 12H), 2.13 (brs, 6H), 7.53 (d, J=8.7 Hz, 4H), 7.55-7.63 (m, 6H), 7.74 (d, J=8.5 Hz, 4H), 8.02 (t, J=1.8 Hz, 1H), 8.79 (dd, J=8.2 Hz, 1.9 Hz, 4H), 8.94 (d, J=1.8 Hz, 2H).

Tg of the obtained compound A-49 was 186° C.

Synthesis Example 8

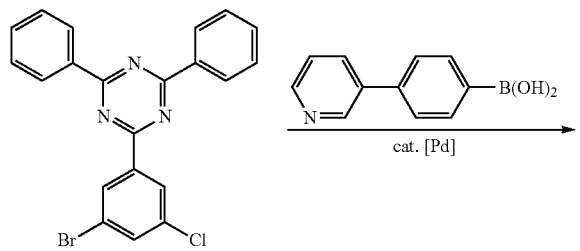

Under an argon stream, 2-(3-bromo-5-chlorophenyl)-4,6-diphenyl-1,3,5-triazine (1.00 g, 2.37 mmol), 4-(3-pyridyl)phenylboronic acid (565 mg, 2.84 mmol), potassium carbonate (981 mg, 7.10 mmol) and tetrakistriphenylphosphine palladium (82.0 mg, 0.0710 mmol) were suspended in a mixed solvent of tetrahydrofuran (28 mL) and water (7 mL), followed by heating to 70° C. and stirring for 20 hours. After cooling to room temperature, water (20 mL) was added to the reaction mixture, and the precipitate was collected by filtration. The obtained precipitate was purified by silica gel chromatography (developing solvent:chloroform) to obtain a white solid of 2-[5-chloro-4'-(3-pyridyl)biphenyl-3-yl]-4,6-diphenyl-1,3,5-triazine (amount: 1.09 g, yield: 92.7%) as the desired product.

$^1$H-NMR (CDCl$_3$): 7.40 (dd, J=7.8 Hz, 0.9 Hz, 1H), 7.56-7.65 (m, 6H), 7.75 (d, J=8.5 Hz, 2H), 7.82-7.84 (m, 3H), 7.95 (ddd, J=7.8 Hz, 2.4 Hz, 1.6 Hz, 1H), 8.63 (dd, J=4.7 Hz, 1.8 Hz, 1H), 8.73 (dd, J=1.9 Hz, 1.6 Hz, 1H), 8.77 (dd, J=8.1 Hz, 1.8 Hz, 4H), 8.90 (t, J=1.6 Hz, 1H), 8.93 (brd, J=1.7 Hz, 1H).

Example 5

Under an argon stream, 2-[5-chloro-4'-(3-pyridyl)biphenyl-3-yl]-4,6-diphenyl-1,3,5-triazine (1.09 g, 2.19 mmol), 2-[4-(1-adamantyl)phenyl]-4,4,5,5-tetramethyl-1,3,2-dioxaborolane (890 mg, 2.63 mmol), palladium acetate (9.84 mg, 0.0438 mmol), 2-dicyclohexylphosphino-2',4',6'-triisopropyl biphenyl (41.8 mg, 0.0877 mmol) and potassium carbonate (909 mg, 6.58 mmol) were suspended in a mixed solvent of tetrahydrofuran (18 mL) and water (6 mL), followed by heating to 70° C. and stirring for 20 hours. After cooling to room temperature, water (30 mL) was added to the reaction mixture, and the precipitate was collected by filtration. The obtained precipitate was purified by silica gel chromatography (developing solvent:chloroform) to obtain a white solid of 2-[4''-(1-adamantyl)-4-(3-pyridyl)-[1,1':3',1'']-terphenyl-5'-yl]-4,6-diphenyl-1,3,5-triazine (Compound A-26) (amount: 1.06 g, yield: 60.6%) as the desired product.

$^1$H-NMR (CDCl$_3$): 1.81 (brt, J=14.7 Hz, 6H), 2.00 (brd, J=2.6 Hz, 6H), 2.14 (brs, 3H), 7.40 (brdd, J=8.1 Hz, 4.8 Hz, 1H), 7.53-7.64 (m, 8H), 7.76 (d, J=7.8 Hz, 4H), 7.91 (d, J=8.5 Hz, 2H), 7.96 (ddd, J=7.9 Hz, 2.3 Hz, 1.6 Hs, 1H), 8.07 (t, J=1.8 Hz, 1H), 8.62 (dd, J=4.7 Hz, 1.3 Hz, 1H), 8.79 (dd, J=8.3 Hz, 1.9 Hz, 4H), 8.95 (d, J=2.1 Hz, 1H), 8.99 (dt, J=5.6 Hz, 1.7 Hz, 2H).

Tg of the obtained compound A-26 was 147° C.

Synthesis Example 9

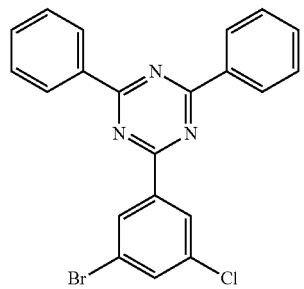
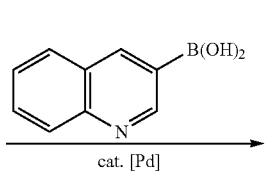
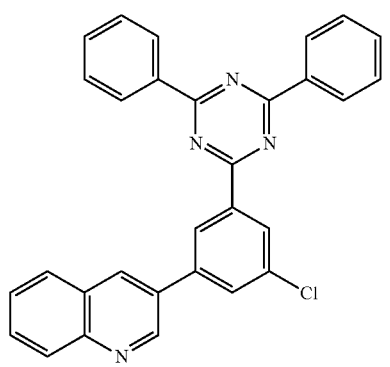
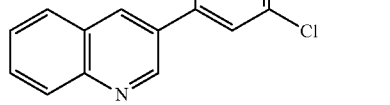

Under an argon stream, 2-(3-bromo-5-chlorophenyl)-4,6-diphenyl-1,3,5-triazine (6.00 g, 14.2 mmol), 3-quinoline boronic acid (2.95 g, 17.0 mmol), potassium carbonate (5.89 g, 42.6 mmol) and tetrakistriphenylphosphine palladium (492 mg, 0.425 mmol) were suspended in a mixed solvent of tetrahydrofuran (120 mL) and water (40 mL), followed by heating to 70° C. and stirring for 24 hours. After cooling to room temperature, water (100 mL) was added to the reaction mixture, and the precipitate was collected by filtration. The obtained precipitate was purified by silica gel chromatography (developing solvent:chloroform) to obtain a white solid of 2-(5-chloro-3-quinolylphenyl)-4,6-diphenyl-1,3,5-triazine (amount: 5.85 g, yield: 87.5%) as the desired product.

¹H-NMR (CDCl₃): 7.56-7.65 (m, 7H), 7.78 (ddd, J=8.7 Hz, 7.7 Hz, 1.5 Hz, 1H), 7.91 (t, J=1.8 Hz, 1H), 7.95 (brd, J=8.2 Hz, 1H), 8.18 (brd, J=8.6 Hz, 1H), 8.43 (brd, J=2.5 Hz, 1H), 8.76 (dd, J=8.6 Hz, 1.6 Hz, 4H), 8.78-8.79 (m, 1H), 8.98 (t, J=1.5 Hz, 1H), 9.31 (d, J=2.3 Hz, 1H).

Example 6

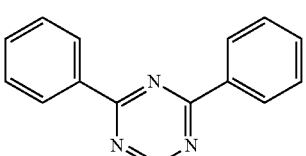
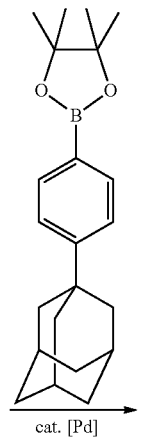
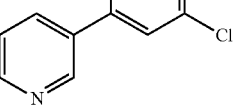
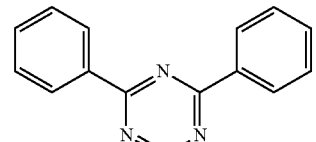
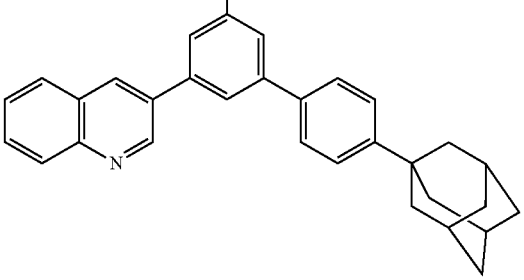

Under an argon stream, 2-(5-chloro-3-quinolylphenyl)-4,6-diphenyl-1,3,5-triazine (1.00 g, 2.12 mmol), 2-[4-(1-adamantyl)phenyl]-4,4,5,5-tetramethyl-1,3,2-dioxaborolane (1.08 g, 3.18 mmol), palladium acetate (9.53 mg, 0.0424 mmol), 2-dicyclohexylphosphino-2',4',6'-triisopropyl biphenyl (40.5 mg, 0.0849 mmol) and potassium carbonate (880 mg, 6.37 mmol) were suspended in a mixed solvent of tetrahydrofuran (18 mL) and water (6 mL), followed by heating to 70° C. and stirring for 18 hours. After cooling to room temperature, water (20 mL) was added to the reaction mixture, and the precipitate was collected by filtration. The obtained precipitate was purified by silica gel chromatography (developing solvent:chloroform) to obtain a white solid of 2-[4'-(1-adamantyl)-5-(3-pyridyl)biphenyl-3-yl]-4,6-diphenyl-1,3,5-triazine (compound A-19) (amount: 600 mg, yield: 43.7%) as the desired product.

¹H-NMR (CDCl₃): 1.81 (brt, J=14.2 Hz, 6H), 2.01 (brd, J=2.8 Hz, 6H), 2.14 (brs, 3H), 7.55-7.64 (m, 9H), 7.74-7.79 (m, 3H), 7.96 (brd, J=8.1 Hz, 1H), 8.14 (t, J=1.7 Hz, 1H), 8.19 (d, J=8.2 Hz, 1H), 8.50 (brd, J=2.3 Hz, 1H), 8.80 (dd, J=8.2 Hz, 1.4 Hz, 4H), 9.06 (dt, J=5.7 Hz, 1.6 Hz, 2H), 9.39 (d, J=2.4 Hz, 1H).

Tg of the obtained compound A-19 was 139° C.

Synthesis Example 10

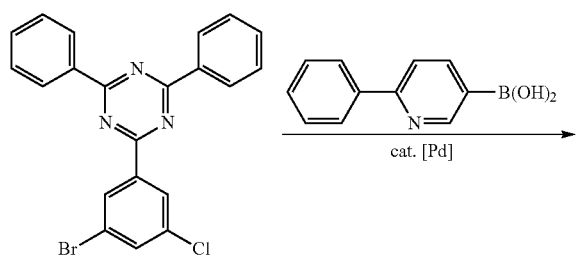

Example 7

Under an argon stream, 2-(3-bromo-5-chlorophenyl)-4,6-diphenyl-1,3,5-triazine (1.00 g, 2.37 mmol), 6-phenyl-3-(4,4,5,5-tetramethyl-1,3,2-dioxaborolan-2-yl)pyridine (798 mg, 2.84 mmol), potassium carbonate (980 mg, 7.10 mmol) and tetrakistriphenylphosphine palladium (82.0 mg, 0.0710 mmol) were suspended in a mixed solvent of tetrahydrofuran (28 mL) and water (7 mL), followed by heating to 70° C. and stirring for 21 hours. After cooling to room temperature, water (20 mL) was added to the reaction mixture, and the precipitate was collected by filtration. The obtained precipitate was purified by silica gel chromatography (developing solvent:chloroform) to obtain a white solid of 2-[5-chloro-3-(6-phenylpyridin-3-yl)phenyl]-4,6-diphenyl-1,3,5-triazine (amount: 997 mg, yield: 84.9%) as the desired product.

$^1$H-NMR (CDCl$_3$): 7.45 (t, J=7.2 Hz, 1H), 7.51 (d, J=7.6 Hz, 1H), 7.50-7.54 (m, 1H), 7.57-7.65 (m, 6H), 7.84 (t, J=1.8 Hz, 1H), 7.90 (dd, J=8.4 Hz, 0.8 Hz, 1H), 8.07-8.08 (m, 1H), 8.08 (dd, J=8.4 Hz, 1.6 Hz, 2H), 8.77-8.78 (m, 1H), 8.78 (dd, J=8.5 Hz, 1.4 Hz, 4H), 8.94 (t, J=1.6 Hz, 1H), 9.08 (dd, J=2.5 Hz, 0.8 Hz, 1H).

Under an argon stream, 2-[5-chloro-3-(6-phenylpyridin-3-yl)phenyl]-4,6-diphenyl-1,3,5-triazine (900 mg, 1.81 mmol), 2-[4-(1-adamantyl)phenyl]-4,4,5,5-tetramethyl-1,3,2-dioxaborolane (735 mg, 2.17 mmol), palladium acetate (8.13 mg, 0.0362 mmol), 2-dicyclohexylphosphino-2',4',6'-triisopropyl biphenyl (34.5 mg, 0.0724 mmol) and potassium carbonate (750 mg, 5.43 mmol) were suspended in a mixed solvent of tetrahydrofuran (20 mL) and water (5 mL), followed by heating to 70° C. and stirring for 30 hours. Then, 2-[4-(1-adamantyl)phenyl]-4,4,5,5-tetramethyl-1,3,2-dioxaborolane (306 mg, 0.905 mmol), palladium acetate (8.13 mg, 0.0362 mmol) and 2-dicyclohexylphosphino-2',4',6'-triisopropyl biphenyl (34.5 mg, 0.0724 mmol) were added, followed by stirring at 70° C. for 20 hours. After cooling to room temperature, the reaction mixture was stirred by addition of water (40 mL) and chloroform (60 mL), and only the organic layer was taken out. The organic layer was dehydrated with magnesium sulfate, and then, low-boiling point components were distilled off to obtain a crude product. The obtained crude product was purified by silica gel chromatography (developing solvent:chloroform)

to obtain a white solid of 2-[4'-(1-adamantyl)-5-(6-phenylpyridin-3-yl)biphenyl-3-yl]-4,6-diphenyl-1,3,5-triazine (compound A-28) (amount: 600 mg, yield: 43.7%) as the desired product.

$^1$H-NMR (CDCl$_3$): 1.81 (brt, J=14.2 Hz, 6H), 2.01 (brd, J=2.9 Hz, 6H), 2.14 (brs, 3H), 7.45 (brt, J=7.1 Hz, 1H), 7.51-7.64 (m, 10H), 7.76 (d, J=8.5 Hz, 2H), 7.91 (brd, J=8.3 Hz, 1H), 8.06 (t, J=1.8 Hz, 1H), 8.10 (brd, J=7.3 Hz, 2H), 8.17 (brd, J=8.0 Hz, 1H), 8.79 (dd, J=8.3 Hz, 1.7 Hz, 4H), 9.00 (t, J=1.7 Hz, 1H), 9.03 (t, J=1.6 Hz, 1H), 9.16 (brd, J=2.0 Hz, 1H).

Tg of the obtained compound A-28 was 145° C.

Example 8

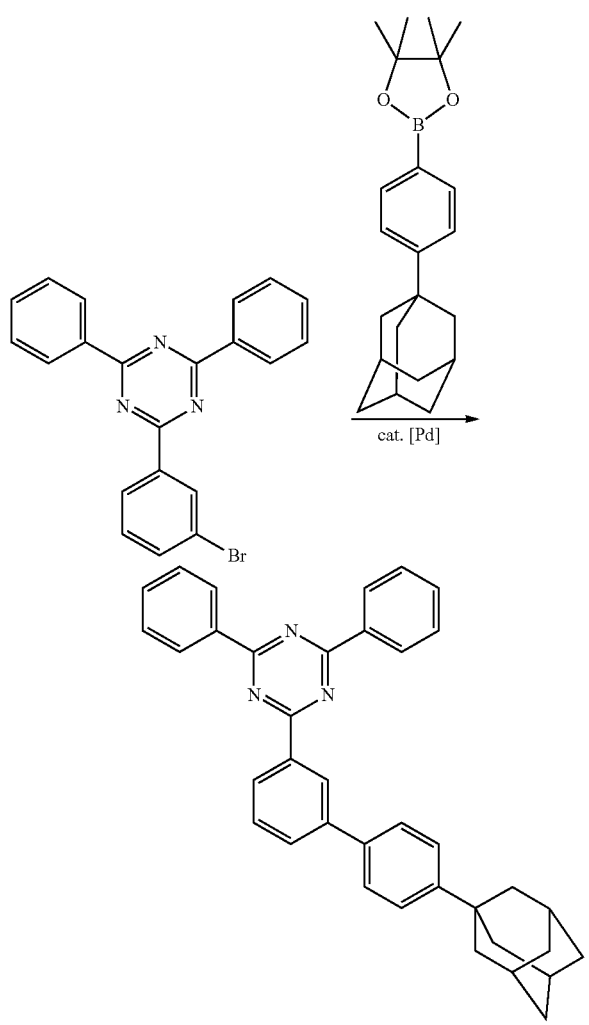

Under an argon stream, 2-(3-bromophenyl)-4,6-diphenyl-1,3,5-triazine (2.00 g, 5.15 mmol), 2-[4-(1-adamantyl)phenyl]-4,4,5,5-tetramethyl-1,3,2-dioxaborolane (3.49 g, 10.3 mmol), tetrakistriphenylphosphine palladium (119 mg, 0.103 mmol) and potassium carbonate (2.14 g, 15. The 5 mmol) were suspended in a mixed solvent of tetrahydrofuran (30 mL) and water (15 mL), followed by heating to 70° C. and stirring for 18 hours. After cooling to room temperature, water (30 mL) was added to the reaction mixture, and the precipitate was collected by filtration. The obtained precipitate was purified by recrystallization with toluene, to obtain a white solid of 2-[4'-(1-adamantyl) biphenyl-3-yl]-4,6-diphenyl-1,3,5-triazine (Compound A-50) (amount: 2.24 g, yield: 83.8%) as the desired product.

$^1$H-NMR (CDCl$_3$): 1.81 (brt, J=14.6 Hz, 6H), 2.01 (brd, J=2.8 Hz, 6H), 2.15 (brs, 3H), 7.53 (d, J=8.5 Hz, 2H), 7.57-7.66 (m, 7H), 7.72 (d, J=8.7 Hz, 2H), 7.84 (ddd, J=7.7 Hz, 1.8 Hz, 1.1 Hz, 1H), 8.74 (d, t, J=8.1 Hz, 1.4 Hz, 1H), 8.80 (dd, J=8.2 Hz, 1.8 Hz, 4H), 9.01 (brt, J=1.8 Hz, 1H).

Tg of the obtained compound A-50 was 102° C.

Synthesis Example 11

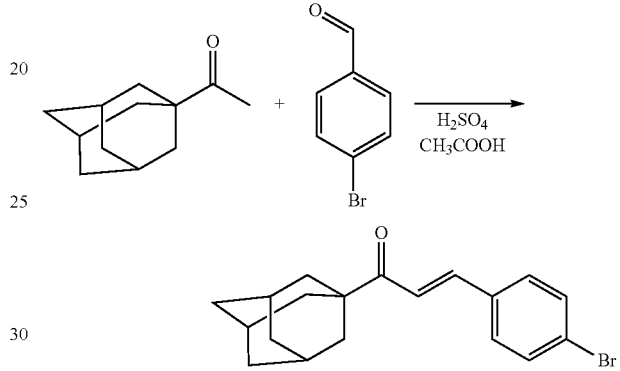

In the air, 1-adamantyl methyl ketone (5.00 g, 28.0 mol) and 4-bromobenzaldehyde (5.19 g, 28.0 mol) were dissolved in acetic acid (50 mL), and concentrated sulfuric acid (7.5 mL, 140 mol) was dropped, followed by stirring at 60° C. for 19 hours. After the stirring, 100 mL of water was added, and the precipitated solid was collected by filtration. The obtained solid was washed with water (200 mL), to obtain a yellow solid of 1-(1-adamantyl)-3-(4-bromophenyl)propenone (amount: 8.54 g, yield: 88.2%) as the desired product.

Synthesis Example 12

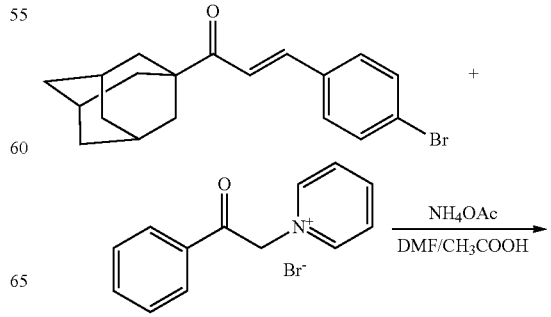

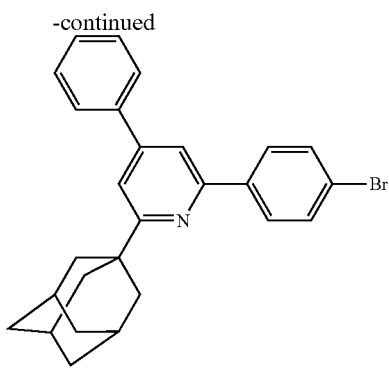

In the air, 1-(1-adamantyl)-3-(4-bromophenyl)propenone (1.00 g, 2.90 mmol), phenacyl pyridinium bromide (1.21 g, 4.34 mol) and ammonium acetate (4.46 g, 57.9 mol) were suspended in a mixed solvent of acetic acid (50 mL) and dimethylformamide (50 mL), followed by stirring at 150° C. for 19 hours. After cooling to room temperature, water (100 mL) was added, and the precipitated solid was collected by filtration. The obtained solid was washed with water (100 mL) and methanol (100 mL), to obtain a white solid of 6-(1-adamantyl)-2-(4-bromophenyl)-4-phenylpyridine (amount: 1.20 g, yield: 92.9%) as the desired product.

$^1$H-NMR (CDCl$_3$): 1.71-2.13 (brm, 15H), 7.33 (d, J=1.4 Hz, 1H), 7.39 (t, J=7.2 Hz, 1H), 7.46 (t, J=7.7 Hz, 2H), 7.53 (d, J=8.7 Hz, 2H), 7.60 (d, J=8.5 Hz, 2H), 7.68 (d, J=1.5 Hz, 1H), 8.12 (dd, J=8.4 Hz, 1.5 Hz, 2H).

Synthesis Example 13

Under an argon stream, 6-(1-adamantyl)-2-(4-bromophenyl)-4-phenylpyridine (8.00 g, 18.0 mmol), bis(pinacolato) diboron (4.80 g, 18.9 mmol), potassium acetate (4.24 g, 43.2 mmol) and bis(triphenylphosphine) palladium (II) dichloride (649 mg, 0.720 mmol) were suspended in 1,4-dioxane (80 mL), followed by heating to 100° C. and stirring for 22 hours. Then, after cooling to room temperature, 200 mL of chloroform and 50 mL of water were added to the reaction solution and mixed by shaking, whereupon only the organic layer was taken out. The organic layer was dehydrated by addition of magnesium sulfate and filtered. Low boiling point components in the obtained organic layer were distilled off to obtain a crude product. The obtained crude product was purified by silica gel column chromatography (developing solvent:mixed solution of chloroform:hexane=1:1), to obtain a white solid of 6-(1-adamantyl)-4-phenyl-2-[4-(4,4,5,5-tetramethyl-1,3,2-dioxaborolan-2-yl) phenyl]pyridine (7.34 g, yield: 83.0%) as the desired product.

Example 9

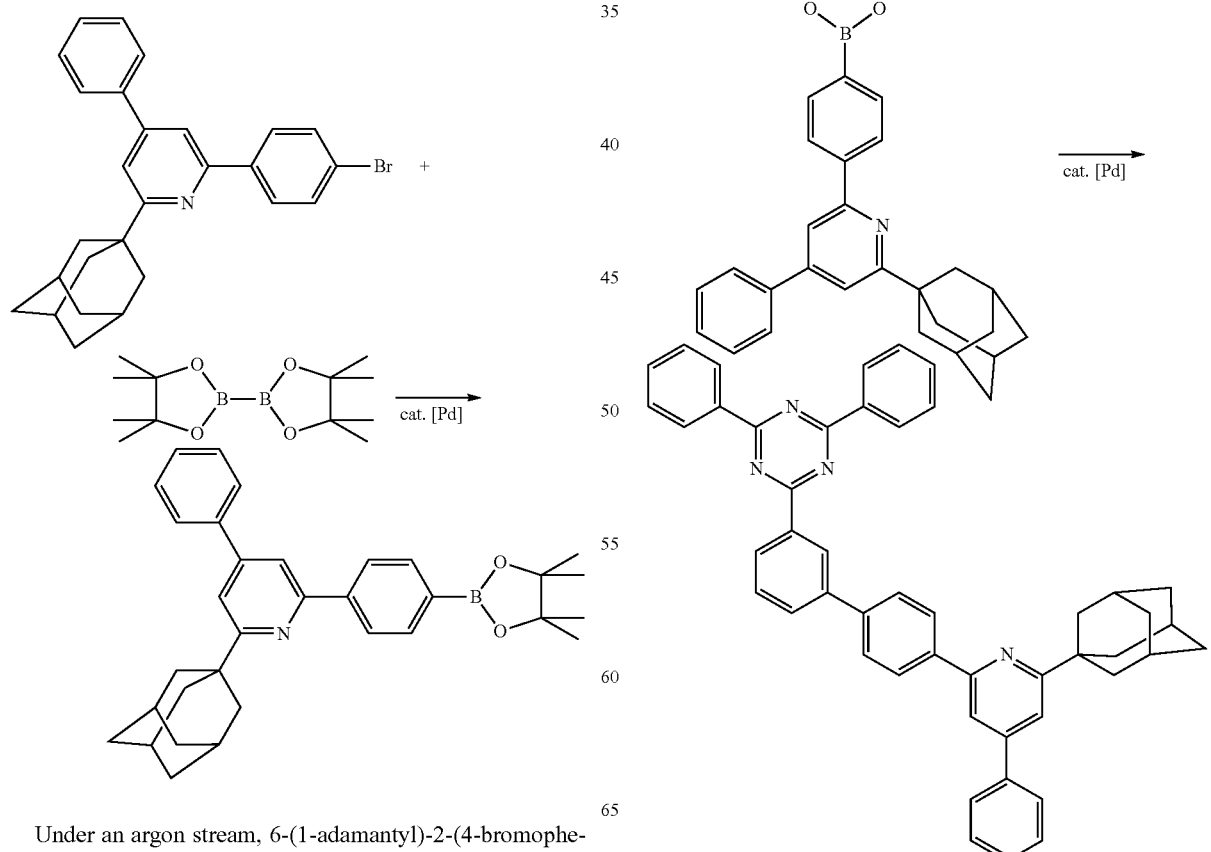

Under an argon stream, 2-(3-bromophenyl)-4,6-diphenyl-1,3,5-triazine (300 mg, 0.772 mmol), 6-(1-adamantyl)-4-phenyl-2-[4-(4,4,5,5-tetramethyl-1,3,2-dioxaborolan-2-yl)phenyl]pyridine (456 mg, 0.927 mmol), tetrakistriphenylphosphine palladium (26.8 mg, 0.0232 mmol) and potassium carbonate (320 mg, 2.32 mmol) were suspended in a mixed solvent of tetrahydrofuran (6 mL) and water (2 mL), followed by heating to 70° C. and stirring for 18 hours. After cooling to room temperature, water (8 mL) and chloroform (20 mL) were added to the reaction mixture and mixed by shaking. Then, only the organic layer was taken out, and low-boiling point components were distilled off, to obtain a crude product. The obtained crude product was sequentially washed with methanol (10 mL) and hexane (10 mL), to obtain a white solid of 2-{4'-[6-(1-adamantyl)-4-phenylpyridin-2-yl]biphenyl-3-yl}-4,6-diphenyl-1,3,5-triazine (compound A-433) (amount: 2.24 g, yield: 83.8%) as the desired product.

$^1$H-NMR (CDCl$_3$): 1.52 (brs, 6H), 1.83 (brs, 6H), 2.16 (brs, 3H), 7.41 (brt, J=7.6 Hz, 1H), 7.47-7.51 (m, 3H), 7.56-7.64 (m, 6H), 7.68 (t, J=7.8 Hz, 1H), 7.82-7.90 (m, 6H), 8.17 (dd, J=8.1 Hz, 1.6 Hz, 2H), 8.79 (dd, J=8.2 Hz, 1.9 Hz, 4H), 8.79-8.80 (m, 1H), 9.05 (t, 1.8 Hz, 1H).

Tg of the obtained compound A-433 was 135° C.

Synthesis Example 14

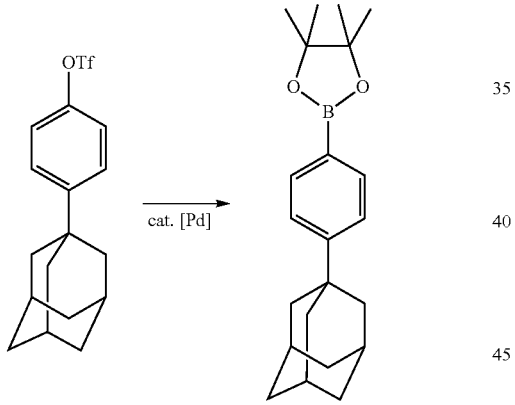

Under an argon stream, 4-(1-adamantyl)phenyl triflate (23.0 g, 74.9 mmol), bis (pinacolato)diboron (19.0 g, 74.9 mmol), palladium acetate (168 mg, 0.749 mmol), 2-dicyclohexylphosphino-2',4',6'-triisopropyl biphenyl (714 mg, 1.50 mmol), potassium acetate (15.4 g, 157 mmol) and lithium chloride (635 mg, 15.0 mmol) were suspended in dioxane (140 mL), followed by heating to 100° C. and stirring for 22 hours. After cooling to room temperature, water (100 mL) and chloroform (200 mL) were added to the reaction mixture and mixed by shaking. Then, only the organic layer was taken out and dehydrated with magnesium sulfate, whereupon low-boiling point components were distilled off to obtain a crude product. The obtained crude product was purified by silica gel column chromatography (developing solvent:chloroform) to obtain a white solid of 2-[4-(1-adamantyl)phenyl]-4,4,5,5-tetramethyl-1,3,2-dioxaborolane (amount: 23.4 g, yield: 92.4%) as the desired product.

$^1$H-NMR (CDCl$_3$): 1.75 (brt, J=15 Hz, 6H), 1.90 (brd, J=2.6 Hz, 6H), 2.07 (brs, 3H), 7.36 (d, J=8.3 Hz, 2H), 7.75 (d, J=8.4 Hz, 2H).

Reference Example 1

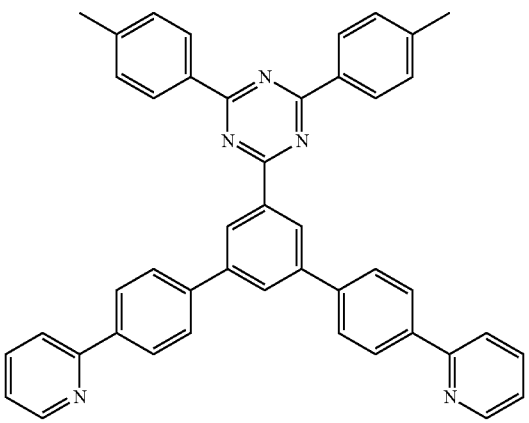 [SMILES: Cc1ccc(-c2nc(-c3ccc(C)cc3)nc(-c3cc(-c4ccc(-c5ccccn5)cc4)cc(-c4ccc(-c5ccccn5)cc4)c3)n2)cc1]

A thermal analysis of 2-[4,4"-di(2-pyridyl)-1,1':3',1"-terphenyl-5'-yl]-4,6-di-p-tolyl-1,3,5-triazine being the above compound that can be synthesized by the production method disclosed in JP-A-2008-280330, was carried out, and as a result, Tg was 108° C.

Reference Example 2

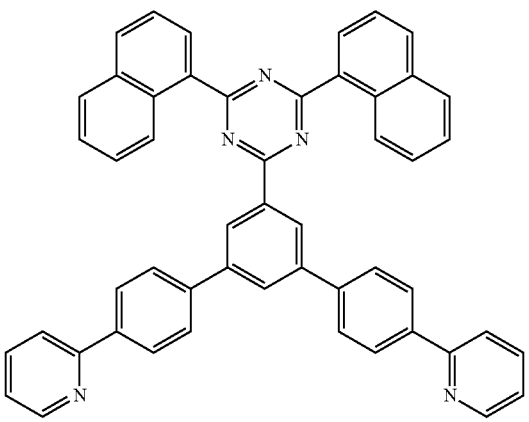 [SMILES: c1ccc(-c2ccc(-c3cc(-c4ccc(-c5ccccn5)cc4)cc(-c4nc(-c5cccc6ccccc56)nc(-c5cccc6ccccc56)n4)c3)cc2)nc1]

A thermal analysis of 2,4-bis(1-naphthyl)-6-[4,4"-bis(2-pyridyl)-[1,1':3',1"]-terphenyl-5'-yl]-1,3,5-triazine being the above compound disclosed in JP-A-2008-280330, was carried out, and as a result, Tg was 104° C.

The structural formulae and abbreviations of the compounds used in evaluations of the devices are as follows.

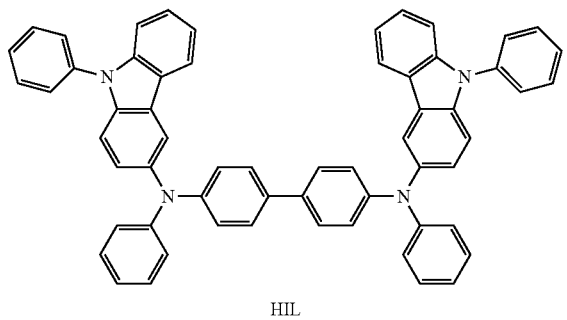

HIL

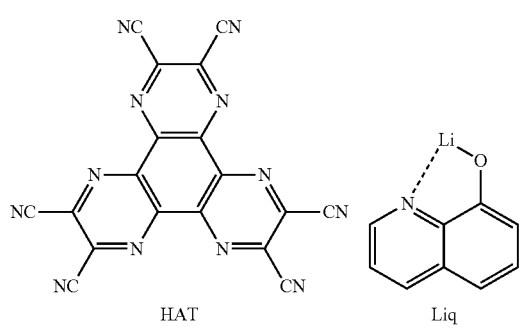

HAT    Liq

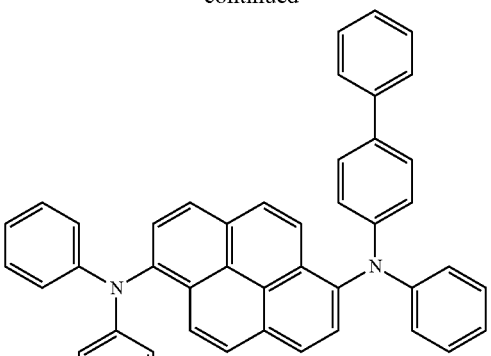

EML-2

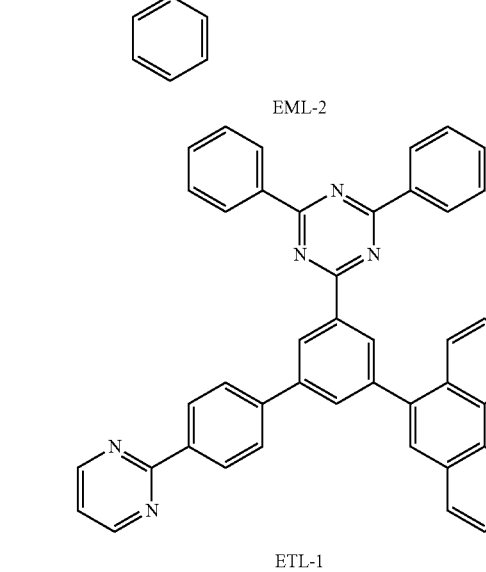

ETL-1

HTL

EML-1

Device Example 1

As the substrate, an ITO transparent electrode-attached glass substrate having an indium-tin oxide (ITO) film (thickness 110 nm) with a width of 2 mm patterned in a stripe shape, was used. This substrate was washed with isopropyl alcohol and then subjected to surface treatment by ozone UV cleaning. The substrate after the cleaning, was subjected to vacuum vapor deposition of each layer by a vacuum vapor deposition method, to prepare an organic electroluminescent device with a light-emitting area of 4 mm², as shown by a cross-sectional schematic view in FIG. 1. Here, each organic material was film-deposited by a resistance heating method.

Firstly, the glass substrate was introduced into a vacuum vapor deposition chamber, and the pressure was reduced to $1.0 \times 10^{-4}$ Pa. Then, on the ITO transparent electrode-attached glass substrate shown by 1 in FIG. 1, a hole injection layer 2, a charge generation layer 3, a hole transport layer 4, a luminous layer 5, an electron transport layer 6, an electron injection layer 7 and a cathode layer 8, were sequentially formed as organic compound layers as laminated in this order, each by vacuum vapor deposition.

As the hole injection layer 2, HIL purified by sublimation was deposited at a rate of 0.15 nm/sec in a film thickness of 65 nm.

As the charge generating layer 3, HAT purified by sublimation was deposited at a rate of 0.05 nm/sec in a film thickness of 5 nm.

As the hole transport layer 4, HTL was deposited at a rate of 0.15 nm/sec in a film thickness of 10 nm.

As the luminous layer 5, EML-1 and EML-2 were deposited at a ratio of 95:5 in a film thickness of 25 nm (deposition rate: 0.18 nm/sec).

As the electron transport layer 6, 2-[4"-(1-adamantyl)-4-(2-pyridyl)-[1,1':3',1"]-terphenyl-5'-yl]-4,6-diphenyl-1,3,5-triazine (Compound A-25) obtained in Example 3 and Liq were deposited at a ratio of 50:50 (weight ratio) in a film thickness of 30 nm (co-vapor deposition, deposition rate: 0.15 nm/sec).

Finally, a metal mask was placed to be orthogonal to the ITO stripe, and the cathode layer 7 was formed. For the cathode layer 7, silver/magnesium (weight ratio 1/10) and silver were deposited in this order in the film thicknesses of 80 nm (deposition rate: 0.5 nm/sec.) and 20 nm (deposition rate: 0.2 nm/sec.), respectively, to obtain a two-layer structure.

Each film thickness was measured by a contact type thickness meter (DEKTAK).

Further, the device was sealed in a nitrogen atmosphere glove box having an oxygen and moisture concentration of at most 1 ppm. For the sealing, a sealing cap made of glass and the above-mentioned film forming substrate epoxy type ultraviolet curable resin (manufactured by Nagase ChemteX Corporation) were used.

Device Example 2

An organic electroluminescent device was prepared in the same manner as in Device Example 1 except that in Device Example 1, for the electron transport layer 6, 2-[4'-(1-adamantyl)-5-(3-pyridyl)biphenyl-3-yl]-4,6-diphenyl-1,3,5-triazine (Compound A-14) obtained in Example 1, was used.

Device Example 3

An organic electroluminescent device was prepared in the same manner as in Device Example 1 except that in Device Example 1, for the electron transport layer 6, 4,6-bis(biphenyl-4-yl)-2-[4'-(1-adamantyl)-5-(3-pyridyl)biphenyl-3-yl]-1,3,5-triazine (Compound A-170) obtained in Example 2, was used.

Device Example 4

An organic electroluminescent device was prepared in the same manner as in Device Example 1 except that in Device Example 1, for the electron transport layer 6, 2-[4,4"-bis(1-adamantyl)-[1,1':3',1"]-terphenyl-5'-yl]-4,6-diphenyl-1,3,5-triazine (Compound A-49) obtained in Example 4, was used.

Device Example 5

An organic electroluminescent device was prepared in the same manner as in Device Example 1 except that in Device Example 1, for the electron transport layer 6, 2-[4"-(1-adamantyl)-4-(3-pyridyl)-[1,1':3',1"]-terphenyl-5'-yl]-4,6-diphenyl-1,3,5-triazine (Compound A-26) obtained in Example 5, was used.

Device Example 6

An organic electroluminescent device was prepared in the same manner as in Device Example 1 except that in Device Example 1, for the electron transport layer 6, 2-[4'-(1-adamantyl)-5-(3-pyridyl)biphenyl-3-yl]-4,6-diphenyl-1,3,5-triazine (Compound A-19) obtained in Example 6, was used.

Device Example 7

An organic electroluminescent device was prepared in the same manner as in Device Example 1 except that in Device Example 1, for the electron transport layer 6, 2-[4'-(1-adamantyl)-5-(6-phenylpyridin-3-yl)biphenyl-3-yl]-4,6-diphenyl-1,3,5-triazine (Compound A-28) obtained in Example 7, was used.

Device Example 8

An organic electroluminescent device was prepared in the same manner as in Device Example 1 except that in Device Example 1, for the electron transport layer 6, 2-{4'-[6-(1-adamantyl)-4-phenylpyridin-2-yl]biphenyl-3-yl}-4,6-diphenyl-1,3,5-triazine (Compound A-433) obtained in Example 9, was used.

Device Reference Example 1

An organic electroluminescent device was prepared in the same manner as in Device Example 1 except that in Device Example 1, for the electron transport layer 6, 2-[5-(9-phenanthryl)-4'-(2-pyrimidyl)biphenyl-3-yl]-4,6-diphenyl-1,3,5-triazine (ETL-1) disclosed in JP-A-2010-183145, was used.

A direct electric current was applied to the prepared organic electroluminescent device, whereby the light emitting characteristics were evaluated by means of a luminance meter i.e. LUMINANCE METER (BM-9) manufactured by TOPCON Corp. As the light emitting characteristics, the voltage (V) and current efficiency (cd/A) when the current (current density: 10 mA/cm$^2$) was applied, were measured. Further, when the device was driven at an initial luminance of 800 cd/m$^2$, the luminance decay time during continuous lighting was measured. For the device service life, the time required when the luminance (cd/m$^2$) was reduced 30%, was measured, and the service life was represented by a relative value when that of Device Reference Example 1 was taken as 100.

TABLE 1

| | Compound | Voltage (V) | Current efficiency (cd/A) | Device service life |
|---|---|---|---|---|
| Device Example 1 | A-25 | 4.44 | 5.13 | 172 |
| Device Example 2 | A-14 | 4.95 | 4.91 | 126 |
| Device Example 3 | A-170 | 4.48 | 4.26 | 116 |
| Device Example 4 | A-49 | 4.28 | 5.44 | 133 |
| Device Example 5 | A-26 | 4.15 | 4.86 | 216 |
| Device Example 6 | A-19 | 4.02 | 4.83 | 176 |
| Device Example 7 | A-28 | 3.99 | 4.78 | 261 |
| Device Example 8 | A-433 | 3.97 | 5.30 | 146 |
| Device Reference Example 1 | ETL-1 | 4.52 | 4.01 | 100 |

From Table 1, it is evident that as compared with Reference Example, the organic electroluminescent devices using the cyclic azine compounds of the present invention are improved in the characteristics such as the voltage, current efficiency and device service life.

INDUSTRIAL APPLICABILITY

The cyclic azine compound (1) of the present invention is excellent in thermal stability during the sublimation purification or vapor deposition process, etc. and can be provided as a material with less impurities, and when it is used as a material for an organic electroluminescent device, the device degradation will be less, the stability of the deposited film will be good, and the thermal resistance, long service life and luminous efficiency will be excellent, and in particular, it is useful as an electron transport material for an organic electroluminescent device excellent in low driving voltage.

Further, a thin film formed from the cyclic azine compound (1) of the present invention has an electron transport ability, a hole blocking ability, oxidation-reduction resistance, water resistance, oxygen resistance, an electron injection characteristic, etc. and thus is useful as a material for an organic electroluminescent device. Especially, it is useful as an electron transport material, hole blocking material, light-emitting host material, etc., and since the cyclic azine compound (1) is a wide band gap material, it not only is useful for applications as conventional fluorescent device material, but also has potential applications as phosphorescent device material.

The entire disclosure of Japanese Patent Application No. 2013-143909 filed on Jul. 9, 2013 including specification, claims, drawings and summary is incorporated herein by reference in its entirety.

REFERENCE SYMBOLS

1: ITO transparent electrode-attached glass substrate, 2: hole injection layer, 3: charge generating layer, 4: hole transport layer, 5: luminous layer, 6: electron transport layer, 7: cathode layer.

The invention claimed is:

1. A cyclic azine compound represented by the formula (1):

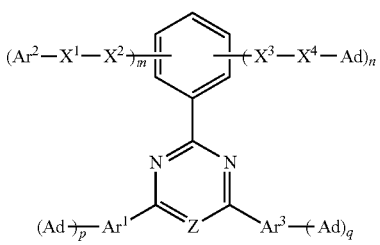

(1)

wherein Ad each independently represents a 1-adamantyl group (Ad$^1$) or a 2-adamantyl group (Ad$^2$):

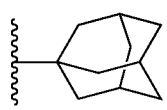

(Ad$^1$)

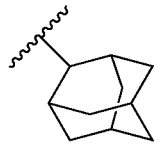

(Ad$^2$)

p and q are each independently 0 or 1,

Ar$^1$ and Ar$^a$ are each independently a single bond but only when p is 1 or q is 1, a C$_{6-30}$ aromatic hydrocarbon group, which may have, as a substituent, a fluorine atom, a C$_{1-4}$ alkyl group, a C$_{6-18}$ aromatic hydrocarbon group, a C$_{6-18}$ aromatic hydrocarbon group substituted by a fluorine atom, a C$_{6-18}$ aromatic hydrocarbon group substituted by a C$_{1-4}$ alkyl group, a C$_{6-18}$ aromatic hydrocarbon group substituted by a C$_{3-13}$ heteroaromatic group, a C$_{3-13}$ heteroaromatic group, or a C$_{3-13}$ heteroaromatic group substituted by a C$_{1-4}$ alkyl group, or a pyridyl group which may be substituted by a phenyl group or a methyl group, Ad groups on Ar$^1$ and Ar$^3$ are each independently bonded to said C$_{6-30}$ aromatic hydrocarbon group or said pyridyl group, Ar$^2$ is each independently a C$_{3-13}$ heteroaromatic group or a C$_{6-18}$ aromatic hydrocarbon group, wherein these groups each independently may have, as a substituent, a fluorine atom, a C$_{1-4}$ alkyl group, a C$_{6-18}$ aromatic hydrocarbon group, a C$_{6-18}$ aromatic hydrocarbon group substituted by a fluorine atom, a C$_{6-18}$ aromatic hydrocarbon group substituted by a C$_{1-4}$ alkyl group, a C$_{6-18}$ aromatic hydrocarbon group substituted by a C$_{3-13}$ heteroaromatic group, a C$_{3-13}$ heteroaromatic group, or a C$_{3-13}$ heteroaromatic group substituted by a C$_{1-4}$ alkyl group, X$^1$, X$^2$, X$^3$ and X$^4$ are each independently a single bond or a C$_{4-14}$ arylene group, which may be substituted by a fluorine atom, a C$_{1-4}$ alkyl group, a phenyl group, a biphenyl group or a naphthyl group, m is 0, 1 or 2, n is 0, 1 or 2, Z is a nitrogen atom, and n+p+q is 1, 2 or 3.

2. The cyclic azine compound according to claim 1, wherein Ar$^1$ and Ar$^3$ are each independently a phenyl group, a biphenyl group, a naphthyl group, a phenanthryl group, an anthryl group, a pyrenyl group, a triphenylenyl group, a chrysenyl group, a fluoranthenyl group, an acenaphthylenyl group, a pyridyl group, a pyrazyl group, a pyrimidyl group, a pyridazyl group, a triazyl group, a quinolyl group or an isoquinolyl group, wherein these groups each independently may have, as a substituent, a methyl group, an ethyl group, a propyl group, an isopropyl group, an n-butyl group or a t-butyl group.

3. The cyclic azine compound according to claim 1, wherein Ar$^2$ is a pyridyl group, a pyrazyl group, a pyridazyl group, a pyrimidyl group, a triazyl group, a quinolyl group, an isoquinolyl group, a naphthyridyl group, a quinazolyl group, a quinoxalyl group, a benzoquinolyl group, an acridyl group, a phenanthridyl group, a phenanthrolyl group, a phenyl group, a biphenyl group, a naphthyl group, a phenanthryl group, an anthryl group, a pyrenyl group, a triphenylenyl group, a chrysenyl group, a fluoranthenyl group or an acenaphthylenyl group, wherein these groups each independently may have, as a substituent, a methyl group, a phenyl group, a naphthyl group, a phenanthryl group, an anthryl group, a pyrenyl group, a triphenylenyl group, a pyridyl group, a pyrimidyl group, a pyrazyl group, a triazyl group, a quinolyl group or an isoquinolyl group.

4. The cyclic azine compound according to claim 1, wherein $X^1$, $X^2$, $X^3$ and $X^4$ are, each independently, a phenylene group, a naphthylene group, a pyridylene group, a pyrazylene group, a pyrimidylene group, wherein these groups may be substituted by a fluorine atom, a methyl group or a phenyl group, or a single bond.

5. The cyclic azine compound according to claim 1, wherein Ad is a 1-adamantyl group.

6. The cyclic azine compound according to claim 1, wherein m is 1.

7. The cyclic azine compound according to claim 1, wherein n is 1.

8. A method for producing a cyclic azine compound represented by the formula (1) as defined in claim 1, which comprises sequentially or simultaneously subjecting a compound represented by the formula (2), and compounds represented by the formulae (3) and (4), to a coupling reaction in the presence or absence of a base and in the presence of a palladium catalyst,

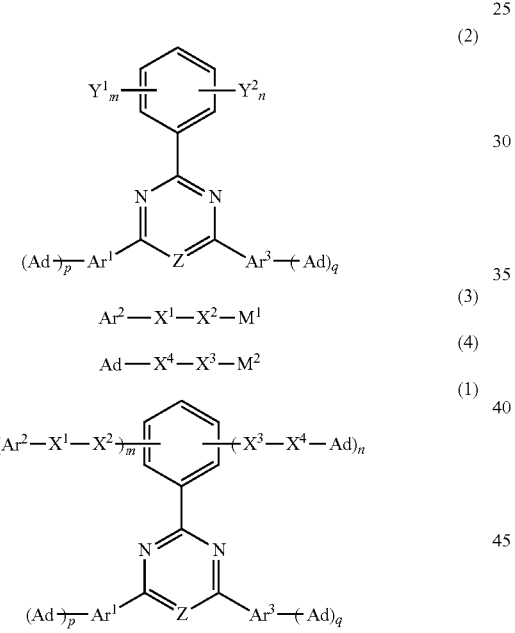

wherein Ad, p, q, $Ar^1$, $Ar^2$, $Ar^3$, $X^1$, $X^2$, $X^3$, $X^4$, m, n and Z are as defined in claim 1, and
n+p+q is 1, 2 or 3,
$Y^1$ and $Y^2$ each independently represents a leaving group,
$M^1$ and $M^2$ each independently represents a $ZnR^1$, $MgR^2$, $Sn(R^3)_3$ or $B(OR^4)_2$, wherein
$R^1$ and $R^2$ are each independently a chlorine atom, a bromine atom or an iodine atom, $R^3$ is a $C_{1-4}$ alkyl group or a phenyl group, $R^4$ is a hydrogen atom, a $C_{1-4}$ alkyl group or a phenyl group, two $R^4$ in $B(OR^4)_2$ may be the same or different, or the two $R^4$ may together form a ring containing an oxygen atom and a boron atom.

9. A method for producing a cyclic azine compound represented by the formula (1) as defined in claim 1, which comprises subjecting a compound represented by the formula (5) and a compound represented by the formula (6), to a coupling reaction in the presence or absence of a base and in the presence of a palladium catalyst,

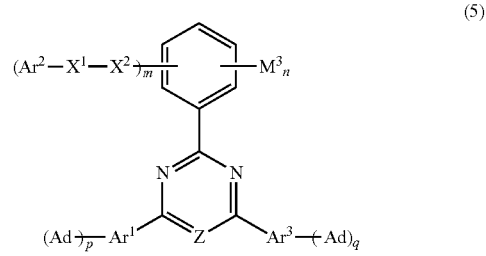

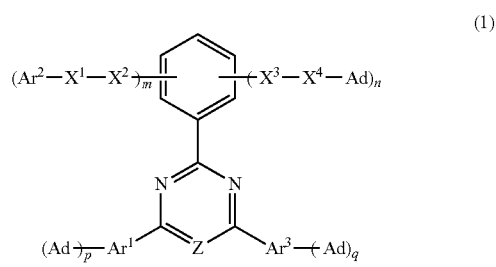

wherein Ad, p, q, $Ar^1$, $Ar^2$, $Ar^3$, $X^1$, $X^2$, $X^3$, $X^4$, m, n and Z are as defined in claim 1, and
n+p+q is 1, 2 or 3,
$Y^3$ represents a leaving group,
$M^3$ represents a $ZnR^1$, $MgR^2$, $Sn(R^3)_3$ or $B(OR^4)_2$, wherein $R^1$ and $R^2$ are each independently a chlorine atom, a bromine atom or an iodine atom, $R^3$ is a $C_{1-4}$ alkyl group or a phenyl group, $R^4$ is a hydrogen atom, a $C_{1-4}$ alkyl group or a phenyl group, two $R^4$ in $B(OR^4)_2$ may be the same or different, or the two $R^4$ may together form a ring containing an oxygen atom and a boron atom.

10. A method for producing a cyclic azine compound represented by the formula (1) as defined in claim 1, which comprises subjecting a compound represented by the formula (7) and a compound represented by the formula (8), to a coupling reaction in the presence or absence of a base and in the presence of a palladium catalyst,

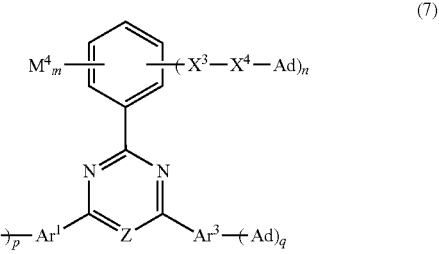

-continued

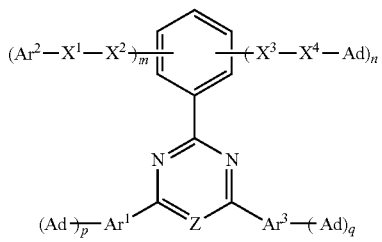
(1)

wherein Ad, p, q, Ar¹, Ar², Ar³, X¹, X², X³, X⁴, m, n and Z are as defined in claim 1, and
n+p+q is 1, 2 or 3,
Y⁴ represents a leaving group,
M⁴ represents a ZnR¹, MgR², Sn(R³)₃ or B(OR⁴)₂, wherein R¹ and R² are each independently a chlorine atom, a bromine atom or an iodine atom, R³ is a $C_{1-4}$ alkyl group or a phenyl group, R⁴ is a hydrogen atom, a $C_{1-4}$ alkyl group or a phenyl group, two R⁴ in B(OR⁴)₂ may be the same or different, or the two R⁴ may together form a ring containing an oxygen atom and a boron atom.

11. The method according to claim 8, wherein the palladium catalyst is a palladium catalyst having a tertiary phosphine as a ligand.

12. The method according to claim 11, wherein the palladium catalyst is a palladium catalyst having triphenylphosphino or 2-dicyclohexylphosphino-2',4',6'-triisopropylbiphenyl as a ligand.

13. A method for producing a cyclic azine compound represented by the formula (1), which comprises reacting a compound represented by the formula (11) and/or (12), and a compound represented by the formula (2') in the presence of a palladium catalyst, or in the presence of a base and a palladium catalyst,

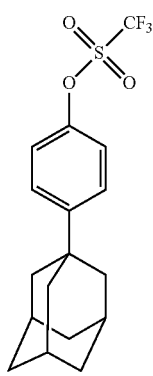
(11)

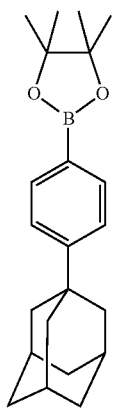
(12)

-continued

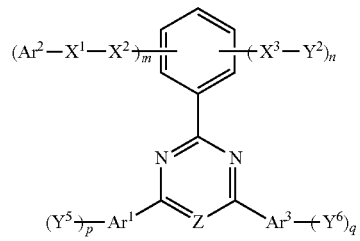
(2')

wherein p and q are each independently 0 or 1,
Ar¹ and Ar³ are each independently a single bond, but only when p is 1, or q is 1, a $C_{6-30}$ aromatic hydrocarbon group, which may have, as a substituent, a fluorine atom, a $C_{1-4}$ alkyl group, a $C_{6-18}$ aromatic hydrocarbon group, a $C_{6-18}$ aromatic hydrocarbon group substituted by a fluorine atom, a $C_{6-18}$ aromatic hydrocarbon group substituted by a $C_{1-4}$ alkyl group, a $C_{6-18}$ aromatic hydrocarbon group substituted by a $C_{3-13}$ heteroaromatic group, a $C_{3-13}$ heteroaromatic group, or a $C_{3-13}$ heteroaromatic group substituted by a $C_{1-4}$ alkyl group, or a pyridyl group which may be substituted by a phenyl group or a methyl group,
Ad groups on Ar¹ and Ar³ are each independently bonded to said $C_{6-30}$ aromatic hydrocarbon group or said pyridyl group,
Ar² is each independently a $C_{3-13}$ heteroaromatic group or a $C_{6-18}$ aromatic hydrocarbon group, wherein these groups each independently may have, as a substituent, a fluorine atom, a $C_{1-4}$ alkyl group, a $C_{6-18}$ aromatic hydrocarbon group, a $C_{6-18}$ aromatic hydrocarbon group substituted by a fluorine atom, a $C_{6-18}$ aromatic hydrocarbon group substituted by a $C_{1-4}$ alkyl group, a $C_{6-18}$ aromatic hydrocarbon group substituted by a $C_{3-13}$ heteroaromatic group, a $C_{3-13}$ heteroaromatic group, or a $C_{3-13}$ heteroaromatic group substituted by a $C_{1-4}$ alkyl group,
m is 0, 1 or 2,
n is 0, 1 or 2,
Z is a nitrogen atom,
n+p+q is 1, 2 or 3,
X¹, X² and X³ are each independently a single bond or a $C_{4-14}$ arylene group, which may be substituted by a fluorine atom, a $C_{1-4}$ alkyl group, a phenyl group, a biphenyl group or a naphthyl group,
Y², Y⁵ and Y⁶ each independently represents a leaving group,

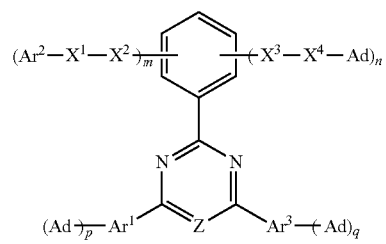
(1)

wherein Ad represents a 1-adamantyl group,
p and q are each independently 0 or 1,
Ar¹ and Ar³ are the same as above,
Ar² is the same as above, $X^1$, $X^2$ and $X^3$ is the same as above,
$X^4$ is a phenylene group,
m is 0, 1 or 2,
n is 0, 1 or 2,
Z is a nitrogen atom,
n+p+q is 1, 2 or 3.

14. An organic electroluminescent device containing the cyclic azine compound as defined in claim 1, as a constituent component.

15. The organic electroluminescent device according to claim 14, wherein the cyclic azine compound is an electron transport layer.

* * * * *